US 10,112,953 B2

(12) United States Patent
Mulcahy et al.

(10) Patent No.: US 10,112,953 B2
(45) Date of Patent: Oct. 30, 2018

(54) 11,13-MODIFIED SAXITOXINS FOR THE TREATMENT OF PAIN

(71) Applicants: SITEONE THERAPEUTICS, INC., Bozeman, MT (US); THE BOARD OF TRUSTEES OF THE LELAND STANFORD JUNIOR UNIVERSITY, Stanford, CA (US)

(72) Inventors: John Mulcahy, Redwood City, CA (US); Hassan Pajouhesh, Mountain View, CA (US); Grant Masaaki Shibuya, South San Francisco, CA (US); Anton Delwig, Albany, CA (US); George Miljanich, Redwood City, CA (US); Justin Du Bois, Menlo Park, CA (US)

(73) Assignees: SITEONE THERAPEUTICS, INC., Bozeman, MT (US); THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 15/283,187

(22) Filed: Sep. 30, 2016

(65) Prior Publication Data

US 2017/0233398 A1    Aug. 17, 2017

Related U.S. Application Data

(60) Provisional application No. 62/235,412, filed on Sep. 30, 2015.

(51) Int. Cl.
*C07D 487/14*    (2006.01)

(52) U.S. Cl.
CPC ................. *C07D 487/14* (2013.01)

(58) Field of Classification Search
CPC .................................................. C07D 487/14
See application file for complete search history.

(56) References Cited

U.S. PATENT DOCUMENTS

| | | | |
|---|---|---|---|
| 3,957,996 | A | 5/1976 | Adams et al. |
| 6,030,974 | A | 2/2000 | Schwartz et al. |
| 6,326,020 | B1 | 12/2001 | Kohane |
| 7,576,202 | B2 | 8/2009 | Myasoedov |
| 2002/0161013 | A1 | 10/2002 | Liu et al. |
| 2005/0137177 | A1 | 6/2005 | Shafer |
| 2005/0202093 | A1 | 9/2005 | Kohane et al. |
| 2006/0057647 | A1 | 3/2006 | Robillot |
| 2007/0280970 | A1 | 12/2007 | Wilson |
| 2008/0021051 | A1 | 1/2008 | Wilson |
| 2008/0045553 | A1 | 2/2008 | Wilson |

FOREIGN PATENT DOCUMENTS

| | | | |
|---|---|---|---|
| CN | 1192903 | A | 9/1998 |
| CN | 1363275 | A | 8/2002 |
| CN | 101513408 | A | 8/2009 |
| EP | 0857972 | A1 | 8/1998 |
| WO | WO 2003/006507 | A1 | 1/2003 |
| WO | WO 2010/027641 | A2 | 3/2010 |
| WO | WO 2010/129864 | * | 11/2010 .......... C07D 487/14 |
| WO | WO 2010/129864 | A2 | 11/2010 |
| WO | WO 2011/098539 | A1 | 8/2011 |
| WO | WO 2015/157559 | A2 | 10/2015 |

OTHER PUBLICATIONS

West, Anthony R., Solid State Chemistry and Its Applications, Wiley, New York, 1988, 358.*
Cox et al., "An SCN9A channelopathy causes congenital inability to experience pain," Nature, vol. 444, Dec. 14, 2006, pp. 894-898.
Akimoto et al., "Synthesis of Saxitoxin Derivatives Bearing Guanidine and Urea Groups At C13 and Evaluation of Their Inhinary Activity on Voltage-Gated Sodium Channels", Org. Biomol. Chem., Jan. 1, 2013, vol. 11, No. 38, pp. 6642-6649.
Anderson, et al., "Voltage-Gated Sodium Channel Blockers As Cytostatic Inhibitors of the Androgen-Independent Prostate Cancer Cell Line PC-3", Mol. Cancer Ther., Nov. 14, 2003, vol. 2, pp. 1149-1154.
Arakawa et al., "Occurrence of carbamoyl-N-hydroxy derivatives of saxitoxin and neosaxitoxin in a xanthid crab Zosimus aeneus", Toxicon, 1994, vol. 32, pp. 175-183.
Arakawa et al., "A New Saxitoxin Analogue from a Xanthid Crab Atergatis Floridus", Toxicon, 1995, vol. 33, pp. 1577-1584.
Bennett et al., "Contribution of Sialic Acid to the Voltage Dependence of Sodium Channel Gating", J. Gen. Physiol., Mar. 1997, vol. 109, No. 3, pp. 327-343.

(Continued)

*Primary Examiner* — Erich A Leeser
(74) *Attorney, Agent, or Firm* — Squire Patton Boggs (US) LLP

(57) ABSTRACT

Provided herein are compounds, pharmaceutical compositions comprising the compounds, methods of preparing the compounds, and methods of using the compounds and compositions in treating conditions associated with voltage-gated sodium channel function where the compounds are 11,13-modified saxitoxins according to Formula (I):

(I)

where $R^1$, $X^1$ and $X^3$ are as described herein.

32 Claims, No Drawings

(56) References Cited

OTHER PUBLICATIONS

Dell'Aversano et al., "Isolation and Structure Elucidation of New and Unusual Saxitoxin Analogues from Mussels", *Journal of Natural Products*, 2008, vol. 71, pp. 1518-1523.
Fleming et al. "(+)-Saxitoxin: A First and Second Generation Stereoselective Synthesis", *J. Am. Chemical Society*, 2007, vol. 129, pp. 9964-9975.
Hall et al., "Dinoflagellate Neurotoxins Related to Saxitoxin: structures of toxins C3 and C4, and confirmation of the structure of neosaxitoxin", *Tet Lett*, 1984; vol. 25, pp. 3537-3538.
Harada et al., "Natural Occurrence of Decarbamoylsaxitoxin in Tropical Dinoflagellate and Bivalves", *Agric Biol Chem*, 1983; vol. 47, pp. 191-193.
Iwamoto et al., "Total synthesis of (−)- and (+)-decarbamoyloxysaxitoxin and (+)-saxitoxin", *Chem Asian J*, 2009, vol. 4, pp. 277-285.
Jacobi et al., "Total Synthesis of +/−Saxitoxin", *J Am Chem Soc*, 1984, vol. 106, pp. 5594-5598.
Klugbauer et al, "Structure and Functional Expression of a New Member of the Tetrodotoxin-Sensitive Voltageactivated Sodium Channel Family From Human Neuroendocrine Cells", *The EMBO Journal*, 1995, vol. 14 No. 6, pp. 1084-1090.
Koehn Fe et al., "Dinoflagellate Neurotoxins Related to Saxitoxin: Structure and Latent Activity of Toxins B1 and B2", *Tetrahedron Letters*, 1982; vol. 23, pp. 2247-2248.
Llewellyn Le, "Saxitoxin, a Toxic Marine Natural Product that Targets a Multitude of Receptors", *Nat Prod Rep*, 2006, vol. 23, pp. 200-222.
Mao et al., "Novel modulator of NaV1.1 and NaV1.2 Na+ channels in rat neuronal cells", *Med Chem Lett*, 2010, vol. 1, pp. 135-138.
Momin et al., "Sensory Neuron Voltage-Gated Sodium Channels As Analgesic Drug Targets", *Current Opinion in Neurobiology*, 2008, vol. 18, pp. 383-388.
Mulcahy et al., "A Stereoselective Synthesis of (+)-Gonyautoxin 3", *J Am Chem Soc.*, Sep. 24, 2008; vol. 130, No. 38, pp. 12630-12631.
Negri et al., "Three Novel Hydroxybenzoate Saxitoxin Analogues Isolated From the Dinoflagellate Gyninodinium Catenatum", *Chem Res Toxicol*, 2003, vol. 16, pp. 1029-1033.
Nishikawa et al., "Synthesis of an Advanced Model of Zetekitoxin AB Focusing on the N-Acylisoxazolidine Amide Structure Corresponding to C13-C17", *Asian Journal of Organic Chemistry*, Oct. 23, 2014, vol. 3, No. 12, pp. 1308-1311.
Ogata et al., "Molecular Diversity of Structure and Function of the Voltage-Gated Na+ Channels", *Jpn. J. Pharmacol.*, 2002, vol. 88, pp. 365-377.
Onodera et al., "New Saxitoxin Analogues from the Freshwater Filamentous Cyanobacterium Lyngbya wollei", *Natural Toxins*, 1997, vol. 5, pp. 146-151.
Robillot et al., "Synthesis of Bifunctional Saxitoxin Analogues by Biotinylation", *Toxicon*, 2009; vol. 53, pp. 460-465.
Rush et al. "Multiple Sodium Channels and their Roles in electrogenesis within Dorsal Root Ganglion Neurons", *J. Physiol*, 2007, 579 (Pt 1), pp. 1-14.
Sato et al., "Identification of Thioether Intermediates in the Reductive Transformation of Gonyautoxins Into Saxitoxins by Thiols", *Bioorganic & Medicinal Chemistry Letters*, vol. 10, No. 6, Aug. 21, 2000, pp. 1787-1789.
Schlager et al., "Micromole scale biotinylation of saxitoxin (STX) for use as a screening moiety for peptide binding libraries", *Medical Defense Bioscience Proceedings*, May 16, 1996, vol. 12, No. 3, pp. 1590-1597.
Shimizu et al., "Isolation of Side-Chain Sulfated Saxitoxin Analogs", *Tetrahedron*, 1984; vol. 40, pp. 539-544.
Shimizu et al., Structure of Saxitoxin in Solutions and Stereochemistry of Dihydrosaxitoxins. *J Am Chem Soc*, 1981, vol. 103, pp. 605-609.
Shimuzu et al., "Toxigenesis and Biosynthesis of Saxitoxin Analogues," *Pure and Applied Chemistry*, 1986, vol. 58, No. 2, pp. 257-262.
Strichartz GR et al., "The Potencies of Synthetic Analogues of Saxitoxin and the Absolute Stereoselectivity of Decarbamoyl Saxitoxin", *Toxicon*, 1995, vol. 33, pp. 723-737.
Tanino et al., "A Stereospecific Total Synthesis of d,l-Saxitoxin", *J Am Chem Soc*, 1977, vol. 99, pp. 2818-2819.
Vale P., "Metabolites of Saxitoxin Analogues in Bivalves Contaminated by Gyrrinodinium Catenatum", *Toxicon*, 2010; vol. 55, pp. 162-165.
Vale P., "New Saxitoxin Analogues in the Marine Environment: Developments in Toxin Chemistry, Detection and Biotransformation During the 2000s", *Phytochem Rev*, 2010, vol. 9, pp. 525-535.
Walls, et al., "Synthesis and Biological Evaluation of a Fluorescent Analog of Phenytoin As a Potential Inhibitor of Neuropathic Pain and Imaging Agent", *Bioorg. Med. Chem.*, Jul. 3, 2012, vol. 20, pp. 5269-5276.
Yotsu-Yamashita et al., "The Structure of Zetekitoxin Ab, A Saxitoxin Analog From the Panamian Golden Frog Atelopus Zeteki: A Potent Sodium-Channel Blocker", *PNAS*, 2004; vol. 101, pp. 4346-4351.
Zaman et al., "Occurrence of a Methyl Derivative of Saxitoxin in Bangladeshi Freshwater Puffers", *Toxicon*, 1998, vol. 36, pp. 627-630.
International Search Report and Written Opinion for PCT/US2016/055050 dated Nov. 28, 2016, 12 pages.
West, Anthony R., "Solid State Chemistry and its Applications", *Wiley, New York*, (1998), p. 358 and p. 365.
Biotinylation web site (http://www.piercenet.com/browse.cfm?fldID.84EBE112-F871-4CA5-807F-47327153CFCB retrieved Apr. 5, 2012).
Biswal et al. "Molecular Imaging: Integration of Molecular Imaging into the Musculoskeletal Imaging Practice", Radiology 244(3):651-671 (2007).
Bundgaard, Design of Prodrugs, 1985, Elsevier, Chapter 1, p. 1-4.
Dib-Hajj et al. "From genes to pain: Na v 1.7 and human pain disorders", Trends Neurosci. 30(11):555-563.
Dorr et al. "Intriguing differences in the gas-phase dissociation behavior of protonated and deprotonated gonyautoxin epimers", J. American Society Mass. Spec. 22:2011-2020.
Fleming et al. "A synthesis of (+)-saxitoxin", J. Am. Chem. Soc. 128:3926-3927 (2006).
Goldberg et al. "Loss-of-function mutations in the Nav1.7 gene underlie congenital indifference to pain in multiple human populations", Clinical Genetics 71(4):311-319 (2007).
Han, Targeted Prodrug Design to Optimize Drug Deliver, 2000, AAPS Pharmsci, vol. 2(1), p. 1-11.
Watanabe et al., "Development of Saxitoxin-Conjugated Affinity Gels" Bioconjugate Chem., 17:459-465 (2006).
Waxman, Stephen G., "A Channel Sets the Gain on Pain" Nature, 444:831-832.

\* cited by examiner

`US 10,112,953 B2`

11,13-MODIFIED SAXITOXINS FOR THE TREATMENT OF PAIN

CROSS-REFERENCE TO RELATED APPLICATIONS

This application claims the benefit of U.S. Provisional Application No. 62/235,412, filed Sep. 30, 2015, which is hereby incorporated by reference in its entirety.

STATEMENT OF GOVERNMENT RIGHTS

This invention was made with Government support under contract NS081887 and NS045684 awarded by the National Institutes of Health. The U.S. Government has certain rights in this invention.

FIELD

Provided herein are compounds, pharmaceutical compositions comprising the compounds, and methods of using the compounds and compositions in treating conditions associated with voltage-gated sodium channel function, for example conditions associated with pain. The compounds are 11,13-modified saxitoxins. Also provided herein are methods of treating pain in a mammal comprising administering a therapeutically or prophylactically effective amount of a 11,13-modified saxitoxin or composition to a mammal. In an embodiment, the mammal is a human.

BACKGROUND

The voltage-gated sodium channel is a large integral membrane protein complex present in neurons and excitable tissues where it contributes to processes such as membrane excitability and muscle contraction (Ogata et al., *Jpn. J. Pharmacol.* (2002) 88(4) 365-77). It has been identified as a primary target for the treatment of pain. Genes encoding for nine distinct mammalian isoforms of Nav channels (Nav isoforms 1.1-1.9) have been sequenced. Variation in the gating properties of different Nav isoforms, cellular distributions, and expression levels influence the physiology of nerve cell conduction. A mounting body of evidence suggests that individual Nav isoforms Nav 1.3, 1.7, and 1.8 are disproportionately involved in pain signaling and nociception, and that an isoform-specific inhibitor of Nav could provide pain relief without the accompanying undesirable effects of a non-specific Nav antagonist or an opioid drug (Momin et al., *Curr Opin Neurobiol.* 18(4): 383-8, 2008; Rush et al., *J. Physiol.* 579(Pt 1): 1-14, 2007).

A human genetic disorder resulting in a loss of function mutation in Na$_V$ 1.7 has been correlated with congenital insensitivity to pain (Cox et al., Nature. (2006) 444(7121) 894-898). The design of a drug which selectively inhibits Na$_V$ 1.7 over the other Na$_V$ channels is therefore desirable. Such a drug design is challenging given the high structural homology (75-96%) of the mammalian Na$_V$ isoforms. There exists a need for compounds which treat pain and conditions associated with voltage-gated sodium channel function, particularly which selectively inhibit Na$_V$ 1.7 over other Na$_V$ isoforms.

SUMMARY

Provided herein are compounds, pharmaceutical compositions comprising the compounds, and methods of using the compounds and compositions for the treatment of conditions modulated by voltage-gated sodium channels, in certain embodiments, in the treatment of pain. The compounds are 11,13-modified saxitoxins. Also provided herein are methods of treating pain and/or conditions modulated by voltage-gated sodium channels in a mammal comprising administering a therapeutically or prophylactically effective amount of a 11,13-modified saxitoxin or composition to a mammal. In an embodiment, the mammal is a human.

In one aspect, provided is a Compound of Formula (I):

(I)

[Chemical structure]

where
$R^1$ is H, OH, $-OS(O)_3^-$, $-OS(O)_2R^5$, $-OC(O)R^6$, $-NR^7C(O)R^{7a}$, $-OC(O)NR^{10}R^{10a}$, $-NR^{11}R^{11a}$, $-NH_3^+$, $-NR^{13}S(O)_2R^{13a}$, $-NR^{14}C(O)NR^{14a}R^{14b}$, or heterocycloalkyl;

$X^1$ is $R^3$ and $X^2$ is $R^9$; or $X^1$ and $X^2$ together with the $-NC(O)-$ to which they are attached form a 5 or 6-membered ring where $X^1$, $X^2$, and the one or two additional ring atoms are independently selected from $-C(O)-$, $-O-$, $-S-$, $-NR^8-$, and $-C(R^4)(R^{4a})-$ provided that only one is selected from $-O-$, $-S-$, and $-NR^8-$; and where the 5 or 6-membered ring is optionally fused at two adjacent carbon atoms, or is optionally fused at one carbon atom and one nitrogen atom which are adjacent to each other, to a form a saturated or unsaturated 6-12 membered bicyclic ring; where the 1, 2, 3, 4, 5, or 6 additional bicyclic ring atoms are independently $-CR^{12}=$ or $-C(R^{12})_2-$; or $X^1$ and $X^2$ together with the $-NC(O)-$ to which they are attached form 1,3-dioxo-hexahydro-1H-4,7-methanoisoindolyl;

each $R^4$ and $R^{4a}$ is independently H; $C_{1-6}$alkyl; or when the 6-12 membered ring is fused at a $-C(R^4)(R^{4a})-$, one or both of the $R^4$ and $R^{4a}$ on the $-C(R^4)(R^{4a})-$ form a single or double bond with an adjacent ring atom;

$R^8$ is hydrogen; $C_{1-6}$alkyl; phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano; or when the 6-12 membered ring is fused at an $-NR^8-$, the $R^8$ forms a single bond with an adjacent ring atom;

each $R^{12}$ is independently hydrogen, halo, $C_{1-6}$alkyl, halo-$C_{1-6}$alkyl, or aryl;

$R^3$ is $-C(O)C_{1-6}$alkyl, $-C(O)OC_{1-6}$alkyl, or $-C(O)$phenyl where the phenyl is optionally substituted with one or two groups independently selected from halo, $C_{1-6}$alkyl, halo-$C_{1-6}$alkyl, $C_{1-6}$alkoxy, and aryl;

$R^5$ is H, $C_{1-6}$alkyl, or aryl optionally substituted with 1, 2, 3, or 4 $R^{5a}$;

each $R^{5a}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo- $C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;

$R^9$ is $C_{1-6}$alkyl, $C_{1-6}$alkoxy, or phenyl where the phenyl is optionally substituted with one or two groups independently selected from halo, $C_{1-6}$alkyl, halo-$C_{1-6}$alkyl, $C_{1-6}$alkoxy, and aryl;

$R^6$ is $C_{1-6}$alkyl; aryl optionally substituted with 1, 2, or 3 $R^{6a}$; aralkyl where the aryl is optionally substituted with 1, 2, 3, or 4 $R^{6a}$; heteroaryl optionally substituted with 1, 2, 3, or 4 $R^{6a}$; heterocyclic optionally substituted with 1, 2, 3, or 4 $R^{6a}$; biphenyl optionally substituted on either ring with 1, 2, 3, or 4 $R^{6a}$; or cycloalkyl optionally substituted with 1, 2, 3, or 4 groups independently selected from $C_{1-6}$alkyl and halo-$C_{1-6}$alkyl;

each $R^{6a}$, when present, is independently halo, $C_{1-6}$alkyl, halo-$C_{1-6}$alkyl, hydroxy, $C_{1-6}$alkoxy, halo-$C_{1-6}$alkoxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, phenyl, or cyano;

$R^7$ is hydrogen or $C_{1-6}$alkyl;

$R^{7a}$ is $C_{1-6}$alkyl; aryl optionally substituted with 1, 2, 3, or 4 $R^{7b}$; aralkyl where the aryl is optionally substituted with 1, 2, 3, or 4 $R^{7b}$; heteroaryl optionally substituted with 1, 2, 3, or 4 $R^{7b}$; heterocyclic optionally substituted with 1, 2, 3, or 4 $R^{7b}$; biphenyl optionally substituted on either ring with 1, 2, 3, or 4 $R^{7b}$; or cycloalkyl optionally substituted with 1, 2, 3, or 4 groups independently selected from $C_{1-6}$alkyl and halo-$C_{1-6}$alkyl;

each $R^{7b}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;

$R^{10}$ is hydrogen or $C_{1-6}$alkyl;

$R^{10a}$ is $C_{1-6}$alkyl; aryl optionally substituted with 1, 2, 3, or 4 $R^{10b}$; aralkyl where the aryl is optionally substituted with 1, 2, 3, or 4 $R^{10b}$; phenylcarbonyl where the phenyl is optionally substituted with 1, 2, 3, or 4 $R^{10b}$; heteroaryl optionally substituted with 1, 2, 3, or 4 $R^{10b}$; heterocyclic optionally substituted with 1, 2, 3, or 4 $R^{10b}$; biphenyl optionally substituted on either ring with 1, 2, 3, or 4 $R^{10b}$; or cycloalkyl optionally substituted with 1, 2, 3, or 4 groups independently selected from $C_{1-6}$alkyl and halo-$C_{1-6}$alkyl;

each $R^{10b}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;

$R^1$ is hydrogen or $C_{1-6}$alkyl;

$R^{11a}$ is $C_{1-6}$alkyl; aryl optionally substituted with 1, 2, 3, or 4 $R^{11b}$; aralkyl where the aryl is optionally substituted with 1, 2, 3, or 4 $R^{11b}$; heteroaryl optionally substituted with 1, 2, 3, or 4 $R^{11b}$; heterocyclic optionally substituted with 1, 2, 3, or 4 $R^{11b}$; biphenyl optionally substituted on either ring with 1, 2, 3, or 4 $R^{11b}$; or cycloalkyl optionally substituted with 1, 2, 3, or 4 groups independently selected from $C_{1-6}$alkyl and halo-$C_{1-6}$alkyl;

each $R^{11b}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;

$R^{13}$ is hydrogen or $C_{1-6}$alkyl;

$R^{13a}$ is $C_{1-6}$alkyl; aryl optionally substituted with 1, 2, 3, or 4 $R^{13b}$; aralkyl where the aryl is optionally substituted with 1, 2, 3, or 4 $R^{13b}$; heteroaryl optionally substituted with 1, 2, 3, or 4 $R^{13b}$; heterocyclic optionally substituted with 1, 2, 3, or 4 $R^{13b}$; biphenyl optionally substituted on either ring with 1, 2, 3, or 4 $R^{13b}$; or cycloalkyl optionally substituted with 1, 2, 3, or 4 groups independently selected from $C_{1-6}$alkyl and halo-$C_{1-6}$alkyl;

each $R^{13b}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;

$R^{14}$ is hydrogen or $C_{1-6}$alkyl;

$R^{14a}$ is hydrogen or $C_{1-6}$alkyl;

$R^{14b}$ is $C_{1-6}$alkyl; aryl optionally substituted with 1, 2, 3, or 4 $R^{14c}$; aralkyl where the aryl is optionally substituted with 1, 2, 3, or 4 $R^{14c}$; heteroaryl optionally substituted with 1, 2, 3, or 4 $R^{14c}$; heterocyclic optionally substituted with 1, 2, 3, or 4 $R^{14c}$; biphenyl optionally substituted on either ring with 1, 2, 3, or 4 $R^{14c}$; or cycloalkyl optionally substituted with 1, 2, 3, or 4 groups independently selected from $C_{1-6}$alkyl and halo-$C_{1-6}$alkyl; and each $R^{14c}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano; or a pharmaceutically acceptable salt, hydrate, solvate, stereoisomer, tautomer, or mixture thereof.

In another aspect, provided herein are pharmaceutical compositions, single unit dosage forms, and kits suitable for use in treating pain and/or conditions modulated by voltage-gated sodium channels which comprise a therapeutically or prophylactically effective amount of a compound provided herein, e.g., of some or any of the embodiments, of Formula (I)-(Ik) and I-P and compounds 1-122.

In an aspect, a method of treatment of pain and/or conditions modulated by voltage-gated sodium channels is provided comprising administering to an individual in need thereof a therapeutically or prophylactically effective amount of a 11,13-modified saxitoxin described herein, e.g., of some or any of the embodiments, of Formula (I)-(Ik) and I-P and compounds 1-122.

In another aspect, provided herein is a compound of Formula Xe

Xe 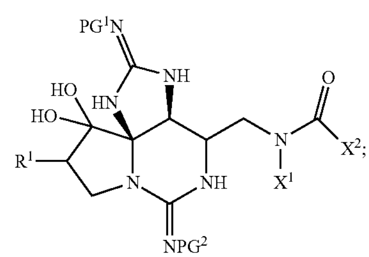 or a salt thereof, where $PG^1$ is a nitrogen-protecting group;

$PG^2$ is a nitrogen-protecting group;

$R^1$ is —OS(O)$_2$R$^5$, —OC(O)R$^6$, —NR$^7$C(O)R$^{7a}$, —OC(O) NR$^{10}$R$^{10a}$, —NR$^{11}$R$^{11a}$, —NR$^{13}$S(O)$_2$R$^{13a}$, or —NR$^{14}$C(O)NR$^{14a}$R$^{14b}$;

$X^1$ is $R^3$ and $X^2$ is $R^9$; or $X^1$ and $X^2$ together with the —NC(O)— to which they are attached form a 5 or 6-membered ring where $X^1$, $X^2$, and the one or two additional ring atoms are independently selected from —C(O)—, —O—, —S—, —NR$^8$—, and —C(R$^4$)(R$^{4a}$)— provided that only one is selected from —O—, —S—, and —NR$^8$—; and where the 5 or 6-membered ring is optionally fused at two adjacent carbon atoms, or is optionally fused at one carbon atom and one nitrogen atom which are adjacent to each other, to a form a saturated or unsaturated 6-12 membered bicyclic ring; where the 1, 2, 3, 4, 5, or 6 additional bicyclic ring atoms are independently —CR$^{12}$= or —C(R$^{12}$)$_2$—;

each $R^4$ and $R^{4a}$ is independently H; C$_{1-6}$alkyl; or when the 6-12 membered ring is fused at a —C(R$^4$)(R$^{4a}$)—, one or both of the $R^4$ and $R^{4a}$ on the —C(R$^4$)(R$^{4a}$)— form a single or double bond with an adjacent ring atom;

$R^8$ is hydrogen; C$_{1-6}$alkyl; phenyl optionally substituted with 1, 2, or 3 groups independently selected from halo, C$_{1-6}$alkyl, halo-C$_{1-6}$alkyl, hydroxy, C$_{1-6}$alkoxy, halo-C$_{1-6}$alkoxy, nitro, and cyano; or when the 6-12 membered ring is fused at an —NR$^8$—, the $R^8$ forms a single bond with an adjacent ring atom;

each $R^{12}$ is independently hydrogen, halo, C$_{1-6}$alkyl, halo-C$_{1-6}$alkyl, or aryl;

$R^3$ is —C(O)C$_{1-6}$alkyl, —C(O)OC$_{1-6}$alkyl, or —C(O)phenyl where the phenyl is optionally substituted with one or two groups independently selected from halo, C$_{1-6}$alkyl, halo-C$_{1-6}$alkyl, C$_{1-6}$alkoxy, and aryl;

$R^9$ is C$_{1-6}$alkyl, C$_{1-6}$alkoxy, or phenyl where the phenyl is optionally substituted with one or two groups independently selected from halo, C$_{1-6}$alkyl, halo-C$_{1-6}$alkyl, C$_{1-6}$alkoxy, and aryl;

$R^5$ is H, C$_{1-6}$alkyl, or aryl optionally substituted with 1, 2, 3, or 4 R$^{5a}$;

each R$^{5a}$, when present, is independently halo, C$_{1-6}$alkyl, halo-C$_{1-6}$alkyl, hydroxy, C$_{1-6}$alkoxy, halo-C$_{1-6}$alkoxy, C$_{1-6}$alkylthio, halo-C$_{1-6}$alkylthio, C$_{1-6}$alkylsulfinyl, halo-C$_{1-6}$alkylsulfinyl, C$_{1-6}$alkylsulfonyl, halo-C$_{1-6}$alkylsulfonyl, nitro, amino, C$_{1-6}$alkylamino, di-C$_{1-6}$alkylamino, phenyl, or cyano;

$R^6$ is C$_{1-6}$alkyl; aryl optionally substituted with 1, 2, or 3 R$^{6a}$; aralkyl where the aryl is optionally substituted with 1, 2, 3, or 4 R$^{6a}$; heteroaryl optionally substituted with 1, 2, 3, or 4 R$^{6a}$; heterocyclic optionally substituted with 1, 2, 3, or 4 R$^{6a}$; biphenyl optionally substituted on either ring with 1, 2, 3, or 4 R$^{6a}$; or cycloalkyl optionally substituted with 1, 2, 3, or 4 groups independently selected from C$_{1-6}$alkyl and halo-C$_{1-6}$alkyl;

each R$^{6a}$, when present, is independently halo, C$_{1-6}$alkyl, halo-C$_{1-6}$alkyl, hydroxy, C$_{1-6}$alkoxy, halo-C$_{1-6}$alkoxy, nitro, C$_{1-6}$alkylthio, halo-C$_{1-6}$alkylthio, C$_{1-6}$alkylsulfinyl, halo-C$_{1-6}$alkylsulfinyl, C$_{1-6}$alkylsulfonyl, halo-C$_{1-6}$alkylsulfonyl, amino, C$_{1-6}$alkylamino, di-C$_{1-6}$alkylamino, phenyl, or cyano;

$R^7$ is hydrogen or C$_{1-6}$alkyl;

$R^{7a}$ is C$_{1-6}$alkyl; aryl optionally substituted with 1, 2, 3, or 4 R$^{7b}$; aralkyl where the aryl is optionally substituted with 1, 2, 3, or 4 R$^{7b}$; heteroaryl optionally substituted with 1, 2, 3, or 4 R$^{7b}$; heterocyclic optionally substituted with 1, 2, 3, or 4 R$^{7b}$; biphenyl optionally substituted on either ring with 1, 2, 3, or 4 R$^{7b}$; or cycloalkyl optionally substituted with 1, 2, 3, or 4 groups independently selected from C$_{1-6}$alkyl and halo-C$_{1-6}$alkyl;

each R$^{7b}$, when present, is independently halo, C$_{1-6}$alkyl, halo-C$_{1-6}$alkyl, hydroxy, C$_{1-6}$alkoxy, halo-C$_{1-6}$alkoxy, nitro, C$_{1-6}$alkylthio, halo-C$_{1-6}$alkylthio, C$_{1-6}$alkylsulfinyl, halo-C$_{1-6}$alkylsulfinyl, C$_{1-6}$alkylsulfonyl, halo-C$_{1-6}$alkylsulfonyl, amino, C$_{1-6}$alkylamino, di-C$_{1-6}$alkylamino, phenyl, or cyano;

$R^{10}$ is hydrogen or C$_{1-6}$alkyl;

$R^{10a}$ is C$_{1-6}$alkyl; aryl optionally substituted with 1, 2, 3, or 4 R$^{10b}$; aralkyl where the aryl is optionally substituted with 1, 2, 3, or 4 R$^{10b}$; phenylcarbonyl where the phenyl is optionally substituted with 1, 2, 3, or 4 R$^{10b}$; heteroaryl optionally substituted with 1, 2, 3, or 4 R$^{10b}$; heterocyclic optionally substituted with 1, 2, 3, or 4 R$^{10b}$; biphenyl optionally substituted on either ring with 1, 2, 3, or 4 R$^{10b}$; or cycloalkyl optionally substituted with 1, 2, 3, or 4 groups independently selected from C$_{1-6}$alkyl and halo-C$_{1-6}$alkyl;

each R$^{10b}$, when present, is independently halo, C$_{1-6}$alkyl, halo-C$_{1-6}$alkyl, hydroxy, C$_{1-6}$alkoxy, halo-C$_{1-6}$alkoxy, nitro, C$_{1-6}$alkylthio, halo-C$_{1-6}$alkylthio, C$_{1-6}$alkylsulfinyl, halo-C$_{1-6}$alkylsulfinyl, C$_{1-6}$alkylsulfonyl, halo-C$_{1-6}$alkylsulfonyl, amino, C$_{1-6}$alkylamino, di-C$_{1-6}$alkylamino, phenyl, or cyano;

$R^{11}$ is hydrogen or C$_{1-6}$alkyl;

$R^{11a}$ is C$_{1-6}$alkyl; aryl optionally substituted with 1, 2, 3, or 4 R$^{11b}$; aralkyl where the aryl is optionally substituted with 1, 2, 3, or 4 R$^{11b}$; heteroaryl optionally substituted with 1, 2, 3, or 4 R$^{11b}$; heterocyclic optionally substituted with 1, 2, 3, or 4 R$^{11b}$; biphenyl optionally substituted on either ring with 1, 2, 3, or 4 R$^{11b}$; or cycloalkyl optionally substituted with 1, 2, 3, or 4 groups independently selected from C$_{1-6}$alkyl and halo-C$_{1-6}$alkyl;

each R$^{11b}$, when present, is independently halo, C$_{1-6}$alkyl, halo-C$_{1-6}$alkyl, hydroxy, C$_{1-6}$alkoxy, halo-C$_{1-6}$alkoxy, nitro, C$_{1-6}$alkylthio, halo-C$_{1-6}$alkylthio, C$_{1-6}$alkylsulfinyl, halo-C$_{1-6}$alkylsulfinyl, C$_{1-6}$alkylsulfonyl, halo-C$_{1-6}$alkylsulfonyl, amino, C$_{1-6}$alkylamino, di-C$_{1-6}$alkylamino, phenyl, or cyano;

$R^{13}$ is hydrogen or C$_{1-6}$alkyl;

$R^{13a}$ is C$_{1-6}$alkyl; aryl optionally substituted with 1, 2, 3, or 4 R$^{13b}$; aralkyl where the aryl is optionally substituted with 1, 2, 3, or 4 R$^{13b}$; heteroaryl optionally substituted with 1, 2, 3, or 4 R$^{13b}$; heterocyclic optionally substituted with 1, 2, 3, or 4 R$^{13b}$; biphenyl optionally substituted on either ring with 1, 2, 3, or 4 R$^{13b}$; or cycloalkyl optionally substituted with 1, 2, 3, or 4 groups independently selected from C$_{1-6}$alkyl and halo-C$_{1-6}$alkyl;

each R$^{13b}$, when present, is independently halo, C$_{1-6}$alkyl, halo-C$_{1-6}$alkyl, hydroxy, C$_{1-6}$alkoxy, halo-C$_{1-6}$alkoxy, C$_{1-6}$alkylthio, halo-C$_{1-6}$alkylthio, C$_{1-6}$alkylsulfinyl, halo-C$_{1-6}$alkylsulfinyl, C$_{1-6}$alkylsulfonyl, halo-C$_{1-6}$alkylsulfonyl, nitro, amino, C$_{1-6}$alkylamino, di-C$_{1-6}$alkylamino, phenyl, or cyano;

$R^{14}$ is hydrogen or C$_{1-6}$alkyl;

$R^{14a}$ is hydrogen or C$_{1-6}$alkyl;

$R^{14b}$ is C$_{1-6}$alkyl; aryl optionally substituted with 1, 2, 3, or 4 R$^{14c}$; aralkyl where the aryl is optionally substituted with 1, 2, 3, or 4 R$^{14c}$; heteroaryl optionally substituted with 1, 2, 3, or 4 R$^{14c}$; heterocyclic optionally substituted with 1, 2, 3, or 4 R$^{14c}$; biphenyl optionally substituted on either ring with 1, 2, 3, or 4 R$^{14c}$; or cycloalkyl optionally substituted with 1, 2, 3, or 4 groups independently selected from C$_{1-6}$alkyl and halo-C$_{1-6}$alkyl; and each R$^{14c}$, when present, is independently halo, C$_{1-6}$alkyl, halo-C$_{1-6}$alkyl, hydroxy, C$_{1-6}$alkoxy, halo-C$_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano.

In another aspect, provided is a method of preparing a compound of Formula I comprising a) deprotecting a compound of Formula Xe

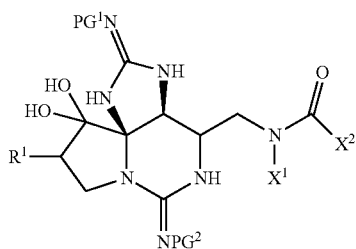

Xe where

PG$^1$ is a nitrogen-protecting group;

PG$^2$ is a nitrogen-protecting group;

R$^1$ is —OS(O)$_2$R$^5$, —OC(O)R$^6$, —NR$^7$C(O)R$^{7a}$, —OC(O)NR$^{10}$R$^{10a}$, —NR$^{11}$R$^{11a}$, —NR$^{13}$S(O)$_2$R$^{13a}$, or —NR$^{14}$C(O)NR$^{14a}$R$^{14b}$;

X$^1$ is R$^3$ and X$^2$ is R$^9$; or

X$^1$ and X$^2$ together with the —NC(O)— to which they are attached form a 5 or 6-membered ring where X$^1$, X$^2$, and the one or two additional ring atoms are independently selected from —C(O)—, —O—, —S—, —NR$^8$—, and —C(R$^4$)(R$^{4a}$)— provided that only one is selected from —O—, —S—, and —NR$^8$—; and where the 5 or 6-membered ring is optionally fused at two adjacent carbon atoms, or is optionally fused at one carbon atom and one nitrogen atom which are adjacent to each other, to a form a saturated or unsaturated 6-12 membered bicyclic ring; where the 1, 2, 3, 4, 5, or 6 additional bicyclic ring atoms are independently —CR$^{12}$= or —C(R$^{12}$)$_2$—;

each R$^4$ and R$^{4a}$ is independently H; $C_{1-6}$alkyl; or when the 6-12 membered ring is fused at a —C(R$^4$)(R$^{4a}$)—, one or both of the R$^4$ and R$^{4a}$ on the —C(R$^4$)(R$^{4a}$)— form a single or double bond with an adjacent ring atom;

R$^8$ is hydrogen; $C_{1-6}$alkyl; phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano; or when the 6-12 membered ring is fused at an —NR$^8$—, the R$^8$ forms a single bond with an adjacent ring atom;

each R$^{12}$ is independently hydrogen, halo, $C_{1-6}$alkyl, halo-$C_{1-6}$alkyl, or aryl;

R$^3$ is —C(O)$C_{1-6}$alkyl, —C(O)O$C_{1-6}$alkyl, or —C(O)phenyl where the phenyl is optionally substituted with one or two groups independently selected from halo, $C_{1-6}$alkyl, halo-$C_{1-6}$alkyl, $C_{1-6}$alkoxy, and aryl;

R$^9$ is $C_{1-6}$alkyl, $C_{1-6}$alkoxy, or phenyl where the phenyl is optionally substituted with one or two groups independently selected from halo, $C_{1-6}$alkyl, halo-$C_{1-6}$alkyl, $C_{1-6}$alkoxy, and aryl;

R$^5$ is H, $C_{1-6}$alkyl, or aryl optionally substituted with 1, 2, 3, or 4 R$^{5a}$;

each R$^{5a}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;

R$^6$ is $C_{1-6}$alkyl; aryl optionally substituted with 1, 2, 3, or 4 R$^{6a}$; aralkyl where the aryl is optionally substituted with 1, 2, 3, or 4 R$^{6a}$; heteroaryl optionally substituted with 1, 2, 3, or 4 R$^{6a}$; heterocyclic optionally substituted with 1, 2, 3, or 4 R$^{6a}$; biphenyl optionally substituted on either ring with 1, 2, 3, or 4 R$^{6a}$; or cycloalkyl optionally substituted with 1, 2, 3, or 4 groups independently selected from $C_{1-6}$alkyl and halo-$C_{1-6}$alkyl;

each R$^{6a}$, when present, is independently halo, $C_{1-6}$alkyl, halo-$C_{1-6}$alkyl, hydroxy, $C_{1-6}$alkoxy, halo-$C_{1-6}$alkoxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, phenyl, or cyano;

R$^7$ is hydrogen or $C_{1-6}$alkyl;

R$^{7a}$ is $C_{1-6}$alkyl; aryl optionally substituted with 1, 2, 3, or 4 R$^{7b}$; aralkyl where the aryl is optionally substituted with 1, 2, 3, or 4 R$^{7b}$; heteroaryl optionally substituted with 1, 2, 3, or 4 R$^{7b}$; heterocyclic optionally substituted with 1, 2, 3, or 4 R$^{7b}$; biphenyl optionally substituted on either ring with 1, 2, 3, or 4 R$^{7b}$; or cycloalkyl optionally substituted with 1, 2, 3, or 4 groups independently selected from $C_{1-6}$alkyl and halo-$C_{1-6}$alkyl;

each R$^{7b}$, when present, is independently halo, $C_{1-6}$alkyl, halo-$C_{1-6}$alkyl, hydroxy, $C_{1-6}$alkoxy, halo-$C_{1-6}$alkoxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, phenyl, or cyano; and R$^{10}$ is hydrogen or $C_{1-6}$alkyl;

R$^{10a}$ is $C_{1-6}$alkyl; aryl optionally substituted with 1, 2, 3, or 4 R$^{10b}$; aralkyl where the aryl is optionally substituted with 1, 2, 3, or 4 R$^{10b}$; phenylcarbonyl where the phenyl is optionally substituted with 1, 2, 3, or 4 R$^{10b}$; heteroaryl optionally substituted with 1, 2, 3, or 4 R$^{10b}$; heterocyclic optionally substituted with 1, 2, 3, or 4 R$^{10b}$; biphenyl optionally substituted on either ring with 1, 2, 3, or 4 R$^{10b}$; or cycloalkyl optionally substituted with 1, 2, 3, or 4 groups independently selected from $C_{1-6}$alkyl and halo-$C_{1-6}$alkyl;

each R$^{10b}$, when present, is independently halo, $C_{1-6}$alkyl, halo-$C_{1-6}$alkyl, hydroxy, $C_{1-6}$alkoxy, halo-$C_{1-6}$alkoxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, phenyl, or cyano;

R$^{11}$ is hydrogen or $C_{1-6}$alkyl;

R$^{11a}$ is $C_{1-6}$alkyl; aryl optionally substituted with 1, 2, 3, or 4 R$^{11b}$; aralkyl where the aryl is optionally substituted with 1, 2, 3, or 4 R$^{11b}$; heteroaryl optionally substituted with 1, 2, 3, or 4 R$^{11b}$; heterocyclic optionally substituted with 1, 2, 3, or 4 R$^{11b}$; biphenyl optionally substituted on either ring with 1, 2, 3, or 4 R$^{11b}$; or cycloalkyl optionally substituted with 1, 2, or 3 groups independently selected from $C_{1-6}$alkyl and halo-$C_{1-6}$alkyl;

each R$^{11b}$, when present, is independently halo, $C_{1-6}$alkyl, halo-$C_{1-6}$alkyl, hydroxy, $C_{1-6}$alkoxy, halo-$C_{1-6}$alkoxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, phenyl, or cyano;

R$^{13}$ is hydrogen or $C_{1-6}$alkyl;

R$^{13a}$ is $C_{1-6}$alkyl; aryl optionally substituted with 1, 2, 3, or 4 R$^{13b}$; aralkyl where the aryl is optionally substituted with 1, 2, 3, or 4 R$^{13b}$; heteroaryl optionally substituted with 1, 2, 3, or 4 R$^{13b}$; heterocyclic optionally substituted with 1, 2, 3, or 4 R$^{13b}$; biphenyl optionally substituted on either ring with 1, 2, 3, or 4 $R^{13b}$; or cycloalkyl optionally substituted with 1, 2, 3, or 4 groups independently selected from $C_{1-6}$alkyl and halo-$C_{1-6}$alkyl;

each $R^{13b}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;

$R^{14}$ is hydrogen or $C_{1-6}$alkyl;

$R^{14a}$ is hydrogen or $C_{1-6}$alkyl;

$R^{14b}$ is $C_{1-6}$alkyl; aryl optionally substituted with 1, 2, 3, or 4 $R^{14c}$; aralkyl where the aryl is optionally substituted with 1, 2, 3, or 4 $R^{14c}$; heteroaryl optionally substituted with 1, 2, 3, or 4 $R^{14c}$; heterocyclic optionally substituted with 1, 2, 3, or 4 $R^{14c}$; biphenyl optionally substituted on either ring with 1, 2, 3, or 4 $R^{14c}$; or cycloalkyl optionally substituted with 1, 2, 3, or 4 groups independently selected from $C_{1-6}$alkyl and halo-$C_{1-6}$alkyl; and each $R^{14c}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{6}$alkylsulfonyl, nitro, amino, $C_{1-6}$alkylamino, di-$C_{1-6}$alkylamino, phenyl, or cyano;

to yield a compound of Formula I; and b) optionally isolating the compound of Formula I.

DESCRIPTION OF EXEMPLARY EMBODIMENTS

Provided herein are compounds, pharmaceutical compositions comprising the compounds, and methods of using the compounds and compositions in the treatment of pain and/or conditions modulated by voltage-gated sodium channels. The compounds are 11,13-modified saxitoxins. Also provided herein are methods of treating pain in a mammal comprising administering a therapeutically or prophylactically effective amount of a 11,13-modified saxitoxin or composition to a mammal. In an embodiment, the mammal is a human.

Definitions

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise. Unless specified otherwise, where a term is defined as being substituted, the groups in the list of substituents are themselves unsubstituted. For example, a substituted alkyl group can be substituted, for example, with a cycloalkyl group, and the cycloalkyl group is not further substituted unless specified otherwise.

The term "alkyl," as used herein, unless otherwise specified, refers to a saturated straight or branched hydrocarbon. In certain embodiments, the alkyl group is a primary, secondary, or tertiary hydrocarbon. In certain embodiments, the alkyl group includes one to ten carbon atoms, i.e., $C_1$ to $C_{10}$ alkyl. In certain embodiments, the alkyl is a $C_{1-6}$alkyl. In certain embodiments, the alkyl group is selected from the group consisting of methyl, ethyl, propyl, isopropyl, butyl, isobutyl, secbutyl, t-butyl, pentyl, isopentyl, neopentyl, hexyl, isohexyl, 3-methylpentyl, 2,2-dimethylbutyl, and 2,3-dimethylbutyl.

The term "alkoxy" as used herein, and unless otherwise specified, refers to the group —OR' where R' is alkyl. Alkoxy groups include, in certain embodiments, methoxy, ethoxy, n-propoxy, isopropoxy, n-butoxy, tert-butoxy, sec-butoxy, n-pentoxy, n-hexoxy, 1,2-dimethylbutoxy, and the like.

The term "alkylthio" as used herein, and unless otherwise specified, refers to the group —SR' where R' is $C_{1-10}$alkyl. In some embodiments, alkylthio is $C_{1-6}$alkylthio. In some embodiments, alkylthio is methylthio.

The term "alkylsulfinyl" as used herein, and unless otherwise specified, refers to the group —S(O)R' where R' is $C_{1-10}$alkyl. In some embodiments, the alkylsulfinyl is $C_{1-6}$alkylsulfinyl.

The term "alkylsulfonyl" as used herein, and unless otherwise specified, refers to the group —S(O)$_2$R' where R' is $C_{1-10}$alkyl. In some embodiments, the alkylsulfonyl is $C_{1-6}$alkylsulfonyl.

The term "amino" means —NH$_2$.

The term "alkylamino," as used herein, and unless otherwise specified, refers to the group —NHR' where R' is $C_{1-10}$alkyl, as defined herein. In some embodiments, the alkylamino is $C_{1-6}$alkylamino.

The term "dialkylamino," as used herein, and unless otherwise specified, refers to the group —NR'R' where each R' is independently $C_{1-10}$alkyl, as defined herein. In some embodiments, the dialkylamino is di-$C_{1-6}$alkylamino.

The term "aryl," as used herein, and unless otherwise specified, refers to a monovalent $C_6$-$C_{14}$ carbocyclic ring system which comprises at least one aromatic ring wherein the aryl ring system is mono, di, or tricyclic. The aryl may be attached to the main structure through any of its rings, i.e. any aromatic or nonaromatic ring. In certain embodiments, aryl is phenyl, naphthyl, bicyclo[4.2.0]octa-1,3,5-trienyl, indanyl, fluorenyl, or tetrahydronaphthyl. When aryl is substituted, it can be substituted on any ring, i.e. on any aromatic or nonaromatic ring comprised by aryl. In some or any embodiments, aryl is phenyl, naphthyl, tetrahydronaphthyl, fluorenyl, or indanyl; each of which is optionally substituted with 1, 2, 3, or 4 groups as defined throughout the specification, including in some embodiments with group(s) independently selected from amino, hydroxy, halo, halo-$C_{1-6}$alkoxy, $C_{1-6}$alkoxy, $C_{1-6}$alkyl, halo-$C_{1-6}$alkyl, $C_{1-6}$alkylthio, $C_{1-6}$alkylsulfonyl, and phenyl.

The term "aralkyl," as used herein, and unless otherwise specified, refers to an alkyl group substituted with one or two aryl groups as defined herein, where the alkyl group is the point of attachment to the remainder of the molecule. In some embodiments, aralkyl is phenylmethyl, phenyleth-1-yl, phenyleth-2-yl, diphenylmethyl, 2,2-diphenylethyl, 3,3-diphenylpropyl, or 3-phenylpropyl; each of which is optionally substituted on the ring with 1, 2, 3, or 4 groups as defined throughout the specification.

The term "biphenyl," as used herein, unless otherwise specified, refers to a phenyl group substituted with a second phenyl group.

The term "cycloalkyl," as used herein, unless otherwise specified, refers to a monovalent, saturated or partially unsaturated (but not aromatic) mono or multi-cyclic hydrocarbon. In certain embodiments, the cycloalkyl group may be a bridged or non-bridged, spirocyclic or not spirocyclic, and/or fused or not fused bicyclic group. In certain embodiments, the cycloalkyl group includes three to ten carbon atoms, i.e., $C_3$ to $C_{10}$ cycloalkyl. In some embodiments, the cycloalkyl has from 3 to 15 ($C_{3-15}$), from 3 to 10 ($C_{3-10}$), or from 3 to 7 ($C_{3-7}$) carbon atoms. In certain embodiments, the cycloalkyl group is monocyclic or bicyclic. In certain embodiments, the cycloalkyl group is monocyclic. In certain embodiments, the cycloalkyl group is bicyclic. In certain embodiments, the cycloalkyl group is tricyclic. In certain embodiments, the cycloalkyl group is fully saturated. In certain embodiments, the cycloalkyl group is partially unsaturated. In certain embodiments, the cycloalkyl group is cyclopropyl, cyclobutyl, cyclopentyl, cyclohexyl, cycloheptyl, bicyclo[2.1.1]hexyl, bicyclo[2.2.1]heptyl, decalinyl or adamantyl. When cycloalkyl is substituted, it can be substituted on any ring, i.e. on any aromatic or nonaromatic ring comprised by cycloalkyl, with 1, 2, 3, or 4 groups as defined throughout the specification.

The term "haloalkyl," as used herein, and unless otherwise specified, refers to an alkyl group substituted with 1, 2, 3, 4, or 5 halo groups. In certain embodiments, the haloalkyl is a halo-$C_{1-6}$alkyl.

The term "haloalkylthio," as used herein, and unless otherwise specified, refers to an —SR group where R is halo-$C_{1-10}$alkyl as defined herein. In certain embodiments, the haloalkylthio is a halo-$C_{1-6}$alkylthio.

The term "haloalkoxy," as used herein, and unless otherwise specified, refers to an —OR group where R is halo-$C_{1-10}$alkyl as defined herein. In certain embodiments, the haloalkoxy is a halo-$C_{1-6}$alkoxy.

The term "haloalkylsulfinyl," as used herein, and unless otherwise specified, refers to an —S(O)R group where R is halo-$C_{1-10}$alkyl as defined herein. In certain embodiments, the haloalkylsulfinyl is a halo-$C_{1-6}$alkylsulfinyl.

The term "haloalkylsulfonyl," as used herein, and unless otherwise specified, refers to an —S(O)$_2$R group where R is halo-$C_{1-10}$alkyl as defined herein. In certain embodiments, the haloalkylsulfonyl is a halo-$C_{1-6}$alkylsulfonyl.

The terms "halogen" and "halo," as used herein, and unless otherwise specified, are synonymous and refer to chloro, bromo, fluoro or iodo.

The term "heterocyclic," as used herein, and unless otherwise specified, refers to a monovalent monocyclic non-aromatic ring system and/or a multicyclic ring system that contains at least one non-aromatic ring; wherein one or more (in certain embodiments, 1, 2, 3, or 4) of the non-aromatic monocyclic ring atoms is a heteroatom independently selected from O, S(O)$_{0-2}$, and N, and the remaining ring atoms are carbon atoms; and wherein one or more (in certain embodiments, 1, 2, 3, or 4) of any of the ring atoms in the multicyclic ring system is a heteroatom(s) independently selected from O, S(O)$_{0-2}$, and N, and the remaining ring atoms are carbon. In certain embodiments, the heterocyclic ring comprises one or two heteroatom(s) which are nitrogen. In certain embodiments, heterocyclic is multicyclic and comprises one heteroatom in a non-aromatic ring, or comprises one heteroatom in an aromatic ring, or comprises two heteroatoms in an aromatic ring, or comprises two heteroatoms where one is in an aromatic ring and the other is in a non-aromatic ring. In certain embodiments, the heterocyclic group has from 3 to 20, 3 to 15, 3 to 10, 3 to 8, 4 to 7, or 5 to 6 ring atoms. In certain embodiments, the heterocyclic is a monocyclic, bicyclic, tricyclic, or tetracyclic ring system. In certain embodiments, the heterocyclic group may be a bridged or non-bridged, spirocyclic or not spirocyclic, and/or fused or not fused bicyclic group. One or more of the nitrogen and sulfur atoms may be optionally oxidized, one or more of the nitrogen atoms may be optionally quaternized, one or more of the carbon atoms may be optionally replaced with

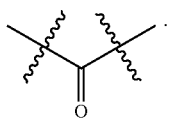 [SMILES: *C(*)=O]

Some rings may be partially or fully saturated, or aromatic provided that heterocyclic is not fully aromatic. The monocyclic and multicyclic heterocyclic rings may be attached to the main structure at any heteroatom or carbon atom which results in a stable compound. The multicyclic heterocyclic may be attached to the main structure through any of its rings, including any aromatic or nonaromatic ring, regardless of whether the ring contains a heteroatom. In certain embodiments, heterocyclic is "heterocycloalkyl" which is 1) a saturated or partially unsaturated (but not aromatic) monovalent monocyclic group which contains at least one ring heteroatom, as described herein, or 2) a saturated or partially unsaturated (but not aromatic) monovalent bi- or tri-cyclic group in which at least one ring contains at least one heteroatom as described herein. When heterocyclic and heterocycloalkyl are substituted, they can be substituted on any ring, i.e. on any aromatic or nonaromatic ring comprised by heterocyclic and heterocycloalkyl. In certain embodiments, such heterocyclic includes, but are not limited to, azepinyl, benzodioxanyl, benzodioxolyl, benzofuranonyl, benzopyranonyl, benzopyranyl, dihydrobenzofuranyl, benzotetrahydrothienyl, benzothiopyranyl, benzoxazinyl, β-carbolinyl, chromanyl, chromonyl, cinnolinyl, coumarinyl, decahydroquinolinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, 2,4-dioxo-imidazolidinyl, imidazolinyl, indolinyl, 2-oxo-indolinyl, isobenzotetrahydrofuranyl, isobenzotetrahydrothienyl, isochromanyl, isocoumarinyl, isoindolinyl, 1-oxo-isoindolinyl, 1,3-dioxo-isoindolinyl, isothiazolidinyl, isoxazolidinyl, 3-oxo-isoxazolidinyl, morpholinyl, 3,5-dioxo-morpholinyl, octahydroindolyl, octahydroisoindolyl, 1-oxo-octahydroisoindolyl, 1,3-dioxo-hexahydroisoindolyl, oxazolidinonyl, oxazolidinyl, oxiranyl, piperazinyl, 2,6-dioxo-piperazinyl, piperidinyl, 2,6-dioxopiperidinyl, 4-piperidonyl, pyrazolidinyl, pyrazolinyl, pyrrolidinyl, pyrrolinyl, 2-oxopyrrolidinyl, 2,5-dioxopyrrolidinyl, quinuclidinyl, tetrahydrofuryl, tetrahydroisoquinolinyl, tetrahydropyranyl, tetrahydrothienyl, thiamorpholinyl, thiomorpholinyl, 3,5-dioxo-thiomorpholinyl, thiazolidinyl, 2,4-dioxo-thiazolidinyl, tetrahydroquinolinyl, phenothiazinyl, phenoxazinyl, xanthenyl, and 1,3,5-trithianyl. In some or any embodiments, heterocyclic is benzo-1,4-dioxanyl, benzodioxolyl, indolinyl, 2-oxo-indolinyl, pyrrolidinyl, piperidinyl, 2,3-dihydrobenzofuranyl, or decahydroquinolinyl; each of which is optionally substituted with 1, 2, 3, or 4 groups as defined throughout the specification, including in some embodiments with group(s) independently selected from halo, alkyl, and phenyl.

The term "heteroaryl," as used herein, and unless otherwise specified, refers to a monovalent monocyclic or multicyclic aromatic group, wherein at least one (in certain embodiments, 1, 2, 3, or 4) ring atom is a heteroatom independently selected from O, S(O)$_{0-2}$, and N in the ring. The heteroaryl group is bonded to the rest of the molecule through any atom in the ring system, valency rules permitting. In certain embodiments, each ring of a heteroaryl group can contain one or two O atoms, one or two S atoms, and/or one to four N atoms, or a combination thereof, provided that the total number of heteroatoms in each ring is four or less and each ring contains at least one carbon atom. In certain embodiments, the heteroaryl has from 5 to 20, from 5 to 15, or from 5 to 10 ring atoms. When heteroaryl is substituted, it can be substituted on any ring. In certain embodiments, monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl and triazolyl. In certain embodiments, bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. In certain embodiments, tricyclic heteroaryl groups include, but are not limited to, acridinyl, benzindolyl, carbazolyl, dibenzofuranyl, perimidinyl, phenanthrolinyl, phenanthridinyl, and phenazinyl. In some or any embodiments, heteroaryl is indolyl, furanyl, pyridinyl, pyrimidinyl, imidazolyl, or pyrazolyl; each of which is optionally substituted with 1, 2, 3, or 4 groups as defined throughout the specification, including in some embodiments with group(s) independently selected from halo, $C_{1-6}$alkyl, halo-$C_{1-6}$alkyl, $C_{1-6}$alkoxy, halo-$C_{1-6}$alkoxy, and phenyl.

The term "phenylcarbonyl," refers to a —C(O)R group where R is phenyl.

The term "protecting group," as used herein, and unless otherwise specified, refers to a group that is added to an oxygen, nitrogen or phosphorus atom to prevent its further reaction or for other purposes. A wide variety of oxygen and nitrogen protecting groups are known to those skilled in the art of organic synthesis. (See for example those described in Greene, et al., Protective Groups in Organic Synthesis, John Wiley and Sons, Fourth Edition, 2006, hereby incorporated by reference.) In some embodiments, a nitrogen-protecting group (e.g. for $PG^1$ and $PG^2$) is 9-fluorenylmethyloxycarbonyl (Fmoc), tert-butoxycarbonyl (Boc), benzyloxycarbonyl (CBz), acetyl, trichloroacetyl, trifluoroacetyl, —C(O)OCH$_2$CCl$_3$ (Troc), p-methoxyphenyl, benzyl, p-methoxybenzyl, p-methoxybenzylcarbonyl, triphenylmethyl, benzylidenyl, 2,2,2-trichloroethoxysulfonyl (Tces), p-methoxybenzenesulfonyl (Mbs) or p-toluenesulfonyl (tosyl). In some embodiments, an oxygen-protecting group (e.g. for $X^1$) is methoxymethyl (MOM), ethoxyethyl, methoxyethoxymethyl, tetrahydrofuranyl, tetrahydropyranyl, methyl, tert-butyl, allyl, benzyl, trimethylsilyl, triethylsilyl, triisopropylsilyl, tert-butyldimethylsilyl, tert-butyldiphenylsilyl, acetyl, pivalyl, benzoyl, dimethoxytrityl, trityl, methoxytrityl, p-methoxybenzyl, or methylthiomethyl.

The term "pharmaceutically acceptable salt," as used herein, and unless otherwise specified, refers to any salt of a compound provided herein which retains its biological properties and which is not toxic or otherwise desirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; and (2) base addition salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, omithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutically acceptable salts further include, in certain embodiments, and without limitation, sodium, potassium, calcium, magnesium, ammonium, tetraalkylammonium salts and the like. When the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

The term "substantially free of" or "substantially in the absence of" stereoisomers with respect to a composition refers to a composition that includes at least 85 or 90% by weight, in certain embodiments 95%, 98%, 99% or 100% by weight, of a designated stereoisomer of a compound in the composition. In certain embodiments, in the methods and compounds provided herein, the compounds are substantially free of stereoisomers.

Similarly, the term "isolated" with respect to a composition refers to a composition that includes at least 85, 90%, 95%, 98%, 99% to 100% by weight, of a specified compound, the remainder comprising other chemical species or stereoisomers.

The term "solvate," as used herein, and unless otherwise specified, refers to a compound provided herein or a salt thereof, that further includes a stoichiometric or non-stoichiometric amount of solvent bound by non-covalent intermolecular forces. Where the solvent is water, the solvate is a hydrate.

The term "isotopic composition," as used herein, and unless otherwise specified, refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

The term "isotopic enrichment," as used herein, and unless otherwise specified, refers to the percentage of incorporation of an amount of a specific isotope at a given atom in a molecule in the place of that atom's natural isotopic abundance. In certain embodiments, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

The term "isotopically enriched," as used herein, and unless otherwise specified, refers to an atom having an isotopic composition other than the natural isotopic composition of that atom. "Isotopically enriched" may also refer to a compound containing at least one atom having an isotopic composition other than the natural isotopic composition of that atom.

As used herein, the term "local anesthetic" means a drug which provides local numbness or pain relief. In some embodiments, local anesthetic includes aminoacylanilide compounds (in some embodiments, lidocaine, prilocaine, bupivacaine, ropivacaine, and mepivacaine) and related local anesthetic compounds having various substituents on the ring system or amine nitrogen; aminoalkyl benzoate compounds (in some embodiments, procaine, chloroprocaine, propoxycaine, hexylcaine, tetracaine, cyclomethycaine, benoxinate, butacaine, and proparacaine) and related local anesthetic compounds; cocaine; amino carbonate compounds (in some embodiments, diperodon); N-phenylamidine compounds (in some embodiments, phenacaine); N-aminoalkyl amide compounds (in some embodiments, dibucaine); aminoketone compounds (in some embodiments, falicaine and dyclonine); and amino ether compounds (in some embodiments, pramoxine and dimethisoquien).

As used herein, "alkyl," "cycloalkyl," "aryl," "alkoxy," "heterocycloalkyl," "heterocyclic," and "heteroaryl," groups optionally comprise deuterium at one or more positions where hydrogen atoms are present, and wherein the deuterium composition of the atom or atoms is other than the natural isotopic composition.

Also as used herein, "alkyl," "cycloalkyl," "aryl," "alkoxy," "heterocycloalkyl," "heterocyclic," and "heteroaryl," groups optionally comprise carbon-13 at an amount other than the natural isotopic composition.

As used herein, and unless otherwise specified, the term "$IC_{50}$" refers to an amount, concentration or dosage of a particular test compound that achieves a 50% inhibition of a maximal response in an assay that measures such response.

As used herein, the terms "subject" and "patient" are used interchangeably. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and in certain embodiments, a human. In certain embodiments, the subject is a farm animal (e.g., a horse, a cow, a pig, etc.) or a pet (e.g., a dog or a cat). In certain embodiments, the subject is a human.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In certain embodiments, a therapeutic agent is an agent which is known to be useful for, or has been or is currently being used for the treatment or prevention of a disorder or one or more symptoms thereof.

"Therapeutically effective amount" refers to an amount of a compound or composition that, when administered to a subject for treating a condition, is sufficient to effect such treatment for the condition. A "therapeutically effective amount" can vary depending on, inter alia, the compound, the condition and its severity, and the age, weight, etc., of the subject to be treated.

"Treating" or "treatment" of any condition or disorder refers, in certain embodiments, to ameliorating a condition or disorder that exists in a subject, including prophylactically. In another embodiment, "treating" or "treatment" includes ameliorating at least one physical parameter, which may be indiscernible by the subject. In yet another embodiment, "treating" or "treatment" includes modulating the condition or disorder, either physically (e.g., stabilization of a discernible symptom) or physiologically (e.g., stabilization of a physical parameter) or both. In yet another embodiment, "treating" or "treatment" includes delaying the onset of the condition or disorder. In yet another embodiment, "treating" or "treatment" includes the reduction or elimination of either the condition (e.g. pain) or one or more symptoms (e.g. pain) of the condition (e.g. sciatica), or to retard the progression of the condition (e.g. pain) or of one or more symptoms (e.g. pain) of the condition (e.g. sciatica), or to reduce the severity of the condition (e.g. pain) or of one or more symptoms (e.g. pain) of the condition (e.g. sciatica). In yet another embodiment, "treating" or "treatment" includes administering a compound described herein prophylactically.

As used herein, the terms "prophylactic agent" and "prophylactic agents" refer to any agent(s) which can be used in the prevention of a condition or one or more symptoms thereof and/or which prevents or impedes the onset, development, progression and/or severity of a condition. In certain embodiments, the term "prophylactic agent" includes a compound provided herein. In certain other embodiments, the term "prophylactic agent" does not refer a compound provided herein.

As used herein, the phrase "prophylactically effective amount" refers to the amount of a therapy (e.g., prophylactic agent) which is sufficient to result in the prevention or reduction of the development, recurrence or onset of one or more symptoms associated with a condition, or to enhance or improve the prophylactic effect(s) of another therapy (e.g., another prophylactic agent).

Compounds

Provided herein are compounds that can modulate the activity of voltage-gated ion channels (e.g., voltage-gated sodium channels). The 11,13-modified saxitoxins can be formed as described herein and used for the treatment of conditions associated with voltage-gated sodium channel function. In certain embodiments, the condition is associated with pain. In certain embodiments, the condition is pain, epilepsy, Parkinson's disease, mood disorders, psychosis, amyotropic lateral sclerosis, glaucoma, ischemia, spasticity disorders and obsessive compulsive disorder. Saxitoxin has the chemical structure provided below with selected atom numbering used herein:

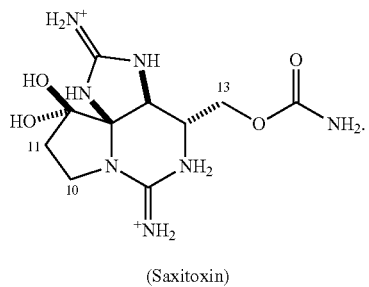

(Saxitoxin)

The embodiments described herein include the recited compounds as well as a pharmaceutically acceptable salt, hydrate, solvate, stereoisomer, tautomer, or mixture thereof.

In some or any embodiments, provided is a Compound of Formula (I-P):

(I-P)

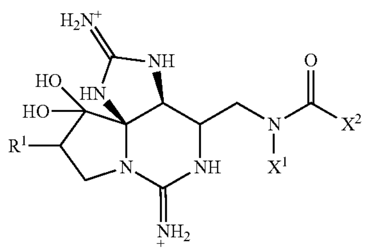

where $R^1$ is H, OH, —$OS(O)_3^-$, —$OS(O)_2R^5$, —$OC(O)R^6$, —$NR^7C(O)R^{7a}$, —$OC(O)NR^{10}R^{10a}$, —$NR^{11}R^{11a}$, or heterocycloalkyl;

$X^1$ is $R^3$ and $X^2$ is $R^9$; or $X^1$ and $X^2$ together with the —NC(O)— to which they are attached form a 5 or 6-membered ring where $X^1$, $X^2$, and the one or two additional ring atoms are independently selected from —C(O)—, —O—, —S—, —$NR^8$—, and —$C(R^4)(R^{4a})$— provided that only one is selected from —O—, —S—, and —$NR^8$—; and where the 5 or 6-membered ring is optionally fused at two adjacent carbon atoms, or is optionally fused at one carbon atom and one nitrogen atom which are adjacent to each other, to a form a saturated or unsaturated 6-12 membered bicyclic ring; where the 1, 2, 3, 4, 5, or 6 additional ring atoms are independently —$CR^{12}$═ or —$C(R^{12})_2$—;

each $R^4$ and $R^{4a}$ is independently H; $C_{1-6}$alkyl; or when the 6-12 membered ring is fused at a —$C(R^4)(R^{4a})$—, one or both of the $R^4$ and $R^{4a}$ on the —$C(R^4)(R^{4a})$— form a single or double bond with an adjacent ring atom;

$R^8$ is hydrogen; $C_{1-6}$alkyl; phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano; or when the 6-12 membered ring is fused at an —$NR^8$—, the $R^8$ forms a single bond with an adjacent ring atom;

each $R^{12}$ is independently hydrogen, halo, $C_{1-6}$alkyl, halo-$C_{1-6}$alkyl, or aryl;

$R^3$ is —$C(O)C_{1-6}$alkyl, —$C(O)OC_{1-6}$alkyl, or —C(O)phenyl where the phenyl is optionally substituted with one or two groups independently selected from halo, $C_{1-6}$alkyl, halo-$C_{1-6}$alkyl, $C_{1-6}$alkoxy, and aryl;

$R^5$ is H or $C_{1-6}$alkyl;

$R^9$ is $C_{1-6}$alkyl, $C_{1-6}$alkoxy, or phenyl where the phenyl is optionally substituted with one or two groups independently selected from halo, $C_{1-6}$alkyl, halo-$C_{1-6}$alkyl, $C_{1-6}$alkoxy, and aryl;

$R^6$ is $C_{1-6}$alkyl; aryl optionally substituted with 1, 2, or 3 $R^{6a}$; aralkyl where the aryl is optionally substituted with 1, 2, or 3 $R^{6a}$; heteroaryl optionally substituted with 1, 2, or 3 $R^{6a}$; heterocyclic optionally substituted with 1, 2, or 3 $R^{6a}$; biphenyl optionally substituted with 1, 2, or 3 $R^{6a}$; or cycloalkyl optionally substituted with 1, 2, or 3 groups independently selected from $C_{1-6}$alkyl and halo-$C_{1-6}$alkyl;

each $R^{6a}$, when present, is independently halo, $C_{1-6}$alkyl, halo-$C_{1-6}$alkyl, hydroxy, $C_{1-6}$alkoxy, halo-$C_{1-6}$alkoxy, nitro, or cyano;

$R^7$ is hydrogen or $C_{1-6}$alkyl;

$R^{7a}$ is $C_{1-6}$alkyl; aryl optionally substituted with 1, 2, or 3 $R^{7b}$; aralkyl where the aryl is optionally substituted with 1, 2, or 3 $R^{7b}$; heteroaryl optionally substituted with 1, 2, or 3 $R^{7b}$; heterocyclic optionally substituted with 1, 2, or 3 $R^{7b}$; biphenyl optionally substituted with 1, 2, or 3 $R^{7b}$; or cycloalkyl optionally substituted with 1, 2, or 3 groups independently selected from $C_{1-6}$alkyl and halo-$C_{1-6}$alkyl;

each $R^{7b}$, when present, is independently halo, $C_{1-6}$alkyl, halo-$C_{1-6}$alkyl, hydroxy, $C_{1-6}$alkoxy, halo-$C_{1-6}$alkoxy, nitro, or cyano; and $R^{10}$ is hydrogen or $C_{1-6}$alkyl;

$R^{10a}$ is $C_{1-6}$alkyl; aryl optionally substituted with 1, 2, or 3 $R^{10b}$; aralkyl where the aryl is optionally substituted with 1, 2, or 3 $R^{10b}$; phenylcarbonyl where the phenyl is optionally substituted with 1, 2, or 3 $R^{10b}$; heteroaryl optionally substituted with 1, 2, or 3 $R^{10b}$; heterocyclic optionally substituted with 1, 2, or 3 $R^{10b}$; biphenyl optionally substituted with 1, 2, or 3 $R^{10b}$; or cycloalkyl optionally substituted with 1, 2, or 3 groups independently selected from $C_{1-6}$alkyl and halo-$C_{1-6}$alkyl;

each $R^{10b}$, when present, is independently halo, $C_{1-6}$alkyl, halo-$C_{1-6}$alkyl, hydroxy, $C_{1-6}$alkoxy, halo-$C_{1-6}$alkoxy, nitro, or cyano;

$R^{11}$ is hydrogen or $C_{1-6}$alkyl;

$R^{11a}$ is $C_{1-6}$alkyl; aryl optionally substituted with 1, 2, or 3 $R^{11b}$; aralkyl where the aryl is optionally substituted with 1, 2, or 3 $R^{11b}$; heteroaryl optionally substituted with 1, 2, or 3 $R^{11b}$; heterocyclic optionally substituted with 1, 2, or 3 $R^{11b}$; biphenyl optionally substituted with 1, 2, or 3 $R^{11b}$; or cycloalkyl optionally substituted with 1, 2, or 3 groups independently selected from $C_{1-6}$alkyl and halo-$C_{1-6}$alkyl; and each $R^{11b}$, when present, is independently halo, $C_{1-6}$alkyl, halo-$C_{1-6}$alkyl, hydroxy, $C_{1-6}$alkoxy, halo-$C_{1-6}$alkoxy, nitro, or cyano; or a pharmaceutically acceptable salt, hydrate, solvate, stereoisomer, tautomer, or mixture thereof.

In some or any embodiments, provided is a Compound of Formula (I), (Ia), (Ib), (Ie), (If), (Ij), or (Ik) where $R^1$ is H, OH, —$OS(O)_3^-$, —$OS(O)_2R^5$, —$OC(O)R^6$, —$NR^7C(O)R^{7a}$, —$OC(O)NR^{10}R^{10a}$, —$NR^{11}R^{11a}$, or heterocycloalkyl;

$X^1$ is $R^3$ and $X^2$ is $R^9$; or $X^1$ and $X^2$ together with the —NC(O)— to which they are attached form

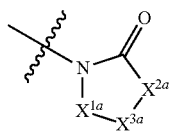

where $X^{1a}$ is —O—, —CH$_2$—, or —C(O)—; $X^{2a}$ is —S—, —NR$^8$—, or —C(R$^4$)(R$^{4a}$)—; and $X^{3a}$ is one or two groups independently selected from —O—, —S—, —NR$^8$—, and —C(R$^4$)(R$^{4a}$)— provided that only one atom of $X^{1a}$, $X^{2a}$, and $X^{3a}$ is selected from —O—, —S—, and —NR$^8$—; and where the

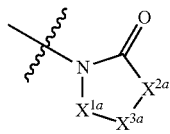

ring is optionally fused at $X^{2a}$ and at the adjacent atom in $X^{3a}$ to form a saturated or unsaturated, 6-12 membered bicyclic ring when 1) $X^{2a}$ is —NR$^8$— and $X^{3a}$ is —C(R$^4$)(R$^{4a}$)— or —C(R$^4$)(R$^{4a}$)—C(R$^4$)(R$^{4a}$)— or 2) $X^{2a}$ is —C(R$^4$)(R$^{4a}$)—, and $X^{3a}$ is —C(R$^4$)(R$^{4a}$)—, —NR$^8$—, —C(R$^4$)(R$^{4a}$)—C(R$^4$)(R$^{4a}$)—, —C(R$^4$)(R$^{4a}$)—NR$^8$—, or —NR$^8$—C(R$^4$)(R$^{4a}$)—; and where the 1, 2, 3, 4, 5, or 6 additional ring atoms are independently —CR$^{12}$= or —C(R$^{12}$)$_2$—;

each R$^4$ and R$^{4a}$ is independently H; C$_{1-6}$alkyl; or when the 6-12 membered ring is fused at a —C(R$^4$)(R$^{4a}$)—, one or both of the R$^4$ and R$^{4a}$ on the —C(R$^4$)(R$^{4a}$)— form a single or double bond with an adjacent ring atom;

R$^8$ is hydrogen; C$_{1-6}$alkyl; phenyl optionally substituted with 1, 2, or 3 groups independently selected from halo, C$_{1-6}$alkyl, halo-C$_{1-6}$alkyl, hydroxy, C$_{1-6}$alkoxy, halo-C$_{1-6}$alkoxy, nitro, and cyano; or when the 6-12 membered ring is fused at an —NR$^8$—, the R$^8$ forms a single bond with an adjacent ring atom;

each R$^{12}$ is independently hydrogen, halo, C$_{1-6}$alkyl, halo-C$_{1-6}$alkyl, or aryl;

R$^3$ is —C(O)C$_{1-6}$alkyl, —C(O)OC$_{1-6}$alkyl, or —C(O)phenyl where the phenyl is optionally substituted with one or two groups independently selected from halo, C$_{1-6}$alkyl, halo-C$_{1-6}$alkyl, C$_{1-6}$alkoxy, and aryl;

R$^5$ is H or C$_{1-6}$alkyl;

R$^9$ is C$_{1-6}$alkyl, C$_{1-6}$alkoxy, or phenyl where the phenyl is optionally substituted with one or two groups independently selected from halo, C$_{1-6}$alkyl, halo-C$_{1-6}$alkyl, C$_{1-6}$alkoxy, and aryl;

R$^6$ is C$_{1-6}$alkyl; aryl optionally substituted with 1, 2, or 3 R$^{6a}$; aralkyl where the aryl is optionally substituted with 1, 2, or 3 R$^{6a}$; heteroaryl optionally substituted with 1, 2, or 3 R$^{6a}$; heterocyclic optionally substituted with 1, 2, or 3 R$^{6a}$; biphenyl optionally substituted with 1, 2, or 3 R$^{6a}$; or cycloalkyl optionally substituted with 1, 2, or 3 groups independently selected from C$_{1-6}$alkyl and halo-C$_{1-6}$alkyl;

each R$^{6a}$, when present, is independently halo, C$_{1-6}$alkyl, halo-C$_{1-6}$alkyl, hydroxy, C$_{1-6}$alkoxy, halo-C$_{1-6}$alkoxy, nitro, or cyano;

R$^7$ is hydrogen or C$_{1-6}$alkyl;

R$^{7a}$ is C$_{1-6}$alkyl; aryl optionally substituted with 1, 2, or 3 R$^{7b}$; aralkyl where the aryl is optionally substituted with 1, 2, or 3 R$^{7b}$; heteroaryl optionally substituted with 1, 2, or 3 R$^{7b}$; heterocyclic optionally substituted with 1, 2, or 3 R$^{7b}$; biphenyl optionally substituted with 1, 2, or 3 R$^{7b}$; or cycloalkyl optionally substituted with 1, 2, or 3 groups independently selected from C$_{1-6}$alkyl and halo-C$_{1-6}$alkyl;

each R$^{7b}$, when present, is independently halo, C$_{1-6}$alkyl, halo-C$_{1-6}$alkyl, hydroxy, C$_{1-6}$alkoxy, halo-C$_{1-6}$alkoxy, nitro, or cyano; and R$^{10}$ is hydrogen or C$_{1-6}$alkyl;

R$^{10a}$ is C$_{1-6}$alkyl; aryl optionally substituted with 1, 2, or 3 R$^{10b}$; aralkyl where the aryl is optionally substituted with 1, 2, or 3 R$^{10b}$; phenylcarbonyl where the phenyl is optionally substituted with 1, 2, or 3 R$^{10b}$; heteroaryl optionally substituted with 1, 2, or 3 R$^{10b}$; heterocyclic optionally substituted with 1, 2, or 3 R$^{10b}$; biphenyl optionally substituted with 1, 2, or 3 R$^{10}$b; or cycloalkyl optionally substituted with 1, 2, or 3 groups independently selected from C$_{1-6}$alkyl and halo-C$_{1-6}$alkyl;

each R$^{10b}$, when present, is independently halo, C$_{1-6}$alkyl, halo-C$_{1-6}$alkyl, hydroxy, C$_{1-6}$alkoxy, halo-C$_{1-6}$alkoxy, nitro, or cyano;

R$^{11}$ is hydrogen or C$_{1-6}$alkyl;

R$^{11a}$ is C$_{1-6}$alkyl; aryl optionally substituted with 1, 2, or 3 R$^{11b}$; aralkyl where the aryl is optionally substituted with 1, 2, or 3 R$^{11b}$; heteroaryl optionally substituted with 1, 2, or 3 R$^{11b}$; heterocyclic optionally substituted with 1, 2, or 3 R$^{11b}$; biphenyl optionally substituted with 1, 2, or 3 R$^{11b}$; or cycloalkyl optionally substituted with 1, 2, or 3 groups independently selected from C$_{1-6}$alkyl and halo-C$_{1-6}$alkyl; and each R$^{11b}$, when present, is independently halo, C$_{1-6}$alkyl, halo-C$_{1-6}$alkyl, hydroxy, C$_{1-6}$alkoxy, halo-C$_{1-6}$alkoxy, nitro, or cyano; or a pharmaceutically acceptable salt, hydrate, solvate, stereoisomer, tautomer, or mixture thereof.

In some or any embodiments, provided is a Compound of Formula (I), (Ia), (Ib), (Ie), (If), (Ij), or (Ik) where R$^1$ is H, OH, —OS(O)$_3^-$, —OS(O)$_2$R$^5$, —OC(O)R$^6$, —NR$^7$C(O)R$^{7a}$, —OC(O)NR$^{10}$R$^{10a}$, —NR$^{11}$R$^{11a}$, —NH$_3^+$, —NR$^{13}$S(O)$_2$R$^{13a}$, —NR$^{14}$C(O)NR$^{14a}$R$^{14b}$, or heterocycloalkyl;

X$^1$ is R$^3$ and X$^2$ is R$^9$; or

X$^1$ and X$^2$ together with the —NC(O)— to which they are attached form

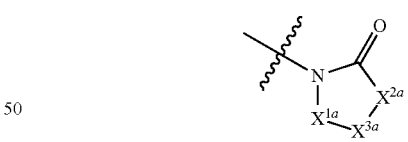

where $X^{1a}$ is —O—, —CH$_2$—, or —C(O)—; $X^{2a}$ is —S—, —NR$^8$—, or —C(R$^4$)(R$^{4a}$)—; and $X^{3a}$ is one or two groups independently selected from —O—, —S—, —NR$^8$—, and —C(R$^4$)(R$^{4a}$)— provided that only one atom of $X^{1a}$, $X^{2a}$, and $X^{3a}$ is selected from —O—, —S—, and —NR$^8$—; and where the

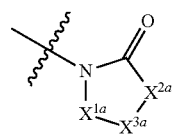

ring is optionally fused at $X^{2a}$ and at the adjacent atom in $X^{3a}$ to form a saturated or unsaturated, 6-12 membered bicyclic ring when 1) $X^{2a}$ is $-NR^8-$ and $X^{3a}$ is $-C(R^4)(R^{4a})-$ or $-C(R^4)(R^{4a})-C(R^4)(R^{4a})-$ or 2) $X^{2a}$ is $-C(R^4)(R^{4a})-$ and $X^{3a}$ is $-C(R^4)(R^{4a})-$, $-NR^8-$, $-C(R^4)(R^{4a})-C(R^4)(R^{4a})-$, $-C(R^4)(R^{4a})-NR^8-$, or $-NR^8-C(R^4)(R^{4a})-$; and where the 1, 2, 3, 4, 5, or 6 additional ring atoms are independently $-CR^{12}=$ or $-C(R^{12})_2-$;

each $R^4$ and $R^{4a}$ is independently H; $C_{1-6}$alkyl; or when the 6-12 membered ring is fused at a $-C(R^4)(R^{4a})-$, one or both of the $R^4$ and $R^{4a}$ on the $-C(R^4)(R^{4a})-$ form a single or double bond with an adjacent ring atom;

$R^8$ is hydrogen; $C_{1-6}$alkyl; phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano; or when the 6-12 membered ring is fused at an $-NR^8-$, the $R^8$ forms a single bond with an adjacent ring atom;

each $R^{12}$ is independently hydrogen, halo, $C_{1-6}$alkyl, halo-$C_{1-6}$alkyl, or aryl;

$R^3$ is $-C(O)C_{1-6}$alkyl, $-C(O)OC_{1-6}$alkyl, or $-C(O)$phenyl where the phenyl is optionally substituted with one or two groups independently selected from halo, $C_{1-6}$alkyl, halo-$C_{1-6}$alkyl, $C_{1-6}$alkoxy, and aryl;

$R^5$ is H, $C_{1-6}$alkyl, or aryl optionally substituted with 1, 2, 3, or 4 $R^{5a}$;

each $R^{5a}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;

$R^9$ is $C_{1-6}$alkyl, $C_{1-6}$alkoxy, or phenyl where the phenyl is optionally substituted with one or two groups independently selected from halo, $C_{1-6}$alkyl, halo-$C_{1-6}$alkyl, $C_{1-6}$alkoxy, and aryl;

$R^6$ is $C_{1-6}$alkyl; aryl optionally substituted with 1, 2, or 3 $R^{6a}$; aralkyl where the aryl is optionally substituted with 1, 2, 3, or 4 $R^{6a}$; heteroaryl optionally substituted with 1, 2, 3, or 4 $R^{6a}$; heterocyclic optionally substituted with 1, 2, 3, or 4 $R^{6a}$; biphenyl optionally substituted on either ring with 1, 2, 3, or 4 $R^{6a}$; or cycloalkyl optionally substituted with 1, 2, 3, or 4 groups independently selected from $C_{1-6}$alkyl and halo-$C_{1-6}$alkyl;

each $R^{6a}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$ alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;

$R^7$ is hydrogen or $C_{1-6}$alkyl;

$R^{7a}$ is $C_{1-6}$alkyl; aryl optionally substituted with 1, 2, 3, or 4 $R^{7b}$; aralkyl where the aryl is optionally substituted with 1, 2, 3, or 4 $R^{7b}$; heteroaryl optionally substituted with 1, 2, 3, or 4 $R^{7b}$; heterocyclic optionally substituted with 1, 2, 3, or 4 $R^{7b}$; biphenyl optionally substituted on either ring with 1, 2, 3, or 4 $R^{7b}$; or cycloalkyl optionally substituted with 1, 2, 3, or 4 groups independently selected from $C_{1-6}$alkyl and halo-$C_{1-6}$alkyl;

each $R^{7b}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;

$R^{10}$ is hydrogen or $C_{1-6}$alkyl;

$R^{10a}$ is $C_{1-6}$alkyl; aryl optionally substituted with 1, 2, 3, or 4 $R^{10b}$; aralkyl where the aryl is optionally substituted with 1, 2, 3, or 4 $R^{10b}$; phenylcarbonyl where the phenyl is optionally substituted with 1, 2, 3, or 4 $R^{10b}$; heteroaryl optionally substituted with 1, 2, 3, or 4 $R^{10b}$; heterocyclic optionally substituted with 1, 2, 3, or 4 $R^{10b}$; biphenyl optionally substituted on either ring with 1, 2, 3, or 4 $R^{10b}$; or cycloalkyl optionally substituted with 1, 2, 3, or 4 groups independently selected from $C_{1-6}$alkyl and halo-$C_{1-6}$alkyl;

each $R^{10b}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;

$R^{11}$ is hydrogen or $C_{1-6}$alkyl;

$R^{11a}$ is $C_{1-6}$alkyl; aryl optionally substituted with 1, 2, 3, or 4 $R^{11b}$; aralkyl where the aryl is optionally substituted with 1, 2, 3, or 4 $R^{11b}$; heteroaryl optionally substituted with 1, 2, 3, or 4 $R^{11b}$; heterocyclic optionally substituted with 1, 2, 3, or 4 $R^{11b}$; biphenyl optionally substituted on either ring with 1, 2, 3, or 4 $R^{11b}$; or cycloalkyl optionally substituted with 1, 2, 3, or 4 groups independently selected from $C_{1-6}$alkyl and halo-$C_{1-6}$alkyl;

each $R^{11b}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;

$R^{13}$ is hydrogen or $C_{1-6}$alkyl;

$R^{13a}$ is $C_{1-6}$alkyl; aryl optionally substituted with 1, 2, 3, or 4 $R^{13b}$; aralkyl where the aryl is optionally substituted with 1, 2, 3, or 4 $R^{13b}$; heteroaryl optionally substituted with 1, 2, 3, or 4 $R^{13b}$; heterocyclic optionally substituted with 1, 2, 3, or 4 $R^{13b}$; biphenyl optionally substituted on either ring with 1, 2, 3, or 4 $R^{13b}$; or cycloalkyl optionally substituted with 1, 2, 3, or 4 groups independently selected from $C_{1-6}$alkyl and halo-$C_{1-6}$alkyl;

each $R^{13b}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;

$R^{14}$ is hydrogen or $C_{1-6}$alkyl;

$R^{14a}$ is hydrogen or $C_{1-6}$alkyl;

$R^{14b}$ is $C_{1-6}$alkyl; aryl optionally substituted with 1, 2, 3, or 4 $R^{14c}$; aralkyl where the aryl is optionally substituted with 1, 2, 3, or 4 $R^{14c}$; heteroaryl optionally substituted with 1, 2, 3, or 4 $R^{14c}$; heterocyclic optionally substituted with 1, 2, 3, or 4 $R^{14c}$; biphenyl optionally substituted on either ring with 1, 2, 3, or 4 $R^{14c}$; or cycloalkyl optionally substituted with 1, 2, 3, or 4 groups independently selected from $C_{1-6}$alkyl and halo-$C_{1-6}$alkyl; and each $R^{14c}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano; or a pharmaceutically acceptable salt, hydrate, solvate, stereoisomer, tautomer, or mixture thereof.

In some or any embodiments, the compound of Formula I is according to Formula (Ia):

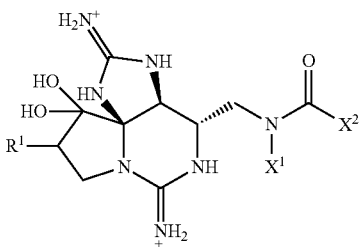

(Ia)

where $R^1$, $X^1$, and $X^2$ are as defined in Formula (I) in the Summary of the Invention or as defined in some or any embodiments described herein.

In some or any embodiments, the compound of Formula I is according to Formula (Ib):

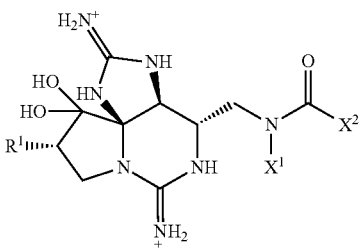

(Ib)

where $R^1$, $X^1$, and $X^2$ are as defined in Formula (I) in the Summary of the Invention or as defined in some or any embodiments described herein.

Embodiment A: In some or any embodiments, the compound is according to Formula (I), (Ia), or (Ib) where
$R^1$ is H, OH, —OS(O)$_3^-$, —OS(O)$_2R^5$, —OC(O)$R^6$, —NHC(O)$R^{7a}$, —N(CH$_3$)C(O)$R^{7a}$, —OC(O)NHR$^{10a}$, —OC(O)N(CH$_3$)R$^{10a}$, —NHR$^{11a}$, —NH$_3^+$, —NHS(O)$_2R^{13a}$, or —NHC(O)NHR$^{14b}$;
$X^1$ is $R^3$ and $X^2$ is $R^9$ or
$X^1$ and $X^2$ together with the —NC(O)— to which they are attached form

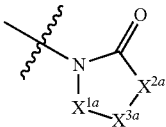

where $X^{1a}$ is —O—, —CH$_2$—, or —C(O)—; $X^{2a}$ is —S—, —NR$^8$—, or —C(R$^4$)(R$^{4a}$)—; and $X^{3a}$ is one or two groups independently selected from —O—, —S—, —NR$^8$—, and —C(R$^4$)(R$^{4a}$)— provided that only one atom of $X^{1a}$, $X^{2a}$, and $X^{3a}$ is selected from —O—, —S—, and —NR$^8$—; and where the

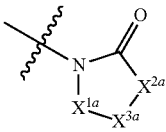

ring is optionally fused at $X^{2a}$ and at the adjacent atom in $X^{3a}$ to form a saturated or unsaturated, 9 or 10-membered bicyclic ring when $X^{2a}$ is —C(R$^4$)(R$^{4a}$)— and $X^{3a}$ is —C(R$^4$)(R$^{4a}$)— or —C(R$^4$)(R$^{4a}$)—C(R$^4$)(R$^{4a}$)—; and where there are four additional ring atoms which are independently —CR$^{12}$= or —C(R$^{12}$)$_2$—;
each $R^4$ and $R^{4a}$ is independently H; C$_{1-3}$alkyl; or when the 6-12 membered ring is fused at a —C(R$^4$)(R$^{4a}$)—, one or both of the $R^4$ and $R^{4a}$ on the —C(R$^4$)(R$^{4a}$)— form a single or double bond with an adjacent ring atom;
$R^8$ is hydrogen, C$_{1-3}$alkyl, or phenyl;
each $R^{12}$ is independently hydrogen, halo, C$_{1-6}$alkyl, halo-C$_{1-6}$alkyl, or aryl;
$R^3$ is —C(O)C$_{1-3}$alkyl or —C(O)OC$_{1-3}$alkyl;
$R^5$ is H, C$_{1-3}$alkyl, or phenyl optionally substituted with 1 or 2 $R^{5a}$;
each $R^{5a}$, when present, is independently halo, C$_{1-6}$alkyl, halo-C$_{1-6}$alkyl, hydroxy, C$_{1-6}$alkoxy, or halo-C$_{1-6}$alkoxy;
$R^9$ is C$_{1-3}$alkyl or phenyl;
$R^6$ is aryl optionally substituted with 1, 2, or 3 $R^{6a}$; or heterocyclic optionally substituted with 1 or 2 $R^{6a}$;
each $R^{6a}$, when present, is independently halo, C$_{1-6}$alkyl, halo-C$_{1-6}$alkyl, C$_{1-6}$alkoxy, halo-C$_{1-6}$alkoxy, or phenyl;
$R^{7a}$ is C$_{1-6}$alkyl; aryl optionally substituted with 1, 2, or 3 $R^{7b}$; aralkyl where the aryl is optionally substituted with 1, 2, or 3 $R^{7b}$; heteroaryl optionally substituted with 1, 2, or 3 $R^{7b}$; heterocyclic optionally substituted with 1, 2, or 3 $R^{7b}$; biphenyl optionally substituted with 1, 2, or 3 $R^{7b}$; or cycloalkyl optionally substituted with 1, 2, or 3 groups independently selected from C$_{1-6}$alkyl and halo-C$_{1-6}$alkyl;
each $R^{7b}$, when present, is independently halo, hydroxy, C$_{1-6}$alkyl, halo-C$_{1-6}$alkyl, C$_{1-6}$alkoxy, halo-C$_{1-6}$alkoxy, C$_{1-6}$alkylthio, C$_{1-6}$alkylsulfonyl, or amino; and
$R^{10a}$ is C$_{1-6}$alkyl; aryl optionally substituted with 1 or 2 $R^{10b}$; aralkyl where the aryl is optionally substituted with 1, 2, or 3 $R^{10b}$; phenylcarbonyl where the phenyl is optionally substituted with 1 or 2 $R^{10b}$; or cycloalkyl optionally substituted with 1, 2, or 3 $R^{10b}$;
each $R^{10b}$, when present, is independently halo, C$_{1-6}$alkyl, halo-C$_{1-6}$alkyl, C$_{1-6}$alkoxy, or halo-C$_{1-6}$alkoxy;
$R^{11a}$ is aryl optionally substituted with 1, 2, or 3 $R^{11b}$; or heteroaryl optionally substituted with 1, 2, or 3 $R^{11b}$;
each $R^{11b}$, when present, is independently halo, C$_{1-6}$alkyl, halo-C$_{1-6}$alkyl, C$_{1-6}$alkoxy, or halo-C$_{1-6}$alkoxy;
$R^{13a}$ is aryl optionally substituted with 1, 2, 3, or 4 $R^{13b}$; or heterocyclic optionally substituted with 1, 2, 3, or 4 $R^{13b}$; and
$R^{14b}$ is aryl optionally substituted with 1, 2, 3, or 4 $R^{14c}$; or heterocyclic optionally substituted with 1, 2, 3, or 4 $R^{14c}$.

In some or any embodiments of Embodiment A, $X^1$ is $R^3$ and $X^2$ is $R^9$. In some or any embodiments of Embodiment A, $X^1$ and $X^2$ together with the —NC(O)— to which they are attached form

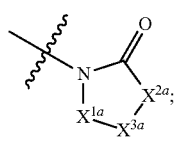

in some or any embodiments of Embodiment A, the ring formed by $X^1$ and $X^2$ and the —NC(O)— to which they are attached is

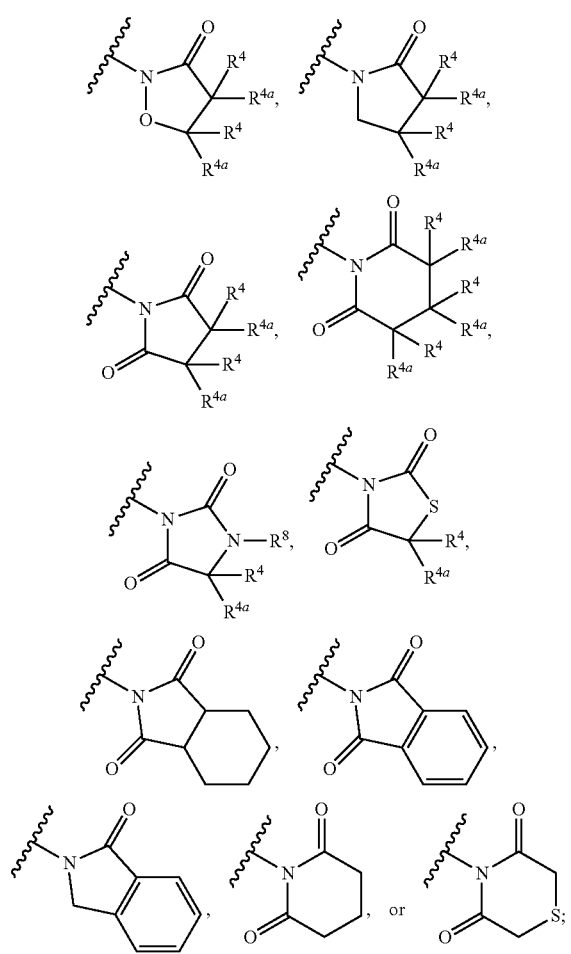

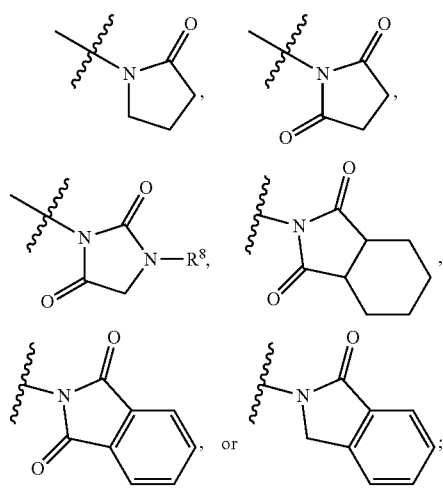

in some or any embodiments of Embodiment A, the ring formed by $X^1$ and $X^2$ and the —NC(O)— to which they are attached is

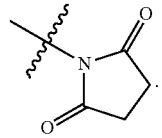

In some or any embodiments of Embodiment A, including any of the foregoing embodiments, $R^1$ is H, OH, —OS(O)$_3^-$, —OS(O)$_2R^5$, —OC(O)$R^6$, —NHC(O)$R^{7a}$, —OC(O)NHR$^{10a}$, —NHR$^{11a}$, —NH$_3^+$, —NHS(O)$_2R^{13a}$, —NHC(O)NHR$^{14b}$, or 2,5-dioxo-pyrrolidinyl. In some or any embodiments of Embodiment A, including any of the foregoing embodiments, $R^1$ is —OC(O)$R^6$ or —NHC(O)$R^{7a}$. In some or any embodiments, the aryl in $R^6$, $R^{7a}$, $R^{10a}$, $R^{11a}$, $R^{13a}$, and $R^{14b}$ is phenyl, naphthyl, tetrahydronaphthyl, fluorenyl, or indanyl; each of which is optionally substituted as described above. In some or any embodiments, the heterocyclic in $R^6$, $R^{7a}$, $R^{13a}$, and $R^{14b}$ is benzo-1,4-dioxanyl, benzodioxolyl, indolinyl, 2-oxo-indolinyl, pyrrolidinyl, piperidinyl, 2,3-dihydrobenzofuranyl, or decahydroquinolinyl; each of which is optionally substituted as described above. In some or any embodiments, the heteroaryl in $R^6$ and $R^{7a}$ is indolyl, furanyl, pyridinyl, or pyrazolyl; each of which is optionally substituted as described above.

In some or any embodiments, the compound of Formula I is according to Formula (Ic):

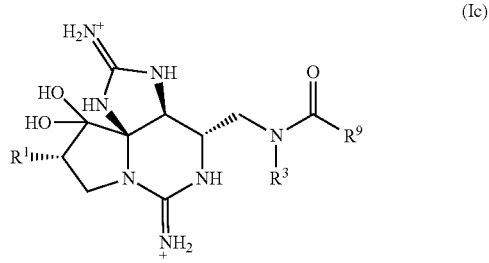

(Ic)

where $R^1$, $R^3$, and $R^9$ are as defined in Formula (I) in the Summary of the Invention or as defined in some or any embodiments described herein. In some or any embodiments, the Compound of Formula (Ic) is that where $R^3$ is —C(O)C$_{1-6}$alkyl and $R^9$ is C$_{1-6}$alkyl; or $R^3$ is —C(O)C$_{1-6}$alkyl and $R^9$ is phenyl; or $R^3$ is —C(O)OC$_{1-6}$alkyl and $R^9$ is phenyl; and all other groups are as defined in Formula (I) in the Summary of the Invention or as defined in some or any embodiments described herein.

In some or any embodiments, the compound of Formula I is according to Formula (Id):

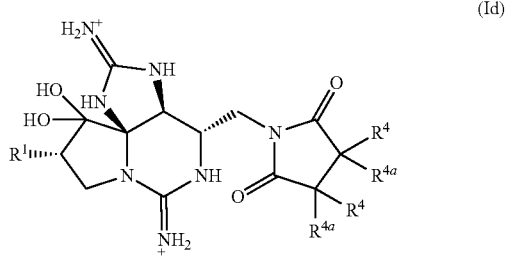

(Id)

where R$^1$ is as defined in Formula (I) in the Summary of the Invention or as defined in some or any embodiments described herein. In some or any embodiments, provided is a Compound of Formula (Id) where each R$^4$ and R$^{4a}$ are independently hydrogen or methyl; and all other groups are as defined in the Summary of the Invention or in some or any embodiments described herein. In some or any embodiments, provided is a Compound of Formula (Id) where each R$^4$ and R$^{4a}$ are hydrogen; and all other groups are as defined in the Summary of the Invention or in some or any embodiments described herein.

In some or any embodiments, the compound of Formula I is according to Formula (Ig):

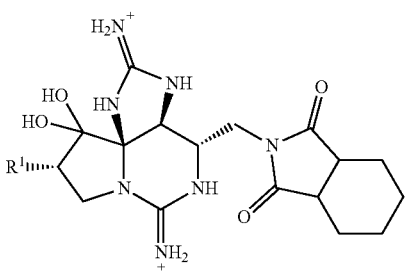

(Ig)

where R$^1$ is as defined in Formula (I) in the Summary of the Invention or as defined in some or any embodiments described herein. In some or any embodiments, provided is a Compound of Formula (Ig) where R$^1$ is —OC(O)R$^6$ or —NR$^7$C(O)R$^{7a}$; and all other groups are as defined in the Summary of the Invention or in some or any embodiments described herein. In some or any embodiments, provided is a Compound of Formula (Ig) where R$^1$ is —OC(O)R$^6$ or —NR$^7$C(O)R$^{7a}$; R$^6$ is aryl optionally substituted with 1 or 2 R$^{6a}$; R$^7$ is hydrogen or methyl; R$^{7a}$ is aryl optionally substituted with 1 or 2 R$^{7b}$; and all other groups are as defined in the Summary of the Invention or in some or any embodiments described herein.

In some or any embodiments, the compound of Formula I is according to Formula (Ih):

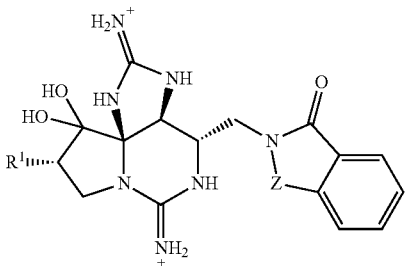

(Ih)

where Z is CH$_2$ or C(O) and R$^1$ is as defined in Formula (I) in the Summary of the Invention or as defined in some or any embodiments described herein. In some or any embodiments, provided is a Compound of Formula (Ih) where R$^1$ is —OC(O)R$^6$ or —NR$^7$C(O)R$^{7a}$; and all other groups are as defined in the Summary of the Invention or in some or any embodiments described herein. In some or any embodiments, provided is a Compound of Formula (Ih) where R$^1$ is —OC(O)R$^6$ or —NR$^7$C(O)R$^{7a}$; R$^6$ is aryl optionally substi- tuted with 1 or 2 R$^{6a}$; R$^7$ is hydrogen; R$^{7a}$ is aryl optionally substituted with 1 or 2 R$^{7b}$; and all other groups are as defined in the Summary of the Invention or in some or any embodiments described herein.

In some or any embodiments, the compound of Formula I is according to Formula (Ii):

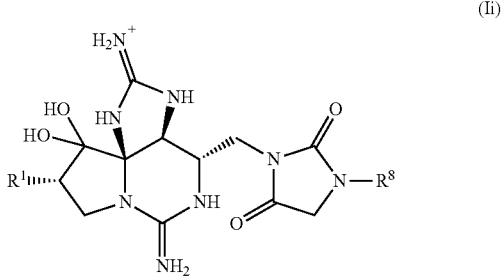

(Ii)

where R$^1$ is as defined in Formula (I) in the Summary of the Invention or as defined in some or any embodiments described herein. In some or any embodiments, provided is a Compound of Formula (Ii) where R$^8$ is C$_{1-6}$alkyl or phenyl; and all other groups are as defined in the Summary of the Invention or in some or any embodiments described herein. In some or any embodiments, provided is a Compound of Formula (Ii) where R$^8$ is C$_{1-3}$alkyl or phenyl; and all other groups are as defined in the Summary of the Invention or in some or any embodiments described herein. In some or any embodiments, provided is a Compound of Formula (Ii) where R$^8$ is methyl or phenyl; and all other groups are as defined in the Summary of the Invention or in some or any embodiments described herein.

In some or any embodiments, the Compound is according to (I), (Ia), (Ib), (Ic), (Id), (Ig), (Ih), or (Ii) where R$^1$ is H, OH, —OS(O)$_3^-$, —OS(O)$_2$R$^5$, —OC(O)R$^6$, —NHC(O)R$^{7a}$, —N(CH$_3$)C(O)R$^{7a}$, —OC(O)NHR$^{10a}$, —OC(O)N(CH$_3$) R$^{10a}$, —NHR$^{11a}$, —NH$_3^+$, —NHS(O)$_2$R$^{13a}$, —NHC(O)NHR$^{14b}$, or 2,5-dioxo-pyrrolidinyl; and all other groups are as defined in Formula (I) in the Summary of the Invention or as defined in some or any embodiments described herein. In some or any embodiments, the Compound is according to (I), (Ia), (Ib), (Ic), (Id), (Ig), (Ih), or (Ii) where R$^1$ is H, OH, —OS(O)$_3^-$, —OS(O)$_2$R$^5$, —OC(O)R$^6$, —NHC(O)R$^{7a}$, —N(CH$_3$)C(O)R$^{7a}$, —OC(O)NHR$^{10a}$, —OC(O)N(CH$_3$)R$^a$, —NHR$^{11a}$, —NH$_3^+$, —NHS(O)$_2$R$^{13a}$, or —NHC(O)NHR$^{14b}$; and all other groups are as defined in Formula (I) in the Summary of the Invention or as defined in some or any embodiments described herein. In some or any embodiments, the Compound is according to (I), (Ia), (Ib), (Ic), (Id), (Ig), (Ih), or (Ii) where R$^1$ is OH, —OS(O)$_3^-$, —OS(O)$_2$R$^5$, —OC(O)R$^6$, —NHC(O)R$^{7a}$, or —N(CH$_3$)C(O)R$^{7a}$; and all other groups are as defined in Formula (I) in the Summary of the Invention or as defined in some or any embodiments described herein. In some or any embodiments, the Compound is according to (I), (Ia), (Ib), (Ic), (Id), (Ig), (Ih), or (Ii) where R$^1$ is H, OH, —OS(O)$_3^-$, —OS(O)$_2$R$^5$, —OC(O) R$^6$, —NHC(O)R$^{7a}$, —OC(O)NHR$^{10a}$, or —NHR$^{11a}$; R$^5$ is C$_{1-6}$alkyl or aryl optionally substituted with 1, 2, 3, or 4 R$^{5a}$; R$^6$ is aryl, heterocyclic, or heteroaryl, each of which is optionally substituted with 1 or 2 R$^{6a}$ groups; R$^{7a}$ is aryl optionally substituted with 1, 2, or 3 R$^{7b}$, R$^{7a}$ is aralkyl optionally substituted with 1, 2, or 3 R$^{7b}$, R$^{7a}$ is biphenyl optionally substituted with 1, 2, or 3 R$^{7b}$, heteroaryl option- ally substituted with 1, 2, or 3 R$^{7b}$, heterocyclic optionally substituted with 1, 2, or 3 $R^{7b}$, or cycloalkyl optionally substituted with 1, 2, or 3 groups independently selected from $C_{1-6}$alkyl and halo-$C_{1-6}$alkyl; $R^{10a}$ is aryl, aralkyl, or heteroaryl, each of which is optionally substituted with 1 or 2 $R^{10b}$ groups or $R^{10a}$ is cycloalkyl optionally substituted with 1 or 2 groups independently selected from $C_{1-6}$alkyl and halo-$C_{1-6}$alkyl; $R^{11a}$ is aryl or heteroaryl, each of which is optionally substituted with 1 or 2 $R^{11b}$ groups; $R^{13a}$ is aryl optionally substituted with 1 or 2 $R^{13b}$; $R^{14b}$ is aryl optionally substituted with 1 or 2 $R^{13b}$; and all other groups are as defined in Formula (I) in the Summary of the Invention or as defined in some or any embodiments described herein. In some or any embodiments, the Compound is according to (I), (Ia), (Ib), (Ic), (Id), (Ig), (Ih), or (Ii) where $R^1$ is OH, —OS(O)$_3^-$, —OS(O)$_2$ $R^5$, —OC(O)$R^6$, or —NHC(O)$R^{7a}$; $R^5$ is $C_{1-6}$alkyl or aryl optionally substituted with 1, 2, 3, or 4 $R^{5a}$; $R^6$ is aryl, heterocyclic, or heteroaryl, each of which is optionally substituted with 1 or 2 $R^{6a}$ groups; $R^{7a}$ is aryl optionally substituted with 1 or 2 $R^{7b}$, $R^{7a}$ is aralkyl optionally substituted with 1, 2, or 3 $R^{7b}$, $R^{7a}$ is biphenyl optionally substituted with 1, 2, or 3 $R^{7b}$, heteroaryl optionally substituted with 1 or 2 $R^{7b}$, heterocyclic optionally substituted with 1, 2, or 3 $R^{7b}$, or cycloalkyl optionally substituted with 1 or 2 groups independently selected from $C_{1-6}$alkyl and halo-$C_{1-6}$alkyl; and all other groups are as defined in Formula (I) in the Summary of the Invention or as defined in some or any embodiments described herein. In some or any embodiments, the Compound is according to (I), (Ia), (Ib), (Ic), (Id), (Ig), (Ih), or (Ii) where $R^1$ is OH, —OS(O)$_3^-$, —OS(O)$_2$ $R^5$, —OC(O)$R^6$, or —NHC(O)$R^{7a}$; $R^5$ is $C_{1-6}$alkyl or aryl optionally substituted with 1 or 2 groups independently selected from halo, $C_{1-6}$alkyl, halo-$C_{1-6}$alkyl, $C_{1-6}$alkoxy, and halo-$C_{1-6}$alkoxy; $R^6$ is aryl, heterocyclic, or heteroaryl, each of which is optionally substituted with 1 or 2 groups independently selected from phenyl, halo, $C_{1-6}$alkyl, halo-$C_{1-6}$alkyl, $C_{1-6}$alkoxy, and halo-$C_{1-6}$alkoxy; $R^{7a}$ is aryl optionally substituted with 1 or 2 groups independently selected from halo, hydroxy, alkylthio, alkylsulfonyl, $C_{1-6}$alkyl, halo-$C_{1-6}$alkyl, $C_{1-6}$alkoxy, and halo-$C_{1-6}$alkoxy; $R^{7a}$ is aralkyl optionally substituted with 1 or 2 groups independently selected from halo, $C_{1-6}$alkyl, halo-$C_{1-6}$alkyl, $C_{1-6}$alkoxy, and halo-$C_{1-6}$alkoxy; or $R^{7a}$ is biphenyl optionally substituted with 1 or 2 groups independently selected from halo, $C_{1-6}$alkyl, halo-$C_{1-6}$alkyl, $C_{1-6}$alkoxy, and halo-$C_{1-6}$alkoxy; $R^{7a}$ is heterocyclic optionally substituted with 1 or 2 groups independently selected from halo, $C_{1-6}$alkyl, halo-$C_{1-6}$alkyl, $C_{1-6}$alkoxy, and halo-$C_{1-6}$alkoxy; or $R^{7a}$ is heteroaryl optionally substituted with 1 or 2 groups independently selected from halo, halo-$C_{1-6}$alkyl, and halo-$C_{1-6}$alkoxy; or $R^{7a}$ is cycloalkyl optionally substituted with 1 or 2 halo-$C_{1-6}$alkyl; and all other groups are as defined in Formula (I) in the Summary of the Invention or as defined in some or any embodiments described herein.

In some or any embodiments, the compound of Formula I is according to Formula (Ie):

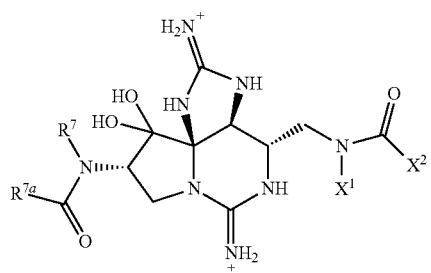
(Ie)

where $R^7$, $R^{7a}$, $X^1$, and $X^2$ are as defined in Formula (I) in the Summary of the Invention or as defined in some or any embodiments described herein. In some or any embodiments, the Compound of Formula (Ie) is that wherein $R^7$ is hydrogen or methyl; and all other groups are as defined in Formula (I) in the Summary of the Invention or as defined in some or any embodiments described herein. In some or any embodiments, the Compound of Formula (Ie) is that wherein $R^7$ is hydrogen; and all other groups are as defined in Formula (I) in the Summary of the Invention or as defined in some or any embodiments described herein. In some or any embodiments, the Compound of Formula (Ie) is that wherein $R^7$ is hydrogen; $R^{7a}$ is aryl optionally substituted with 1, 2, or 3 $R^{7b}$, $R^{7a}$ is heterocyclic optionally substituted with 1, 2, or 3 $R^{7b}$, $R^{7a}$ is biphenyl optionally substituted on either ring with 1, 2, or 3 $R^{7b}$, $R^{7a}$ is aralkyl optionally substituted with 1, 2, or 3 $R^{7b}$, heteroaryl optionally substituted with 1, 2, or 3 $R^{7b}$, or cycloalkyl optionally substituted with 1, 2, or 3 groups independently selected from $C_{1-6}$alkyl and halo-$C_{1-6}$alkyl; and all other groups are as defined in Formula (I) in the Summary of the Invention or as defined in some or any embodiments described herein. In some or any embodiments, the Compound of Formula (Ie) is that wherein $R^7$ is hydrogen; $R^{7a}$ is aryl optionally substituted with 1, 2, or 3 $R^{7b}$, $R^{7a}$ is heterocyclic optionally substituted with 1, 2, or 3 $R^{7b}$, $R^{7a}$ is biphenyl optionally substituted on either ring with 1, 2, or 3 $R^{7b}$, $R^{7a}$ is aralkyl optionally substituted with 1, 2, or 3 $R^{7b}$, heteroaryl optionally substituted with 1, 2, or 3 $R^{7b}$, or cycloalkyl optionally substituted with 1, 2, or 3 groups independently selected from $C_{1-6}$alkyl and halo-$C_{1-6}$alkyl; each $R^{7b}$ is independently halo, hydroxy, $C_{1-6}$alkyl, halo-$C_{1-6}$alkyl, $C_{1-6}$alkoxy, or halo-$C_{1-6}$alkoxy; and all other groups are as defined in Formula (I) in the Summary of the Invention or as defined in some or any embodiments described herein. In some or any embodiments, the Compound of Formula (Ie) is that wherein $R^7$ is hydrogen; $R^{7a}$ is aryl optionally substituted with 1, 2, or 3 $R^{7b}$, $R^{7a}$ is heterocyclic optionally substituted with 1, 2, or 3 $R^{7b}$, $R^{7a}$ is biphenyl optionally substituted on either ring with 1, 2, or 3 $R^{7b}$, $R^{7a}$ is aralkyl optionally substituted with 1, 2, or 3 $R^{7b}$, heteroaryl optionally substituted with 1, 2, or 3 $R^{7b}$, or cycloalkyl optionally substituted with 1, 2, or 3 groups independently selected from $C_{1-6}$alkyl and halo-$C_{1-6}$alkyl; each $R^{7b}$ is independently halo, halo-$C_{1-6}$alkyl, or halo-$C_{1-6}$alkoxy; and all other groups are as defined in Formula (I) in the Summary of the Invention or as defined in some or any embodiments described herein. In some or any embodiments, provided is a Compound of Formula (Ie) where the ring formed by $X^1$ and $X^2$ and the —NC(O)— to which they are attached is

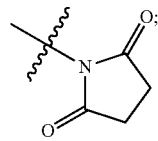 [SMILES: *N1C(=O)CCC1=O]

and all other groups are as defined in Formula (I) in the Summary of the Invention or as defined in some or any embodiments described herein. In some or any embodiments, provided is a Compound of Formula (Ie) where the aryl in $R^{7a}$ is phenyl, naphthyl, tetrahydronaphthyl, fluorenyl, or indanyl; each of which is optionally substituted with 1, 2, or 3 groups independently selected from halo, $C_{1-6}$alkyl, halo-$C_{1-6}$alkyl, hydroxy, $C_{1-6}$alkoxy, halo- $C_{1-6}$alkoxy, $C_{1-6}$alkylthio, $C_{1-6}$alkylsulfonyl, and amino; and all other groups are as defined in Formula (I) in the Summary of the Invention or as defined in some or any embodiments described herein. In some or any embodiments, provided is a Compound of Formula (Ie) where the heterocyclic in $R^{7a}$ is benzo-1,4-dioxanyl, benzodioxolyl, indolinyl, 2-oxo-indolinyl, pyrrolidinyl, piperidinyl, 2,3-dihydrobenzofuranyl, or decahydroquinolinyl; each of which is optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, and phenyl; and all other groups are as defined in Formula (I) in the Summary of the Invention or as defined in some or any embodiments described herein.

In some or any embodiments, the compound of Formula I is according to Formula (If):

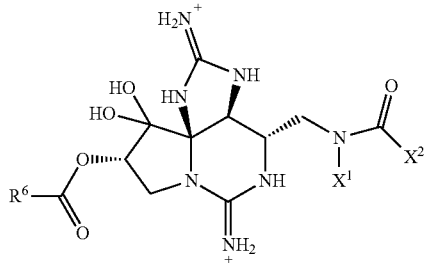

(If)

where $R^6$, $X^1$, and $X^2$ are as defined in Formula (I) in the Summary of the Invention or as defined in some or any embodiments described herein. In some or any embodiments, the Compound of Formula (If) is that wherein $R^6$ is aryl, heterocyclic, or heteroaryl, each of which is optionally substituted with 1 or 2 $R^{6a}$; and all other groups are as defined in Formula (I) in the Summary of the Invention or as defined in some or any embodiments described herein. In some or any embodiments, the Compound of Formula (If) is that wherein $R^6$ is aryl, heterocyclic, or heteroaryl, each of which is optionally substituted with 1 or 2 $R^{6a}$; each $R^{6a}$ is independently phenyl, halo, $C_{1-6}$alkyl, halo-$C_{1-6}$alkyl, or halo-$C_{1-6}$alkoxy; and all other groups are as defined in Formula (I) in the Summary of the Invention or as defined in some or any embodiments described herein. In some or any embodiments, provided is a Compound of Formula (If) where the ring formed by $X^1$ and $X^2$ and the —NC(O)— to which they are attached is

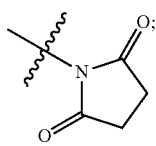

and all other groups are as defined in Formula (I) in the Summary of the Invention or as defined in some or any embodiments described herein. In some or any embodiments, provided is a Compound of Formula (If) where the aryl in $R^6$ is phenyl, naphthyl, tetrahydronaphthyl, fluorenyl, or indanyl; each of which is optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, $C_{1-6}$alkylthio, $C_{1-6}$alkylsulfonyl, and amino; and all other groups are as defined in Formula (I) in the Summary of the Invention or as defined in some or any embodiments described herein. In some or any embodiments, provided is a Compound of Formula (If) where the heterocyclic in $R^6$ is benzo-1,4-dioxanyl, benzodioxolyl, indolinyl, 2-oxo-indolinyl, pyrrolidinyl, piperidinyl, 2,3-dihydrobenzofuranyl, or decahydroquinolinyl; each of which is optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, and phenyl; and all other groups are as defined in Formula (I) in the Summary of the Invention or as defined in some or any embodiments described herein.

In some or any embodiments, the compound of Formula I is according to Formula (Ij):

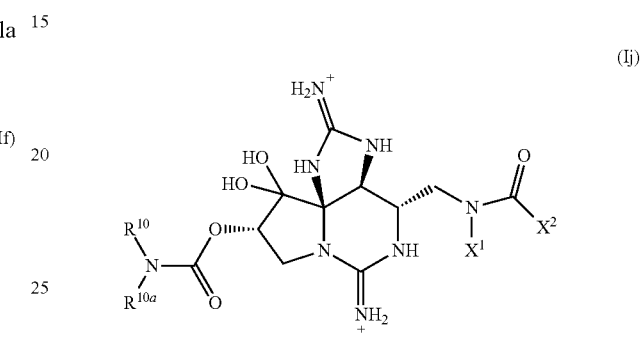

(Ij)

where $R^{10}$, $R^{10a}$, $X^1$, and $X^2$ are as defined in Formula (I) in the Summary of the Invention or as defined in some or any embodiments described herein. In some or any embodiments, the Compound of Formula (Ij) is that wherein $R^{10}$ is hydrogen or methyl; and all other groups are as defined in Formula (I) in the Summary of the Invention or as defined in some or any embodiments described herein. In some or any embodiments, the Compound of Formula (Ij) is that wherein $R^{10}$ is hydrogen; and all other groups are as defined in Formula (I) in the Summary of the Invention or as defined in some or any embodiments described herein. In some or any embodiments, the Compound of Formula (Ij) is that wherein $R^7$ is hydrogen; $R^{10a}$ is aryl or aralkyl, each of which is optionally substituted with 1 or 2 $R^{10b}$ or $R^{10a}$ is cycloalkyl optionally substituted with 1 or 2 groups independently selected from $C_{1-6}$alkyl and halo-$C_{1-6}$alkyl; and all other groups are as defined in Formula (I) in the Summary of the Invention or as defined in some or any embodiments described herein. In some or any embodiments, the Compound of Formula (Ij) is that wherein $R^7$ is hydrogen; $R^{10a}$ is aryl or aralkyl, each of which is optionally substituted with 1 or 2 $R^{10b}$ or $R^{10a}$ is cycloalkyl optionally substituted with 1 or 2 groups independently selected from $C_{1-6}$alkyl and halo-$C_{1-6}$alkyl; each $R^{10b}$ is independently selected from halo, $C_{1-6}$alkyl, halo-$C_{1-6}$alkyl, $C_{1-6}$alkoxy, or halo-$C_{1-6}$alkoxy; and all other groups are as defined in Formula (I) in the Summary of the Invention or as defined in some or any embodiments described herein. In some or any embodiments, provided is a Compound of Formula (Ij) where the ring formed by $X^1$ and $X^2$ and the —NC(O)— to which they are attached is

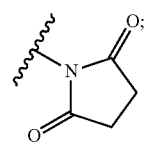 [SMILES: *N1C(=O)CCC1=O]

and all other groups are as defined in Formula (I) in the Summary of the Invention or as defined in some or any embodiments described herein. In some or any embodiments, provided is a Compound of Formula (Ij) where the aryl in $R^{10a}$ is phenyl, naphthyl, tetrahydronaphthyl, fluorenyl, or indanyl; each of which is optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, $C_{1-6}$alkylthio, $C_{1-6}$alkylsulfonyl, and amino; and all other groups are as defined in Formula (I) in the Summary of the Invention or as defined in some or any embodiments described herein. In some or any embodiments, provided is a Compound of Formula (Ij) where the heterocyclic in $R^{10a}$ is benzo-1,4-dioxanyl, benzodioxolyl, indolinyl, 2-oxo-indolinyl, pyrrolidinyl, piperidinyl, 2,3-dihydrobenzofuranyl, or decahydroquinolinyl; each of which is optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, and phenyl; and all other groups are as defined in Formula (I) in the Summary of the Invention or as defined in some or any embodiments described herein.

In some or any embodiments, the compound of Formula I is according to Formula (Ik):

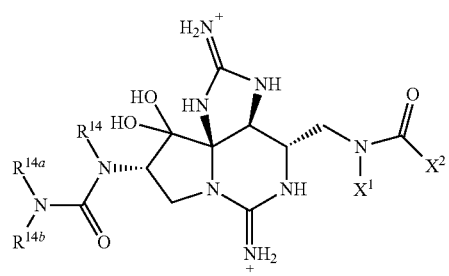

(Ik)

where $R^{14}$, $R^{14a}$, $R^{14b}$, $X^1$, and $X^2$ are as defined in Formula (I) in the Summary of the Invention or as defined in some or any embodiments described herein. In some or any embodiments, the Compound of Formula (Ik) is that wherein $R^{14}$ and $R^{14a}$ are independently hydrogen or methyl; and all other groups are as defined in Formula (I) in the Summary of the Invention or as defined in some or any embodiments described herein. In some or any embodiments, the Compound of Formula (Ik) is that wherein $R^{14}$ and $R^{14a}$ are hydrogen; and all other groups are as defined in Formula (I) in the Summary of the Invention or as defined in some or any embodiments described herein. In some or any embodiments, the Compound of Formula (Ik) is that wherein $R^{14}$ and $R^{14a}$ are hydrogen; $R^{14b}$ is aryl optionally substituted with 1 or 2 $R^{14c}$; and all other groups are as defined in Formula (I) in the Summary of the Invention or as defined in some or any embodiments described herein. In some or any embodiments, the Compound of Formula (Ik) is that wherein $R^{14}$ and $R^{14a}$ are hydrogen; $R^{14b}$ is aryl optionally substituted with 1 or 2 $R^{14c}$; each $R^{14c}$ is independently selected from halo, $C_{1-6}$alkyl, halo-$C_{1-6}$alkyl, $C_{1-6}$alkoxy, and halo-$C_{1-6}$alkoxy; and all other groups are as defined in Formula (I) in the Summary of the Invention or as defined in some or any embodiments described herein. In some or any embodiments, provided is a Compound of Formula (Ik) where the ring formed by $X^1$ and $X^2$ and the —NC(O)— to which they are attached is

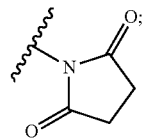

and all other groups are as defined in Formula (I) in the Summary of the Invention or as defined in some or any embodiments described herein. In some or any embodiments, provided is a Compound of Formula (Ik) where the aryl in $R^{14a}$ is phenyl, naphthyl, tetrahydronaphthyl, fluorenyl, or indanyl; each of which is optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, $C_{1-6}$alkylthio, $C_{1-6}$alkylsulfonyl, and amino; and all other groups are as defined in Formula (I) in the Summary of the Invention or as defined in some or any embodiments described herein. In some or any embodiments, provided is a Compound of Formula (Ik) where the heterocyclic in $R^{14a}$ is benzo-1,4-dioxanyl, benzodioxolyl, indolinyl, 2-oxo-indolinyl, pyrrolidinyl, piperidinyl, 2,3-dihydrobenzofuranyl, or decahydroquinolinyl; each of which is optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, and phenyl; and all other groups are as defined in Formula (I) in the Summary of the Invention or as defined in some or any embodiments described herein.

In some or any embodiments, the Compound is according to Formula (I), (Ia), (Ib), I-P, (Ie), (If), (Ij), or (Ik) where $X^1$ and $X^2$ together with the —NC(O)— to which they are attached form a 5 or 6-membered ring where $X^1$, $X^2$, and the one or two additional ring atoms are independently selected from —C(O)—, —O—, —S—, —NR$^8$—, and —C(R$^4$)(R$^{4a}$)— provided that only one is selected from —O—, —S—, and —NR$^8$—; and where the 5 or 6-membered ring is optionally fused at two adjacent carbon atoms, or is optionally fused at one carbon atom and one nitrogen atom which are adjacent to each other, to a form a saturated or unsaturated 6-12 membered bicyclic ring; where the 1, 2, 3, 4, 5, or 6 additional ring atoms are independently —CR$^{12}$═ or —C(R$^{12}$)$_2$—; each $R^4$ and $R^{4a}$ is independently H; $C_{1-6}$alkyl; or when the 6-12 membered ring is fused at a —C(R$^4$)(R$^{4a}$)—, one or both of the $R^4$ and $R^{4a}$ on the —C(R$^4$)(R$^{4a}$)— form a single or double bond with an adjacent ring atom; $R^8$ is hydrogen; $C_{1-6}$alkyl; phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano; or when the 6-12 membered ring is fused at an —NR$^8$—, the $R^8$ forms a single bond with an adjacent ring atom; each $R^{12}$ is independently hydrogen, halo, $C_{1-6}$alkyl, halo-$C_{1-6}$alkyl, or aryl; and all other groups are as defined in Formula (I) in the Summary of the Invention or as defined in some or any embodiments described herein.

In some or any embodiments, the Compound is according to Formula (I), (Ia), (Ib), I-P, (Ie), (If), (Ij), or (Ik) where $X^1$ and $X^2$ together with the —NC(O)— to which they are attached form a 5 or 6-membered ring where $X^1$, $X^2$, and the one or two additional ring atoms are independently selected from —C(O)—, —O—, —S—, —NR$^8$—, and —C(R$^4$)(R$^{4a}$)— provided that only one is selected from —O—, —S—, and —NR$^8$—; wherein when the 5 or 6-membered ring comprises two adjacent —C(R$^4$)(R$^{4a}$)— or comprises a —C(R$^4$)(R$^{4a}$)— which is adjacent to —NR$^8$—, then the 5 or 6-membered ring is optionally fused at the two adjacent atoms to form a saturated or unsaturated 6-12 membered bicyclic ring; where the 1, 2, 3, 4, 5, or 6 additional ring atoms are independently —CR$^{12}$═ or —C(R$^{12}$)$_2$—;

each R$^4$ and R$^{4a}$ is independently H; C$_{1-6}$alkyl; or when the 6-12 membered ring is fused at a —C(R$^4$)(R$^{4a}$)—, one or both of the R$^4$ and R$^{4a}$ on the —C(R$^4$)(R$^{4a}$)— form a single or double bond with an adjacent ring atom;

R$^8$ is hydrogen; C$_{1-6}$alkyl; phenyl optionally substituted with 1, 2, or 3 groups independently selected from halo, C$_{1-6}$alkyl, halo-C$_{1-6}$alkyl, hydroxy, C$_{1-6}$alkoxy, halo-C$_{1-6}$alkoxy, nitro, and cyano; or when the 6-12 membered ring is fused at an —NR$^8$—, the R$^8$ forms a single bond with an adjacent ring atom;

each R$^{12}$ is independently hydrogen, halo, C$_{1-6}$alkyl, halo-C$_{1-6}$alkyl, or aryl; and all other groups are as defined in Formula (I) in the Summary of the Invention or as defined in some or any embodiments described herein.

In some or any embodiments, provided is a Compound of Formula (I), (Ia), (Ib), I-P, (Ie), (If), (Ij), or (Ik) where X$^1$ is R$^3$ and X$^2$ is R$^9$; or X$^1$ and X$^2$ together with the —NC(O)— to which they are attached form a 5 or 6-membered ring where X$^1$, X$^2$, and the one or two additional ring atoms are independently selected from —C(O)—, —O—, —S—, —NR$^8$—, and —C(R$^4$)(R$^{4a}$)— provided that only one is selected from —O—, —S—, and —NR$^8$—; and where the 5 or 6-membered ring is optionally fused at two adjacent carbon atoms, or is optionally fused at one carbon atom and one nitrogen atom which are adjacent to each other, to a form a saturated or unsaturated 6-12 membered bicyclic ring; where the 1, 2, 3, 4, 5, or 6 additional bicyclic ring atoms are independently —CR$^{12}$═ or —C(R$^{12}$)$_2$—; where all other groups are as defined in Formula (I) in the Summary of the Invention or as defined in some or any embodiments described herein. In some or any embodiments, provided is a Compound of Formula (I), (Ia), (Ib), I-P, (Ie), (If), (Ij), or (Ik) where X$^1$ is R$^3$ and X$^2$ is R$^9$; or X$^1$ and X$^2$ together with the —NC(O)— to which they are attached form a 5 or 6-membered ring where X$^1$, X$^2$, and the one or two additional ring atoms are independently selected from —C(O)—, —O—, —S—, —NR$^8$—, and —C(R$^4$)(R$^{4a}$)— provided that only one is selected from —O—, —S—, and —NR$^8$— and provided that one and only one is —C(O)— and is attached to the nitrogen of the; and where the 5 or 6-membered ring is optionally fused at two adjacent carbon atoms, or is optionally fused at one carbon atom and one nitrogen atom which are adjacent to each other, to a form a saturated or unsaturated 6-12 membered bicyclic ring; where the 1, 2, 3, 4, 5, or 6 additional bicyclic ring atoms are independently —CR$^{12}$═ or —C(R$^{12}$)$_2$—; where all other groups are as defined in Formula (I) in the Summary of the Invention or as defined in some or any embodiments described herein. In some or any embodiments, provided is a Compound of Formula (I), (Ia), (Ib), I-P, (Ie), (If), (Ij), or (Ik) where X$^1$ is R$^3$ and X$^2$ is R$^9$; or X$^1$ and X$^2$ together with the —NC(O)— to which they are attached form a 5 or 6-membered ring where X$^1$, X$^2$, and the one or two additional ring atoms are independently selected from —C(O)—, —O—, —S—, —NR$^8$—, and —C(R$^4$)(R$^{4a}$)— provided that only one is selected from —O—, —S—, and —NR$^8$— and provided that X$^1$ and only X$^1$ is —C(O)—; and where the 5 or 6-membered ring is optionally fused at two adjacent carbon atoms, or is optionally fused at one carbon atom and one nitrogen atom which are adjacent to each other, to a form a saturated or unsaturated 6-12 membered bicyclic ring; where the 1, 2, 3, 4, 5, or 6 additional bicyclic ring atoms are independently —CR$^{12}$═ or —C(R$^{12}$)$_2$—; where all other groups are as defined in Formula (I) in the Summary of the Invention or as defined in some or any embodiments described herein.

In some or any embodiments, the Compound is according to Formula (I), (Ia), (Ib), I-P, (Ie), (If), (Ij), or (Ik) where X$^1$ and X$^2$ together with the —NC(O)— to which they are attached form a 5 or 6-membered ring where X$^1$, X$^2$, and the one or two additional ring atoms are independently selected from —C(O)—, —O—, —S—, —NR$^8$—, and —C(R$^4$)(R$^{4a}$)— provided that only one is selected from —O—, —S—, and —NR$^8$—; each R$^4$ and R$^{4a}$ is independently H; C$_{1-6}$alkyl; R$^8$ is hydrogen, C$_{1-6}$alkyl, or phenyl optionally substituted with 1, 2, or 3 groups independently selected from halo, C$_{1-6}$alkyl, halo-C$_{1-6}$alkyl, hydroxy, C$_{1-6}$alkoxy, halo-C$_{1-6}$alkoxy, nitro, and cyano; and all other groups are as defined in Formula (I) in the Summary of the Invention or as defined in some or any embodiments described herein.

In some or any embodiments, provided is a Compound according to Formula (I), (Ia), (Ib), I-P, (Ie), (If), (Ij), or (Ik) where one and only one of X$^1$, X$^2$, and the one or two additional ring atoms is —C(O)—; and all other groups are as defined in Formula (I) in the Summary of the Invention or as defined in some or any embodiments described herein.

In some or any embodiments, provided is a Compound according to Formula (I), (Ia), (Ib), I-P, (Ie), (If), (Ij), or (Ik) where X$^1$ and only X$^1$ is —C(O)—; and all other groups are as defined in Formula (I) in the Summary of the Invention or as defined in some or any embodiments described herein.

In some or any embodiments, the Compound is according to Formula (I), (Ia), (Ib), I-P, (Ie), (If), (Ij), or (Ik) where X$^1$ and X$^2$ together with the —NC(O)— to which they are attached form a 5 or 6-membered ring where X$^1$, X$^2$, and the one or two additional ring atoms are independently selected from —C(O)—, —O—, —S—, —NR$^8$—, and —C(R$^4$)(R$^{4a}$)— provided that only one is selected from —O—, —S—, and —NR$^8$—; wherein the 5 or 6-membered ring comprises two adjacent —C(R$^4$)(R$^{4a}$)— or comprises a —C(R$^4$)(R$^{4a}$)— which is adjacent to —NR$^8$—, and the 5 or 6-membered ring is fused at the two adjacent atoms to form a saturated or unsaturated 6-12 membered bicyclic ring; where the 1, 2, 3, 4, 5, or 6 additional bicyclic ring atoms are independently —CR$^{12}$═ or —C(R$^{12}$)$_2$—;

each R$^4$ and R$^{4a}$ is independently H; C$_{1-6}$alkyl; or when the 6-12 membered ring is fused at a —C(R$^4$)(R$^{4a}$)—, one or both of the R$^4$ and R$^{4a}$ on the —C(R$^4$)(R$^{4a}$)— form a single or double bond with an adjacent ring atom;

R$^8$ is hydrogen; C$_{1-6}$alkyl; phenyl optionally substituted with 1, 2, or 3 groups independently selected from halo, C$_{1-6}$alkyl, halo-C$_{1-6}$alkyl, hydroxy, C$_{1-6}$alkoxy, halo-C$_{1-6}$alkoxy, nitro, and cyano; or when the 6-12 membered ring is fused at an —NR$^8$—, the R$^8$ forms a single bond with an adjacent ring atom;

each R$^{12}$ is independently hydrogen, halo, C$_{1-6}$alkyl, halo-C$_{1-6}$alkyl, or aryl; and all other groups are as defined in Formula (I) in the Summary of the Invention or as defined in some or any embodiments described herein.

In some or any embodiments, the Compound is according to Formula (I), (Ia), (Ib), I-P, (Ie), (If), (Ij), or (Ik) where X$^1$ and X$^2$ together with the —NC(O)— to which they are attached form

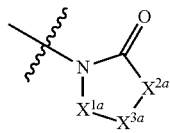

and $X^{1a}$ is —O—, $X^{2a}$ is —C(R$^4$)(R$^{4a}$)—, and $X^{3a}$ is —C(R$^4$)(R$^{4a}$)—; R$^4$ and R$^{4a}$ are independently H or alkyl; and all other groups are as defined in Formula (I) in the Summary of the Invention or as defined in some or any embodiments described herein. In some or any embodiments, the Compound is according to Formula (I), (Ia), (Ib), (Ic), (Ie), (If), (Ij), or (Ik) where $X^{1a}$ is —C(O)—; $X^{2a}$ is —C(R$^4$)(R$^{4a}$)—; $X^{3a}$ is —C(R$^4$)(R$^{4a}$)—S—, —C(R$^4$)(R$^{4a}$)—O—, —C(R$^4$)(R$^{4a}$)—NH—, or —C(R$^4$)(R$^{4a}$)—N(CH$_3$)—; R$^4$ and R$^{4a}$ are independently H or alkyl; and all other groups are as defined in Formula (I) in the Summary of the Invention or as defined in some or any embodiments described herein. In some or any embodiments, the Compound is according to Formula (I), (Ia), (Ib), I-P, (Ie), (If), (Ij), or (Ik) where $X^{1a}$ is —C(O)—; $X^{2a}$ is —C(R$^4$)(R$^{4a}$)—; $X^{3a}$ is —C(R$^4$)(R$^{4a}$)— or —C(R$^4$)(R$^{4a}$)—C(R$^4$)(R$^{4a}$)—; R$^4$ and R$^{4a}$ are independently H or alkyl; and all other groups are as defined in Formula (I) in the Summary of the Invention or as defined in some or any embodiments described herein. In some or any embodiments, the Compound is according to Formula (I), (Ia), (Ib), I-P, (Ie), (If), (Ij), or (Ik) where $X^{1a}$ is —CH$_2$— or —C(O)—; $X^{2a}$ is —C(R$^4$)(R$^{4a}$)—; $X^{3a}$ is —C(R$^4$)(R$^{4a}$)—; and where the

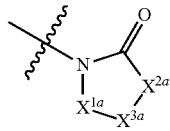

ring is optionally fused at $X^{2a}$ and at the adjacent atom in $X^{3a}$ to form a saturated or unsaturated, 6-12 membered bicyclic ring when 1) $X^{2a}$ is —NR$^8$— and $X^{3a}$ is —C(R$^4$)(R$^{4a}$)— or —C(R$^4$)(R$^{4a}$)—C(R$^4$)(R$^{4a}$)— or 2) $X^{2a}$ is —C(R$^4$)(R$^{4a}$)— and $X^{3a}$ is —C(R$^4$)(R$^{4a}$)—, —NR$^8$—, —C(R$^4$)(R$^{4a}$)—C(R$^4$)(R$^{4a}$)—, —C(R$^4$)(R$^{4a}$)—NR$^8$—, or —NR—C(R$^4$)(R$^{4a}$)—; and where the three or four additional ring atoms are independently —CR$^{12}$= or —C(R$^{12}$)$_2$—; each R$^4$ and R$^{4a}$ is independently H; C$_{1-6}$alkyl; or absent when the 6-12 membered bicyclic ring is fused at a —C(R$^4$)(R$^{4a}$)—; R$^8$ is hydrogen, C$_{1-6}$alkyl, or phenyl optionally substituted with 1, 2, or 3 groups independently selected from halo, C$_{1-6}$alkyl, halo-C$_{1-6}$alkyl, hydroxy, C$_{1-6}$alkoxy, halo-C$_{1-6}$alkoxy, nitro, and cyano; or R$^8$ is absent when the 6-12 membered bicyclic ring is fused at an —NR$^8$— atom; each R$^{12}$ is independently hydrogen, halo, C$_{1-6}$alkyl, halo-C$_{1-6}$alkyl, or aryl; and all other groups are as defined in Formula (I) in the Summary of the Invention or as defined in some or any embodiments described herein. In some or any embodiments, the Compound is according to Formula (I), (Ia), (Ib), I-P, (Ie), (If), (Ij), or (Ik) where $X^{1a}$ is —C(O)—, $X^{2a}$ is —S— or —NR$^8$—, and $X^{3a}$ is —C(R$^4$)(R$^{4a}$)—; R$^4$ and R$^{4a}$ are independently H or alkyl; and all other groups are as defined in Formula (I) in the Summary of the Invention or as defined in some or any embodiments described herein. In some or any embodiments for the Compound according to Formula (I), (Ia), (Ib), I-P, (Ie), (If), (Ij), or (Ik), the ring

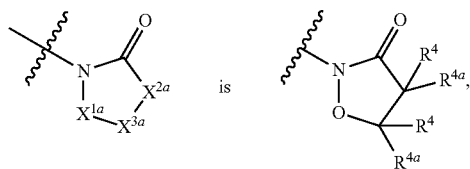

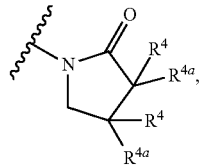

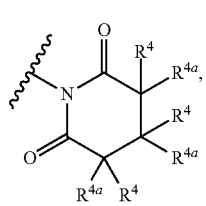

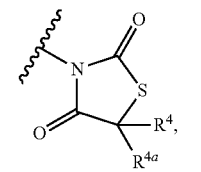

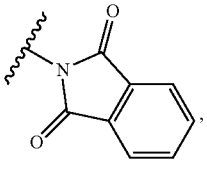

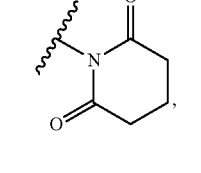

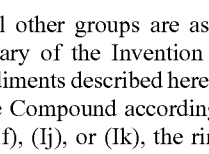

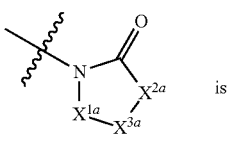

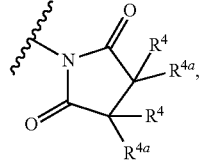

and all other groups are as defined in Formula (I) in the Summary of the Invention or as defined in some or any embodiments described herein. In some or any embodiments for the Compound according to Formula (I), (Ia), (Ib), I-P, (Ie), (If), (Ij), or (Ik), the ring -continued

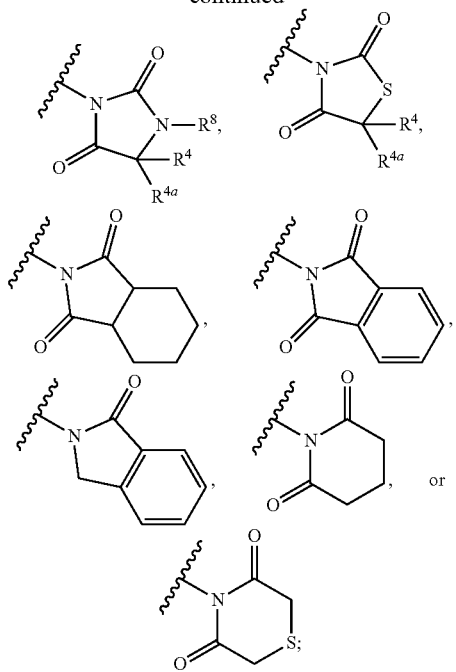

and all other groups are as defined in Formula (I) in the Summary of the Invention or as defined in some or any embodiments described herein. In some or any embodiments for the Compound according to Formula (I), (Ia), (Ib) I-P, (Ie), (If), (Ij), or (Ik), the ring

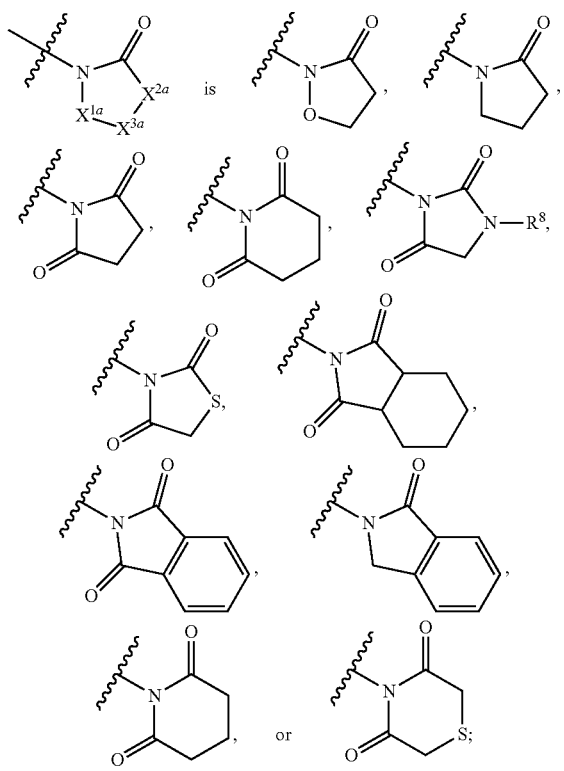

and all other groups are as defined in Formula (I) in the Summary of the Invention or as defined in some or any embodiments described herein. In some or any embodiments for the Compound according to Formula (I), (Ia), (Ib), I-P, (Ie), (If), (Ij), or (Ik), the ring

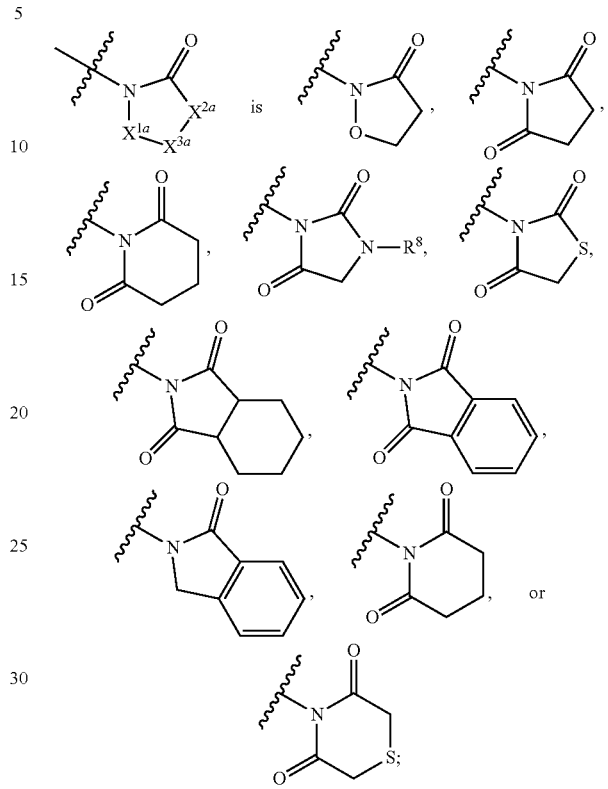

and all other groups are as defined in Formula (I) in the Summary of the Invention or as defined in some or any embodiments described herein. In some or any embodiments for the Compound according to Formula (I), (Ia), (Ib), I-P, (Ie), (If), (Ij), or (Ik), the ring

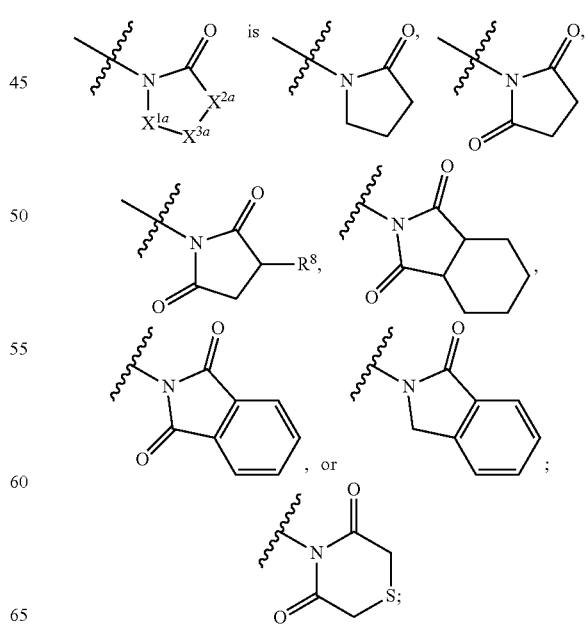

and all other groups are as defined in Formula (I) in the Summary of the Invention or as defined in some or any embodiments described herein. In some or any embodiments for the Compound according to Formula (I), (Ia), (Ib), I-P, (Ie), (If), (Ij), or (Ik), the ring

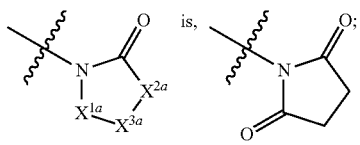

and all other groups are as defined in Formula (I) in the Summary of the Invention or as defined in some or any embodiments described herein.

In some or any embodiments, the Compound of Formula (I), (Ia), (Ib), I-P, (Ie), (If), (Ij), or (Ik) is that where $R^3$ is —C(O)$C_{1-6}$alkyl and $R^9$ is $C_{1-6}$alkyl; or $R^3$ is —C(O)$C_{1-6}$alkyl and $R^9$ is phenyl; or $R^3$ is —C(O)O$C_{1-6}$alkyl and $R^9$ is phenyl; and all other groups are as defined in Formula (I) in the Summary of the Invention or as defined in some or any embodiments described herein.

In some or any embodiments for the Compound according to Formula (I), (Ia), (Ib), (Id), (Ig), (Ih), or (Ii), $R^1$ is —OS(O)$_2R^5$, —OC(O)$R^6$, —NR$^7$C(O)$R^{7a}$, —OC(O)NR$^{10}R^{10a}$, —NR$^{11}R^{11a}$, —NR$^{13}S(O)_2R^{13a}$, or —NR$^{14}C(O)NR^{14a}R^{14b}$; and all other groups are as defined in Formula (I) in the Summary of the Invention or as defined in some or any embodiments described herein. In some or any embodiments for the Compound according to Formula (I), (Ia), (Ib), (Id), (Ig), (Ih), or (Ii), $R^1$ is —OS(O)$_2R^5$, —OC(O)$R^6$, —NR$^7$C(O)$R^{7a}$, —OC(O)NR$^{10}R^{10a}$, —NR$^{11}R^{11a}$, —NR$^{13}S(O)_2R^{13a}$, or —NR$^{14}C(O)NR^{14a}R^{14b}$; $R^5$ is $C_{1-6}$alkyl or aryl optionally substituted with 1, 2, 3, or 4 $R^{5a}$; $R^6$ is aryl optionally substituted with 1, 2, 3, or 4 $R^{6a}$; or heterocyclic optionally substituted with 1, 2, 3, or 4 $R^{6a}$; $R^{7a}$ is aryl optionally substituted with 1, 2, 3, or 4 $R^{7b}$; or heterocyclic optionally substituted with 1, 2, 3, or 4 $R^{7b}$; $R^{10a}$ is aryl optionally substituted with 1, 2, 3, or 4 $R^{10b}$; or heterocyclic optionally substituted with 1, 2, 3, or 4 $R^{10b}$; $R^{11a}$ is aryl optionally substituted with 1, 2, 3, or 4 $R^{11b}$; or heterocyclic optionally substituted with 1, 2, 3, or 4 $R^{11b}$; $R^{13a}$ is aryl optionally substituted with 1, 2, 3, or 4 $R^{13b}$; or heterocyclic optionally substituted with 1, 2, 3, or 4 $R^{13b}$; and $R^{14b}$ is aryl optionally substituted with 1, 2, 3, or 4 $R^{14c}$; or heterocyclic optionally substituted with 1, 2, 3, or 4 $R^{14c}$; and all other groups are as defined in Formula (I) in the Summary of the Invention or as defined in some or any embodiments described herein.

In some or any embodiments for the Compound according to Formula (I), (Ia), (Ib), (Ic), (Id), (Ig), (Ih), or (Ii), $R^1$ is —OC(O)$R^6$ or —NR$^7$C(O)$R^{7a}$. and all other groups are as defined in Formula (I) in the Summary of the Invention or as defined in some or any embodiments described herein. In some or any embodiments for the Compound according to Formula (I), (Ia), (Ib), (Ic), (Id), (Ig), (Ih), or (Ii), $R^1$ is —OC(O)$R^6$ or —NR C(O)$R^{7a}$; $R^6$ is aryl optionally substituted with 1, 2, 3, or 4 $R^{6a}$, or heterocyclic optionally substituted with 1, 2, 3, or 4 $R^{6a}$; $R^{7a}$ is aryl optionally substituted with 1, 2, 3, or 4 $R^{7b}$, or heterocyclic optionally substituted with 1, 2, 3, or 4 $R^{7b}$; and all other groups are as defined in Formula (I) in the Summary of the Invention or as defined in some or any embodiments described herein.

In some or any embodiments for the Compound according to Formula (I), (Ia), (Ib), (Ic), (Id), (Ie), (If), (Ig), (Ih), (Ii), (Ij), or (Ik), $R^7$, $R^{10}$, $R^{11}$, $R^{13}$, $R^{14}$, and $R^{14a}$ are hydrogen; and all other groups are as defined in Formula (I) in the Summary of the Invention or as defined in some or any embodiments described herein.

In some or any embodiments, provided is a Compound according to Formula (I), (Ia), (Ib), (Ic), (Id), (Ie), (If), (Ig), (Ih), (Ii), (Ij), or (Ik) where the aryl in $R^1$ is phenyl, naphthyl, tetrahydronaphthyl, fluorenyl, or indanyl; each of which is optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, $C_{1-6}$alkylthio, $C_{1-6}$alkylsulfonyl, and amino; or the heterocyclic in $R^1$ is benzo-1,4-dioxanyl, benzodioxolyl, indolinyl, 2-oxo-indolinyl, pyrrolidinyl, piperidinyl, 2,3-dihydrobenzofuranyl, or decahydroquinolinyl; each of which is optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, and phenyl; and all other groups are as defined in Formula (I) in the Summary of the Invention or as defined in some or any embodiments described herein. In some or any embodiments, provided is a Compound according to Formula (I), (Ia), (Ib), (Ic), (Id), (Ie), (If), (Ig), (Ih), (Ii), (Ij), or (Ik) where the aryl in $R^1$ is phenyl, naphthyl, tetrahydronaphthyl, fluorenyl, or indanyl; each of which is optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, $C_{1-6}$alkylthio, $C_{1-6}$alkylsulfonyl, and amino; and all other groups are as defined in Formula (I) in the Summary of the Invention or as defined in some or any embodiments described herein. In some or any embodiments, provided is a Compound according to Formula (I), (Ia), (Ib), (Ic), (Id), (Ie), (If), (Ig), (Ih), (Ii), (Ij), or (Ik) where the heterocyclic in $R^1$ is benzo-1,4-dioxanyl, benzodioxolyl, indolinyl, 2-oxo-indolinyl, pyrrolidinyl, piperidinyl, 2,3-dihydrobenzofuranyl, or decahydroquinolinyl; each of which is optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, and phenyl; and all other groups are as defined in Formula (I) in the Summary of the Invention or as defined in some or any embodiments described herein.

In some or any embodiments of Formula (I), (Ia), (Ib), I-P, (Ic), (Id), (Ig), (Ih), and (Ii), $R^1$ is not hydrogen. In some or any embodiments of Formula (I), (Ia), (Ib), I-P, (Ic), (Id), (Ig), (Ih), and (Ii), $R^1$ is not hydroxy. In some or any embodiments of Formula (I), (Ia), (Ib), I-P, (Ic), (Id), (Ig), (Ih), and (Ii), $R^1$ is not —OS(O)$_3^-$. In some or any embodiments of Formula (I), (Ia), (Ib), I-P, (Ic), (Id), (Ig), (Ih), and (Ii), $R^1$ is not —NH$_3^+$. In some or any embodiments of Formula (I), (Ia), (Ib), I-P, (Ic), (Id), (Ig), (Ih), and (Ii), $R^1$ is not hydrogen, hydroxy, —OS(O)$_3^-$, or —NH$_3^+$.

In some or any embodiments, provided is a Compound of Formula (I), (Ia), (Ib), (Id), (Ie), (If), (Ig), (Ih), (Ii), (Ij), or (Ik) where the $R^5$, $R^6$, $R^{7a}$, $R^{10a}$, $R^{10a}$, $R^{13a}$, and $R^{14b}$ rings are optionally substituted with 1, 2, or 3 groups as defined herein; and all other groups are as defined in Formula (I) in the Summary of the Invention or as defined in some or any embodiments described herein. In some or any embodiments, provided is a Compound of Formula (I), (Ia), (Ib), (Id), (Ie), (If), (Ig), (Ih), (Ii), (Ij), or (Ik) where the $R^5$, $R^6$, $R^{7a}$, $R^{10a}$, $R^{11a}$, $R^{13a}$, and $R^{14b}$ rings are optionally substituted with 1 or 2 groups as defined herein; and all other groups are as defined in Formula (I) in the Summary of the Invention or as defined in some or any embodiments described herein. In some or any embodiments, provided is a Compound of Formula (I), (Ia), (Ib), (Id), (Ie), (If), (Ig), (Ih), (Ii), (Ij), or (Ik) where the $R^5$, $R^6$, $R^{7a}$, $R^{10a}$, $R^{11a}$, $R^{13a}$, and $R^{14b}$ rings are optionally substituted with 2 groups as defined herein; and all other groups are as defined in Formula (I) in the Summary of the Invention or as defined in some or any embodiments described herein. In some or any embodiments, provided is a Compound of Formula (I), (Ia), (Ib), (Id), (Ie), (If), (Ig), (Ih), (Ii), (Ij), or (Ik) where the $R^5$, $R^6$, $R^{7a}$, $R^{10a}$, $R^{11a}$, $R^{13a}$, and $R^{14b}$ rings are optionally substituted with 1 group as defined herein; and all other groups are as defined in Formula (I) in the Summary of the Invention or as defined in some or any embodiments described herein.

In certain embodiments, provided herein is a compound selected from any of Formulas 1-122; or a pharmaceutically acceptable salt, hydrate, solvate, stereoisomer, tautomer, or mixture thereof:

(1)
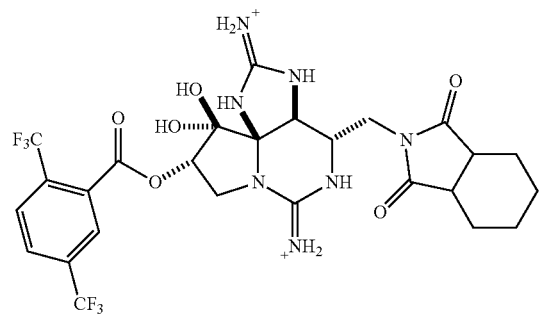

(2)
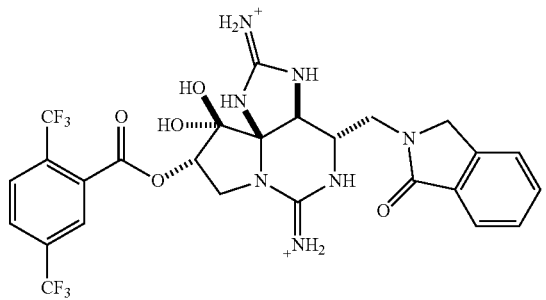

(3)
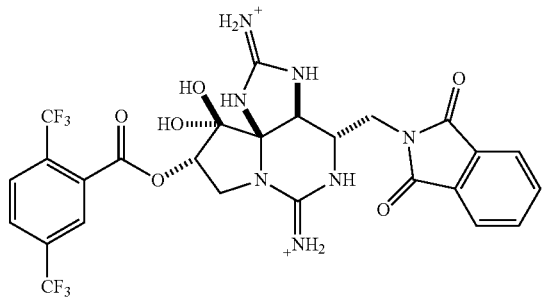

-continued (4)
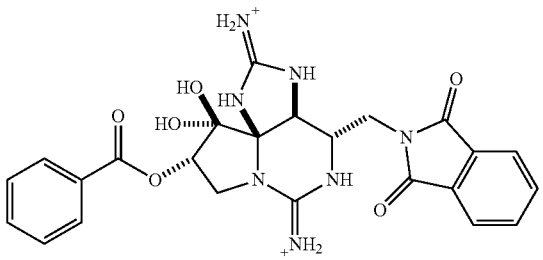

(5)
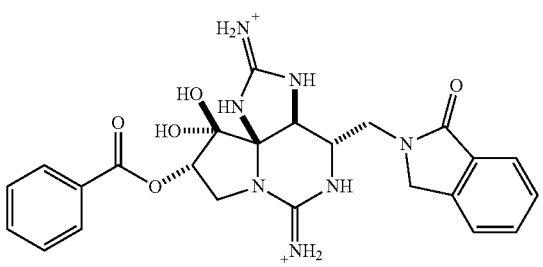

(6)
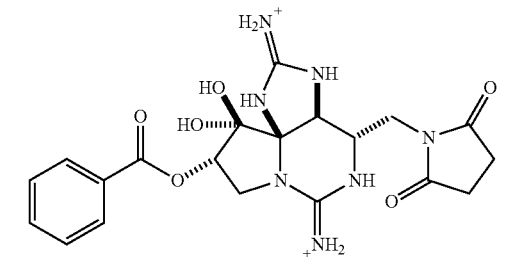

(7)
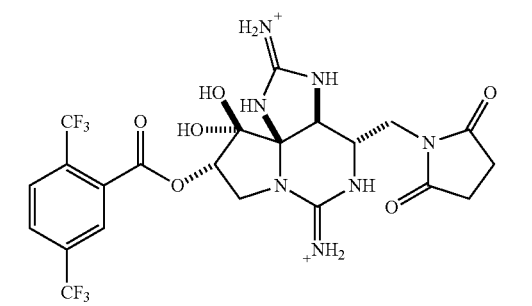

(8)
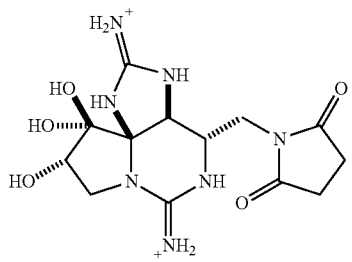

(9)
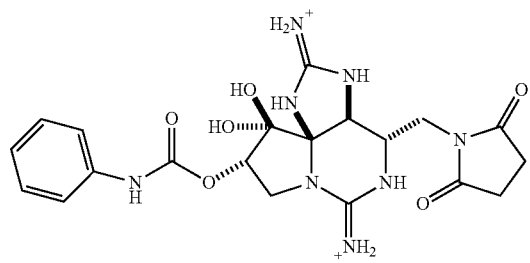
(10)
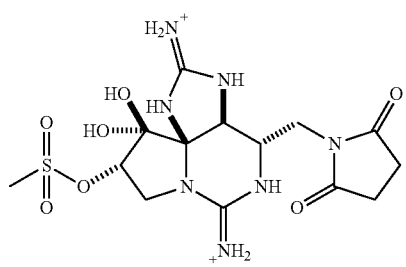
(11)
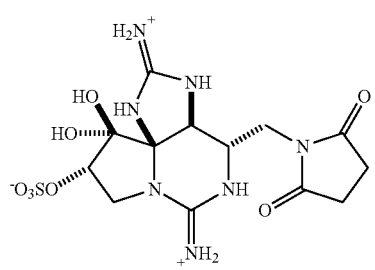
(12)
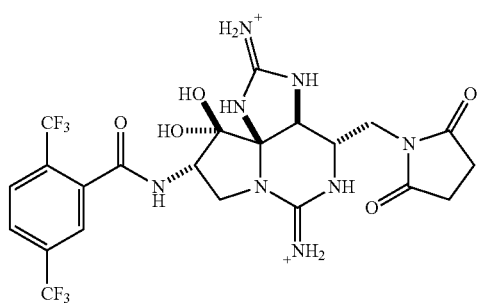
(13)
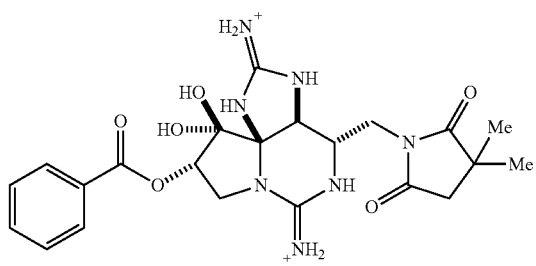
(14)
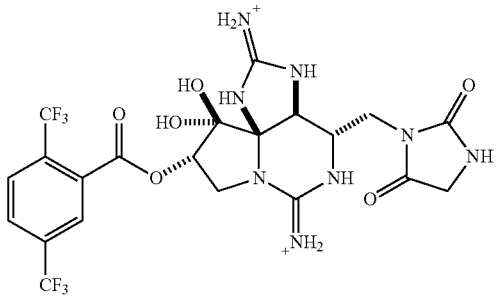
(15)
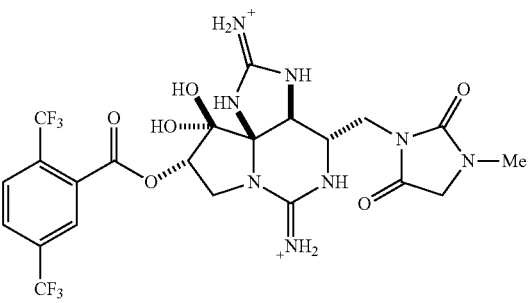
(16)
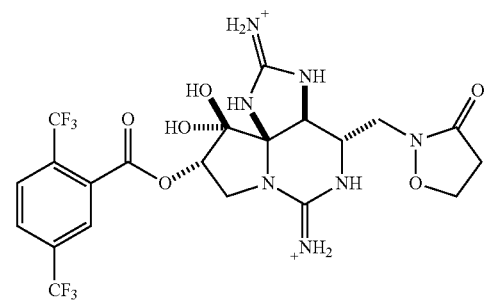
(17)
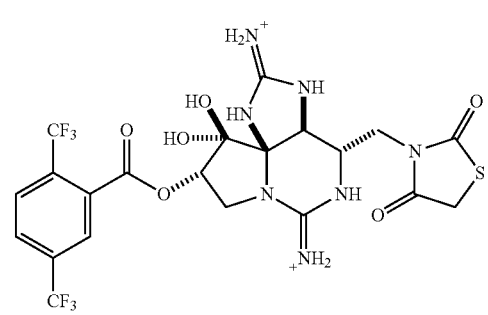
(18)
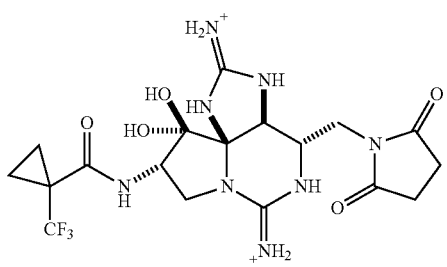

(19) 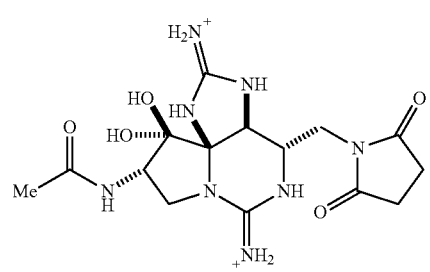
(20) 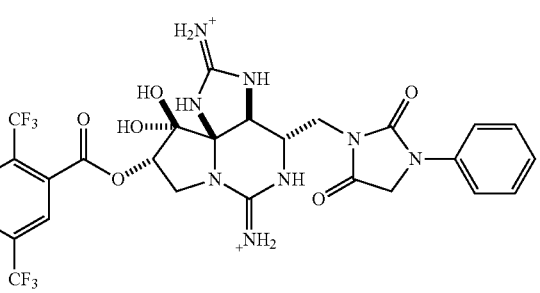
(21) 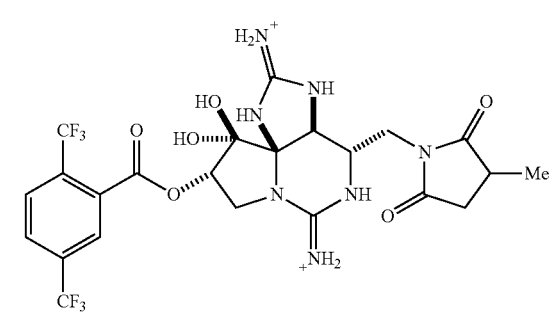
(22) 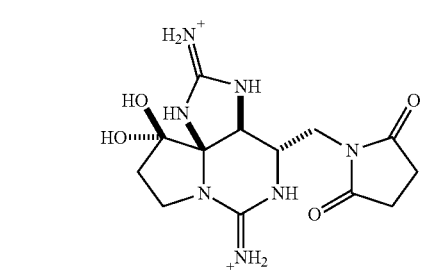
(23) 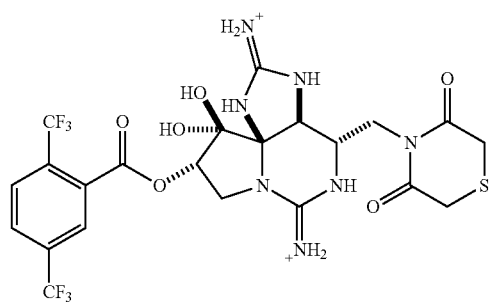
(24) 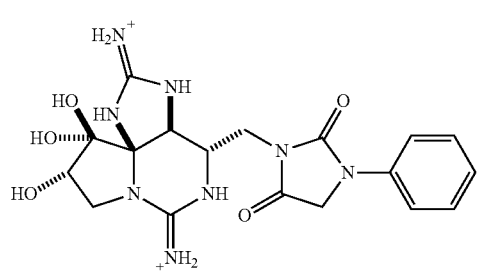
(25) 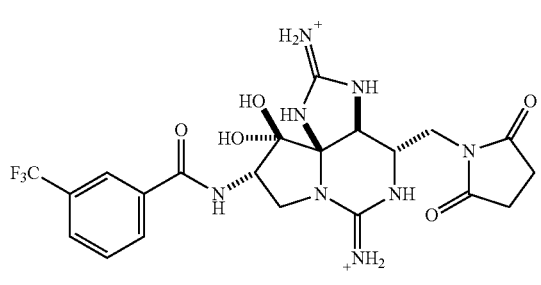
(26) 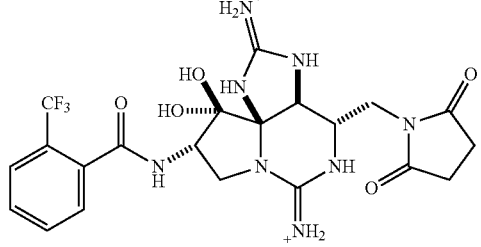
(27) 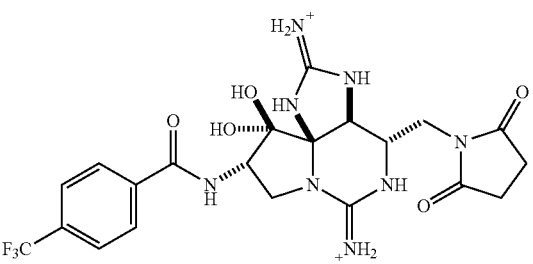
(28) 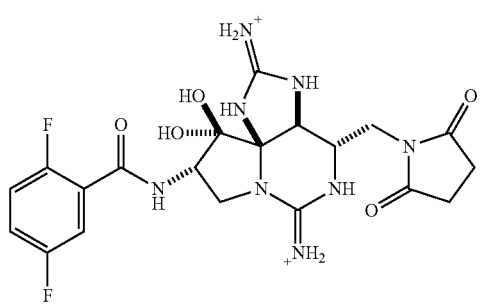

-continued
(29)
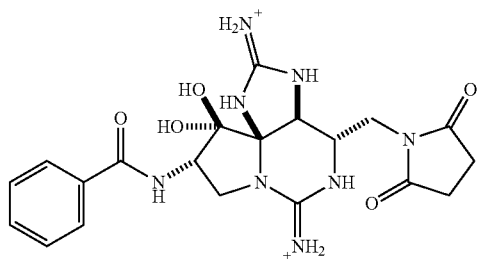
(30)
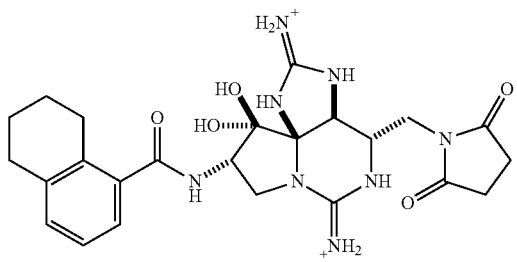
(31)
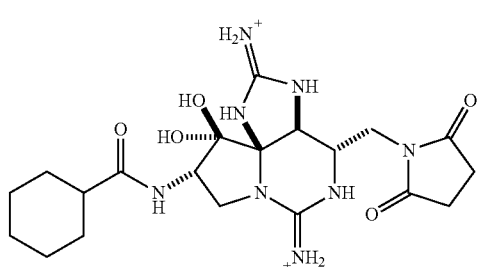
(32)
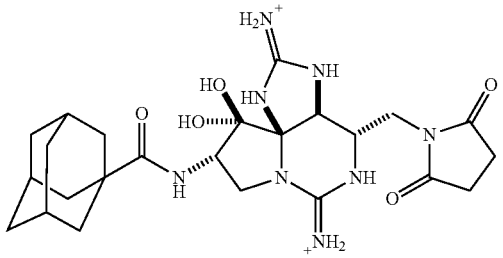
(33)
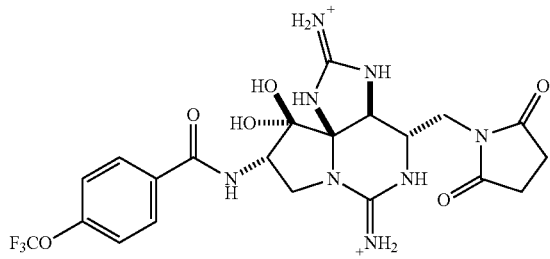
-continued
(34)
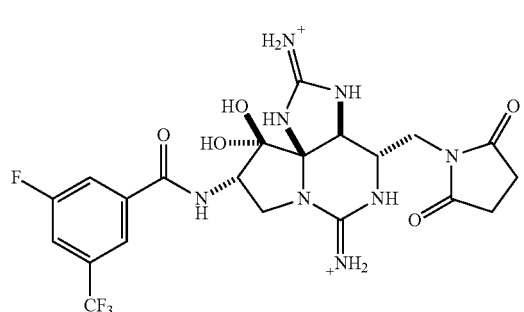
(35)
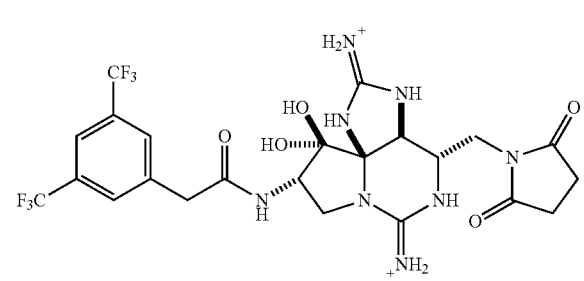
(36)
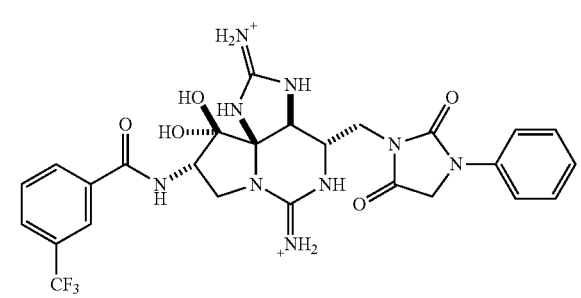
(37)
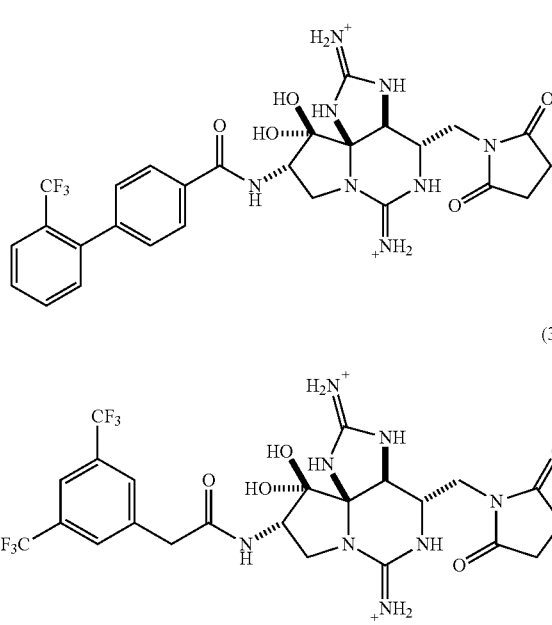
(38)
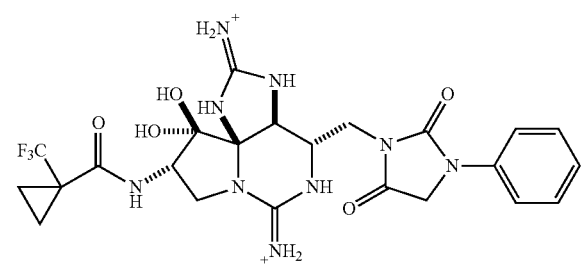

(39) 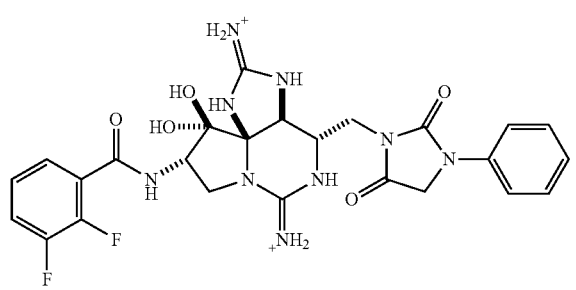
(40) 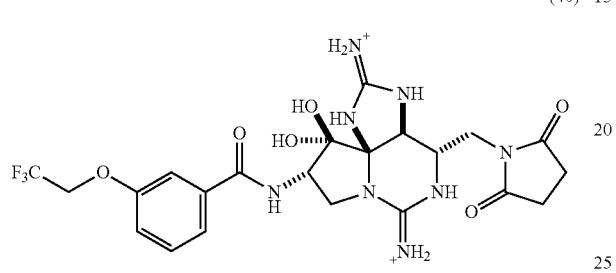
(41) 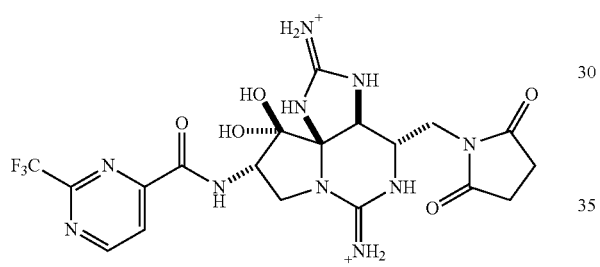
(42) 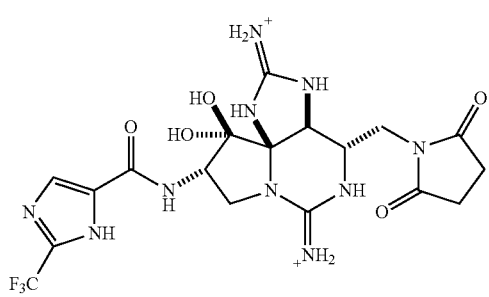
(43) 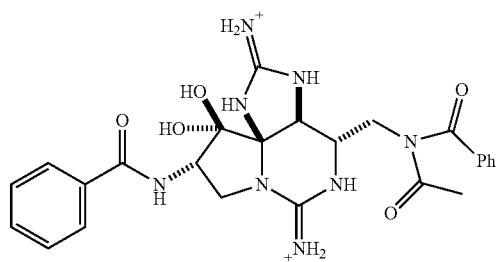
(44) 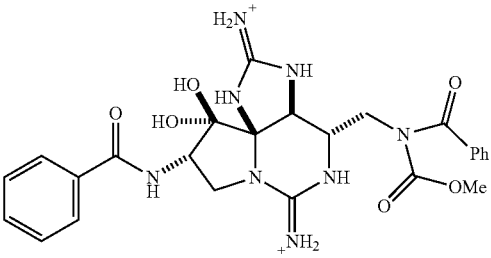
(45) 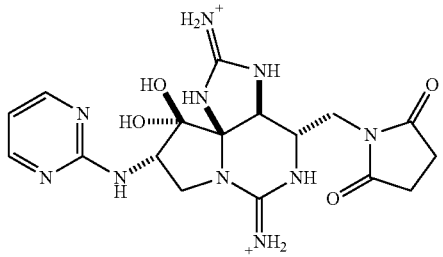
(46) 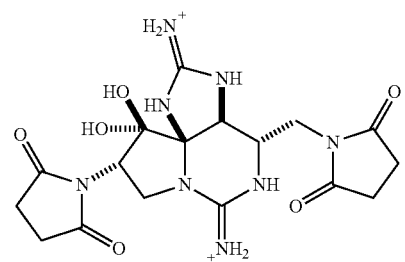
(47) 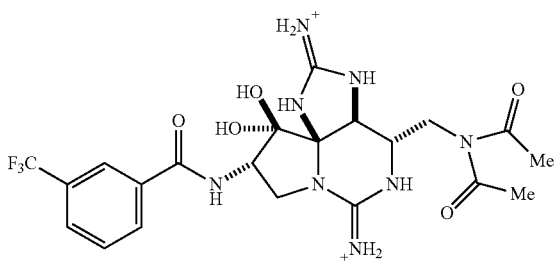
(48) 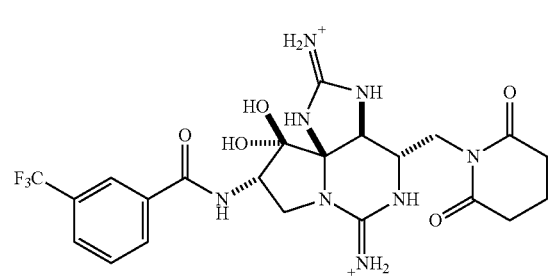

-continued
(49)
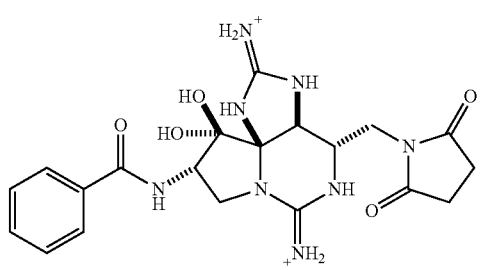
(50)
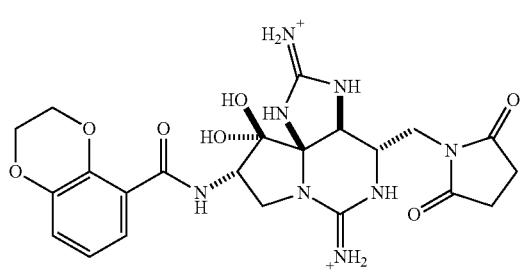
(51)
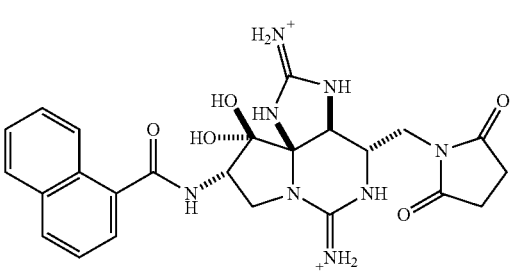
(52)
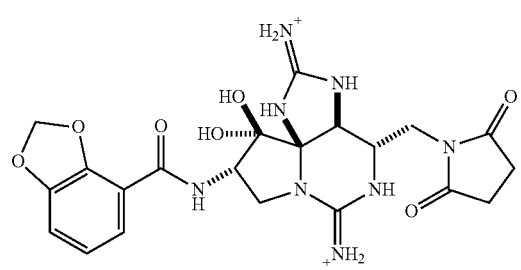
(53)
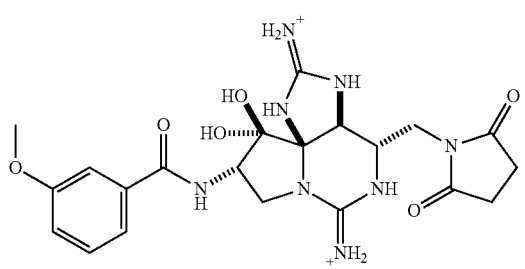
-continued
(54)
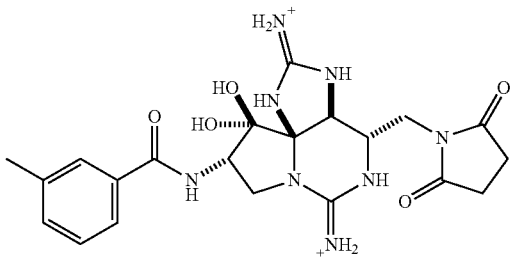
(55)
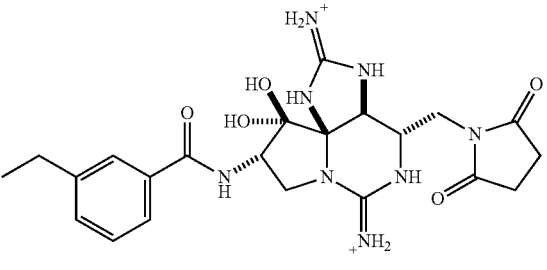
(56)
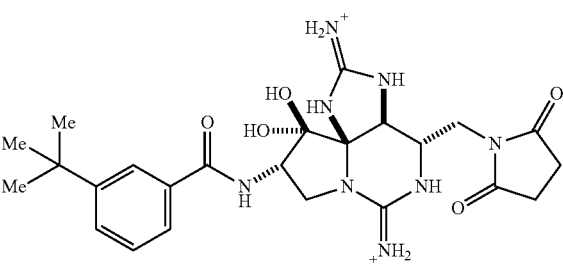
(57)
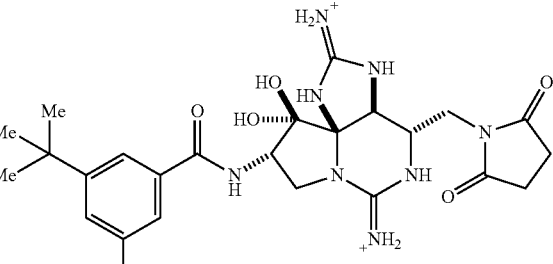
(58)
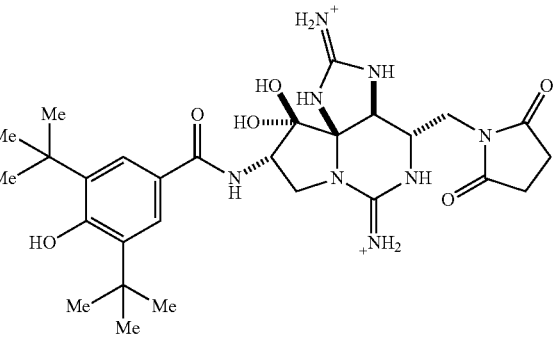

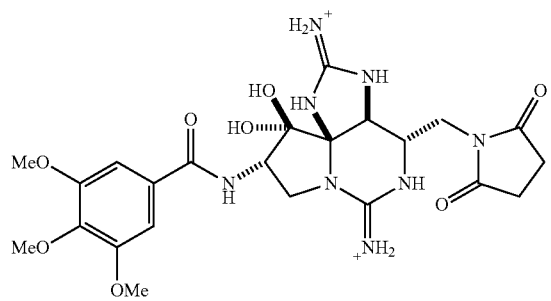
(59)
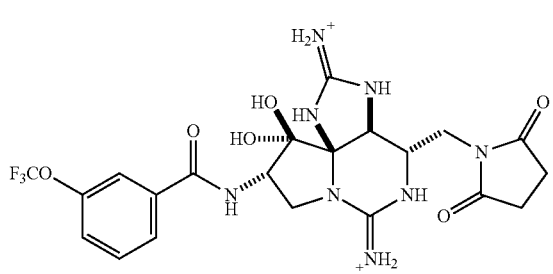
(60)
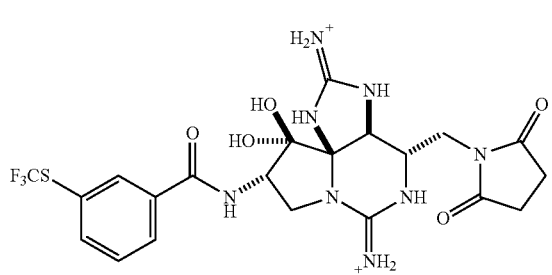
(61)
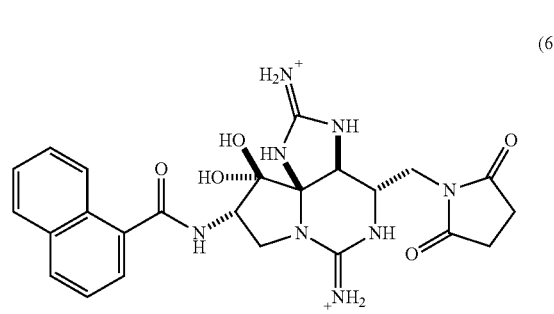
(62)
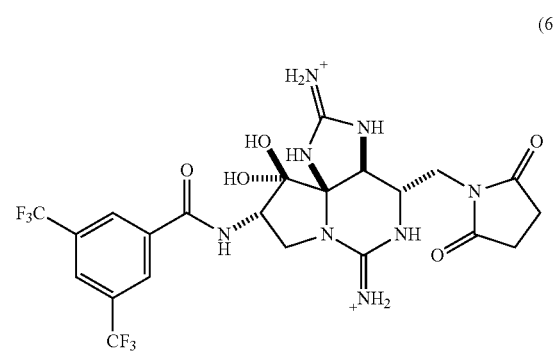
(63)
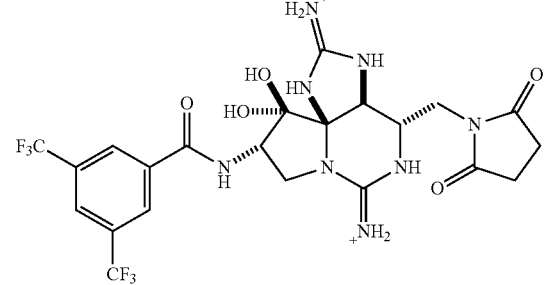
(64)
(65)
(66)
(67)
(68)

(69)
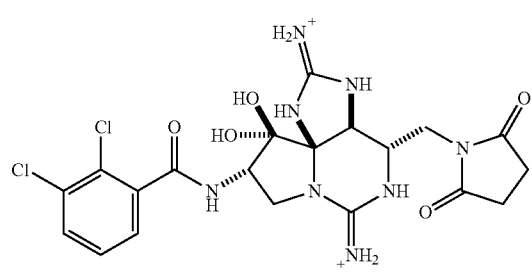
(70)
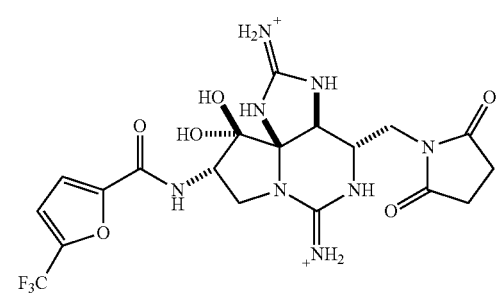
(71)
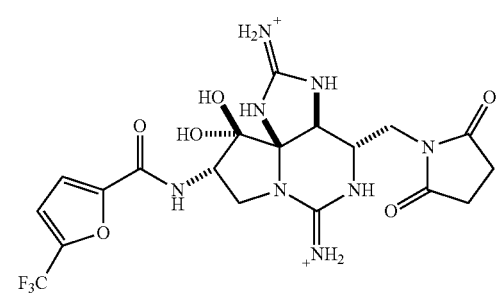
(72)
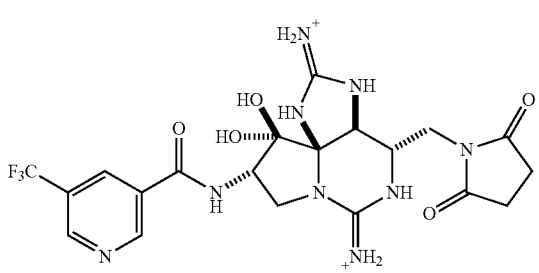
(73)
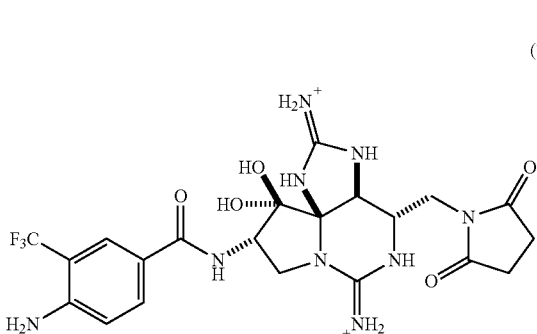
(74)
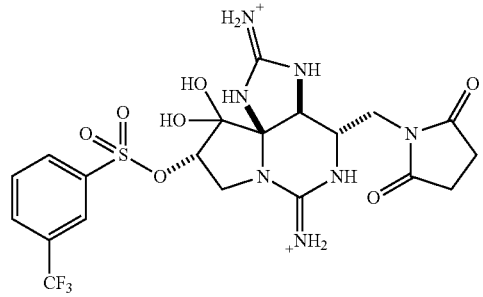
(75)
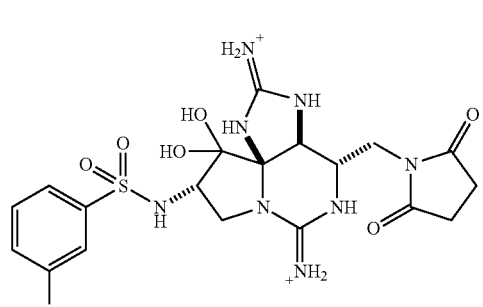
(76)
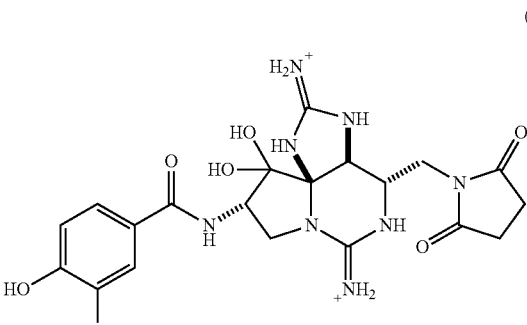
(77)
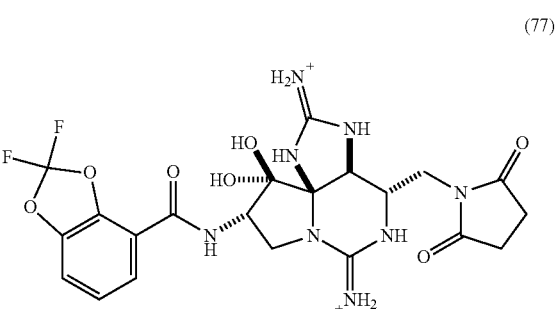
(78)
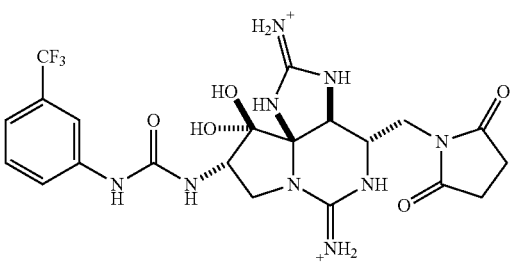

-continued
(79)
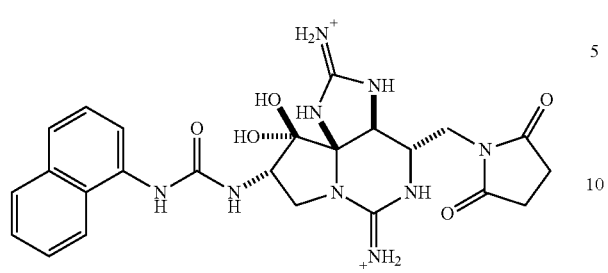
(80)
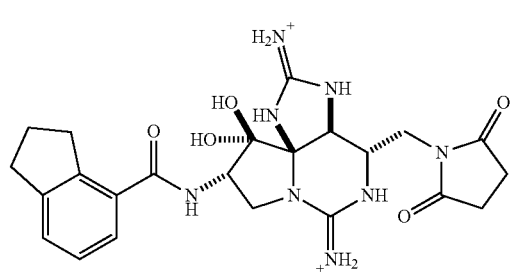
(81)
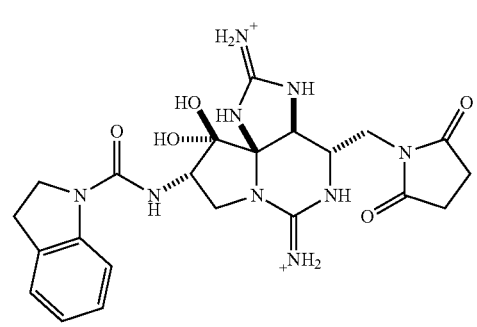
(82)
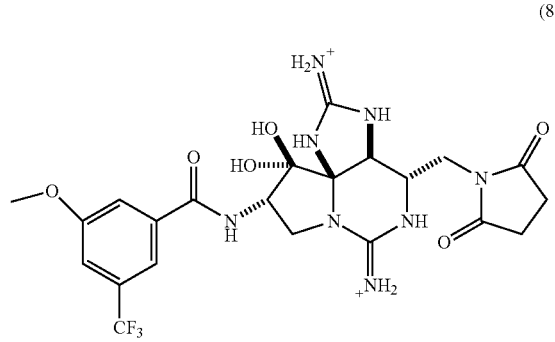
(83)
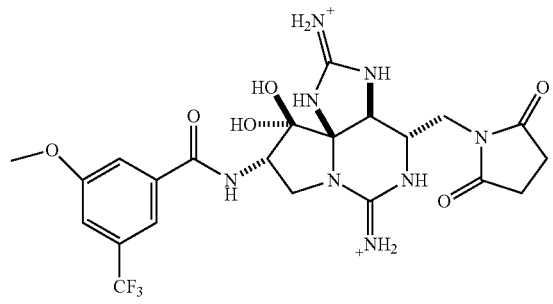
(84)
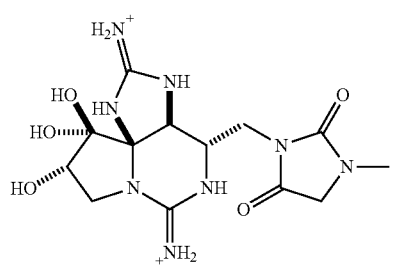
(85)
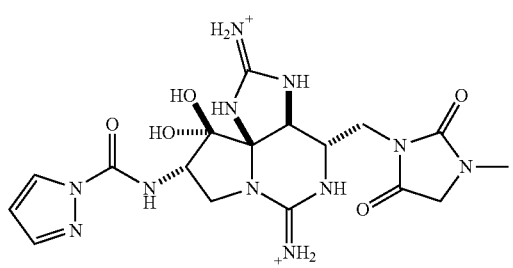
(86)
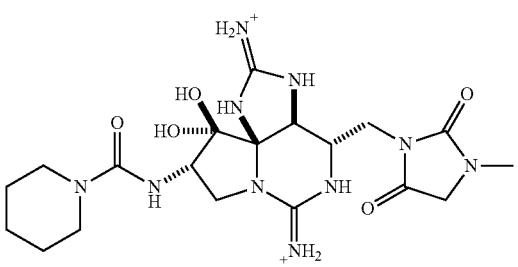
(87)
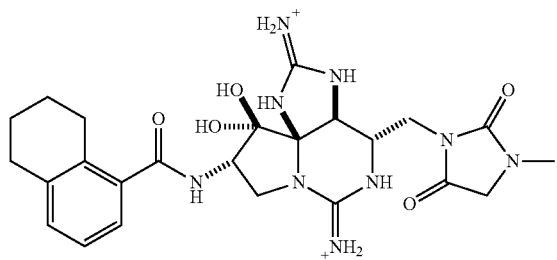
(88)
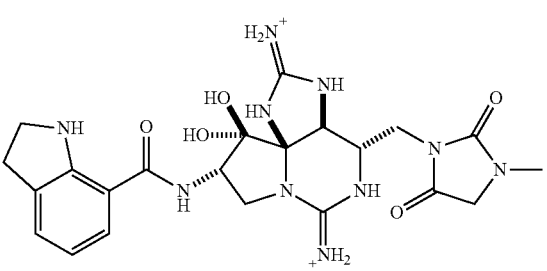

(89)
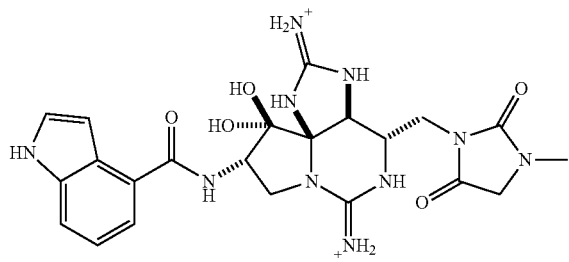
(90)
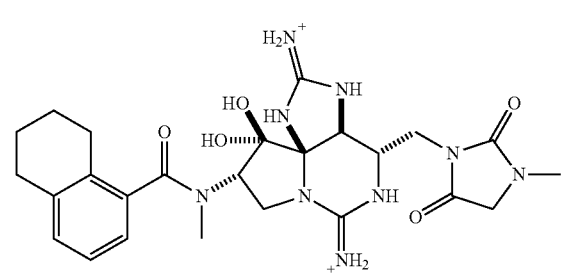
(91)
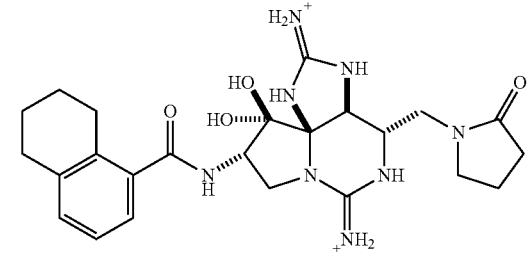
(92)
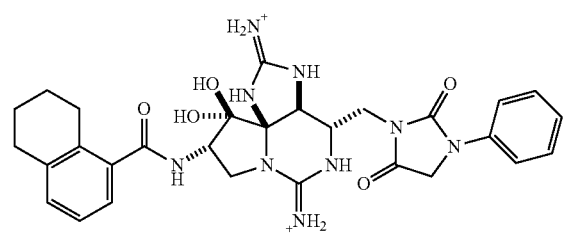
(93)
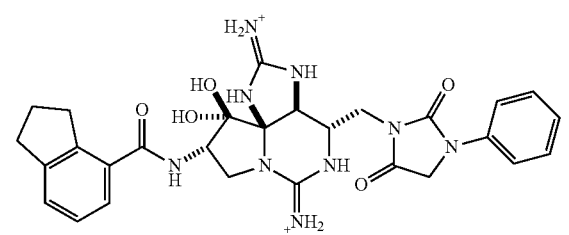
(94)
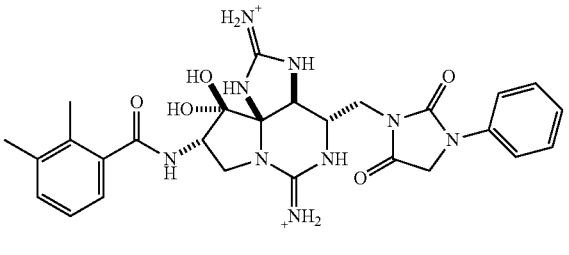
(95)
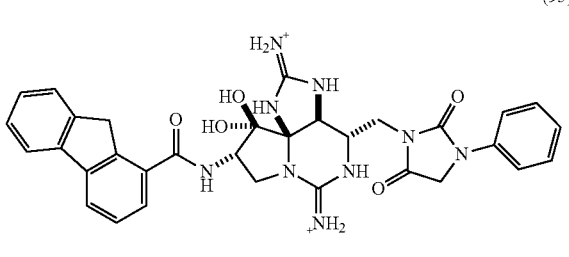
(96)
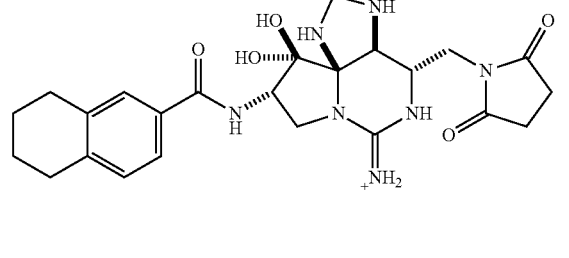
(97)
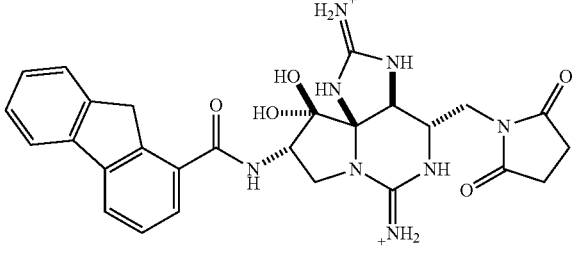
(98)
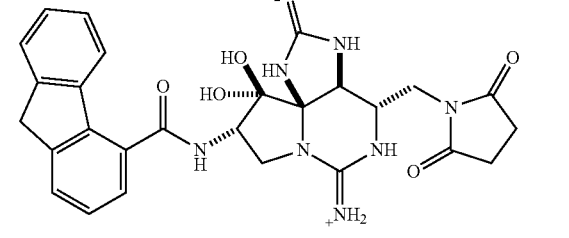

(99)
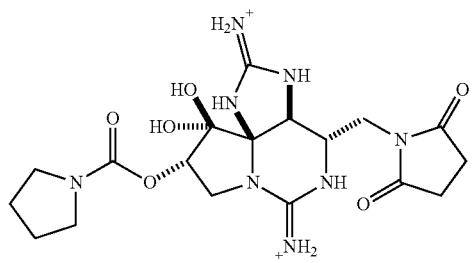
(100)
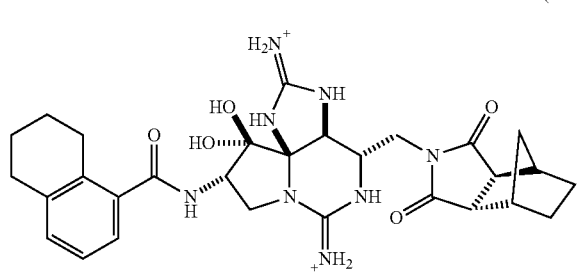
(101)
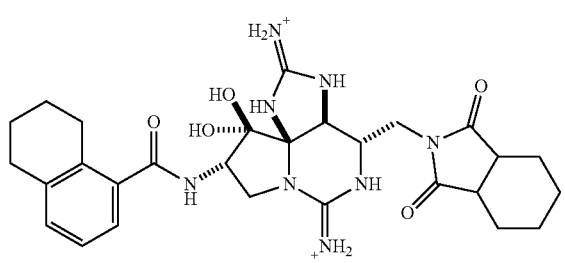
(102)
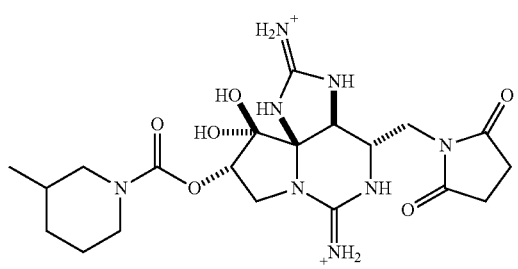
(103)
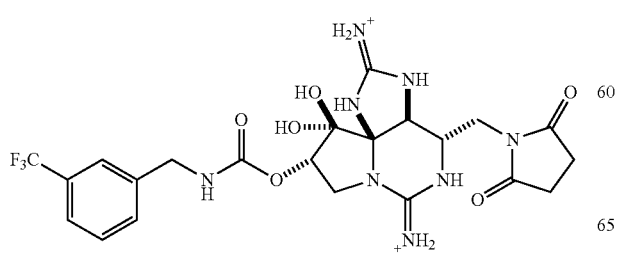
(104)
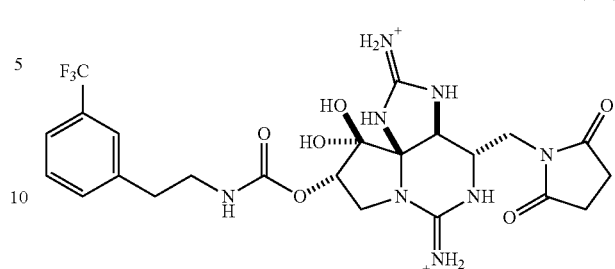
(105)
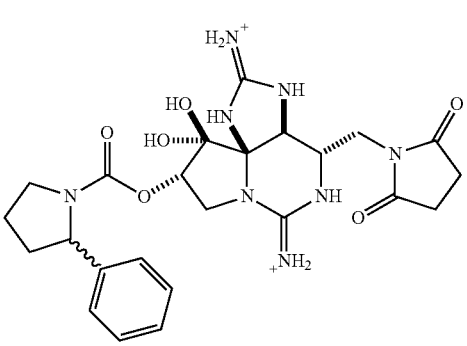
(106)
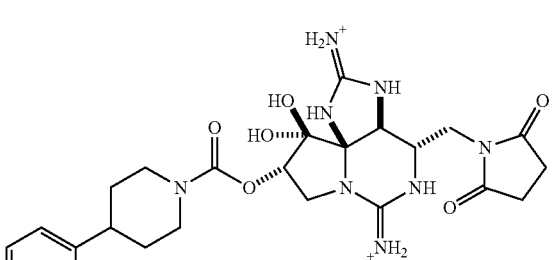
(107)
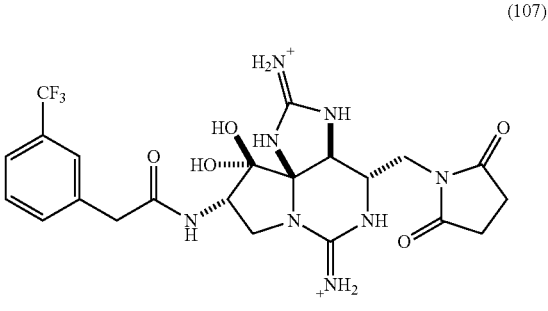
(108)
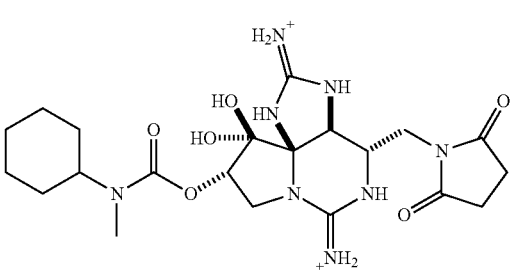

(109)
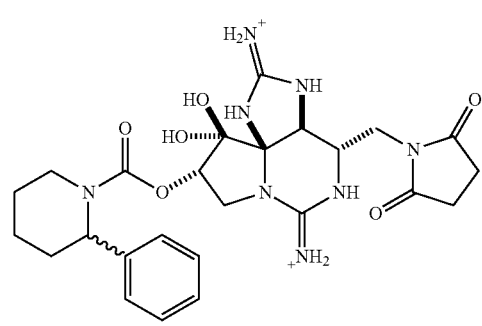
(110)
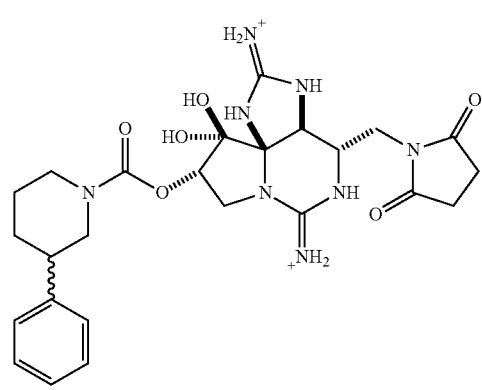
(111)
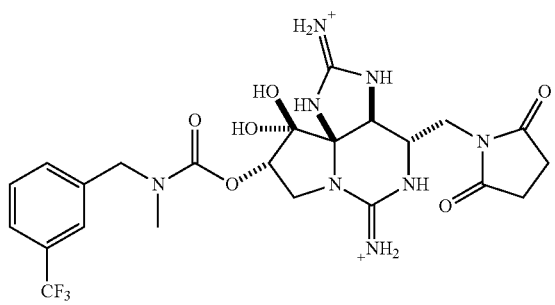
(112)
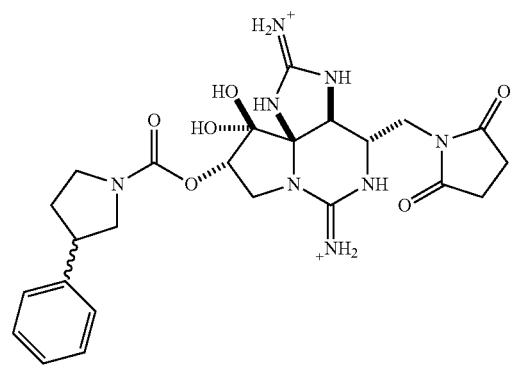
(113)
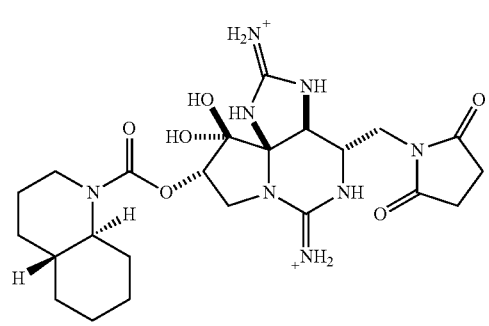
(114)
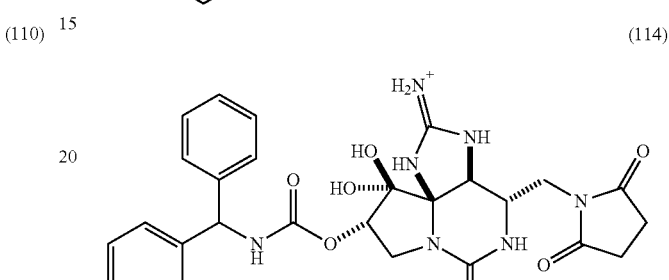
(115)
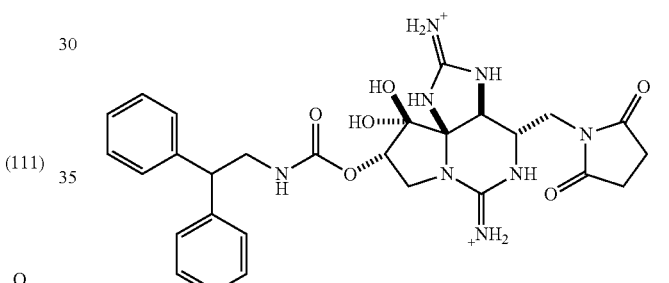
(116)
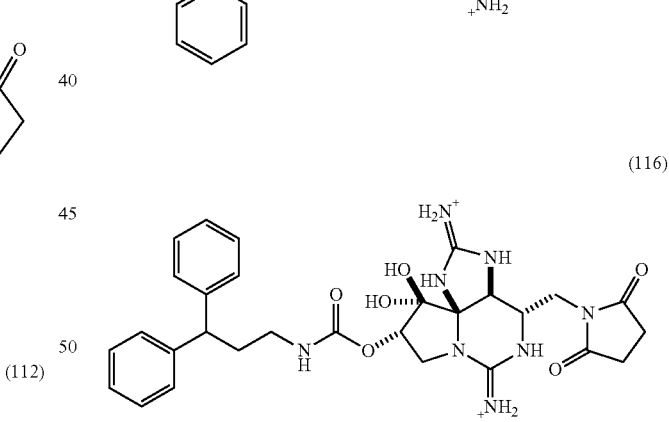
(117)
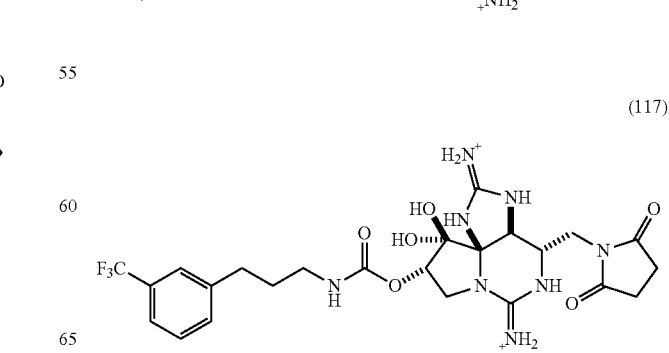

-continued (118)

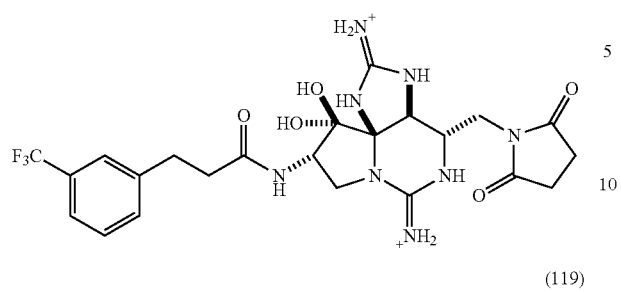

(119)

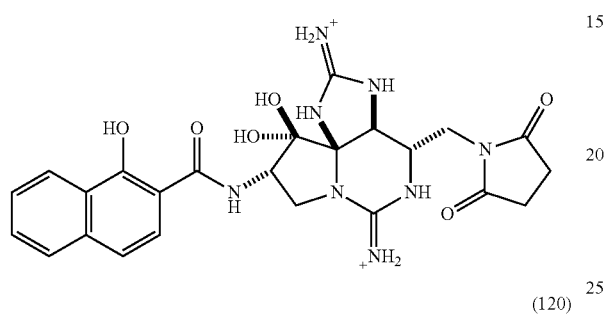

(120)

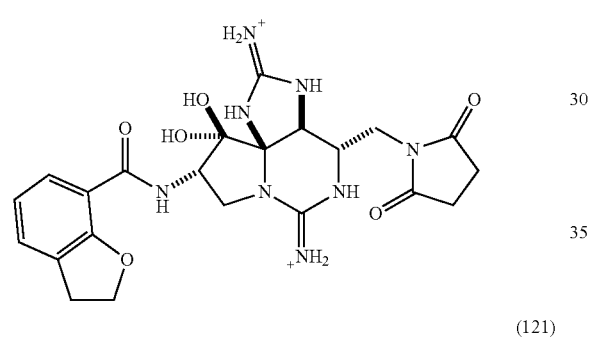

(121)

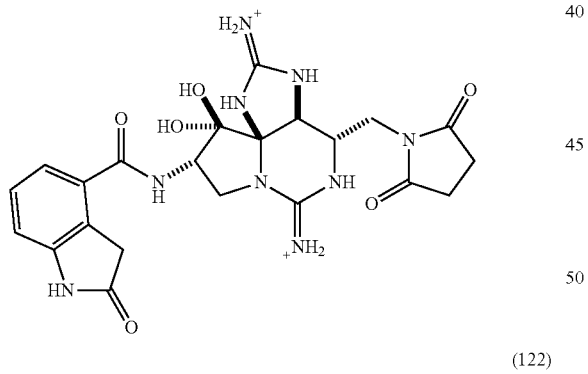

(122)

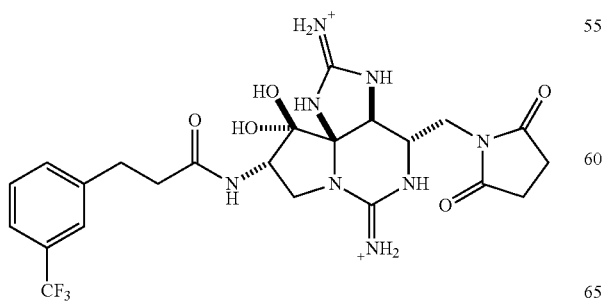

or a pharmaceutically acceptable salt, hydrate, solvate, stereoisomer, tautomer, or mixture thereof.

In some embodiments is a compound of Formula Xb

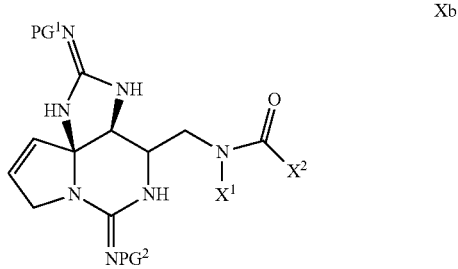

Xb or a salt thereof, where $PG^1$ is a nitrogen-protecting group;
$PG^2$ is a nitrogen-protecting group;
$X^1$ is $R^3$ and $X^2$ is $R^9$; or
$X^1$ and $X^2$ together with the —NC(O)— to which they are attached form a 5 or 6-membered ring where $X^1$, $X^2$, and the one or two additional ring atoms are independently selected from —C(O)—, —O—, —S—, —$NR^8$—, and —C($R^4$)($R^{4a}$)— provided that only one is selected from —O—, —S—, and —$NR^8$—; and where the 5 or 6-membered ring is optionally fused at two adjacent carbon atoms, or is optionally fused at one carbon atom and one nitrogen atom which are adjacent to each other, to a form a saturated or unsaturated 6-12 membered bicyclic ring; where the 1, 2, 3, 4, 5, or 6 additional ring atoms are independently —$CR^{12}$= or —C($R^{12}$)$_2$—;

each $R^4$ and $R^{4a}$ is independently H; $C_{1-6}$alkyl; or when the 6-12 membered ring is fused at a —C($R^4$)($R^{4a}$)—, one or both of the $R^4$ and $R^{4a}$ on the —C($R^4$)($R^{4a}$)— form a single or double bond with an adjacent ring atom;

$R^8$ is hydrogen; $C_{1-6}$alkyl; phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano; or when the 6-12 membered ring is fused at an —$NR^8$—, the $R^8$ forms a single bond with an adjacent ring atom;

each $R^{12}$ is independently hydrogen, halo, $C_{1-6}$alkyl, halo-$C_{1-6}$alkyl, or aryl;

$R^3$ is —C(O)$C_{1-6}$alkyl, —C(O)O$C_{1-6}$alkyl, or —C(O)phenyl where the phenyl is optionally substituted with one or two groups independently selected from halo, $C_{1-6}$alkyl, halo-$C_{1-6}$alkyl, $C_{1-6}$alkoxy, and aryl; and $R^9$ is $C_{1-6}$alkyl, $C_{1-6}$alkoxy, or phenyl where the phenyl is optionally substituted with one or two groups independently selected from halo, $C_{1-6}$alkyl, halo-$C_{1-6}$alkyl, $C_{1-6}$alkoxy, and aryl. In some embodiments is a compound of Formula Xb1:

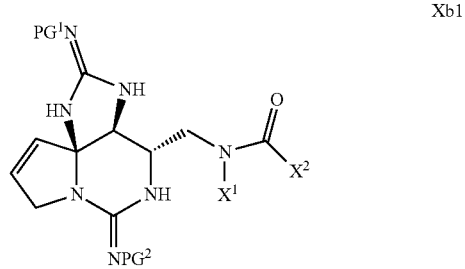

Xb1 or a salt thereof; where PG¹, PG², X¹, and X² are as defined for a compound of formula Xb, above or in any embodiments described herein.

In some embodiments is a compound of Formula Xc

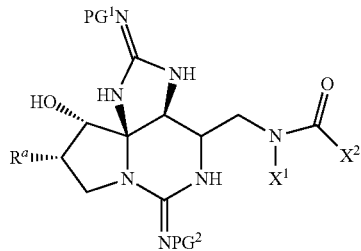

Xc or a salt thereof, where
$R^a$ is OH, —NHPG³, or —NH₂;
PG¹ is a nitrogen-protecting group;
PG² is a nitrogen-protecting group;
PG³ is a nitrogen-protecting group;
$X^1$ is $R^3$ and $X^2$ is $R^9$; or
$X^1$ and $X^2$ together with the —NC(O)— to which they are attached form a 5 or 6-membered ring where $X^1$, $X^2$, and the one or two additional ring atoms are independently selected from —C(O)—, —O—, —S—, —NR⁸—, and —C(R⁴)(R⁴ᵃ)— provided that only one is selected from —O—, —S—, and —NR⁸—; and where the 5 or 6-membered ring is optionally fused at two adjacent carbon atoms, or is optionally fused at one carbon atom and one nitrogen atom which are adjacent to each other, to a form a saturated or unsaturated 6-12 membered bicyclic ring; where the 1, 2, 3, 4, 5, or 6 additional ring atoms are independently —CR¹²═ or —C(R¹²)₂—;
each $R^4$ and $R^{4a}$ is independently H; $C_{1-6}$alkyl; or when the 6-12 membered ring is fused at a —C(R⁴)(R⁴ᵃ)—, one or both of the $R^4$ and $R^{4a}$ on the —C(R⁴)(R⁴ᵃ)— form a single or double bond with an adjacent ring atom;
$R^8$ is hydrogen; $C_{1-6}$alkyl; phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano; or when the 6-12 membered ring is fused at an —NR⁸—, the $R^8$ forms a single bond with an adjacent ring atom;
each $R^{12}$ is independently hydrogen, halo, $C_{1-6}$alkyl, halo-$C_{1-6}$alkyl, or aryl;
$R^3$ is —C(O)$C_{1-6}$alkyl, —C(O)O$C_{1-6}$alkyl, or —C(O)phenyl where the phenyl is optionally substituted with one or two groups independently selected from halo, $C_{1-6}$alkyl, halo-$C_{1-6}$alkyl, $C_{1-6}$alkoxy, and aryl; and
$R^9$ is $C_{1-6}$alkyl, $C_{1-6}$alkoxy, or phenyl where the phenyl is optionally substituted with one or two groups independently selected from halo, $C_{1-6}$alkyl, halo-$C_{1-6}$alkyl, $C_{1-6}$alkoxy, and aryl. In some embodiments is a compound of Formula Xc4:

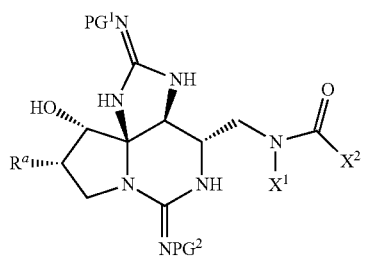

Xc4 or a salt thereof; where $R^a$, PG¹, PG², X¹, and X² are as defined for a compound of formula Xc, above or in any embodiments described herein.

In some embodiments is a compound of Formula Xd

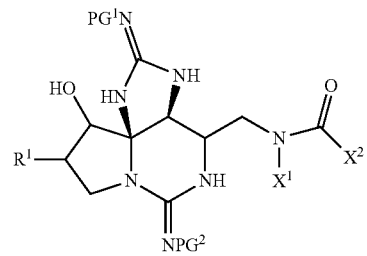

Xd or a salt thereof, where
PG¹ is a nitrogen-protecting group;
PG² is a nitrogen-protecting group;
$R^1$ is —OS(O)₂R⁵, —OC(O)R⁶, —NR⁷C(O)R⁷ᵃ, —OC(O)NR¹⁰R¹⁰ᵃ, —NR¹¹R¹¹ᵃ, —NR¹³S(O)₂R¹³ᵃ, or —NR¹⁴C(O)NR¹⁴ᵃR¹⁴ᵇ;
$X^1$ is $R^3$ and $X^2$ is $R^9$; or
$X^1$ and $X^2$ together with the —NC(O)— to which they are attached form a 5 or 6-membered ring where $X^1$, $X^2$, and the one or two additional ring atoms are independently selected from —C(O)—, —O—, —S—, —NR⁸—, and —C(R⁴)(R⁴ᵃ)— provided that only one is selected from —O—, —S—, and —NR⁸—; and where the 5 or 6-membered ring is optionally fused at two adjacent carbon atoms, or is optionally fused at one carbon atom and one nitrogen atom which are adjacent to each other, to a form a saturated or unsaturated 6-12 membered bicyclic ring; where the 1, 2, 3, 4, 5, or 6 additional ring atoms are independently —CR¹²═ or —C(R¹²)₂—;
each $R^4$ and $R^{4a}$ is independently H; $C_{1-6}$alkyl; or when the 6-12 membered ring is fused at a —C(R⁴)(R⁴ᵃ)—, one or both of the $R^4$ and $R^{4a}$ on the —C(R⁴)(R⁴ᵃ)— form a single or double bond with an adjacent ring atom;
$R^8$ is hydrogen; $C_{1-6}$alkyl; phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano; or when the 6-12 membered ring is fused at an —NR⁸—, the $R^8$ forms a single bond with an adjacent ring atom;
each $R^{12}$ is independently hydrogen, halo, $C_{1-6}$alkyl, halo-$C_{1-6}$alkyl, or aryl;
$R^3$ is —C(O)$C_{1-6}$alkyl, —C(O)O$C_{1-6}$alkyl, or —C(O)phenyl where the phenyl is optionally substituted with one or two groups independently selected from halo, $C_{1-6}$alkyl, halo-$C_{1-6}$alkyl, $C_{1-6}$alkoxy, and aryl;
$R^9$ is $C_{1-6}$alkyl, $C_{1-6}$alkoxy, or phenyl where the phenyl is optionally substituted with one or two groups independently selected from halo, $C_{1-6}$alkyl, halo-$C_{1-6}$alkyl, $C_{1-6}$alkoxy, and aryl;
$R^5$ is H, $C_{1-6}$alkyl, or aryl optionally substituted with 1, 2, 3, or 4 $R^{5a}$;
each $R^{5a}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;
$R^6$ is $C_{1-6}$alkyl; aryl optionally substituted with 1, 2, 3, or 4 $R^{6a}$; aralkyl where the aryl is optionally substituted with 1, 2, 3, or 4 $R^{6a}$; heteroaryl optionally substituted with 1, 2, 3, or 4 $R^{6a}$; heterocyclic optionally substituted with 1, 2, 3, or 4 $R^{6a}$; biphenyl optionally substituted with 1, 2, 3, or 4 $R^{6a}$; or cycloalkyl optionally substituted with 1, 2, 3 groups independently selected from $C_{1-6}$alkyl and halo-$C_{1-6}$alkyl;

each $R^{6a}$, when present, is independently halo, $C_{1-6}$alkyl, halo-$C_{1-6}$alkyl, hydroxy, $C_{1-6}$alkoxy, halo-$C_{1-6}$alkoxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, phenyl, or cyano;

$R^7$ is hydrogen or $C_{1-6}$alkyl;

$R^{7a}$ is $C_{1-6}$alkyl; aryl optionally substituted with 1, 2, 3, or 4 $R^{7b}$; aralkyl where the aryl is optionally substituted with 1, 2, 3, or 4 $R^{7b}$; heteroaryl optionally substituted with 1, 2, 3, or 4 $R^{7b}$; heterocyclic optionally substituted with 1, 2, 3 $R^{7b}$; biphenyl optionally substituted with 1, 2, 3, or 4 $R^{7b}$; or cycloalkyl optionally substituted with 1, 2, 3, or 4 groups independently selected from $C_{1-6}$alkyl and halo-$C_{1-6}$alkyl;

each $R^{7b}$, when present, is independently halo, $C_{1-6}$alkyl, halo-$C_{1-6}$alkyl, hydroxy, $C_{1-6}$alkoxy, halo-$C_{1-6}$alkoxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, phenyl, or cyano; and $R^{10}$ is hydrogen or $C_{1-6}$alkyl;

$R^{10a}$ is $C_{1-6}$alkyl; aryl optionally substituted with 1, 2, 3, or 4 $R^{10b}$; aralkyl where the aryl is optionally substituted with 1, 2, 3, or 4 $R^{10b}$; phenylcarbonyl where the phenyl is optionally substituted with 1, 2, 3, or 4 $R^{10b}$; heteroaryl optionally substituted with 1, 2, 3, or 4 $R^{10b}$; heterocyclic optionally substituted with 1, 2, 3, or 4 $R^{10b}$; biphenyl optionally substituted with 1, 2, 3 $R^{10b}$; or cycloalkyl optionally substituted with 1, 2, 3, or 4 groups independently selected from $C_{1-6}$alkyl and halo-$C_{1-6}$alkyl;

each $R^{10b}$, when present, is independently halo, $C_{1-6}$alkyl, halo-$C_{1-6}$alkyl, hydroxy, $C_{1-6}$alkoxy, halo-$C_{1-6}$alkoxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, phenyl, or cyano;

$R^{11}$ is hydrogen or $C_{1-6}$alkyl;

$R^{11a}$ is $C_{1-6}$alkyl; aryl optionally substituted with 1, 2, 3, or 4 $R^{11b}$; aralkyl where the aryl is optionally substituted with 1, 2, 3, or 4 $R^{11b}$; heteroaryl optionally substituted with 1, 2, 3, or 4 $R^{11b}$; heterocyclic optionally substituted with 1, 2, 3, or 4 $R^{11b}$; biphenyl optionally substituted with 1, 2, 3, or 4 $R^{11b}$; or cycloalkyl optionally substituted with 1, 2, 3, or 4 groups independently selected from $C_{1-6}$alkyl and halo-$C_{1-6}$alkyl;

each $R^{11b}$, when present, is independently halo, $C_{1-6}$alkyl, halo-$C_{1-6}$alkyl, hydroxy, $C_{1-6}$alkoxy, halo-$C_{1-6}$alkoxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, phenyl, or cyano;

$R^{13}$ is hydrogen or $C_{1-6}$alkyl;

$R^{13a}$ is $C_{1-6}$alkyl; aryl optionally substituted with 1, 2, 3, or 4 $R^{13b}$; aralkyl where the aryl is optionally substituted with 1, 2, 3, or 4 $R^{13b}$; heteroaryl optionally substituted with 1, 2, 3, or 4 $R^{13b}$; heterocyclic optionally substituted with 1, 2, 3, or 4 $R^{13b}$; biphenyl optionally substituted on either ring with 1, 2, 3, or 4 $R^{13b}$; or cycloalkyl optionally substituted with 1, 2, 3, or 4 groups independently selected from $C_{1-6}$alkyl and halo-$C_{1-6}$alkyl;

each $R^{13b}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;

$R^{14}$ is hydrogen or $C_{1-6}$alkyl;

$R^{14a}$ is hydrogen or $C_{1-6}$alkyl;

$R^{14b}$ is $C_{1-6}$alkyl; aryl optionally substituted with 1, 2, 3, or 4 $R^{14c}$; aralkyl where the aryl is optionally substituted with 1, 2, 3, or 4 $R^{14c}$; heteroaryl optionally substituted with 1, 2, 3, or 4 $R^{14c}$; heterocyclic optionally substituted with 1, 2, 3, or 4 $R^{14c}$; biphenyl optionally substituted on either ring with 1, 2, 3, or 4 $R^{14c}$; or cycloalkyl optionally substituted with 1, 2, 3, or 4 groups independently selected from $C_{1-6}$alkyl and halo-$C_{1-6}$alkyl; and each $R^{14c}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano.

In some embodiments is a compound of Formula Xd1

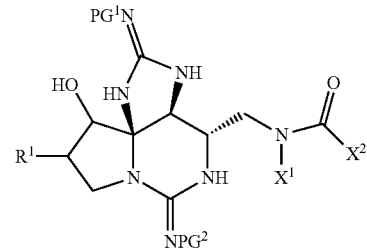

or a salt thereof, where $R^1$, $PG^1$, $PG^2$, $X^1$, and $X^2$ are as defined for a compound of formula Xd, above or in any embodiments described herein.

In some embodiments, the compound of Formula Xb, Xb1, Xc, Xc1, Xc2, Xc3, Xc4, Xd, Xd1, Xe, or Xe1 is that where $PG^1$ is a nitrogen-protecting group selected from Tces, Mbs and tosyl; $PG^2$ is a nitrogen-protecting group selected from —C(O)CCl$_3$ and —C(O)OCH$_2$CCl$_3$; and all other groups are as defined in any of the embodiments. In some embodiments, the compound of Formula Xb, Xb1, Xc, Xc1, Xc2, Xc3, Xc4, Xd, Xd1, Xe, or Xe1 is that where $PG^1$ is Tces, $PG^2$ is —C(O)CCl$_3$, and all other groups are as defined in any of the embodiments. In some or any embodiments, the compound of Formula Xb, Xb1, Xc, Xc1, Xc2, Xc3, Xc4, Xd, Xd1, Xe, or Xe1 is that where $X^1$ and $X^2$ together with the —NC(O)— to which they are attached form

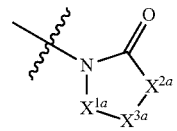

where $X^{1a}$ is —O—, —CH$_2$—, or —C(O)—; $X^{2a}$ is —S—, —NR$^8$—, or —C(R$^4$)(R$^{4a}$)—; and $X^{3a}$ is one or two groups independently selected from —O—, —S—, —NR$^8$—, and —C(R$^4$)(R$^{4a}$)— provided that only one atom of $X^{1a}$, $X^{2a}$, and $X^{3a}$ is selected from —O—, —S—, and —NR$^8$—; and where the

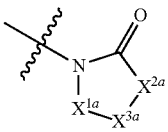

ring is optionally fused at $X^{2a}$ and at the adjacent atom in $X^{3a}$ to form a saturated or unsaturated, 9 or 10-membered bicyclic ring when $X^{2a}$ is —C(R$^4$)(R$^{4a}$)— and $X^{3a}$ is —C(R$^4$)(R$^{4a}$)— or —C(R$^4$)(R$^{4a}$)—C(R$^4$)(R$^{4a}$)—; and where the four additional ring atoms are independently —CH= or —CH$_2$—;

each R$^4$ and R$^{4a}$ is independently H; C$_{1-6}$alkyl; or when the 6-12 membered ring is fused at a —C(R$^4$)(R$^{4a}$)—, one or both of the R$^4$ and R$^{4a}$ on the —C(R$^4$)(R$^{4a}$)— form a single or double bond with an adjacent ring atom;

R$^8$ is hydrogen, C$_{1-6}$alkyl, or phenyl.

In some embodiments, provided herein are:
(a) compounds as described herein, e.g., of Formula (I)-(Ik) and I-P and 1-122, and pharmaceutically acceptable salts and compositions thereof,
(b) compounds as described herein, e.g., of Formula (I)-(Ik) and I-P and 1-122, and pharmaceutically acceptable salts and compositions thereof for use in the treatment of pain and/or conditions modulated by voltage-gated sodium channels;
(c) processes for the preparation of compounds as described herein, e.g., of Formula (I)-(Ik) and I-P and 1-122, as described in more detail elsewhere herein;
(d) pharmaceutical formulations comprising a compound as described herein, e.g., of Formula (I)-(Ik) and I-P and 1-122, or a pharmaceutically acceptable salt thereof together with a pharmaceutically acceptable carrier or diluent;
(e) a method for the treatment of a condition associated with voltage-gated sodium channel function in a subject that includes the administration of a therapeutically or prophylactically effective amount of a compound as described herein, e.g., of Formula (I)-(Ik) and I-P and 1-122, its pharmaceutically acceptable salt or composition;
(f) a method for the treatment of pain in a subject that includes the administration of a therapeutically or prophylactically effective amount of a compound as described herein, e.g., of Formula (I)-(Ik) and I-P and 1-122, its pharmaceutically acceptable salt or composition;
(g) pharmaceutical formulations comprising a compound as described herein, e.g., of Formula (I)-(Ik) and I-P and 1-122, or a pharmaceutically acceptable salt thereof together with one or more other effective agents for treating pain and/or conditions modulated by voltage-gated sodium channels, optionally in a pharmaceutically acceptable carrier or diluent;
(h) a method for the treatment of pain in a subject that includes the administration of a therapeutically or prophylactically effective amount of a compound as described herein, e.g., of Formula (I)-(Ik) and I-P and 1-122, its pharmaceutically acceptable salt or composition in combination and/or alternation with one or more agent for the treatment of pain and/or conditions modulated by voltage-gated sodium channels; and
(i) a method for the treatment of a condition associated with voltage-gated sodium channel function in a subject that includes the administration of a therapeutically or prophylactically effective amount of a compound as described herein, e.g., of Formula (I)-(Ik) and I-P and 1-122, its pharmaceutically acceptable salt or composition in combination and/or alternation with one or more agent for the treatment of pain.

Optically Active Compounds

It is appreciated that compounds provided herein have several chiral centers and may exist in and be isolated in optically active and racemic forms. It is to be understood that any racemic, optically-active, diastereomeric, tautomeric, or stereoisomeric form, or mixtures thereof, of a compound provided herein, which possess the useful properties described herein is within the scope of the invention. It being well known in the art how to prepare optically active forms (in certain embodiments, by resolution of the racemic form by recrystallization techniques, by synthesis from optically-active starting materials, by chiral synthesis, or by chromatographic separation using a chiral stationary phase). In addition, the compounds described herein may epimerize at the C11 position under certain conditions. Such epimers are within the embodiments provided herein.

In certain embodiments, methods to obtain optically active materials are known in the art, and include at least the following.
i) physical separation of crystals—a technique whereby macroscopic crystals of the individual stereoisomers are manually separated. This technique can be used if crystals of the separate stereoisomers exist, i.e., the material is a conglomerate, and the crystals are visually distinct;
ii) simultaneous crystallization—a technique whereby the individual stereoisomers are separately crystallized from a solution of the racemate, possible only if the latter is a conglomerate in the solid state;
iii) enzymatic resolutions—a technique whereby partial or complete separation of a racemate by virtue of differing rates of reaction for the stereoisomers with an enzyme;
iv) enzymatic asymmetric synthesis—a synthetic technique whereby at least one step of the synthesis uses an enzymatic reaction to obtain an stereoisomerically pure or enriched synthetic precursor of the desired stereoisomer;
v) chemical asymmetric synthesis—a synthetic technique whereby the desired stereoisomer is synthesized from an achiral precursor under conditions that produce asymmetry (i.e., chirality) in the product, which may be achieved using chiral catalysts or chiral auxiliaries;
vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;
vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the stereoisomers with a chiral, non-racemic reagent or catalyst under kinetic conditions;

ix) stereospecific synthesis from non-racemic precursors—a synthetic technique whereby the desired stereoisomer is obtained from non-chiral starting materials and where the stereochemical integrity is not or is only minimally compromised over the course of the synthesis;

x) chiral liquid chromatography—a technique whereby the stereoisomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and stereoisomers are separated by virtue of their differing interactions in the gaseous mobile phase with a column containing a fixed non-racemic chiral adsorbent phase;

xii) extraction with chiral solvents—a technique whereby the stereoisomers are separated by virtue of preferential dissolution of one stereoisomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one stereoisomer of the racemate to pass through.

In some embodiments, provided is a composition of a 11,13-modified saxitoxin that comprises a substantially pure designated stereoisomer of the 11,13-modified saxitoxin. In certain embodiments, in the methods and compounds of this invention, the compounds are substantially free of other stereoisomer. In some embodiments, a composition includes a compound that is at least 85%, 90%, 95%, 98%, 99% or 100% by weight, of the 11,13-modified saxitoxin, the remainder comprising other chemical species or stereoisomers.

Isotopically Enriched Compounds

Also provided herein are isotopically enriched compounds, including but not limited to isotopically enriched 11,13-modified saxitoxins.

Isotopic enrichment (in certain embodiments, deuteration) of pharmaceuticals to improve pharmacokinetics ("PK"), pharmacodynamics ("PD"), and toxicity profiles, has been demonstrated previously with some classes of drugs. See, for example, Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999).

Isotopic enrichment of a drug can be used, in certain embodiments, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrees the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). See, e.g., Foster et al., Adv. Drug Res., vol. 14, pp. 1-36 (1985); Kushner et al., Can. J. Physiol. Pharmacol., vol. 77, pp. 79-88 (1999).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

The animal body expresses a variety of enzymes for the purpose of eliminating foreign substances, such as therapeutic agents, from its circulation system. In certain embodiments, such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein will produce a detectable KIE that will affect the pharmacokinetic, pharmacologic, and/or toxicological profiles of a compound provided herein in comparison with a similar compound having a natural isotopic composition.

Preparation of Compounds

The compounds provided herein can be prepared, isolated or obtained by any method apparent to those of skill in the art. Compounds provided herein can be prepared according to the Exemplary Preparation Schemes provided below. Reaction conditions, steps and reactants not provided in the Exemplary Preparation Schemes would be apparent to, and known by, those skilled in the art.

Additional steps and reagents not provided in the Exemplary Preparation Scheme would be known to those of skill in the art. For example, the compound of formula A (depicted below) where $PG^1$ is a nitrogen-protecting group, e.g. Tces, and $PG^2$ is a nitrogen-protecting group, e.g. Troc, can be prepared using procedures known to one of ordinary skill in the art (e.g. see US2010/0284913. It would be appreciated by one of ordinary skill in the art that an intermediate of formula A-1:

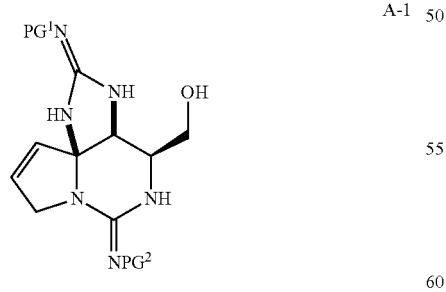

A-1 could be prepared using the procedures known by one of ordinary skill in the art or as disclosed in US2010/0284913 (which is herein incorporated by reference in its entirety, particularly the synthetic methods disclosed therein) but replacing L-serine with D-serine. Exemplary methods of preparation are described in detail in the Examples herein.

General Scheme A

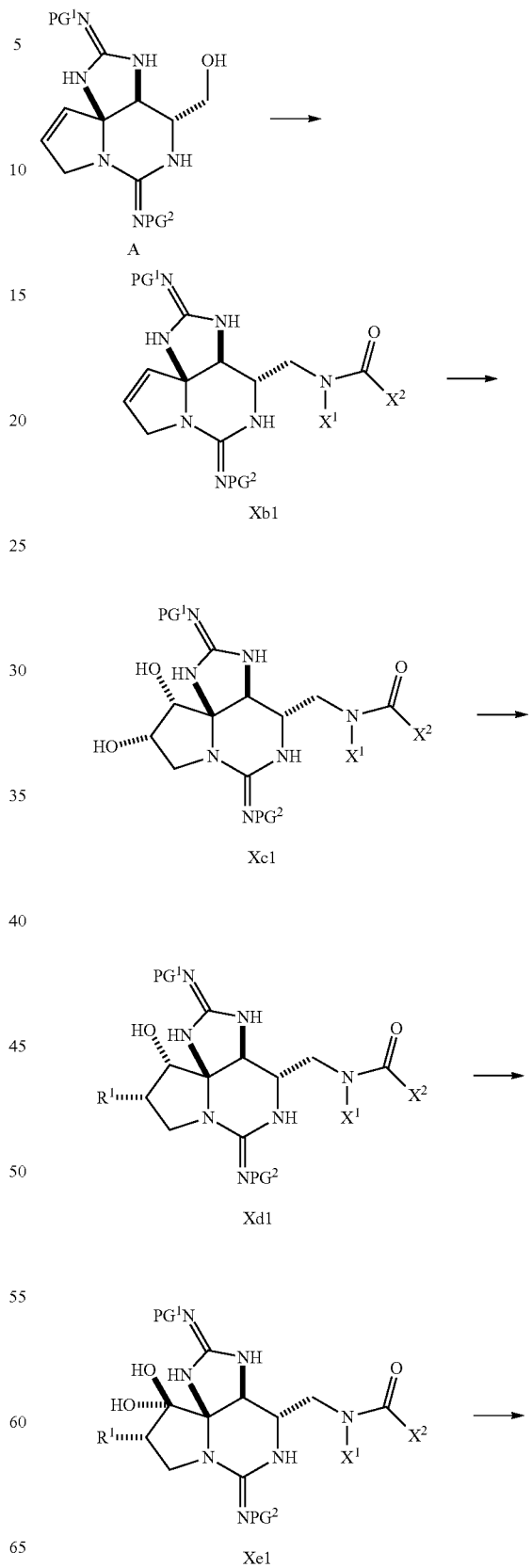

-continued

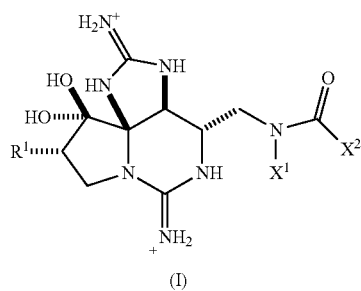

(I)

A Compound of Formula I where $R^1$ is —OC(O)$R^6$ or —OS(O)$_2R^5$; $X^1$, $X^2$, and all other groups are as defined in the Summary of the Invention or in any embodiments can be prepared according to General Scheme A. For example, the compound of formula A where $PG^1$ is a nitrogen-protecting group, e.g. Tces, and $PG^2$ is a nitrogen-protecting group, e.g. Troc, can be prepared using procedures known to one of ordinary skill in the art (e.g. see US2010/0284913. The compound of formula A can be treated with phthalimide or succinimide and triphenylphosphine in the presence of an azodicarboxylate such as diisopropyl azodicarboxylate in a solvent such as THF to form the compound of formula Xb1 which can be optionally purified (for example by chromatography) before proceeding to the next step. The compound Xc1 can be prepared by treating Xb1 with a co-oxidant/catalyst such as N-methylmorpholine-N-oxide and a hydroxylating agent such as $OsO_4$ in a solvent such as THF, where the reaction is optionally quenched, for example with $Na_2S_2O_3$, and where the product is optionally extracted and/or purified by chromatography. The compound of formula Xd1 can be prepared by treating Xc1 with a base such as dimethylaminopyridine or triethylamine and a compound of formula

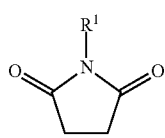

where $R^1$ is —OC(O)$R^6$ (where $R^6$ and all other groups are as defined in the Summary of the Invention or in some or any of the embodiments herein) or of formula ClS(O)$_2R^5$(where $R^5$ and all other groups are as defined in the Summary of the Invention or in some or any of the embodiments herein) in a solvent such as $CH_2Cl_2$ and where the product is optionally purified before using in the next step. The compound of formula Xe1 can be prepared by treating a compound of formula Xd1 with Dess-Martin periodinane in a solvent such as $CH_2Cl_2$ and where the product is optionally purified before using in the next step. The compound of Formula I where $R^1$ is —OC(O)$R^6$ can be prepared by treating the compound of formula Xe1 with a catalyst such as $PdCl_2$ in the presence of an acid such as trifluoroacetic acid in one more solvents such as methanol and/or water and followed by treating with $H_2$, and where the product is removed by filtration and optionally purified by chromatography.

General Scheme B

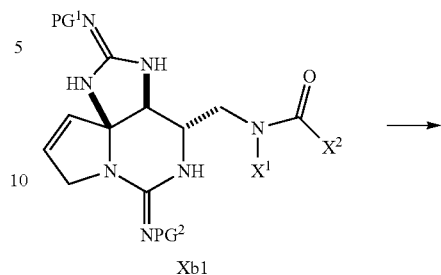

Xb1

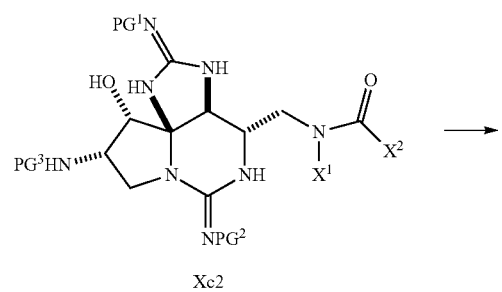

Xc2

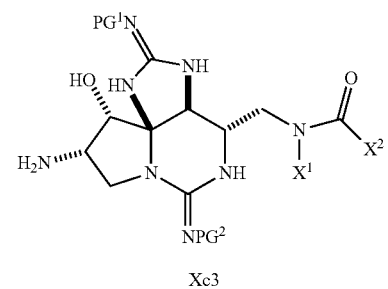

Xc3

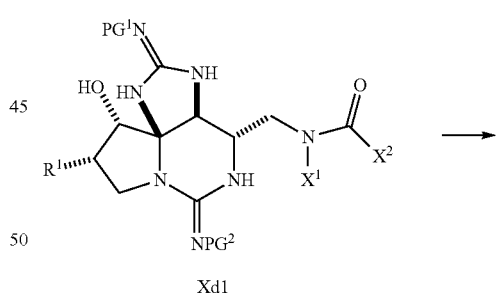

Xd1

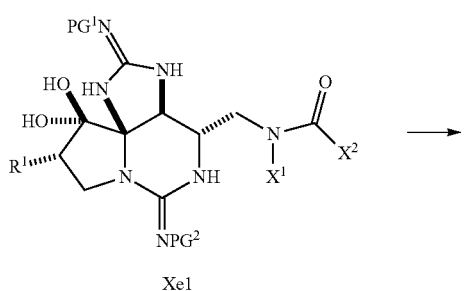

Xe1

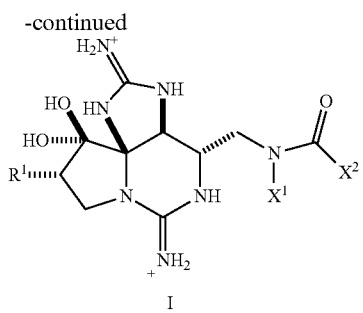

(I)

A Compound of Formula I where R¹ is —NR C(O)R^{7a}, —NR^{11}R^{11a}, —NR^{13}S(O)$_2$R^{13}a or —NR^{14}C(O)R^{14a}R^{14b}; X¹, X², and all other groups are as defined in the Summary of the Invention or in any embodiments can be prepared according to General Scheme B. In some embodiments, R^{13} and R^{14} are hydrogen. For example, the compound of formula Xb1 where PG¹ is a nitrogen-protecting group, e.g. Tces, and PG² is a nitrogen-protecting group, e.g. Troc, can be prepared as described above in General Scheme A or in other embodiments herein. Xb1 can be treated with a compound of formula H$_2$NPG³ where PG³ is as defined in any of the embodiments herein (e.g. PG³ is Boc) in the presence of OsO$_4$ in a solvent such as CH$_3$CN, where the reaction is optionally quenched, for example with NaHCO$_3$ and where the product is optionally extracted and/or purified by chromatography. The PG³ protecting group is then removed using conditions known to one of ordinary skill in the art, e.g. by treating with an acid such as TFA when PG³ is Boc to yield the compound of formula Xc3 or a salt thereof. The product is used in the next step without further purification or is optionally extracted and/or purified by chromatography. Xc3 is then treated with a base such as triethylamine in a solvent such as CH$_2$Cl$_2$ with a compound of formula

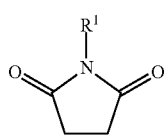

where R¹ is —OC(O)R⁶ (where R⁶ and all other groups are as defined in the Summary of the Invention or in some or any of the embodiments herein), of formula ClS(O)$_2$R^{13a} (where R^{13a} and all other groups are as defined in the Summary of the Invention or in some or any of the embodiments herein) or of formula O=C=N—R^{14a} (where R^{14a} and all other groups are as defined in the Summary of the Invention or in some or any of the embodiments herein) where the product is optionally extracted and/or purified by chromatography. The compound of formula Xe1 can be prepared by treating a compound of formula Xd1 with Dess-Martin periodinane in a solvent such as CH$_2$Cl$_2$ and where the product is optionally purified before using in the next step. The compound of Formula I where R¹ is —OC(O)R⁶ can be prepared by treating the compound of formula Xe1 with a catalyst such as PdCl$_2$ in the presence of an acid such as trifluoroacetic acid in one more solvents such as methanol and/or water and followed by treating with H$_2$, and where the product is removed by filtration and optionally purified by chromatography.

General Scheme C

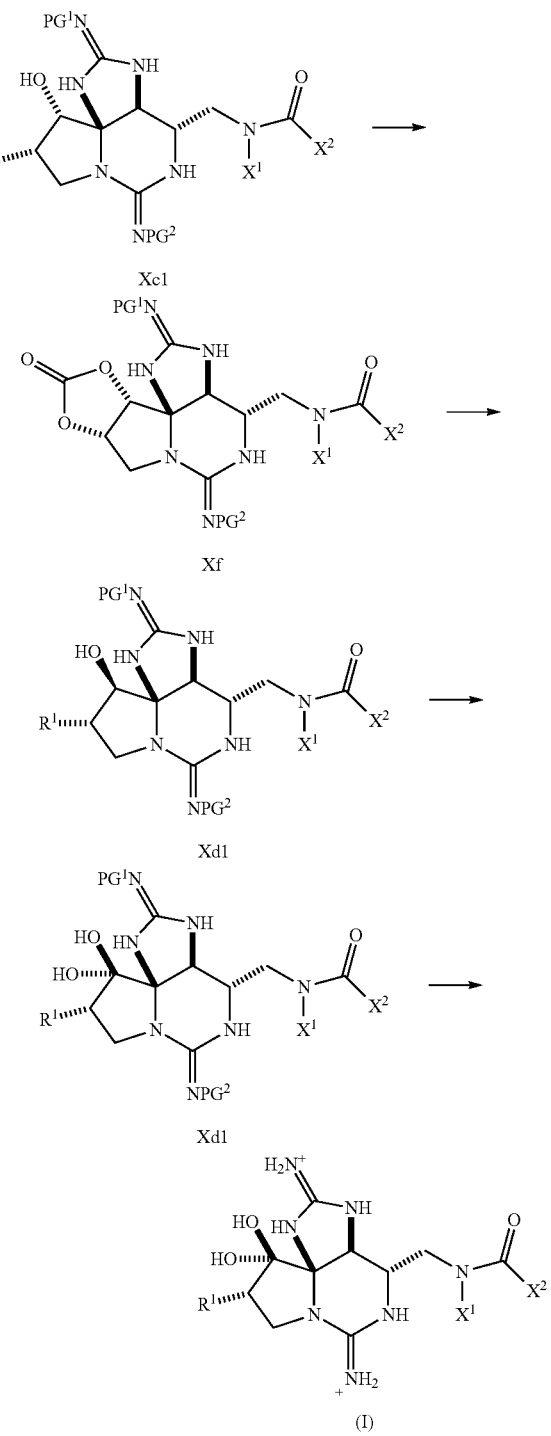

A Compound of Formula I where R¹ is —OC(O)NR^{10}R^{10a}; X¹, X², and all other groups are as defined in the Summary of the Invention or in any embodiments can be prepared according to General Scheme C. For example, the compound of formula Xc1 where PG¹ is a nitrogen-protecting group, e.g. Tces, and PG² is a nitrogen-protecting group, e.g. Troc, can be prepared as described above in General Scheme A or in other embodiments herein. Xc1 can be treated with a coupling agent such as 1,1'-carbonyldiimidazole in a solvent such as THF where the product Xf is optionally purified. Xf is then treated with a compound of formula $HNR^{10}R^{10a}$ to form the compound of formula Xd1 where the product is optionally extracted and/or purified by chromatography. Xe1 is prepared from Xd1 using conditions known to one or ordinary skill in the art or using conditions described for Scheme A. The compound of Formula I where $R^1$ is —OC(O)$NR^{10}R^{10a}$ can be prepared by treating the compound of formula Xe1 with a catalyst such as $PdCl_2$ in the presence of an acid such as trifluoroacetic acid in one more solvents such as methanol and/or water and followed by treating with $H_2$, and where the product is removed by filtration and optionally purified by chromatography.

In another embodiment, provided is a method of preparing a compound of Formula I comprising a) deprotecting a compound of Formula Xe

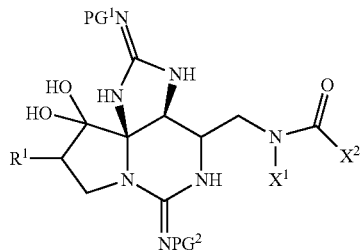

Xe where $PG^1$ is a nitrogen-protecting group selected from Tces, Mbs, and tosyl; $PG^2$ is a nitrogen-protecting group selected from —C(O)$CCl_3$ and —C(O)$OCH_2CCl_3$; and $R^1$, $X^1$, and $X^2$ are as defined in any of the embodiments described herein;

b) optionally isolating the compound of Formula I.

In some or any embodiments the compound of formula Xe is according to formula Xe1.

Pharmaceutical Compositions and Methods of Administration

The compounds provided herein can be formulated into pharmaceutical compositions using methods available in the art and those disclosed herein. Any of the compounds disclosed herein can be provided in the appropriate pharmaceutical composition and be administered by a suitable route of administration.

The methods provided herein encompass administering pharmaceutical compositions containing at least one compound as described herein, including a compound of Formula (I)-(Ik) and I-P and 1-122, if appropriate in a salt form, either used alone or in the form of a combination with one or more compatible and pharmaceutically acceptable carriers, such as diluents or adjuvants, or with another agent for the treatment of pain and/or conditions modulated by voltage-gated sodium channels.

In certain embodiments, the second agent can be formulated or packaged with the compound provided herein. Of course, the second agent will only be formulated with the compound provided herein when, according to the judgment of those of skill in the art, such co-formulation should not interfere with the activity of either agent or the method of administration. In certain embodiments, the compound provided herein and the second agent are formulated separately. They can be packaged together, or packaged separately, for the convenience of the practitioner of skill in the art.

In clinical practice the active agents provided herein may be administered by any conventional route, in particular orally, parenterally, rectally or by inhalation (e.g. in the form of aerosols). In certain embodiments, the compound provided herein is administered orally.

Use may be made, as solid compositions for oral administration, of tablets, pills, hard gelatin capsules, powders or granules. In these compositions, the active product is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, in certain embodiments, wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, in certain embodiments, ethyl oleate. These compositions can also contain adjuvants, in particular wetting, isotonizing, emulsifying, dispersing and stabilizing agents. Sterilization can be carried out in several ways, in certain embodiments, using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, in certain embodiments, dextran, mannitol or lactose.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Remington: The Science and Practice of Pharmacy; Pharmaceutical Press; 22 edition (Sep. 15, 2012).

Typical pharmaceutical compositions and dosage forms comprise one or more excipients. Suitable excipients are well-known to those skilled in the art of pharmacy, and in certain embodiments, suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions provided herein can comprise excipients that are well known in the art and are listed, in certain embodiments, in the U.S. Pharmacopeia (USP 36-NF 31 S2). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, New York, 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. In certain embodiments, suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In a certain embodiment, the pharmaceutical compositions or single unit dosage forms are sterile and in suitable form for administration to a subject, in certain embodiments, an animal subject, such as a mammalian subject, in certain embodiments, a human subject.

A pharmaceutical composition is formulated to be compatible with its intended route of administration. In certain embodiments, routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

In certain embodiments, dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. In certain embodiments, a dosage form used in the initial treatment of pain may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington: The Science and Practice of Pharmacy; Pharmaceutical Press; 22 edition (Sep. 15, 2012).

Generally, the ingredients of compositions are supplied either separately or mixed together in unit dosage form, in certain embodiments, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound.

Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington: The Science and Practice of Pharmacy; Pharmaceutical Press; 22 edition (Sep. 15, 2012).

In certain embodiments, the oral dosage forms are solid and prepared under anhydrous conditions with anhydrous ingredients, as described in detail herein. However, the scope of the compositions provided herein extends beyond anhydrous, solid oral dosage forms. As such, further forms are described herein.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration. In certain embodiments, excipients suitable for use in oral liquid or aerosol dosage forms include, but are not limited to, water, glycols, oils, alcohols, flavoring agents, preservatives, and coloring agents. In certain embodiments, excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

In certain embodiments, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

In certain embodiments, excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

In certain embodiments, fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions is typically present in from about 50 to about 99 weight percent of the pharmaceutical composition or dosage form.

In certain embodiments, suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, in certain embodiments, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds provided herein can be administered by controlled release means or by delivery devices that are well known to those of ordinary skill in the art. In certain embodiments, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500; each of which is incorporated herein by reference in its entirety. Such dosage forms can be used to provide slow or controlled release of one or more active ingredients using, in certain embodiments, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus encompassed herein are single unit dosage forms suitable for oral administration such as, but not limited to, tablets, capsules, gel caps, and caplets that are adapted for controlled release.

All controlled release pharmaceutical products have a common goal of improving drug therapy over that achieved by their non-controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug may be administered using intravenous infusion, an implantable osmotic pump, a transdermal patch, liposomes, or other modes of administration. In certain embodiments, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intra-arterial. Because their administration typically bypasses subjects' natural defenses against contaminants, parenteral dosage forms are typically, sterile or capable of being sterilized prior to administration to a subject. In certain embodiments, parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. In certain embodiments, suitable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington: The Science and Practice of Pharmacy; Pharmaceutical Press; 22 edition (Sep. 15, 2012);

and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are nontoxic and pharmaceutically acceptable. Moisturizers or humectants can also be added to pharmaceutical compositions and dosage forms if desired. Examples of such additional ingredients are well known in the art. See, e.g., Remington: The Science and Practice of Pharmacy; Pharmaceutical Press; 22 edition (Sep. 15, 2012).

Depending on the specific tissue to be treated, additional components may be used prior to, in conjunction with, or subsequent to treatment with active ingredients provided. In certain embodiments, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Dosage and Unit Dosage Forms

In human therapeutics, the doctor will determine the posology which he considers most appropriate according to a preventive or curative treatment and according to the age, weight, stage of the infection and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

In further aspects, provided are methods of treating a condition associated with voltage-gated sodium channel function and/or pain in a subject by administering, to a subject in need thereof, a therapeutically or prophylactically effective amount of a compound provided herein, or a pharmaceutically acceptable salt thereof. The amount of the compound or composition which will be therapeutically or prophylactically effective in the treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in certain embodiments, the dosage administered to a subject is 0.140 mg/kg to 3 mg/kg of the subject's body weight, based on weight of the active compound. In certain embodiments, the dosage administered to a subject is between 0.20 mg/kg and 2.00 mg/kg, or between 0.30 mg/kg and 1.50 mg/kg of the subject's body weight.

In certain embodiments, the recommended daily dose range of a composition provided herein for the conditions described herein lie within the range of from about 0.1 mg to about 1000 mg per day, given as a single once-a-day dose or as divided doses throughout a day. In certain embodiments, the daily dose is administered twice daily in equally divided doses. In certain embodiments, a daily dose range should be from about 10 mg to about 200 mg per day, in other embodiments, between about 10 mg and about 150 mg per day, in further embodiments, between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the herein described dosage amounts and dose frequency schedules. Further, when a subject is administered multiple dosages of a composition provided herein, not all of the dosages need be the same. In certain embodiments, the dosage administered to the subject may be increased to improve the prophylactic or therapeutic effect of the composition or it may be decreased to reduce one or more side effects that a particular subject is experiencing.

In certain embodiment, the dosage of the composition provided herein, based on weight of the active compound, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In certain embodiments, treatment or prevention can be initiated with one or more loading doses of a compound or composition provided herein followed by one or more maintenance doses. In such embodiments, the loading dose can be, for instance, about 60 to about 400 mg per day, or about 100 to about 200 mg per day for one day to five weeks. The loading dose can be followed by one or more maintenance doses. In certain embodiments, each maintenance does is, independently, about from about 10 mg to about 200 mg per day, between about 25 mg and about 150 mg per day, or between about 25 and about 80 mg per day. Maintenance doses can be administered daily and can be administered as single doses, or as divided doses.

In certain embodiments, a dose of a compound or composition provided herein can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound or composition provided herein is administered to achieve a steady-state concentration in blood or serum of the subject of from about 300 to about 4000 ng/mL, from about 400 to about 1600 ng/mL, or from about 600 to about 1200 ng/mL. In some embodiments, loading doses can be administered to achieve steady-state blood or serum concentrations of about 1200 to about 8000 ng/mL, or about 2000 to about 4000 ng/mL for one to five days. In certain embodiments, maintenance doses can be administered to achieve a steady-state concentration in blood or serum of the subject of from about 300 to about 4000 ng/mL, from about 400 to about 1600 ng/mL, or from about 600 to about 1200 ng/mL.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, provided herein are unit dosages comprising a compound, or a pharmaceutically acceptable salt thereof, in a form suitable for administration. Such forms are described in detail herein. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

In certain embodiments, dosages of the second agents to be used in a combination therapy are provided herein. In certain embodiments, dosages lower than those which have been or are currently being used to treat pain are used in the combination therapies provided herein. The recommended dosages of second agents can be obtained from the knowledge of those of skill in the art. For those second agents that are approved for clinical use, recommended dosages are described in, for example, Hardman et al., eds., 1996, Goodman & Gilman's The Pharmacological Basis Of Therapeutics $9^{th}$ Ed, Mc-Graw-Hill, New York; Physician's Desk Reference (PDR) $57^{th}$ Ed., 2003, Medical Economics Co., Inc., Montvale, N.J.; which are incorporated herein by reference in their entirety.

In various embodiments, the therapies (e.g., a compound provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart. In various embodiments, the therapies are administered no more than 24 hours apart or no more than 48 hours apart. In certain embodiments, two or more therapies are administered within the same patient visit. In other embodiments, the compound provided herein and the second agent are administered concurrently.

In other embodiments, the compound provided herein and the second agent are administered at about 2 to 4 days apart, at about 4 to 6 days apart, at about 1 week part, at about 1 to 2 weeks apart, or more than 2 weeks apart.

In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In certain embodiments, a compound provided herein and a second agent are administered to a patient, in certain embodiments, a mammal, such as a human, in a sequence and within a time interval such that the compound provided herein can act together with the other agent to provide an increased benefit than if they were administered otherwise. In certain embodiments, the second active agent can be administered at the same time or sequentially in any order at different points in time; however, if not administered at the same time, they should be administered sufficiently close in time so as to provide the desired therapeutic or prophylactic effect. In certain embodiments, the compound provided herein and the second active agent exert their effect at times which overlap. Each second active agent can be administered separately, in any appropriate form and by any suitable route. In other embodiments, the compound provided herein is administered before, concurrently or after administration of the second active agent.

In certain embodiments, the compound provided herein and the second agent are cyclically administered to a patient. Cycling therapy involves the administration of a first agent (e.g., a first prophylactic or therapeutic agent) for a period of time, followed by the administration of a second agent and/or third agent (e.g., a second and/or third prophylactic or therapeutic agent) for a period of time and repeating this sequential administration. Cycling therapy can reduce the development of resistance to one or more of the therapies, avoid or reduce the side effects of one of the therapies, and/or improve the efficacy of the treatment.

In certain embodiments, the compound provided herein and the second active agent are administered in a cycle of less than about 3 weeks, about once every two weeks, about once every 10 days or about once every week. One cycle can comprise the administration of a compound provided herein and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of the second agent are administered separately yet within a time interval such that the compound provided herein can work together with the second active agent. In certain embodiments, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the compound provided herein. In certain embodiments, the compound provided herein is administered concurrently with one or more second agents in the same pharmaceutical composition. In another embodiment, a compound provided herein is administered concurrently with one or more second agents in separate pharmaceutical compositions. In still another embodiment, a compound provided herein is administered prior to or subsequent to administration of a second agent. Also contemplated are administration of a compound provided herein and a second agent by the same or different routes of administration, e.g., oral and parenteral. In certain embodiments, when the compound provided herein is administered concurrently with a second agent that potentially produces adverse side effects including, but not limited to, toxicity, the second active agent can advantageously be administered at a dose that falls below the threshold that the adverse side effect is elicited.

Kits

Also provided are kits for use in methods of treatment of pain and/or a condition associated with voltage-gated sodium channel function or a pain-related disorder. The kits can include a compound or composition provided herein, a second agent or composition, and instructions providing information to a health care provider regarding usage for treating the pain or a pain-related disorder. Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 day. In some embodiments, a compound or composition can be included as a sterile aqueous pharmaceutical composition or dry powder (e.g., lyophilized) composition.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Methods of Use

Provided herein is a method for treating a condition associated with voltage-gated sodium channel function and/or pain in a subject, which comprises contacting the subject with a therapeutically or prophylactically effective amount of a 11,13-modified saxitoxin disclosed herein, e.g., a 11,13-modified saxitoxin of Formula (I)-(Ik) and I-P and 1-122, including a single enantiomer, a mixture of an enantiomeric pair, an individual diastereomer, a mixture of diastereomers, an individual stereoisomer, a mixture of stereoisomers, or a tautomeric form thereof; or a pharmaceutically acceptable salt, solvate, prodrug, phosphate, or active metabolite thereof.

In certain embodiments, provided herein are methods for treating pain and/or a condition associated with voltage-gated sodium channel function in a subject. In certain embodiments, the methods encompass the step of administering to the subject in need thereof an amount of a compound effective for the treatment pain and/or a condition associated with voltage-gated sodium channel function in combination with a second agent effective for the treatment or prevention of pain and/or a condition associated with voltage-gated sodium channel function. The compound can be any compound as described herein, and the second agent can be any second agent described in the art or herein. In certain embodiments, the compound is in the form of a pharmaceutical composition or dosage form, as described elsewhere herein.

In certain embodiments, provided herein are methods for treating a condition associated with voltage-gated sodium channel function in a subject. In certain embodiments, the methods encompass the step of administering to the subject in need thereof a therapeutically or prophylactically effective amount of a compound effective for the treatment of a condition associated with voltage-gated sodium channel function in combination with a second agent effective for the treatment of a condition associated with voltage-gated sodium channel function. The compound can be any compound as described herein, and the second agent can be any second agent described in the art or herein. In certain embodiments, the compound is in the form of a pharmaceutical composition or dosage form, as described elsewhere herein.

In certain embodiments, the pain to be reduced, ameliorated, treated, or prevented is associated with a condition selected from erythromelalgia, diabetic peripheral neuropathy, paroxysmal extreme pain disorder, complex regional pain syndrome, trigeminal neuralgia, multiple sclerosis, osteoarthritis, postherpetic neuralgia, cancer pain, cluster headache, migraine, sciatica, endometriosis, fibromyalgia, and postsurgical pain In certain embodiments, the condition associated with voltage-gated sodium channel function is selected from epilepsy, Parkinson's disease, a mood disorder, psychosis, amyotropic lateral sclerosis, glaucoma, ischemia, a spasticity disorder, and obsessive compulsive disorder.

In some embodiments, the compounds described herein are used for the reduction of the severity or duration of pain. In some embodiments, the compounds described herein are used for the reduction of the severity or duration of pain associated with voltage-gated sodium channel function.

In some embodiments, the compounds described herein are used for prevention of pain or of a condition associated with voltage-gated sodium channel function.

In some embodiments, the compounds described herein are used for treatment of pain or of a condition associated with voltage-gated sodium channel function.

Assay Methods

Compounds can be assayed for efficacy in treating pain and/or a condition associated with voltage-gated sodium channel function according to any assay known to those of skill in the art. Exemplary assay methods are provided elsewhere herein.

Second Therapeutic Agents

In certain embodiments, the compounds and compositions provided herein are useful in methods of treatment of pain and/or a condition associated with voltage-gated sodium channel function, that comprise further administration of a second agent effective for the treatment of pain and/or a pain-related disorder and/or a condition associated with voltage-gated sodium channel function. The second agent can be any agent known to those of skill in the art to be effective for the treatment of pain and/or a pain-related disorder and/or a condition associated with voltage-gated sodium channel function, including those currently approved by the United States Food and Drug Administration, or other similar body of a country foreign to the United States. In some embodiments, the second agent is a local anesthetic (in some embodiments, a steroid), a vasoconstrictor, a glucocorticoid, adrenergic drugs (in some embodiments, alpha agonists or mixed central-peripheral alpha-2-agonists), vanilloids, or a chemical permeation enhancer. In some embodiments, chemical permeation enhancers include anionic surfactants, cationic surfactants, nonionic surfactants. In some embodiments, the second agent is bupivacaine, levobupivicaine, tetracaine, ropivacaine, epinephrine, phenylephrine, clonidine, sodium lauryl sulfate, sodium octyl sulfate, dodecyltrimethylammonium bromide, octyltrimethylammonium bromide, polyoxyethylene (20) sorbitan monolaurate, and/or polyoxyethylene (20) sorbitan monooleate.

In certain embodiments, a compound provided herein is administered in combination with one second agent. In further embodiments, a compound provided herein is administered in combination with two second agents. In still further embodiments, a compound provided herein is administered in combination with two or more second agents.

As used herein, the term "in combination" includes the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

As used herein, the term "synergistic" includes a combination of a compound provided herein and another therapy (e.g., a prophylactic or therapeutic agent) which has been or is currently being used to prevent, manage or treat a disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The active compounds provided herein can be administered in combination or alternation with another therapeutic agent, in particular an agent effective in the treatment of pain and/or a pain-related disorder and/or a condition associated with voltage-gated sodium channel function. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the pain or a pain-related disorder to be alleviated. It is to be further understood that for any particular subject, specific dosage regimens and schedules should be adjusted over time according to the individual need and the professional judgment of the person administering or supervising the administration of the compositions.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography); THF (tetrahydrofuran); $CDCl_3$ (deuterated chloroform); AcOH (acetic acid); DCM (dichloromethane); DMSO (dimethylsulfoxide); DMSO-$d_6$ (deuterated dimethylsulfoxide); EtOAc (ethyl acetate); MeOH (methanol); Tces (2,2,2-trichloroethoxysulfonyl); —Si(tert-Bu)(Ph)$_2$ and —Si$^t$BuPh$_2$ (tert-butyl-diphenylsilyl); and BOC (t-butyloxycarbonyl).

For all of the following examples, standard work-up and purification methods known to those skilled in the art can be utilized. Unless otherwise indicated, all temperatures are expressed in ° C. (degrees Celsius). All reactions are conducted at room temperature unless otherwise noted. Synthetic methodologies illustrated herein are intended to exemplify the applicable chemistry through the use of specific examples and are not indicative of the scope of the disclosure.

Example 1

Preparation of 11,13-Modified Saxitoxin Compounds

Scheme 1

Preparation of Compounds (1) and (2)

A solution of alcohol A (74.0 mg, 121.5 μmol, 1.0 equiv) which can be prepared using procedures known to one of ordinary skill in the art (e.g. see US2010/0284913), triphenylphosphine (63.8 mg, 243.3 μmol, 2.0 equiv), and phthalimide (35.6 mg, 242.0 μmol, 2.0 equiv) in THF (1.4 mL) was cooled to 0° C. Diisopropyl azodicarboxylate (49 μL, 249.7 μmol, 2.1 equiv) was added dropwise over 5 minutes and the reaction was warmed to room temperature. After 5 hours additional portions triphenylphosphine (63.0 mg), phthalimide (36.0 mg), and diisopropyl azodicarboxylate (49 μL) were added sequentially. The reaction was stirred for 14 hours and concentrated under reduced pressure. Purification of the residue by chromatography on silica gel (gradient elution: hexanes→2:1 EtOAc/hexanes) afforded the phthalimide B as a white solid (80.0 mg, 108.4 μmol, 89%).

To a solution of olefin B (80.0 mg, 108.4 μmol, 1.0 equiv) in 2.0 mL mL of THF were added sequentially N-methylmorpholine-N-oxide (26.0 mg, 230 μmol, 2.1 equiv) and $OsO_4$ (26 μL of a 4% aqueous solution, 4.1 μmol, 0.04 equiv). The reaction mixture was stirred for 14 h and then quenched by the addition of 2.5 mL of saturated aqueous $Na_2S_2O_3$. The contents were diluted with 8.0 mL of EtOAc and transferred to a separatory funnel. The organic layer was collected and the aqueous phase was extracted with 3×8.0 mL of EtOAc. The combined organic extracts were dried over MgSO₄ and concentrated under reduced pressure. Purification of the oily residue by chromatography on silica gel (gradient elution: hexanes→3:1 EtOAc/hexanes) afforded the diol C as a white solid (42.0 mg, 54.3 μmol, 50%).

Dimethylaminopyridine (12.7 mg, 103.6 μmol, 4.0 equiv) and the 2,5-dioxopyrrolidin-1-yl 2,5-bis(trifluoromethyl)benzoate (10.2 mg, 28.4 μmol, 1.1 equiv) were added to a solution of diol C (20.0 mg, 25.9 μmol, 1.0 equiv) in 1.0 mL CH₂Cl₂ at 0° C. The mixture was allowed to warm slowly to room temperature. After 20 h the reaction mixture was loaded directly to a column of silica gel. Purification by chromatography on silica gel (gradient elution: hexanes→2:1 hexanes/EtOAc) afforded the benzoate D as a white solid (14.0 mg, 13.8 μmol, 54%).

To a solution of benzoate D (14.0 mg, 13.8 μmol, 1.0 equiv) in 1.0 mL of CH₂Cl₂ was added Dess-Martin periodinane (23 mg, 55.3 μmol, 4.0 equiv). The reaction was stirred for 15 min and then loaded directly to a column of silica gel. Purification of the residue by chromatography on silica gel (gradient elution: hexanes-3:1 EtOAc/hexanes) afforded intermediate E as a white solid.

Trifluoroacetic acid (50 μL) and PdCl₂ (5.0 mg) were added to a solution of intermediate E in 3:1 MeOH/H₂O (4.0 mL). H₂ gas was bubbled through the reaction mixture for 30 minutes, after which time bubbling was ceased and the reaction was stirred under an atmosphere of H₂ for 20 h. The reaction mixture was sequentially filtered through a 0.2 μm PTFE syringe filter. The flask and filters were washed with 10 mL of MeOH and the filtrate concentrated under reduced pressure. The thin-film residue was dissolved in 4.0 mL of 1:1 MeCN/1.0 M aqueous HCl. After 3 h the reaction mixture was concentrated under reduced pressure, dissolved in 1.5 mL of a 10 mM aqueous heptafluorobutyric acid solution and purified by reversed-phase HPLC (Bonna-Agela Durashell C18, 10 μM, 21.2×250 mm column, eluting with gradient flow over 40 min of 0:100→60:40 MeCN/10 mM aqueous C₃F₇CO₂H, 214 nm UV detection). At a flow rate of 13 mL/min, compound (2) had a retention time of 31.1-31.8 min and was isolated as a white hygroscopic solid (2.7 μmol, 20% over 2 steps). Compound (1) had a retention time of 32.1-32.7 min and was isolated as a white hygroscopic solid (1.3 μmol, 9.4%% over 2 steps). (1): MS (ES+) m/z calcd. for $C_{26}H_{27}F_6N_7O_6$ 647.19 found 648.12 (MH⁺). (2): MS (ES+) m/z calcd. for $C_{26}H_{23}F_6N_7O_5$ 627.17 found 628.09 (MH⁺).

Scheme 2

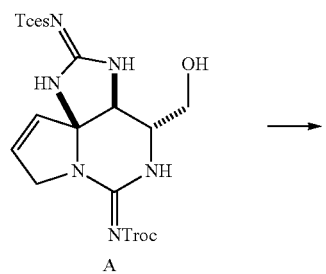

A

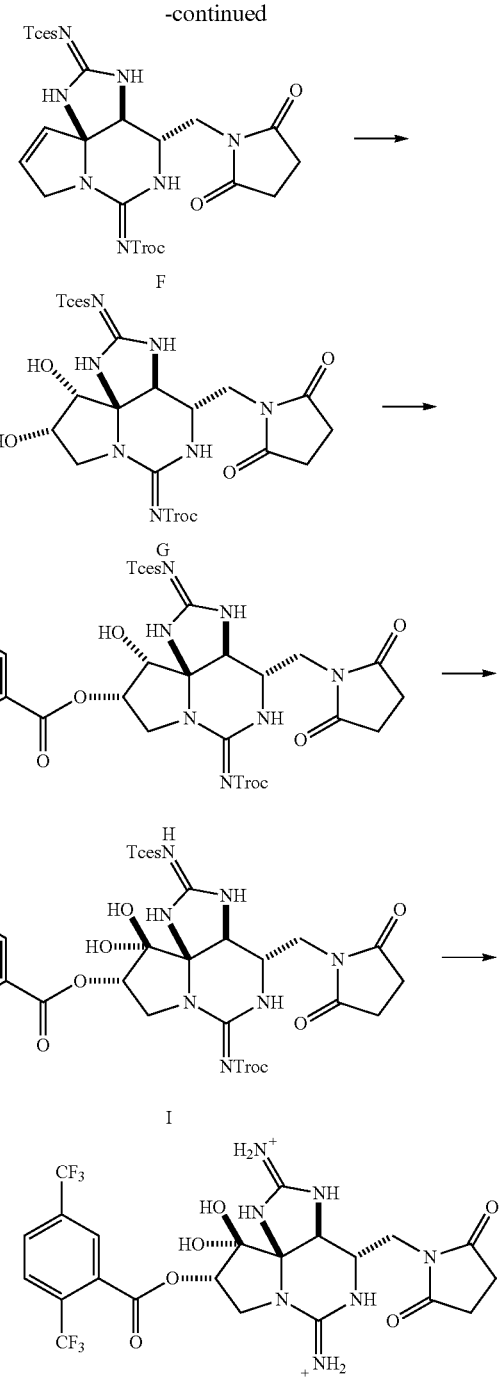

Preparation of Compound (7)

To a solution of triphenylphosphine (376 mg, 1.43 mmol, 2.5 equiv) in THF (9.2 mL) cooled to 0° C. was added diisopropyl azodicarboxylate (283 μL, 1.44 mmol, 2.5 equiv) dropwise over 5 minutes. The mixture was stirred at this temperature for an additional 15 min, during which time a white precipitate formed. In a separate flask, alcohol A (350 mg, 0.575 mmol, 1.0 equiv) was dissolved in 21.5 mL of THF and cooled to 0° C. To the solution of A was added the white suspension of PPh₃/DIAD dropwise over ~5 minutes. After an additional 15 minutes, succinimide (197 mg, 2.0 mmol, 3.5 equiv) was added in a single portion and the reaction was warmed to room temperature. After 4 hours the reaction was concentrated under reduced pressure. Purification of the residue by chromatography on silica gel (gradient elution: hexanes→3:1 EtOAc/hexanes) afforded the succinimide F as a white solid (205 mg, 0.297 mmol, 52%).

To a solution of olefin F (85.7 mg, 124 μmol, 1.0 equiv) in 2.0 mL of THF were added sequentially N-methylmorpholine-N-oxide (30.0 mg, 256 μmol, 2.1 equiv) and $OsO_4$ (30 μL of a 4% aqueous solution, 4.7 μmol, 0.04 equiv). The reaction mixture was stirred for 14 h and then quenched by the addition of saturated aqueous $Na_2S_2O_3$. The contents were diluted with EtOAc and transferred to a separatory funnel. The organic layer was collected and the aqueous phase was extracted with EtOAc. The combined organic extracts were dried over $MgSO_4$ and concentrated under reduced pressure. Purification of the oily residue by chromatography on silica gel (gradient elution: hexanes→4:1 EtOAc/hexanes) afforded the diol G as a white solid (44.0 mg, 61 μmol, 49%).

Dimethylaminopyridine (16 mg, 132.6 μmol, 4.0 equiv) and 2,5-dioxopyrrolidin-1-yl 2,5-bis(trifluoromethyl)benzoate (13 mg, 36.4 μmol, 1.1 equiv) were added to a solution of diol G (24 mg, 33.14 μmol, 1.0 equiv) in 1.5 mL of $CH_2Cl_2$ at 0° C. The mixture was allowed to warm slowly to room temperature. After 20 h the reaction mixture was load directly to a column of silica gel. Purification by chromatography on silica gel (gradient elution: hexanes→2:1 EtOAc/hexanes) afforded the benzoate H as a white solid (14 mg, 14.5 μmol, 44%).

To a solution of benzoate H (14.0 mg, 14.5 μmol, 1.0 equiv) in 1.0 mL of $CH_2Cl_2$ was added Dess-Martin periodinane (24.6 mg, 58.0 μmol, 4.0 equiv). The reaction was stirred for 15 min and then loaded directly to a column of silica gel. Purification by chromatography on silica gel (gradient elution: hexanes→2:1 EtOAc/hexanes) afforded intermediate I as a white solid.

Trifluoroacetic acid (100 μL) and $PdCl_2$ (7.0 mg) were added to a solution of intermediate E in 3:1 MeOH/$H_2O$ (4.0 mL). $H_2$ gas was bubbled through the reaction mixture for 30 minutes, after which time bubbling was ceased and the reaction was stirred under an atmosphere of $H_2$ for 20 h. The reaction mixture was sequentially filtered through a 0.2 μm PTFE syringe filter. The flask and filters were washed with 10 mL of MeOH and the filtrate concentrated under reduced pressure. The thin-film residue was dissolved in 4 mL of 1:1 MeCN/1.0 M aqueous HCl. After 3 h the reaction mixture was concentrated under reduced pressure, dissolved in 1.5 mL of a 10 mM aqueous heptafluorobutyric acid solution and purified by reversed-phase HPLC (Bonna-Agela Durashell C18, 10 μM, 21.2×250 mm column, eluting with gradient flow over 40 min of 0:100→60:40 MeCN/10 mM aqueous $C_3F_7CO_2H$, 214 nm UV detection). At a flow rate of 13 mL/min, compound (7) had a retention time of 29.1-29.9 min and was isolated as a white hygroscopic solid (6.7 μmol, 46% over 2 steps). $^1$H NMR ($D_2O$, 400 MHz) δ 8.47 (s, 1H), 8.35-8.30 (m, 2H), 5.82 (dd, J=7.1, 5.2 Hz, 1H), 5.09 (s, 1H), 4.48 (dd, J=11.3, 7.1 Hz, 1H), 4.08 (dd, J=13.8, 12.0 Hz, 1H), 3.96 (dd, J=11.9, 3.2 Hz, 1H), 3.88 (dd, J=11.3, 5.2 Hz, 1H), 3.63 (dd, J=14.0, 3.3 Hz, 1H), 2.95 (s, 4H) ppm.

Scheme 3

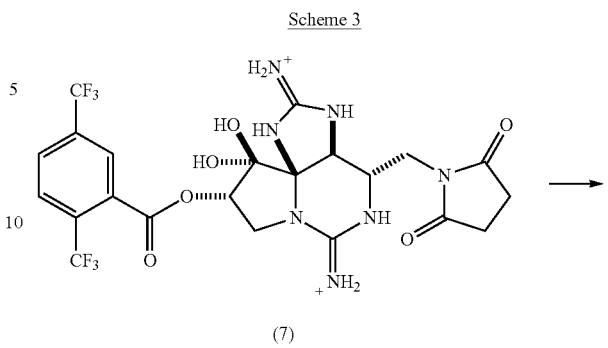

(7)

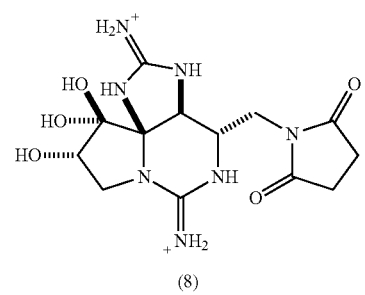

(8)

Preparation of Compound (8)

Compound (7) (2 μmol) was dissolved in 1.0 mL of 2.0 M $NH_3$ in MeOH. The reaction was stirred for 15 minutes, concentrated in vacuo, and immediately redissolved in 1.0 mL of 1.0 M HCl. After 17 h the reaction mixture was concentrated under reduced pressure, dissolved in 1.5 mL of a 10 mM aqueous heptafluorobutyric acid solution and purified by reversed-phase HPLC (Bonna-Agela Durashell C18, 10 μM, 21.2×250 mm column, eluting with gradient flow over 40 min of 10:90→40:60 MeCN/10 mM aqueous $C_3F_7CO_2H$, 214 nm UV detection). At a flow rate of 13 mL/min, compound (8) had a retention time of 15.4-16.4 min and was isolated as a white hygroscopic solid (0.75 μmol, 38%). $^1$H NMR ($D_2O$, 400 MHz) δ 4.96 (s, 1H), 4.58-4.54 (m, 1H), 4.16-4.02 (m, 2H), 3.89-3.85 (m, 1H), 3.67-3.62 (m, 1H), 3.44-3.39 (m, 1H), 2.91 (s, 4H) ppm.

Scheme 4

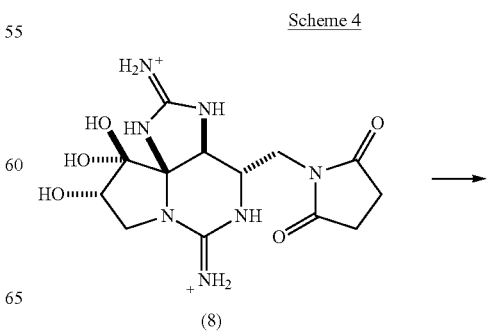

(8)

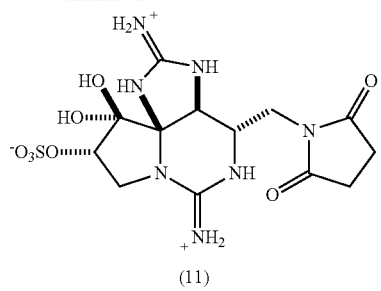

(11)

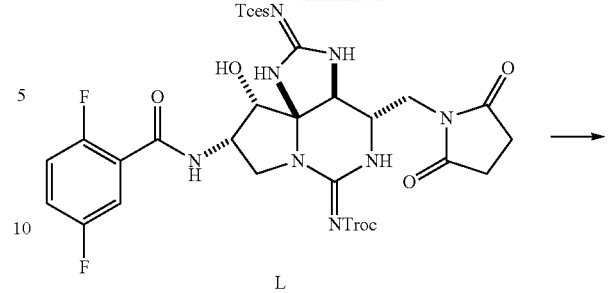

Preparation of Compound (11)

To a solution of (8) (10 mg, 12.8 μmol) and 2,6-di-tert-butyl-4-methylpyridine (72 mg, 352 μmol, 27.5 equiv) was added dropwise DMF.SO$_3$ (1.16 mL of a 0.1 M solution in dimethylformamide, 116.5 μmol, 9.1 equiv). The reaction mixture was stirred for 1 h, then quenched by the addition of 400 μL of H$_2$O. The solution was concentrated in vacuo and the thin-film residue was purified by reversed-phase HPLC (Bonna-Agela Durashell C18, 10 μM, 21.2×250 mm column, eluting with gradient flow over 40 min of 0:100→40:60 MeCN/10 mM aqueous C$_3$F$_7$CO$_2$H, 214 nm UV detection). At a flow rate of 13 mL/min, compound (11) had a retention time of 13.0-13.8 min and was isolated as a white hygroscopic solid (6.7 μmol, 52%). $^1$H NMR (D$_2$O, 400 MHz) δ 5.07-5.03 (m, 1H), 4.97 (s, 1H), 4.28 (dd, J=10.5, 8.1 Hz, 1H), 4.05 (dd, J=14.3, 11.9 Hz, 1H), 3.87-3.84 (m, 1H), 3.70 (dd, J=10.5, 6.8 Hz, 1H), 3.64 (dd J=14.1, 3.4 Hz, 1H), 2.88 (s, 4H) ppm.

Scheme 5

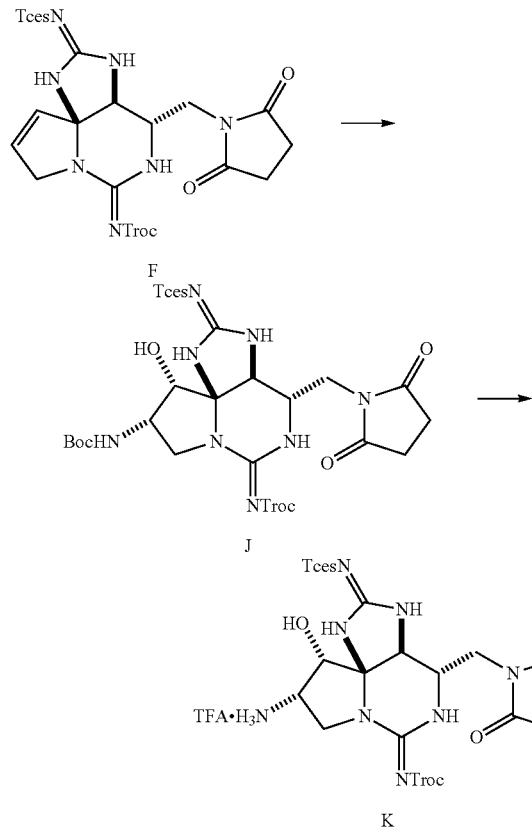

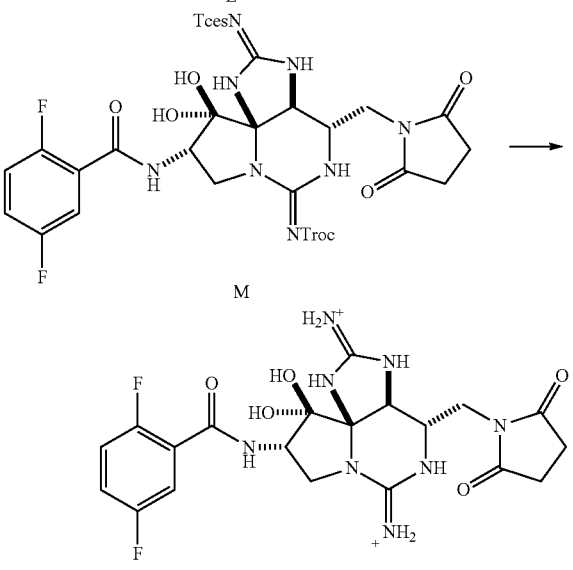

(28)

Preparation of Compound (28)

To solution of tert-butyl 4-chlorobenzoyloxycarbamate (353 mg, 1.30 mmol, 3.4 equiv) in CH$_3$CN (7.8 mL) was added OsO$_4$ (123 μL of a 4% aqueous solution, 19 μmol, 0.05 equiv). After 25 minutes a solution of F (262 mg, 379 μmol, 1.0 equiv) in 3.0 mL of CH$_3$CN was added followed immediately by the addition of 1.08 mL of H$_2$O. The resulting mixture was stirred at room temperature for 3 days, and quenched by the addition of 1.8 mL of 1:1 saturated aqueous Na$_2$S$_2$O$_3$/saturated aqueous NaHCO$_3$. The mixture was stirred for an additional 5 minutes then diluted with H$_2$O (35 mL) and extracted with 3×70 mL of EtOAc. The combined organic layers were washed with 2×28 mL of saturated aqueous NaHCO$_3$, dried with MgSO$_4$ and concentrated in vacuo. Purification of the residue by chromatography on silica gel (gradient elution: hexanes→1:3 hexanes/EtOAc) afforded the carbamate J as a white solid (141 mg, 171 μmol, 45%).

To solution of J (141 mg, 171 μmol) in 6.2 mL of dichloromethane was added trifluoroacetic acid (1.3 mL). The resulting solution was stirred at room temperature for 4 hrs and concentrated in vacuo to afford the trifluoroacetate salt K that was used in the following step without purification.

To a solution of K (21 mg, 25.1 μmol, 1.0 equiv) in 1 mL of CH$_2$Cl$_2$ was added Et$_3$N (14 μL, 100 μmol, 4.0 equiv). The resulting solution was stirred at room temperature for 15 minutes followed by addition of 2,5-dioxopyrrolidin-1-yl 2,5-difluorobenzoate (8.0 mg, 27.6 μmol, 1.1 equiv). The resulting solution was stirred for 20 hours and reaction mixture was loaded directly to a column of silica gel.

Purification by chromatography on silica gel (gradient elution: hexanes→1:2 hexanes/EtOAc) afforded intermediate L as a white solid (14 mg, 16.2 μmol, 65%).

To a solution of amide L (14 mg, 16.2 μmol, 1.0 equiv) in 1.0 mL of CH$_2$Cl$_2$ was added Dess-Martin periodinane (28 mg, 66 μmol, 4.1 equiv). The reaction was stirred at room temperature for 20 min and then loaded directly to a column of silica gel. Purification by chromatography on silica gel (gradient elution: hexanes→1:2 hexanes/EtOAc) afforded intermediate M as a white solid.

Trifluoroacetic acid (140 μL) and PdCl$_2$ (12 mg) were added to a solution of intermediate M in 3:1 MeOH/H$_2$O (4 mL). H$_2$ gas was bubbled through the reaction mixture for 30 minutes, after which time bubbling was ceased and the reaction was stirred under an atmosphere of H$_2$ for 20 h. The reaction mixture was sequentially filtered through a 0.2 μm PTFE syringe filter. The flask and filters were washed with 10 mL of MeOH and the filtrate concentrated under reduced pressure. The thin-film residue was dissolved in 4 mL of 1:1 MeCN/1.0 M aqueous HCl. After 3 h the reaction mixture was concentrated under reduced pressure, dissolved in 1.5 mL of a 10 mM aqueous heptafluorobutyric acid solution and purified by reversed-phase HPLC (Bonna-Agela Durashell C18, 10 μM, 21.2×250 mm column, eluting with gradient flow over 40 min of 0:100→60:40 MeCN/10 mM aqueous C$_3$F$_7$CO$_2$H, 214 nm UV detection). At a flow rate of 13 mL/min, compound (28) had a retention time of 23.9-24.7 min and was isolated as a white hygroscopic solid (2.4 μmol, 15% over 2 steps). $^1$H NMR (D$_2$O, 400 MHz) δ 7.77-7.70 (m, 1H), 7.60-7.48 (m, 2H), 5.17-5.12 (m, 1H), 5.04 (s, 1H), 4.40 (t, J=9.8 Hz, 1H), 4.17-4.05 (m, 1H), 4.01-3.97 (m, 1H), 3.73 (dd, J=14.0, 3.2 Hz, 1H), 3.64 (dd, J=10.0, 8.9 Hz, 1H), 2.99 (s, 4H) ppm.

Scheme 6

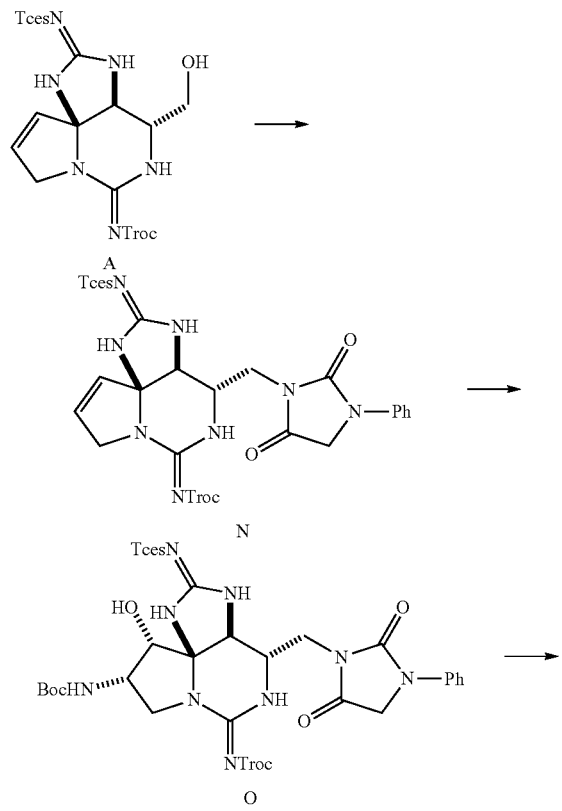

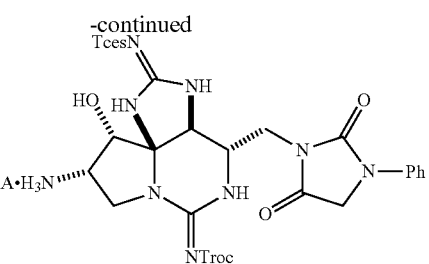

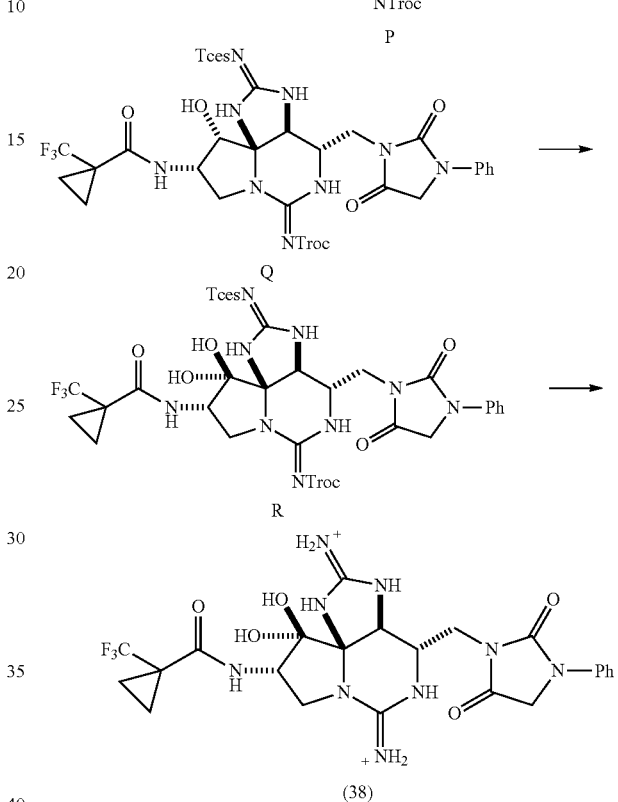

Preparation of Compound (38)

To a solution of triphenylphosphine (118 mg, 0.45 mmol, 2.5 equiv) in 3.0 mL of THF cooled to 0° C. was added diisopropyl azodicarboxylate (89 μL, 0.45 mmol, 2.5 equiv) dropwise over 5 minutes. The mixture was stirred at this temperature for an additional 15 min, during which time a white precipitate formed. In a separate flask, alcohol A (110 mg, 0.18 mmol, 1.0 equiv) was dissolved in 7.0 mL of THF and cooled to 0° C. To the solution of A was added the suspension of PPh$_3$/DIAD dropwise over ~5 minutes. After an additional 15 minutes, 1-phenylhydantoin (111 mg, 0.63 mmol, 3.5 equiv) was added in a single portion and the reaction was warmed to room temperature. After 14 hours the reaction was concentrated under reduced pressure. Purification of the residue by chromatography on silica gel (gradient elution: CH$_2$Cl$_2$→4:1 CH$_2$Cl$_2$/actone) afforded the hydantoin N as a white solid (130 mg, 0.17 mmol, 94%).

To solution of tert-butyl 4-chlorobenzoyloxycarbamate (156 mg, 575 μmol, 3.4 equiv) in 2.8 mL of CH$_3$CN was added OsO$_4$ (53.1 μL of a 4% aqueous solution, 7.8 μmol, 0.05 equiv). After 25 minutes a solution of N (130 mg, 169 μmol, 1.0 equiv) in 2.0 mL of CH$_3$CN was added followed immediately by the addition of 0.48 mL of H$_2$O. The resulting mixture was stirred at room temperature for 3 days, and quenched by the addition of 0.7 mL of 1:1 saturated aqueous Na$_2$S$_2$O$_3$/saturated aqueous NaHCO$_3$. The mixture was stirred for an additional 5 minutes then diluted with H$_2$O (18 mL) and extracted with 3×40 mL of EtOAc. The combined organic layers were washed with 2×14 mL of saturated aqueous NaHCO$_3$, dried with MgSO$_4$ and concentrated in vacuo. Purification of the residue by chromatography on silica gel (gradient elution: CH$_2$Cl$_2$→5:1 CH$_2$Cl$_2$/acetone) afforded the carbamate O as a white solid (83 mg, 89 μmol, 53%).

To solution of O (83 mg, 89 μmol) in 3.5 mL of dichloromethane was added trifluoroacetic acid (0.7 mL). The resulting solution was stirred at room temperature for 4 hrs and concentrated in vacuo to afford the trifluoroacetate salt P that was used in the following step without purification.

To a solution of P (25 mg, 27 μmol, 1.0 equiv) in 1.0 mL of CH$_2$Cl$_2$ was added Et$_3$N (15 μL, 108 μmol, 4.0 equiv). The resulting solution was stirred at room temperature for 15 minutes followed by addition of 2,5-dioxopyrrolidin-1-yl 1-(trifluoromethyl)cyclopropane-1-carboxylate (7.5 mg, 30 μmol, 1.1 equiv). The resulting solution was stirred for 20 hours and reaction mixture was loaded directly to a column of silica gel. Purification by chromatography on silica gel (gradient elution: hexanes→1:2 hexanes/EtOAc) afforded intermediate Q as a white solid (6 mg, 6.4 μmol, 24%).

To a solution of amide Q (6 mg, 6.4 μmol, 1.0 equiv) in 1.0 mL of CH$_2$Cl$_2$ was added Dess-Martin periodinane (11 mg, 26 μmol, 4.1 equiv). The reaction was stirred for 20 min and then loaded directly to a column of silica gel. Purification by chromatography on silica gel (gradient elution: hexanes→1:2 hexanes/EtOAc) afforded intermediate R as a white solid.

Trifluoroacetic acid (60 μL) and PdCl$_2$ (5 mg) were added to a solution of intermediate R in 3:1 MeOH/H$_2$O (4.0 mL). H$_2$ gas was bubbled through the reaction mixture for 30 minutes, after which time bubbling was ceased and the reaction was stirred under an atmosphere of H$_2$ for 20 h. The reaction mixture was sequentially filtered through a 0.2 μm PTFE syringe filter. The flask and filters were washed with 10 mL of MeOH and the filtrate concentrated under reduced pressure. The thin-film residue was dissolved in 4 mL of 1:1 MeCN/1.0 M aqueous HCl. After 3 h the reaction mixture was concentrated under reduced pressure, dissolved in 1.5 mL of a 10 mM aqueous heptafluorobutyric acid solution and purified by reversed-phase HPLC (Bonna-Agela Durashell C18, 10 μM, 21.2×250 mm column, eluting with gradient flow over 40 min of 0:100→60:40 MeCN/10 mM aqueous C$_3$F$_7$CO$_2$H, 214 nm UV detection). At a flow rate of 13 mL/min, compound (38) had a retention time of 28.2-29.3 min and was isolated as a white hygroscopic solid (0.47 μmol, 7.3% over two steps). $^1$H NMR (D$_2$O, 400 MHz) δ 7.84-7.82 (m, 2H), 7.77-7.73 (m, 2H), 7.58-7.54 (m, 1H), 5.09 (s, 1H), 5.05-5.01 (m, 1H), ~4.80 (s, 2H, under solvent peak), 4.39-4.34 (m, 1H), 4.26 (dd, J=14.3, 11.6 Hz, 1H), 4.15-4.11 (m, 1H), 3.90 (dd, J=14.3, 3.5 Hz, 1H), 3.64 (dd, J=10.2, 8.5 Hz, 1H), 1.68 (s, 4H) ppm.

Scheme 7

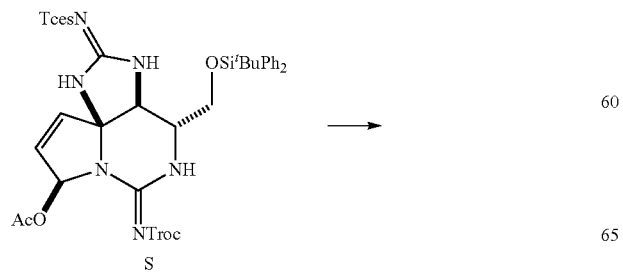

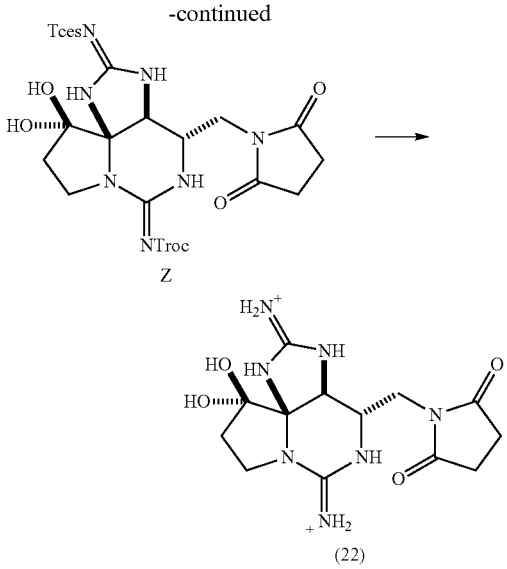

(22)

Preparation of Compound (22)

To a −78° C. solution of acetate S (400 mg, 0.442 mmol, 1.0 equiv) in 10 mL of THF was added dropwise tetrabutylammonium fluoride (530 μL of a 1.0 M solution in THF, 0.53 mmol, 1.2 equiv). The mixture was warmed to 0° C. and stirred at this temperature for 30 min. Following this time, the reaction was quenched by the addition of 10 mL saturated NH$_4$Cl. The contents were diluted with 20 mL of EtOAc and transferred to a separatory funnel. The organic layer was collected and the aqueous phase was extracted with 2×20 mL EtOAc. The combined organic extracts were dried over MgSO$_4$, filtered, and concentrated under reduced pressure. Purification of the residue by chromatography on silica gel (gradient elution: hexanes→2:1 EtOAc/hexanes) afforded the alcohol T as a white solid (176 mg, 0.264 mmol, 60%).

To a solution of triphenylphosphine (344 mg) in THF (8.0 mL) cooled to 0° C. was added diisopropyl azodicarboxylate (256 μL) dropwise over 5 minutes. The mixture was stirred at this temperature for an additional 10 min, during which time a white precipitate formed. In a separate flask, alcohol T (176 mg, 264 μmol, 1.0 equiv) was dissolved in 8.0 mL of THF and cooled to 0° C. To the solution of T was added 3.2 mL (2.0 equiv) of the white PPh$_3$/DIAD suspension dropwise over ~5 minutes. After an additional 10 minutes, succinimide (78 mg, 792 μmol, 3.0 equiv) was added in a single portion and the reaction was warmed to room temperature. After 4 hours the reaction was concentrated under reduced pressure. Purification of the residue by chromatography on silica gel (gradient elution: CH$_2$Cl$_2$→3:1 CH$_2$Cl$_2$/acetone) afforded the succinimide U as a white solid (142 mg, 190 μmol, 72%).

To a solution of N,O-acetal U (142 mg, 190 μmol, 1.0 equiv) in 3.0 mL of CH$_2$Cl$_2$ was added thiophenol (62 μL, 608 mmol, 3.2 equiv) and BF$_3$.OEt$_2$ (54 μL, 438 μmol, 2.3 equiv). The red-brown solution was warmed to 40° C. and stirred at this temperature for 1.5 h. The reaction was then quenched by the addition of 10 mL of saturated aqueous NaHCO$_3$, the mixture stirred vigorously for 10 min and transferred to a separatory funnel containing 10 mL of EtOAc. The organic layer was collected and the aqueous portion was extracted with 3×10 mL of EtOAc. The combined organic extracts were dried over MgSO4, filtered, and concentrated under reduced pressure to a dark brown solid material. Purification by chromatography on silica gel (gradient elution: hexanes→2:1 EtOAc/hexanes) afforded N,S-acetal V (87 mg, 109 μmol, 57%) as a pale yellow foam.

To a solution of N,S-acetal V (87 mg, 109 μmol, 1.0 equiv) in 2.1 mL of hexafluoroisopropanol was added urea hydrogen peroxide (20.5 mg, 218 μmol, 2.0 equiv). The reaction was stirred for 30 min then quenched by the addition of 2 mL of saturated aqueous Na2S2O3. The solution was stirred vigorously for 5 min and transferred to a separatory funnel containing 10 mL of EtOAc. The organic phase was collected and the aqueous layer was extracted with an additional 10 mL of EtOAc. The combined organics extracts were dried over MgSO4, filtered, and concentrated under reduced pressure to a yellow solid. Purification of this material by chromatography on silica gel (gradient elution: hexanes→100% EtOAc) yielded sulfoxide W as a pale yellow foam (50 mg, 61 μmol, 56%).

To a solution of sulfoxide W (50.0 mg, 61 μmol, 1.0 equiv) in 2.5 mL of 2,2,2-trichloroethanol was added sodium thiophenolate (9.0 mg, 67.5 μmol, 1.1 equiv). The solution was stirred at 80° C. for 5 h, then concentrated under reduced pressure. Purification by chromatography on silica gel (gradient elution: hexanes→4:1 EtOAc/hexanes) yielded allylic alcohol X as a white solid (31.7 mg, 45 μmol, 74%).

To a solution of X (31.7 mg, 45 μmol, 1.0 equiv) was added Crabtree's catalyst (7.2 mg, 9 μmol, 0.2 equiv). H$_2$ gas was bubbled through the reaction mixture for 30 minutes, after which time bubbling was ceased and the reaction was stirred under an atmosphere of H$_2$ for 5.5 h. After this time, the reaction was concentrated under reduced pressure. Purification of the residue by chromatography on silica gel (gradient elution: hexanes→4:1 EtOAc/hexanes) afforded intermediate Y as a white solid (31 mg, 44 μmol, 98%).

To a solution of alcohol Y (31 mg, 44 μmol, 1.0 equiv) in 2.0 mL of CH$_2$Cl$_2$ was added Dess-Martin periodinane (28 mg, 65.6 μmol, 1.5 equiv). The reaction was stirred for 20 min and then loaded directly to a column of silica gel. Purification of the residue by chromatography on silica gel (gradient elution: hexanes→100% EtOAc) afforded intermediate Z as a white solid (22 mg, 30 μmol, 71%).

Trifluoroacetic acid (200 μL) and PdCl$_2$ (24 mg) were added to a solution of intermediate Z (22 mg, 30 μmol) in 3:1 MeOH/H$_2$O (8 mL). H$_2$ gas was bubbled through the reaction mixture for 30 minutes, after which time bubbling was ceased and the reaction was stirred under an atmosphere of H$_2$ for 14 h. The reaction mixture was filtered through a 0.2 μm PTFE syringe filter. The flask and filters were washed with 10 mL of MeOH and the filtrate concentrated under reduced pressure. The thin-film residue was dissolved in 4 mL of 1:1 MeCN/1.0 M aqueous HCl. After 3 h the reaction mixture was concentrated under reduced pressure, dissolved in 1.5 mL of a 10 mM aqueous heptafluorobutyric acid solution and purified by reversed-phase HPLC (Bonna-Agela Durashell C18, 10 μM, 21.2×250 mm column, eluting with gradient flow over 40 min of 0:100→40:60 MeCN/10 mM aqueous C$_3$F$_7$CO$_2$H, 214 nm UV detection). At a flow rate of 13 mL/min, compound (22) had a retention time of 22.4-23.6 min and was isolated as a white hygroscopic solid (1.15 μmol, 4%). $^1$H NMR (D$_2$O, 400 MHz) δ 4.95 (s, 1H), 4.08 (dd, J=14.1, 11.8 Hz, 1H), 3.99 (dd, J=10.2, 1.7 Hz, 1H), 3.94 (dd, J=11.4, 2.9 Hz, 1H), 3.78 (td, J=9.8, 8.3 Hz, 1H), 3.70-3.65 (m, 1H), 2.97 (s, 4H), 2.64-2.46 (m, 2H) ppm.

Characterization Data for Additional Compounds

The following compounds were prepared using procedures known to one of ordinary skill in the art or as described herein.

(4): $^1$H NMR (D$_2$O, 400 MHz) δ 8.22-8.16 (m, 2H), 8.01-7.94 (m, 4H) 7.79 (t, J=7.4, 1H), 7.64 (t, J=7.8, 2H), 5.67 (dd, J=7.3, 6.1 Hz, 1H), 5.14 (s, 1H), 4.44 (dd, J=11.2, 7.6 Hz, 1H), 4.26 (dd, J=14.4, 12.0 Hz, 1H), 4.03 (dd, J=11.6, 3.4 Hz, 1H), 3.92-3.84 (m, 2H) ppm.

(5): $^1$H NMR (D$_2$O, 400 MHz) δ 8.27-8.20 (m, 2H), 7.90-7.88 (m, 1H), 7.84-7.78 (m, 2H), 7.75-7.73 (m, 1H), 7.69-7.63 (m, 3H), 5.71 dd, J=7.6, 6.4 Hz, 1H), 5.07 (s, 1H), 4.94-4.86 (m, 1H), 4.58 (d, J=17.6 Hz, 1H), 4.47-4.38 (m, 2H), 4.11 (dd, J=10.8, 3.4 Hz, 1H), 3.88 (dd, J=11.0, 6.2 Hz, 1H), 3.63 (dd, J=14.5, 4.1 Hz, 1H) ppm.

(6): $^1$H NMR (D$_2$O, 400 MHz) δ 8.27-8.21 (m, 2H), 7.89 (m, 1H), 7.73-7.68 (m, 2H), 5.69 (dd, J=7.6, 6.2 Hz, 1H), 5.09 (s, 1H), 4.45 (dd, J=11.2, 7.9 Hz, 1H), 4.13 (dd, J=13.7, 12.5, 1H), 3.95 (dd, J=12.4, 3.9 Hz, 1H), 3.81 (dd, J=11.1, 6.2 Hz, 1H), 3.71 (dd, J=14.4, 3.3 Hz, 1H), 2.91 (s, 4H) ppm.

(10): $^1$H NMR (D$_2$O, 400 MHz) δ 5.36 (dd, J=7.5, 6.7 Hz, 1H), 4.99 (s, 1H), 4.32 (dd, J=10.9, 7.9 Hz, 1H), 4.03 (dd, J=14.4, 11.7 Hz, 1H), 3.90-3.86 (m, 1H), 3.79 (dd, J=11.1, 6.5 Hz, 1H), 3.65 (dd, J=14.4, 3.6 Hz, 1H), 3.44 (s, 3H), 2.89 (s, 4H) ppm.

(12): $^1$H NMR (D$_2$O, 400 MHz) δ 8.31 (s, 3H), 5.15 (m, 1H), 5.08 (s, 1H), 4.50-4.44 (m, 1H), 4.23-4.13 (m, 1H), 4.07-4.01 (m, 1H), 3.76 (dd, J=14.0, 3.4 Hz, 1H), 3.64 (dd, J=9.8, 9.1 Hz, 1H), 3.04 (s, 4H) ppm.

(13): $^1$H NMR (D$_2$O, 400 MHz) δ 8.22-8.20 (m, 2H), 7.85-7.81 (m, 1H), 7.68-7.64 (m, 2H), 5.64 (dd, J=7.2, 5.8 Hz, 1H), 5.08 (s, 1H), 4.39 (dd, J=11.4, 7.5 Hz, 1H), 4.13 (dd, J=14.1, 12.0 Hz, 1H), 3.93 (dd, J=11.9, 3.6 Hz, 1H), 3.81 (dd, J=11.2, 5.8 Hz, 1H), 3.67 (dd, J=14.1, 3.7 Hz, 1H), 2.79 (s, 4H), 1.38 (s, 3H), 1.34 (s, 3H) ppm.

(14): $^1$H NMR (D$_2$O, 400 MHz) δ 8.39 (s, 1H), 8.27-8.22 (m, 2H), 5.75 (dd, J=6.8, 5.0 Hz, 1H), 5.02 (s, 1H), 4.40 (dd, J=11.5, 7.0 Hz, 1H), 4.15 (d, J=1.7 Hz, 2H), 4.01-3.89 (m, 2H), 3.84 (dd, J=11.4, 5.0 Hz, 1H), 3.59 (dd, J=13.6, 2.7 Hz, 1H) ppm.

(15): $^1$H NMR (D$_2$O, 400 MHz) δ 8.56 (s, 1H), 8.42-8.37 (m, 2H), 5.87 (dd, J=7.2, 5.4 Hz, 1H), 5.13 (d, J=0.6 Hz, 1H), 4.55 (dd, J=11.3, 7.2 Hz, 1H), 4.27 (s, 2H), 4.11 (dd, J=14.0, 11.8 Hz, 1H), 4.02 (dd, J=12.0, 2.7 Hz, 1H), 3.92 (dd, J=11.3, 5.4 Hz, 1H), 3.70 (dd, J=14.0, 3.1 Hz, 1H), 3.19 (s, 3H) ppm.

(16): $^1$H NMR (D$_2$O, 400 MHz) δ 8.45 (s, 1H), 8.33-8.27 (m, 2H), 5.77 (dd, J=7.1, 5.4 Hz, 1H), 4.98 (s, 1H), 4.53 (td, J=8.4, 1.7 Hz, 2H), 4.43 (dd, J=11.3, 7.3 Hz, 1H), 4.17-4.03 (m, 2H), 3.83 (dd, J=11.4, 5.4 Hz, 1H), 3.61 (dd, J=14.6, 3.4 Hz, 1H), 3.02-2.97 (m, 2H) ppm.

(17): $^1$H NMR (D$_2$O, 400 MHz) δ 8.45 (s, 1H), 8.34-8.29 (m, 2H), 5.80 (dd, J=7.1, 5.2 Hz, 1H), 5.08 (d, J=0.7 Hz, 1H), 4.47 (dd, J=14.2, 7.2 Hz, 1H), 4.26 (s, 2H), 4.14 (dd, J=14.2, 11.9 Hz, 1H), 3.99 (dd, J=12.1, 3.3 Hz, 1H), 3.84 (dd, J=11.3, 5.3 Hz, 1H), 3.74 (dd, J=14.3, 3.6 Hz, 1H) ppm.

(18): $^1$H NMR (D$_2$O, 400 MHz) δ 5.06 (s, 1H), 5.04-4.97 (m, 1H), 4.38-4.32 (m, 1H), 4.21-4.11 (m, 1H), 4.03 (dd, J=11.5, 3.5 Hz, 1H), 3.77 (dd, J=14.0, 3.4 Hz, 1H), 3.63-3.59 (m, 1H), 3.05 (s, 4H), 1.72-1.64 (m, 4H) ppm.

(19): $^1$H NMR (D$_2$O, 400 MHz) δ 4.90 (s, 1H), ~4.8 (m, 1H, under solvent peak), 4.18-4.13 (m, 1H), 4.01-3.98 (m, 1H), 3.86 (dd, J=12.2, 3.3 Hz, 1H), 3.61 (dd, J=14.2, 3.3 Hz, 1H), 3.39 (dd, J=10.0, 9.4 Hz, 1H), 2.88 (s, 4H), 2.16 (s, 3H) ppm.

(20): $^1$H NMR (D$_2$O, 400 MHz) δ 8.66 (s, 1H), 8.47 (s, 2H), 7.91-7.88 (m, 2H), 7.83-7.79 (m, 2H), 7.63-7.59 (m, 1H), 5.96 (dd, J=7.2, 5.5 Hz, 1H), 5.26 (s, 1H), ~4.8 (s, 1H, under solvent peak), 4.65 (dd, J=11.3, 7.3 Hz, 1H), 4.34-4.28 (m, 1H), 4.20 (dd, J=11.6, 3.4 Hz, 1H), 4.03-3.99 (m, 1H), 3.90 (dd, J=14.2, 3.3 Hz, 1H) ppm.

(21): MS (ES+) m/z calcd. for C$_{23}$H$_{23}$F$_6$N$_7$O$_6$ 607.16 found 608.12 (MH$^+$).

(23): $^1$H NMR (D$_2$O, 400 MHz) δ 8.40 (m, 1H), 8.30-8.27 (m, 2H), 5.77 (dd, J=6.4, 4.3 Hz, 1H), 4.95 (s, 1H), 4.49 (dd, J=13.9, 12.1 Hz, 1H), 4.41 (dd, J=11.4, 6.5 Hz, 1H), 3.97-3.93 (m, 1H), 3.85-3.82 (m, 1H), 3.80 (s, 4H), 3.73-3.69 (m, 1H) ppm.

(24): $^1$H NMR (D$_2$O, 400 MHz) δ 7.71-7.68 (m, 2H), 7.66-7.61 (m, 2H), 7.47-7.42 (m, 1H), 5.04 (d, J=7.3, 1.4 Hz, 1H), 4.71 (s, 2H), 4.61 (dd, J=8.2, 7.1 Hz, 1H), 4.21-4.15 (m, 2H), 4.00 (dd, J=11.6, 3.4 Hz, 1H), 3.81 (dd, J=14.6, 3.5 Hz, 1H), 3.47 (dd, J=104, 7.0 Hz, 1H) ppm.

(25): $^1$H NMR (D$_2$O, 400 MHz) δ 8.38-8.36 (m, 1H), 8.30-8.28 (m, 1H), 8.17-8.14 (m, 1H), 7.94-7.90 (m, 1H), 5.20-5.14 (m, 1H), 5.04 (s, 1H), 4.39 (t, J=9.9 Hz, 1H), 4.23-4.05 (m, 1H), 3.99 (dd, J=11.9, 3.3 Hz, 2H), 3.75-3.66 (m, 2H), 2.98 (s, 4H) ppm.

(26): $^1$H NMR (D$_2$O, 400 MHz) δ 8.12-8.10 (m, 1H), 8.03-7.97 (m, 2H), 7.94-7.91 (m, 1H), 5.17-5.12 (m, 1H), 5.08 (s, 1H), 4.50-4.45 (m, 1H), 4.20-4.14 (m, 1H), 4.06-4.01 (m, 1H), 3.77 (dd, J=13.9, 3.2 Hz, 1H), 3.66-3.61 (m, 1H), 3.04 (s, 4H) ppm.

(27): $^1$H NMR (D$_2$O, 400 MHz) δ 8.26-8.19 (m, 2H), 8.11-8.07 (m, 2H), 5.21-5.16 (m, 1H), 5.00 (s, 1H), 4.40-4.34 (m, 1H), 4.17 (dd, J=14.0, 11.9 Hz, 1H), 4.00-3.96 (m, 1H), 3.76-3.66 (m, 2H), 3.00 (s, 4H) ppm.

(29): $^1$H NMR (D$_2$O, 400 MHz) δ 8.08-8.05 (m, 2H), 7.88-7.84 (m, 1H), 7.78-7.74 (m, 2H), 5.17 (t, J=9.1 Hz, 1H), 5.06 (s, 1H), 4.38 (t, J=9.8 Hz, 1H), 4.23-4.14 (m, 1H), 4.02-3.98 (m, 1H), 3.76-3.67 (m, 2H), 3.00 (s, 4H) ppm.

(30): $^1$H NMR (D$_2$O, 400 MHz) δ 7.42-7.30 (m, 3H), 5.07-5.02 (m, 1H), 4.98 (s, 1H), 4.34 (t, J=9.8 Hz, 1H), 4.11-4.02 (m, 1H), 3.96-3.91 (m, 1H), 3.67 (dd, J=14.0, 3.4 Hz, 1H), 3.57 (t, J=9.6 Hz, 1H), 2.94 (m, 8H), 1.93-1.88 (m, 4H) ppm.

(31): $^1$H NMR (D$_2$O, 400 MHz) δ 5.00 (s, 1H), 4.90-4.83 (m, 1H), 4.29-4.23 (m, 1H), 4.12 (dd, J=13.9, 12.2 Hz, 1H), 4.03-3.89 (m, 1H), 3.71 (dd, J=14.0, 3.4 Hz, 1H), 3.49 (t, J=9.4 Hz, 1H), 2.99 (s, 4H), 2.56-2.49 (m, 1H), 2.04-1.83 (m, 5H), 1.61-1.33 (m, 5H) ppm.

(32): $^1$H NMR (D$_2$O, 400 MHz) δ 5.00 (s, 1H), 4.90-4.83 (m, 1H), 4.29-4.24 (m, 1H), 4.15-4.08 (m, 1H), 3.99-3.95 (m, 1H), 3.74-3.68 (m, 1H), 3.56-3.50 (m, 1H), 2.99 (s, 4H), 2.05 (s, 7H), 1.96-1.86 (m, 8H) ppm.

(33): $^1$H NMR (D$_2$O, 400 MHz) δ 8.14-8.12 (m, 2H), 7.64-7.62 (m, 2H), 5.15 (t, J=9.19 Hz, 1H), 5.03 (s, 1H), 4.37-4.32 (m, 1H), 4.21-4.11 (m, 1H), 3.97 (dd, J=11.8, 3.1 Hz, 1H), 3.74-3.64 (m, 2H), 2.97 (s, 4H) ppm.

(35): $^1$H NMR (D$_2$O, 400 MHz) δ 8.20-8.18 (m, 2H), 8.14-8.10 (m, 2H), 7.98-7.94 (m, 1H), 7.89-7.85 (m, 1H), 7.78-7.76 (m, 1H), 7.68-7.66 (m, 1H), 5.25 (t, J=9.4 Hz, 1H), 5.12 (s, 1H), 4.46-4.40 (m, 1H), 4.24-4.09 (m, 2H), 3.80-3.70 (m, 2H), 3.02 (s, 4H) ppm.

(36): MS (ES+) m/z calcd. for C$_{23}$H$_{24}$F$_6$N$_8$O$_5$ 606.118 found 607.08 (MH$^+$).

(37): $^1$H NMR (D$_2$O, 400 MHz) δ 8.42 (s, 1H) 8.34-8.32 (m, 1H), 8.21-8.17 (m, 1H), 7.98-7.94 (m, 1H), 7.79-7.76 (m, 2H), 7.72-7.68 (m, 2H), 7.54-7.47 (m, 1H), 5.24-5.19 (m, 1H), 5.10 (s, 1H), ~4.8 (s, 2H, under solvent peak), 4.44-4.39 (m, 1H), 4.30-4.23 (m, 1H), 4.13-4.09 (m, 1H), 3.91-3.86 (m, 1H), 3.73 (dd, J=10.1, 8.9 Hz, 1H) ppm.

(39): $^1$H NMR (D$_2$O, 400 MHz) δ 7.77-7.67 (m, 5H), 7.55-7.48 (m, 3H), 5.20-5.16 (m, 1H), 5.09 (s, 1H), ~4.80 (s, 2H, under solvent peak), 4.45-4.40 (m, 1H), 4.23 (dd, J=14.4, 11.9 Hz, 1H), 4.12-4.08 (m, 1H), 3.87 (dd, J=14.4, 3.1 Hz, 1H), 3.68 (dd, J=10.0, 9.1 Hz, 1H) ppm.

Preparation of Compound (104)

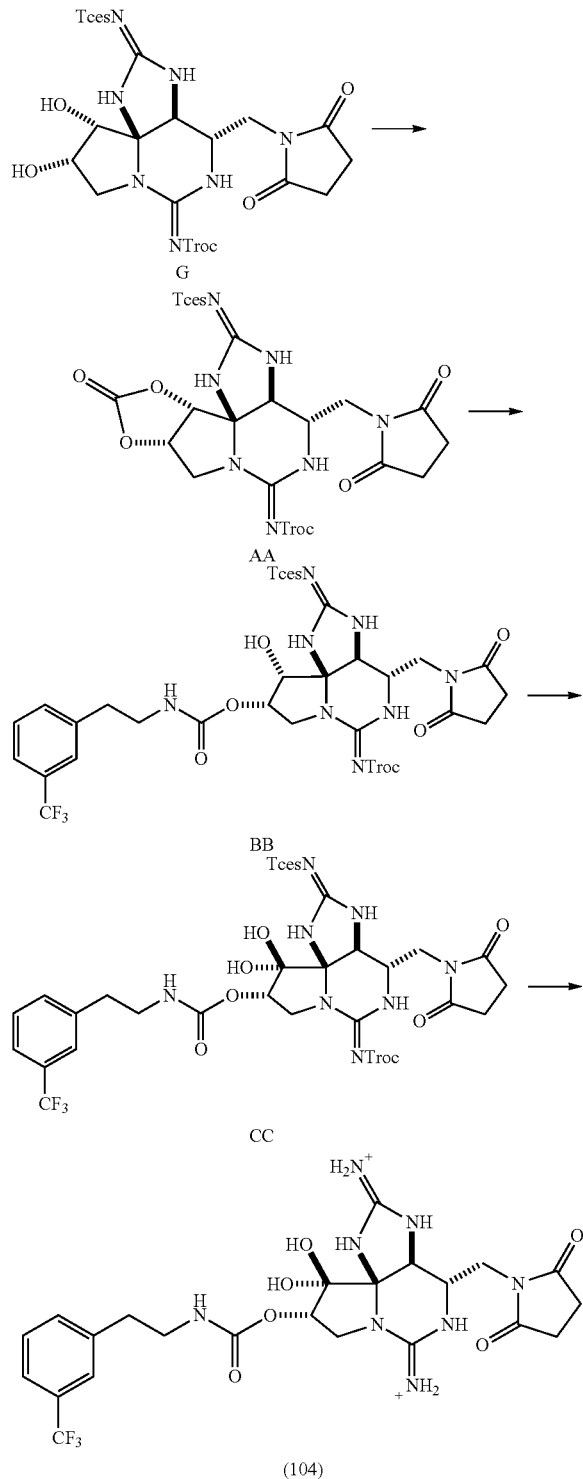

To a solution of diol G (306 mg, 422 µmol, 1.0 equiv) in 4.5 mL of dry THF was added 1,1'-carbonyldiimidazole (104 mg, 633 µmol, 1.5 equiv). The resulting mixture stirred at room temperature for 48 h and then concentrated in vacuo. Purification of residue by chromatography on silica gel (gradient elution: $CH_2Cl_2 \to 4:1$ $CH_2Cl_2$/acetone) afforded cyclic carbonate AA (200 mg, 266 µmol, 63%) as a white solid.

To a suspension of cyclic carbonate AA (70 mg, 93.3 µmol, 1.0 equiv) in 1.5 mL of dry $CH_2Cl_2$ was added 3-[3-(trifluoromethyl)phenyl]ethan-1-amine (88 mg, 466.5 µmol, 5 equiv). The resulting mixture stirred at 45° C. for 48 h. The resulting solution was diluted with $CH_2Cl_2$ (5 mL) and washed successively with 0.01N HCl until the washing becomes neutral. The organics were dried over MgSO4, filtered, and concentrated under reduced pressure to a yellow oil. Purification of residue by chromatography on silica gel (gradient elution: $CH_2Cl_2 \to 4:1$ $CH_2Cl_2$/acetone) afforded desired carbamate BB (63 mg, 67 µmol, 72%) as a white solid.

To a solution of carbamate BB (63 mg, 67 µmol, 1.0 equiv) in 2.0 mL of $CH_2Cl_2$ was added Dess-Martin periodinane (71 mg, 167 µmol, 2.5 equiv). The reaction was stirred for 20 min and then concentrated. The residue was dissolved in 0.2 mL of DMSO, 1.5 mL of MeCN and 0.5 mL of a 10 mM aqueous trifluoroacetic acid solution and purified by reversed-phase HPLC (Bonna-Agela Durashell C18, 10 µM, 21.2×250 mm column, eluting with gradient flow over 30 min of 30 to 70% MeCN/10 mM aqueous $CF_3CO_2H$, 214 nm UV detection). At a flow rate of 13 mL/min, intermediate CC had a retention time of 25.4-27.0 min and afforded 30 mg of oxidized intermediate CC as a white solid.

Trifluoroacetic acid (300 µL) and $PdCl_2$ (15 mg) were added to a solution of intermediate CC in 3:1 MeOH/$H_2O$ (4.0 mL). $H_2$ gas was bubbled through the reaction mixture for 30 minutes, after which time bubbling was ceased and the reaction was stirred under an atmosphere of $H_2$ for 20 h. The reaction mixture was sequentially filtered through a 0.2 µm PTFE syringe filter. The flask and filters were washed with 10 mL of MeOH and the filtrate concentrated under reduced pressure. The thin-film residue was dissolved in 4 mL of 1:1 MeCN/1.0 M aqueous HCl. After 3 h the reaction mixture was concentrated under reduced pressure, dissolved in 0.5 mL of MeCN and 1.5 mL of a 10 mM aqueous trifluoroacetic acid solution and purified by reversed-phase HPLC (Bonna-Agela Durashell C18, 10 µM, 21.2×250 mm column, eluting with gradient flow over 40 min of 0 to 50% MeCN/10 mM aqueous $CF_3CO_2H$, 214 nm UV detection). At a flow rate of 13 mL/min, compound (104) had a retention time of 30.5-33.1 min and was isolated as a white hygroscopic solid (19.3 µmol, 29% over two steps).

Preparation of Compound (80)

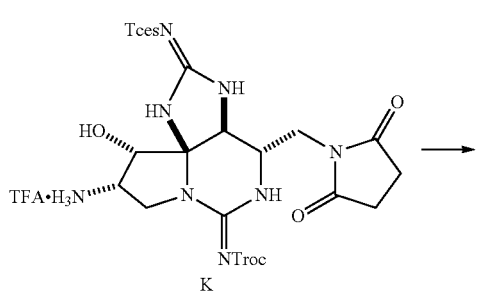

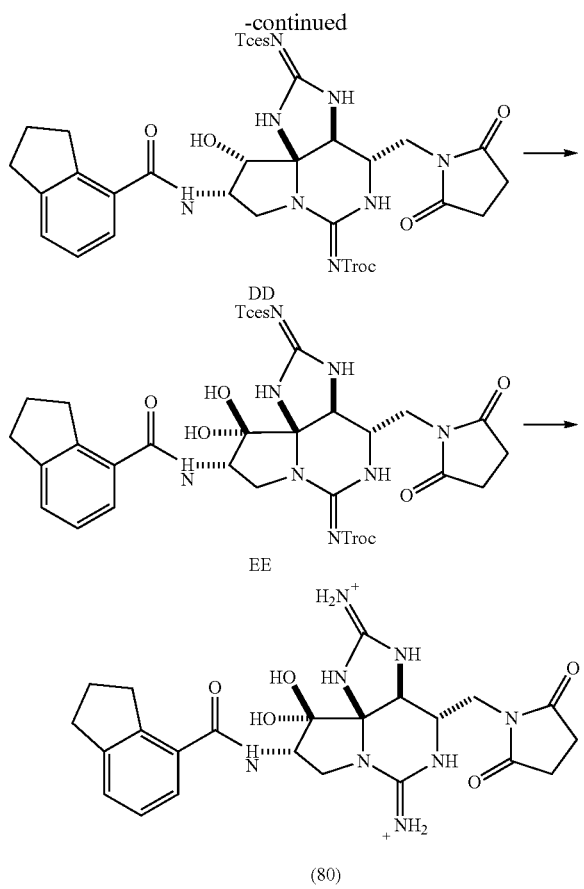

(80)

pressure. The thin-film residue was dissolved in 4 mL of 2:1 MeCN/1.0 M aqueous HCl. After 3 h the reaction mixture was concentrated under reduced pressure, dissolved in 1.5 mL of a 10 mM aqueous trifluoroacetic acid solution and purified by reversed-phase HPLC (Bonna-Agela Durashell C18, 10 μM, 50×250 mm column, eluting with gradient flow over 60 min of 0:100→18-23% MeCN/10 mM aqueous CF$_3$CO$_2$H, 214 nm UV detection). At a flow rate of 25 mL/min, compound (80) had a retention time of 47-54.8 min and was isolated as a white hygroscopic solid (10 μmol, 20% over 2 steps).

Preparation of Compound (93)

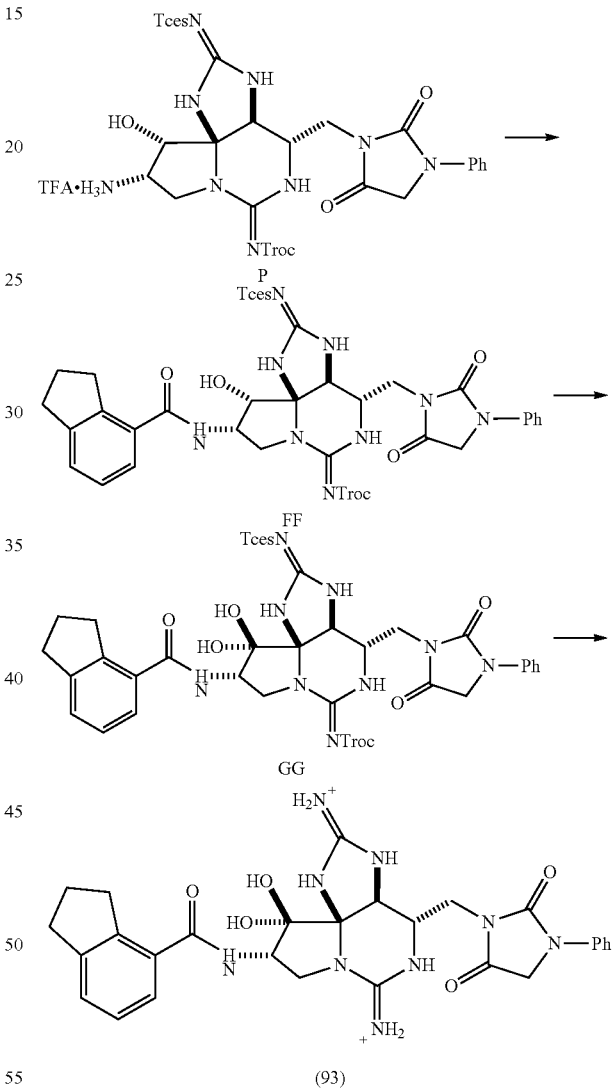

To a solution of K (318 mg, 380 μmol, 1.0 equiv) in 2.5 mL of CH$_2$Cl$_2$ was added Et$_3$N (215 μL, 100 μmol, 4.0 equiv). The resulting solution was stirred at room temperature for 15 minutes followed by addition of 2,5-dioxopyrrolidin-1-yl 2,3-dihydro-1H-indene-4-carboxylate (118 mg, 455.8 μmol, 1.2 equiv). The resulting solution was stirred for 20 hours and reaction mixture was loaded directly to a column of silica gel. Purification by chromatography on silica gel (gradient elution: hexanes→1:2 hexanes/EtOAc) afforded intermediate DD as a white solid (167 mg, 192 μmol, 51%).

To a solution of amide DD (41.5 mg, 47.8 μmol, 1.0 equiv) in 2.0 mL of CH$_2$Cl$_2$ was added Dess-Martin periodinane (35.5 mg, 83.7 μmol, 1.75 equiv). The reaction was stirred at room temperature for 20 min and then concentrated. The residue was dissolved in 0.2 mL of DMSO, 1.5 mL of MeCN and 0.5 mL of a 10 mM aqueous trifluoroacetic acid solution and purified by reversed-phase HPLC (Bonna-Agela Durashell C18, 10 μM, 21.2×250 mm column, eluting with gradient flow over 30 min of 30 to 70% MeCN/10 mM aqueous CF$_3$CO$_2$H, 214 nm UV detection). At a flow rate of 13 mL/min, intermediate EE had a retention time of 23.7-25.2 min and afforded 23 mg of oxidized intermediate EE as a white solid.

Trifluoroacetic acid (230 μL) and PdCl$_2$ (12 mg) were added to a solution of intermediate EE in 3:1 MeOH/H$_2$O (4 mL). H$_2$ gas was bubbled through the reaction mixture for 30 minutes, after which time bubbling was ceased and the reaction was stirred under an atmosphere of H$_2$ for 20 h. The reaction mixture was sequentially filtered through a 0.2 μm PTFE syringe filter. The flask and filters were washed with 10 mL of MeOH and the filtrate concentrated under reduced To a solution of P (50 mg, 54.7 μmol, 1.0 equiv) in 1.5 mL of CH$_2$Cl$_2$ was added Et$_3$N (31 μL, 219 μmol, 4.0 equiv). The resulting solution was stirred at room temperature for 15 minutes followed by addition of 2,5-dioxopyrrolidin-1-yl 2,3-dihydro-1H-indene-4-carboxylate (18.5 mg, 71.2 μmol, 1.3 equiv). The resulting solution was stirred for 20 hours and reaction mixture was loaded directly to a column of silica gel. Purification by chromatography on silica gel (gradient elution: hexanes→1:1.5 hexanes/EtOAc) afforded intermediate FF as a white solid (20 mg, 21 μmol, 39%).

To a solution of amide FF (20 mg, 21.2 µmol, 1.0 equiv) in 1.0 mL of CH$_2$Cl$_2$ was added Dess-Martin periodinane (18 mg, 42.3 µmol, 2 equiv). The reaction was stirred at room temperature for 20 min and then concentrated. The residue was dissolved in 0.2 mL of DMSO, 1.5 mL of MeCN and 0.5 mL of a 10 mM aqueous trifluoroacetic acid solution and purified by reversed-phase HPLC (Bonna-Agela Durashell C18, 10 µM, 21.2×250 mm column, eluting with gradient flow over 30 min of 30 to 70% MeCN/10 mM aqueous CF$_3$CO$_2$H, 214 nm UV detection). At a flow rate of 13 mL/min, intermediate GG had a retention time of 28.5-30.2 min and afforded 12 mg of oxidized intermediate GG as a white solid.

Trifluoroacetic acid (120 µL) and PdCl$_2$ (6 mg) were added to a solution of intermediate GG in 3:1 MeOH/H$_2$O (4 mL). H$_2$ gas was bubbled through the reaction mixture for 30 minutes, after which time bubbling was ceased and the reaction was stirred under an atmosphere of H$_2$ for 20 h. The reaction mixture was sequentially filtered through a 0.2 µm PTFE syringe filter. The flask and filters were washed with 10 mL of MeOH and the filtrate concentrated under reduced pressure. The thin-film residue was dissolved in 4 mL of 3:1 MeCN/1.0 M aqueous HCl. After 3 h the reaction mixture was concentrated under reduced pressure, dissolved in 1.5 mL of a 10 mM aqueous trifluoroacetic acid solution and purified by reversed-phase HPLC (Bonna-Agela Durashell C18, 10 µM, 21.2×250 mm column, eluting with gradient flow over 40 min of 0:100→0-50% MeCN/10 mM aqueous CF$_3$CO$_2$H, 214 nm UV detection). At a flow rate of 13 mL/min, compound (93) had a retention time of 29.5-30.5 min and was isolated as a white hygroscopic solid (4.5 µmol, 21% over 2 steps).

Characterization Data for Additional Compounds

The following compounds were prepared using procedures known to one of ordinary skill in the art or as described herein.

(50): $^1$H NMR (D$_2$O, 400 MHz) δ 7.71 (dd, J=7.9, 1.6 Hz, 1H), 7.36 (dd, J=8.1, 1.7 Hz, 1H) 7.24 (appar. t, J=8.0 Hz, 1H), 5.10 (appar. t, J=8.9 Hz, 1H), 5.04 (s, 1H), 4.68-4.66 (m, 2H), 4.57-4.55 (m, 2H), 4.43 (appar. t, J=9.7 Hz, 1H), 4.15 (dd, J=14.0, 3.6 Hz, 1H), 4.02-4.00 (m, 1H), 3.75 (dd, J=14.0, 3.6 Hz, 1H), 3.62 (dd, J=10.1, 8.6 Hz, 1H), 3.00 (s, 4H) ppm.

(52): $^1$H NMR (D$_2$O, 400 MHz) δ 7.53 (dd, J=8.2, 1.2 Hz, 1H), 7.28 (dd, J=7.8, 1.2 Hz, 1H), 7.18 (appar. t, J=8.0 Hz, 1H), 6.29 (dd, J=6.9, 0.9 Hz, 2H), 5.09 (appar. t, J=8.9 Hz, 1H), 4.99 (d, J=0.7 Hz, 1H), 4.36 (dd, J=10.1, 9.5 Hz, 1H), 4.09 (dd, J=14.1, 11.8 Hz, 1H), 3.95 (dd, J=12.0, 3.2 Hz, 1H), 3.70 (dd, J=14.0, 3.5 Hz, 1H), 3.59 (dd, J=10.2, 8.6 Hz, 1H), 2.95 (s, 4H) ppm.

(60): $^1$H NMR (D$_2$O, 400 MHz) δ 8.12-7.97 (m, 2H), 7.90-7.78 (m, 2H), 5.18 (appar. t, J=9.1 Hz, 1H), 5.06 (s, 1H), 4.38 (appar. t, J=9.8 Hz, 1H), 4.24-4.10 (m, 1H), 4.04-3.92 (m, 1H), 3.77-3.68 (m, 2H), 3.01 (s, 4H) ppm.

(62): $^1$H NMR (D$_2$O, 400 MHz) δ 8.40-8.38 (m, 1H), 8.32-8.29 (m, 1H), 8.24-8.21 (m, 1H), 7.99 (dd, J=7.1, 1.0 Hz, 1H), 7.86-7.78 (m, 3H), 5.25 (appar. t, J=9.1 Hz, 1H), 5.05 (d, J=0.6 Hz, 1H), 4.47 (dd, J=9.7, 9.2 Hz, 1H), 4.17-4.10 (m, 1H), 4.03-3.97 (m, 1H), 3.74-3.67 (m, 2H), 2.98 (s, 4H) ppm.

(64): $^1$H NMR (D$_2$O, 400 MHz) δ 8.53-8.52 (m, 1H), 8.30-8.24 (m, 2H), 8.13-8.11 (m, 2H), 8.01 (m, 1H), 7.93-7.89 (m, 2H), 7.85-7.81 (m, 1H), 5.39-5.35 (m, 1H), 5.26 (s, 1H), 4.59-4.54 (m, 1H), 4.31-4.22 (m, 2H), 3.91-3.83 (m, 2H), 3.14 (s, 4H) ppm.

(54): $^1$H NMR (D$_2$O, 400 MHz) δ 7.96-7.91 (m, 2H), 7.75-7.67 (m, 2H), 5.19 (appar. t, J=9.1 Hz, 1H), 5.10 (s, 1H), 4.42 (appar. t, J=9.7 Hz, 1H), 4.21 (dd, J=14.2, 11.8 Hz, 1H), 4.04 (dd, J=12.0, 3.4 Hz, 1H), 3.78 (dd, J=14.2, 3.6 Hz, 1H), 3.73 (dd, J=9.9, 9.3 Hz, 1H), 3.04 (s, 4H), 2.66 (s, 3H) ppm.

(65): $^1$H NMR (D$_2$O, 400 MHz) δ 8.05 (s, 1H), 7.99-7.96 (m, 1H), 7.83 (d, J=7.7 Hz, 1H), 7.74-7.73 (m, 1H), 5.22 (appar. t, J=9.1 Hz, 1H), 5.12 (s, 1H), 4.44 (appar. t, J=9.7 Hz, 1H), 4.26-4.18 (m, 1H), 4.06 (dd, J=11.6, 3.4 Hz, 1H), 3.82-3.74 (m, 2H), 3.31-3.25 (m, 1H), 3.06 (s, 4H), 1.54 (d, J=6.9 Hz, 6H) ppm.

(53): $^1$H NMR (D$_2$O, 400 MHz) δ 7.70-7.65 (m, 2H), 7.61-7.60 (m, 1H), 7.43-7.40 (m, 1H), 5.15 (appar. t, J=9.1 Hz, 1H), 5.04 (s, 1H), 4.35 (appar. t, J=9.7 Hz, 1H), 4.15 (dd, J=14.3, 11.8 Hz, 1H), 4.06 (s, 3H), 3.98 (dd, J=11.8, 3.4 Hz, 1H), 3.74-3.65 (m, 2H), 2.98 (s, 4H) ppm.

(40): $^1$H NMR (D$_2$O, 400 MHz) δ 7.78-7.66 (m, 3H), 7.53-7.49 (m, 1H), 5.16 (appar. t, J=9.1 Hz, 1H), 5.05 (s, 1H), 4.86 (q, J=8.5 Hz, 2H), 4.37 (appar. t, J=9.8 Hz, 1H), 4.22-4.06 (m, 1H), 3.99 (dd, J=12.0, 3.8 Hz, 1H), 3.75-3.66 (m, 2H), 2.99 (s, 4H) ppm.

(66): $^1$H NMR (D$_2$O, 400 MHz) δ 4.96 (s, 1H), 4.31 (dd, J=10.5, 9.4 Hz, 1H), 4.19 (dd, J=9.3, 7.6 Hz, 1H), 4.05 (dd, J=14.1, 12.0 Hz, 1H), 3.94-3.91 (m, 1H), 3.73 (dd, J=10.6, 7.6 Hz, 1H), 3.64 (dd, J=14.1, 3.5 Hz, 1H), 2.91 (s, 4H) ppm.

(59): MS (ES+) m/z calcd. for C$_{23}$H$_{30}$N$_8$O$_8$ 546.22 found 546.17 (MH$^+$).

(67): $^1$H NMR (D$_2$O, 400 MHz) δ 8.29 (d, J=9.2 Hz, 1H), 8.16 (d, J=8.0 Hz, 1H), 8.06-8.00 (m, 1H), 7.83-7.78 (m, 1H), 7.74-7.67 (m, 1H), 5.26 (appar. t, J=9.0 Hz, 1H), 5.03 (s, 1H), 4.53 (appar. t, J=9.7 Hz, 1H), 4.24 (s, 3H), 4.20-4.12 (m, 1H), 4.07 (dd, J=15.6, 11.9 Hz, 1H), 3.78-3.62 (m, 2H), 3.04 (s, 4H) ppm.

(56): $^1$H NMR (D$_2$O, 400 MHz) δ 8.12-8.10 (m, 1H), 7.95-7.88 (m, 2H), 7.70 (t, J=7.8 Hz, 1H), 5.16 (appar. t, J=9.1 Hz, 1H), 5.05 (s, 1H), 4.38 (appar. t, J=9.8 Hz, 1H), 4.17 (dd, J=14.0, 11.8 Hz, 1H), 4.00 (dd, J=12.0, 3.3 Hz, 1H), 3.76-3.68 (m, 2H), 3.00 (s, 4H), 1.54 (s, 9H) ppm.

(68): $^1$H NMR (D$_2$O, MHz) δ 8.61-8.59 (m, 1H), 8.42-8.36 (m, 2H), 8.04-8.00 (m, 1H), 5.19 (appar. t, J=9.2 Hz, 1H), 5.05 (s, 1H), 4.38 (appar. t, J=9.7 Hz, 1H), 4.16 (dd, J=14.3, 11.8 Hz, 1H), 3.99 (dd, J=11.4, 3.4 Hz, 1H), 3.76-3.67 (m, 2H), 3.47 (s, 3H), 2.99 (s, 4H) ppm.

(69): $^1$H NMR (400 MHz, D$_2$O) δ 7.91 (dt, J=8.0, 1.5 Hz, 1H), 7.69 (ddd, J=12.5, 7.7, 1.6 Hz, 1H), 7.62 (appar. t, J=7.8 Hz, 1H), 5.12 (appar. t, J=9.1 Hz, 1H), 5.03 (s, 1H), 4.42 (appar. t, J=9.7 Hz, 1H), 4.17-4.07 (m, 1H), 4.02-3.97 (m, 1H), 3.72 (dt, J=14.1, 3.8 Hz, 1H), 3.62 (dd, J=9.9, 9.1 Hz, 1H), 2.99 (s, 4H) ppm.

(70): $^1$H NMR (D$_2$O, 400 MHz) δ 7.61-7.57 (m, 1H), 7.44-7.43 (m, 1H), 5.23-5.15 (m, 1H), 5.09 (s, 1H), 4.44-4.33 (m, 1H), 4.27-4.17 (m, 1H), 4.08-4.00 (m, 1H), 3.83-3.68 (m, 2H), 3.01 (s, 4H) ppm.

(72): $^1$H NMR (D$_2$O, 400 MHz) δ 8.244-8.240 (m, 1H), 8.07-8.04 (m, 1H), 7.19-7.14 (m, 1H), 5.13 (appar. t, J=9.1 Hz, 1H), 5.05 (s, 1H), 4.35 (appar. t, J=9.7 Hz, 1H), 4.20-4.14 (m, 1H), 4.00 (dd, J=11.9, 3.6 Hz, 1H), 3.74 (dd, J=14.0, 3.1 Hz, 1H), 3.67 (dd, J=9.7, 9.3 Hz, 1H), 3.00 (s, 4H) ppm.

(58): $^1$H NMR (D$_2$O, 400 MHz) δ 8.04 (s, 2H), 5.25-5.18 (m, 1H), 5.13 (s, 1H), 4.46 (appar q, J=10.0 Hz, 1H), 4.28-4.17 (m, 1H), 4.08 (dd, J=12.2, 3.3 Hz, 1H), 3.86-3.77 (m, 2H), 3.08 (s, 4H), 1.74 (s, 18H) ppm.

(73): $^1$H NMR (D$_2$O, 400 MHz) δ 8.05-8.03 (d, J=8.1 Hz, 1H), 7.88-7.85 (m, 1H), 7.67 (t, J=7.8 Hz, 1H), 5.13 (appar. t, J=9.2 Hz, 1H), 5.03 (s, 1H), 4.41 (appar. t, J=9.7 Hz, 1H), 4.12-4.09 (m, 1H), 3.98 (dd, J=11.7, 2.9 Hz, 1H), 3.71 (dd, J=14.1, 2.9 Hz, 1H), 3.62 (appar. t, J=9.4 Hz, 1H), 2.98 (s, 3H), 2.69 (s, 3H) ppm.

(74): $^1$H NMR (D$_2$O, 400 MHz) δ 8.46 (s, 1H), 8.37 (d, J=8.3 Hz, 1H), 8.27-8.25 (m, 1H), 7.57-7.55 (m, 1H), 5.27-5.24 (m, 1H), 4.91 (s, 1H), 4.16-4.11 (m, 1H), 3.96-3.88 (m, 1H), 3.84-3.80 (m, 1H), 3.66 (dd, J=11.0, 6.1 Hz, 1H), 3.55 (d, J=15.8 Hz, 1H), 2.86 (s, 4H) ppm.

(75): MS (ES+) m/z calcd. for C$_{20}$H$_{23}$F$_3$N$_8$O$_6$S 560.14 found 561.09 (MH$^+$).

(77): $^1$H NMR (D$_2$O, 400 MHz) δ 7.78 (d, J=8.2 Hz, 1H), 7.63-7.61 (m, 1H), 7.51-7.47 (m, 1H), 5.14 (appar. t, J=9.0 Hz, 1H), 5.03 (s, 1H), 4.38 (appar. t, J=9.8 Hz, 1H), 4.14 (appar. t, J=12.9 Hz, 1H), 3.98 (dd, J=11.8, 2.7 Hz, 1H), 3.72 (dd, J=14.4, 2.9 Hz, 1H), 3.65 (appar. t, J=9.5 Hz, 1H), 2.97 (s, 4H) ppm.

(78): $^1$H NMR (D$_2$O, 400 MHz) δ 7.97 (s, 1H), 7.76-7.70 (m, 2H), 7.64-7.62 (m, 1H), 5.01 (s, 1H), 4.85 (appar. t, J=9.2 Hz,), 4.31 (appar. t, J=9.6 Hz, 1H), 4.12 (appar. t, J=12.8 Hz, 1H), 3.97 (dd, J=11.8, 2.7 Hz, 1H), 3.72 (dd, J=13.8, 2.8 Hz, 1H), 3.52 (appar. t, J=9.4 Hz, 1H), 2.99 (s, 4H) ppm.

(79): $^1$H NMR (D$_2$O, 400 MHz) δ 8.38-8.36 (m, 1H), 8.31 (d, J=7.0 Hz, 1H), 8.17 (d, J=8.1 Hz, 1H), 8.00-7.85 (m, 4H), 5.11 (s, 1H), 4.96 (appar. t, J=8.6 Hz, 1H), 4.44 (appar. t, J=9.8 Hz, 1H), 4.21 (appar. t, J=12.9 Hz, 1H), 4.08 (dd, J=11.6, 3.3 Hz, 1H), 3.83-3.79 (m, 1H), 3.64 (appar. t, J=9.6 Hz, 1H), 3.10 (s, 4H) ppm.

(80): $^1$H NMR (D$_2$O, 400 MHz) δ 7.66 (d, J=7.6 Hz, 2H), 7.47 (appar. t, J=7.6 Hz, 1H), 5.10 (appar. t, J=9.1 Hz, 1H), 5.02 (s, 1H), 4.37 (appar. t, J=9.7 Hz, 1H), 4.13 (dd, J=14.1, 12.0 Hz, 1H), 3.97 (dd, J=11.7, 3.4 Hz, 1H), 3.71 (dd, J=14.1, 3.4 Hz, 1H), 3.62 (appar. t, J=9.5 Hz, 1H), 3.26 (td, J=7.3, 4.0 Hz, 2H), 3.12 (appar. t, J=7.5 Hz, 2H), 2.97 (s, 4H), 2.28-2.20 (m, 2H) ppm.

(81): $^1$H NMR (D$_2$O, 400 MHz) δ 7.85 (d, J=7.8 Hz, 1H), 7.38 (d, J=7.2 Hz, 1H), 7.33-7.29 (m, 1H), 7.12 (m, 1H), 4.93 (s, 1H), 4.82 (appar. t, J=8.9 Hz, 1H), 4.21 (appar. t, J=9.6 Hz, 1H), 4.12 (dd, J=17.5, 8.1 Hz, 2H), 4.07-4.01 (m, 1H), 3.89-3.86 (m, 1H), 3.64-3.60 (m, 1H), 3.52 (appar. t, J=9.1 Hz, 1H), 3.30 (appar. t, J=8.2 Hz, 2H), 2.88 (s, 4H) ppm.

(83): $^1$H NMR (D$_2$O, 400 MHz) δ 7.42-7.33 (m, 3H), 5.04 (appar. t, J=9.1 Hz, 1H), 4.97 (s, 1H), 4.33 (appar. t, J=9.7 Hz, 1H), 4.20 (s, 2H), 4.03 (dd, J=14.1, 11.7 Hz, 1H), 3.94 (dd, J=11.7, 2.9 Hz, 1H), 3.68 (dd, J=14.1, 3.1 Hz, 1H), 3.55 (appar. t, J=9.5 Hz, 1H), 3.08 (s, 3H), 2.94-2.90 (m, 4H), 1.91-1.89 (m, 4H) ppm.

(84): $^1$H NMR (D$_2$O, 400 MHz) δ 4.98 (d, J=0.4 Hz, 1H), 4.59 (dd, J=8.1, 7.2 Hz, 1H), 4.21 (s, 2H), 4.16 (dd, J=10.4, 8.3 Hz, 1H), 4.05 (dd, J=14.6, 11.7 Hz, 1H), 3.90 (ddd, J=11.8, 3.2, 0.4 Hz, 1H), 3.71-3.66 (m, 1H), 3.43 (dd, J=10.3, 7.2 Hz, 1H), 3.09 (s, 3H) ppm.

(85): $^1$H NMR (D$_2$O, 400 MHz) δ 7.66 (d, J=7.6 Hz, 2H), 7.48 (appar. t, J=7.6 Hz, 1H), 5.10 (appar. t, J=9.1 Hz, 1H), 5.01 (d, J=0.5 Hz, 1H), 4.37 (appar. t, J=9.8 Hz, 1H), 4.25 (s, 2H), 4.09 (dd, J=14.2, 11.6 Hz, 1H), 3.98 (dd, J=11.6, 2.8 Hz, 1H), 3.73 (dd, J=14.2, 3.2 Hz, 1H), 3.61 (dd, J=10.0, 9.0 Hz, 1H), 3.29-3.24 (m, 2H), 3.14-3.10 (m, 5H), 2.29-2.23 (m, 2H) ppm.

(86): $^1$H NMR (D$_2$O, 400 MHz) δ 8.45 (d, J=2.5 Hz, 1H), 7.98 (d, J=1.0 Hz, 1H), 6.74 (t, J=1.4 Hz, 1H), 5.04-5.00 (m, 2H), 4.33 (appar. t, J=9.8 Hz, 1H), 4.23 (s, 2H), 4.08 (dd, J=14.4, 11.9 Hz, 1H), 3.98-3.94 (m, 1H), 3.74-3.66 (m, 2H), 3.11 (s, 3H) ppm.

(88): $^1$H NMR (D$_2$O, 400 MHz) δ 7.84 (d, J=7.8 Hz, 1H), 7.71 (d, J=7.6 Hz, 1H), 7.41 (appar. t, J=7.7 Hz, 1H), 5.11 (appar. t, J=9.1 Hz, 1H), 5.01 (s, 1H), 4.32 (appar. t, J=9.8 Hz, 1H), 4.24 (s, 2H), 4.09 (dd, J=14.3, 11.9 Hz, 1H), 3.97 (dd, J=11.8, 3.4 Hz, 1H), 3.91 (appar. t, J=8.2 Hz, 2H), 3.72 (dd, J=14.5, 3.6 Hz, 1H), 3.64 (appar. t, J=9.5 Hz, 1H), 3.37 (appar. t, J=8.0 Hz, 2H), 3.11 (s, 3H) ppm.

(90): MS (ES+) m/z calcd. for C$_{25}$H$_{33}$N$_9$O$_5$ 539.26 found 540.14 (MH$^+$).

(91): $^1$H NMR (D$_2$O, 400 MHz) δ 7.41-7.32 (m, 3H), 5.03 (appar. t, J=9.0 Hz, 1H), 4.87 (s, 1H), 4.30 (appar. t, J=9.7 Hz, 1H), 4.07-4.00, (m, 1H), 3.94 (dd, J=11.7, 3.2 Hz, 1H), 3.68 (dt, J=9.0, 7.0 Hz, 1H), 3.57-3.49 (m, 2H), 3.21 (dd, J=13.2, 2.8 Hz, 1H), 2.93-2.89 (m, 4H), 2.53 (appar. t, J=7.5 Hz, 2H), 1.94-1.85 (m, 6H) ppm.

(92): $^1$H NMR (D$_2$O, MHz) δ 7.67 (d, J=7.9 Hz, 2H), 7.61 (appar. t, J=7.9 Hz, 2H), 7.44-7.32 (m, 4H), 5.05 (appar. t, J=9.0 Hz, 1H), 5.00 (s, 1H), 4.69 (s, 2H), 4.34 (appar. t, J=9.6 Hz, 1H), 4.14 (dd, J=14.2, 11.8 Hz, 1H), 4.02 (dd, J=11.5, 3.3 Hz, 1H), 3.78 (dd, J=14.5, 3.5 Hz, 1H), 3.57 (appar. t, J=9.5 Hz, 1H), 2.93-2.89 (m, 4H), 1.90-1.88 (m, 4H) ppm.

(93): $^1$H NMR (D$_2$O, 400 MHz): δ 7.66 (d, J=8.0 Hz, 2H), 7.61 (appar. t, J=6.9 Hz, 4H), 7.41 (appar. t, J=7.5 Hz, 2H), 5.07 (appar. t, J=9.0 Hz, 1H), 5.01 (s, 1H), 4.73-4.64 (m, 2H), 4.33 (appar. t, J=9.7 Hz, 1H), 4.16 (dd, J=14.3, 11.5 Hz, 1H), 4.02 (dd, J=11.6, 3.3 Hz, 1H), 3.79 (dd, J=14.4, 3.4 Hz, 1H), 3.59 (appar. t, J=9.5 Hz, 1H), 3.24-3.20 (m, 2H), 3.06 (appar. t, J=7.5 Hz, 2H), 2.22-2.16 (m, 2H) ppm.

(94): $^1$H NMR (D$_2$O, 400 MHz) δ 7.67 (appar. d, J=7.7 Hz, 2H), 7.61 (appar. t, J=8.0 Hz, 2H), 7.47 (appar. d, J=7.3 Hz, 1H), 7.42 (appar. t, J=7.2 Hz, 2H), 7.34 (appar. t, J=7.6 Hz, 1H), 5.07 (appar. t, J=9.1 Hz, 1H), 5.01 (s, 1H), 4.69 (s, 2H), 4.36 (appar. t, J=9.7 Hz, 1H), 4.14 (dd, J=14.3, 11.7 Hz, 1H), 4.02 (dd, J=11.7, 3.2 Hz, 1H), 3.79 (dd, J=14.4, 3.4 Hz, 1H), 3.59 (appar. t, J=9.5 Hz, 1H), 2.43 (s, 3H), 2.40 (s, 3H) ppm.

(95): $^1$H NMR (D$_2$O, 400 MHz) δ 8.25 (d, J=7.6 Hz, 1H), 8.09 (d, J=7.3 Hz, 1H), 7.87-7.81 (m, 2H), 7.74-7.67 (m, 3H), 7.65-7.55 (m, 4H), 7.42 (appar. t, J=7.3 Hz, 1H), 5.17 (appar. t, J=8.9 Hz, 1H), 5.04 (s, 1H), 4.70 (s, 2H), 4.39 (appar. t, J=9.8 Hz, 1H), 4.33 (d, J=10.7 Hz, 2H), 4.19 (dd, J=14.4, 11.7 Hz, 1H), 4.05 (dd, J=11.5, 3.4 Hz, 1H), 3.82 (dd, J=14.4, 3.4 Hz, 1H), 3.66 (appar. t, J=9.5 Hz, 1H) ppm.

(96): $^1$H NMR (D$_2$O, 400 MHz) δ 7.75-7.71 (m, 2H), 7.40 (d, J=7.9 Hz, 1H), 5.09 (appar. t, J=9.1 Hz, 1H), 5.00 (s, 1H), 4.31 (appar. t, J=9.8 Hz, 1H), 4.12 (dd, J=14.1, 11.9 Hz, 1H), 3.95 (dd, J=11.9, 3.7 Hz, 1H), 3.69 (dd, J=14.3, 3.4 Hz, 1H), 3.62 (dd, J=9.9, 9.2 Hz, 1H), 2.97-2.92 (m, 8H), 1.94-1.92 (m, 4H) ppm.

(98): $^1$H NMR (D$_2$O, 400 MHz) δ 8.26 (appar. d, J=7.6 Hz, 1H), 8.11 (appar. d, J=7.5 Hz, 1H), 7.86 (appar. dd, J=15.0, 7.2 Hz, 2H), 7.74 (appar. t, J=7.7 Hz, 1H), 7.66-7.57 (m, 2H), 5.17 (appar. t, J=9.1 Hz, 1H), 5.02 (s, 1H), 4.42-4.33 (m, 3H), 4.13 (dd, J=14.1, 11.8 Hz, 1H), 3.97 (dd, J=11.8, 3.4 Hz, 1H), 3.73-3.64 (m, 2H), 2.95 (s, 4H) ppm.

(99): $^1$H NMR (D$_2$O, 400 MHz) δ 5.34 (appar. t, J=7.4 Hz, 1H), 5.02 (s, 1H), 4.30 (d, J=10.7, 8.3 Hz, 1H), 4.08 (dd, J=14.0, 12.0 Hz, 1H), 3.90 (dd, J=11.8, 3.3 Hz, 1H), 3.69-3.46 (m, 6H), 2.92 (s, 4H), 2.03-1.97 (m, 4H) ppm.

(101): MS (ES+) m/z calcd. for $C_{28}H_{36}N_8O_5$ 564.28 found 565.34 (MH+).

(102): $^1$H NMR (D$_2$O, 400 MHz) δ 5.35-5.29 (m, 1H), 5.05 (s, 1H), 4.32 (appar. t, J=9.3 Hz, 1H), 4.18-3.90 (m, 4H), 3.72-3.61 (m, 2H), 3.14-3.03 (m, 1H), 3.01-2.93 (m, 4H), 2.76 (appar. t, J=12.3 Hz, 1H), 1.95-1.92 (m, 1H), 1.84-1.58 (m, 3H), 1.34-1.23 (m, 1H), 1.07-0.98 (m, 3H) ppm.

(103): $^1$H NMR (D$_2$O, 400 MHz) δ 7.81 (s, 2H), 7.74-7.70 (m, 2H), 5.36 (appar. t, J=7.0 Hz, 1H), 5.03 (s, 1H), 4.56 (s, 2H), 4.32 (dd, J=10.7, 8.4 Hz, 1H), 4.09 (dd, J=13.4, 12.8 Hz, 1H), 3.93 (dd, J=11.9, 3.2 Hz, 1H), 3.72-3.62 (m, 2H), 2.94 (s, 4H) ppm.

(104): $^1$H NMR (D$_2$O, 400 MHz) δ 7.62 (m, 2H), 7.54-7.53 (m, 2H), 5.12-5.08 (m, 1H), 4.88 (s, 1H), 4.10 (dd, J=10.8, 7.8 Hz, 1H), 3.91 (dd, J=13.6, 12.1 Hz, 1H), 3.82-3.79 (m, 1H), 3.54 (dd, J=14.1, 3.2 Hz, 1H), 3.50-3.45 (m, 2H), 3.38 (dd, J=10.8, 6.1 Hz, 1H), 2.98-2.88 (m, 2H), 2.83 (s, 4H) ppm.

(105): MS (ES+) m/z calcd. for $C_{24}H_{30}N_8O_6$ 526.23 found 527.25 (MH+).

(106): $^1$H NMR (D$_2$O, 400 MHz) δ 7.42 (t, J=7.5 Hz, 2H), 7.35-7.29 (m, 3H), 5.26 (appar. t, J=6.8 Hz, 1H), 4.96 (s, 1H), 4.36-4.28 (m, 1H), 4.22 (dd, J=11.0, 7.8 Hz, 1H), 4.00 (dd, J=13.9, 12.2 Hz, 1H), 3.84 (dd, J=11.9, 3.2 Hz, 1H), 3.64-3.60 (m, 2H), 3.10-3.00 (m, 2H), 2.89-2.76 (m, 6H), 1.94-1.84 (m, 2H), 1.74-1.51 (m, 2H) ppm.

(107): MS (ES+) m/z calcd. for $C_{22}H_{25}F_3N_8O_6$ 538.19 found 539.13 (MH+).

(108): $^1$H NMR (D$_2$O, 400 MHz): δ 5.26-5.22 (m, 1H), 4.95 (s, 1H), 4.24-4.15 (m, 1H), 4.00 (dd, J=14.0, 12.0 Hz, 1H), 3.84 (dd, J=11.8, 3.0 Hz, 1H), 3.66-3.54 (m, 3H), 2.88 (s, 3H), 2.84 (s, 4H), 1.84-1.76 (m, 2H), 1.68-1.60 (m, 2H), 1.55-1.44 (m, 2H), 1.39-1.20 (m, 2H), 1.16-1.05 (m, 2H) ppm.

(110): MS (ES+) m/z calcd. for $C_{25}H_{32}N_8O_6$ 540.24 found 541.18 (MH+).

(111): MS (ES+) m/z calcd. for $C_{23}H_{27}F_3N_8O_6$ 568.20 found 569.14 (MH+).

(115): $^1$H NMR (D$_2$O, 400 MHz) δ 7.45-7.31 (m, 10H), 5.11 (appar. t, J=6.3 Hz, 1H), 4.84 (s, 1H), 4.28 (appar. t, J=8.1 Hz, 1H), 4.07 (dd, J=11.0, 7.1 Hz, 1H), 3.84 (dd, J=13.1, 5.7 Hz, 2H), 3.79-3.76 (m, 2H), 3.42 (dt, J=11.1, 5.6 Hz, 2H), 2.82 (s, 4H) ppm.

(116): $^1$H NMR (D$_2$O, 400 MHz) δ 7.42-7.36 (m, 8H), 7.29-7.25 (m, 2H), 5.12 (appar. t, J=6.6 Hz, 1H), 4.91 (s, 1H), 4.15 (dd, J=10.8, 7.7 Hz, 1H), 4.10-4.05 (m, 1H), 3.98 (dd, J=13.0, 12.0 Hz, 1H), 3.84-3.81 (m, 1H), 3.61 (dd, J=14.0, 2.8 Hz, 1H), 3.47 (dd, J=10.6, 6.5 Hz, 1H), 3.26-3.10 (m, 2H), 2.80 (s, 4H), 2.37-2.32 (m, 2H) ppm.

(117): $^1$H NMR (D$_2$O, 400 MHz) δ 7.62 (appar. s, 1H), 7.61-7.58 (m, 1H), 7.53 (dd, J=6.3, 3.2 Hz, 2H), 5.17 (appar. t, J=6.9 Hz, 1H), 4.91 (s, 1H), 4.17 (dd, J=10.8, 8.0 Hz, 1H), 4.00-3.94 (m, 1H), 3.82 (dd, J=11.9, 3.1 Hz, 1H), 3.61 (dd, J=14.3, 3.3 Hz, 1H), 3.47 (dd, J=10.8, 6.1 Hz, 1H), 3.26-3.12 (m, 2H), 2.81 (s, 4H), 2.81-2.70 (m, 2H), 1.93-1.86 (m, 2H) ppm.

(118): $^1$H NMR (D$_2$O, 400 MHz) δ 7.64-7.54 (m, 4H), 3.97 (appar. t, J=9.7 Hz, 1H), 3.88 (dd, J=13.2, 12.1 Hz, 1H), 3.79 (dd, J=11.5, 2.4 Hz, 1H), 3.53 (dd, J=13.6, 2.5 Hz, 2H), 3.10-3.02 (m, 2H), 2.97 (appar. t, J=9.5 Hz, 1H), 2.84 (s, 4H), 2.74 (appar. t, J=7.0 Hz, 2H) ppm. MS (ES+) m/z calcd. for $C_{23}H_{27}F_3N_8O_5$ 552.21 found 553.14 (MH+).

(120): MS (ES+) m/z calcd. for $C_{22}H_{26}N_7O_6$ 498.19 found 499.14 (MH+).

Example 2

Na$_V$ Inhibition Assay

Electrophysiology experiments were performed on Human Embryonic Kidney 293 cells (HEK) or Chinese hamster ovary cells (CHO) transfected with the full-length cDNA coding for the appropriate human Nay sodium channel α-subunit.

Sodium currents were measured using the patch-clamp technique in the whole-cell configuration with a HEKA EPC 9 amplifier (HEKA Elektronik Dr. Schulze GmbH, Germany) or with an IonFlux 16 automated patch clamp system (Fluxion Biosciences, South San Francisco, USA) as previously described by Moran. See, Moran O, Picollo A, Conti F (2003) Tonic and phasic guanidinium toxin-block of skeletal muscle Na channels expressed in Mammalian cells, Biophys J 84(5):2999-3006. For manual patch-clamp experiments, borosilicate glass micropipettes (Sutter Instruments, Novato, Calif.) were pulled to a tip diameter yielding a resistance of 1.0-2.0 MΩ in the working solutions. The composition of intracellular solution was (in mM): CsF 110, EDTA 20, HEPES 10, NaCl 10, and the pH was adjusted to 7.2 with CsOH. The composition of extracellular solution was (in mM): NaCl 135, KCl 4.5, CaCl$_2$ 2, MgCl$_2$ 1, HEPES 10, and the pH was adjusted to 7.4 with NaOH. Peak currents were generally between 0.5-20 nA.

Lyophilized stock of each of the toxin derivatives were stored at −20° C. and dissolved in the external solution prior to recording. (+)-Saxitoxin and (+)-gonyautoxin-III were synthesized according to routes previously published. (Fleming J J, McReynolds M D, Du Bois J. (+)-saxitoxin: a first and second generation stereoselective synthesis. *J Am Chem Soc.* 2007; 129(32):9964-9975; Mulcahy J V, Du Bois J. A stereoselective synthesis of (+)-gonyautoxin 3. *J Am Chem Soc.* 2008; 130:12630-12631). Current measurements were recorded under continuous perfusion, controlled manually by syringe addition.

The output of the EPC 9 patch-clamp amplifier was filtered with a built-in low-pass, four-pole Bessel filter having a cutoff frequency of 10 kHz and sampled at 20 kHz. For both manual and automated recordings, the membrane was kept at a holding potential of between −120 and −90 mV. Pulse stimulation and data acquisition were controlled with the Pulse software (HEKA Elektronik Dr. Schulze GmbH, Germany) or the IonFlux software (Fluxion Biosciences, South San Francisco, USA). All measurements were performed at room temperature (about 20-22° C.). Recordings were made at least 5 min after establishing the whole-cell and voltage-clamp configuration to allow for stabilization of the voltage-dependent properties of the channels. Currents were elicited by 10 ms step depolarizations from a holding potential to a value between −40 and 0 mV. Data were normalized to control currents, plotted against toxin concentration and analyzed in Microsoft Excel software. Data were fit to a four-parameter logistic equation to determine $IC_{50}$ values and expressed as mean.

TABLE 1

Na$_v$ Isoform Potency and Selectivity
All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 μM < +++ ≤ 100 μM < ++ ≤ 250 μM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| 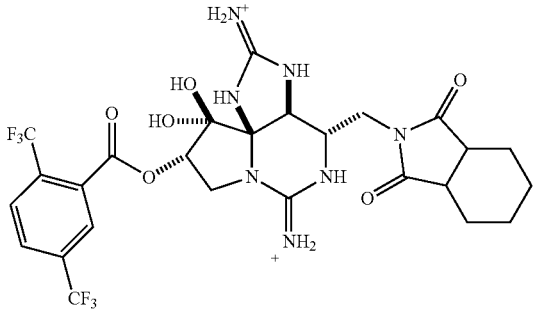 (1) | +++ | ++ | ++ | NT | NT | NT |
| 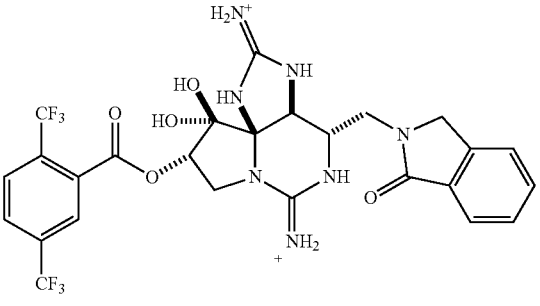 (2) | +++ | +++ | ++ | NT | NT | NT |
| 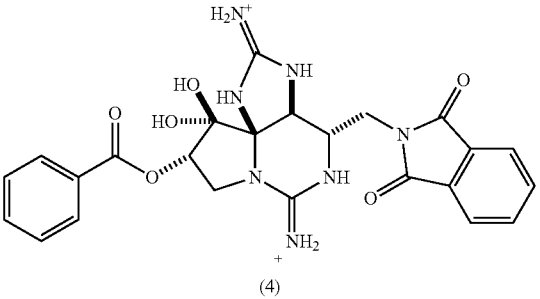 (4) | NT | NT | NT | ++++ | +++ | ++ |
| 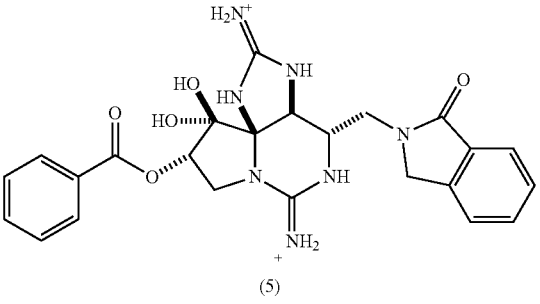 (5) | ++++ | ++++ | + | ++++ | ++++ | + |

TABLE 1-continued

Na$_v$ Isoform Potency and Selectivity
All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 μM < +++ ≤ 100 μM < ++ ≤ 250 μM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| 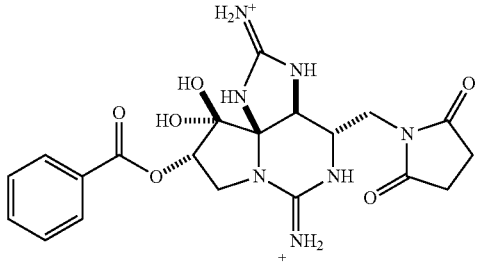 (6) | ++++ | +++ | +++ | +++ | NT | NT |
| 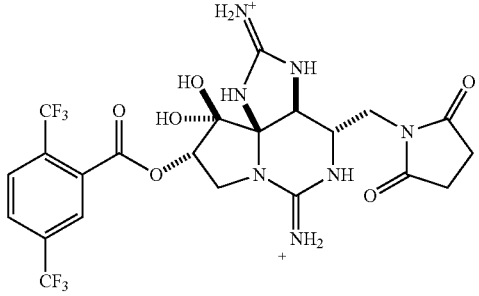 (7) | +++ | +++ | ++ | ++++ | ++ | +++ |
| 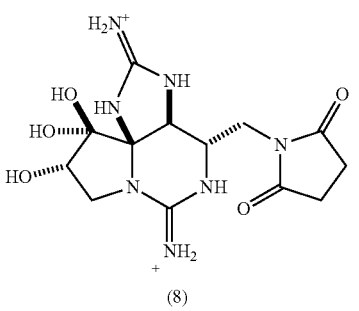 (8) | +++ | ++ | +++ | ++++ | +++ | +++ |
| 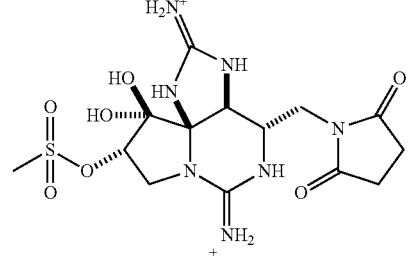 (10) | ++++ | +++ | ++ | ++++ | +++ | ++ |

TABLE 1-continued

Na$_v$ Isoform Potency and Selectivity
All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 μM < +++ ≤ 100 μM < ++ ≤ 250 μM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| 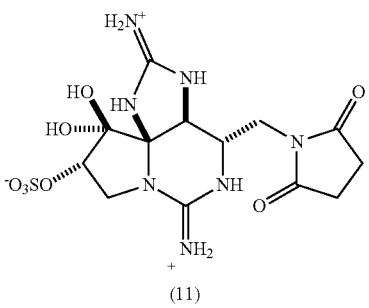 (11) | NT | NT | NT | ++++ | ++ | +++ |
| 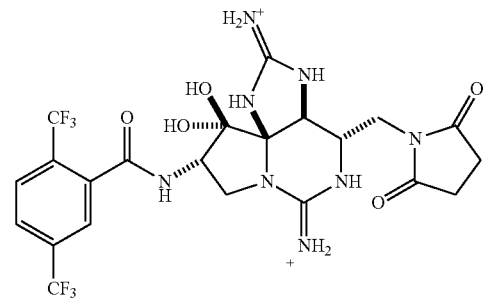 (12) | ++++ | ND | +++ | ++++ | +++ | ++++ |
| 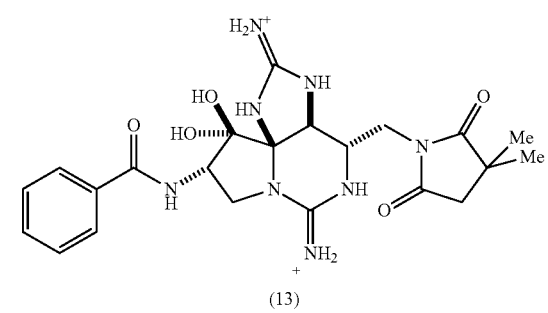 (13) | ++ | ++ | + | NT | NT | NT |
| 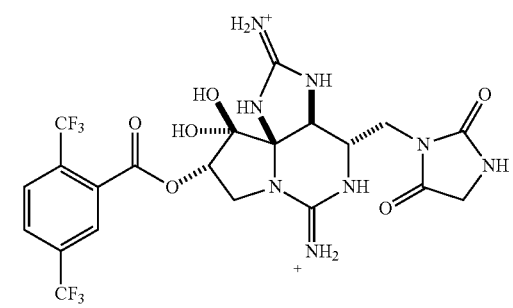 (14) | NT | NT | NT | +++ | +++ | ++ |

TABLE 1-continued

Na$_v$ Isoform Potency and Selectivity

All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 µM < +++ ≤ 100 µM < ++ ≤ 250 µM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| 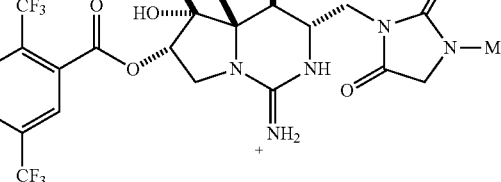 (15) | NT | NT | NT | ++++ | ND | ++ |
| 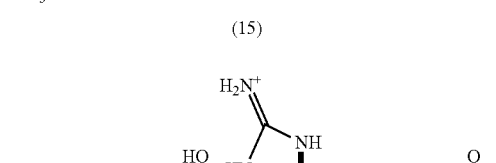 (16) | NT | NT | NT | ++++ | ++++ | ++ |
| 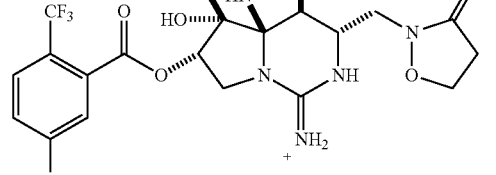 (17) | ++++ | ND | ++ | NT | NT | NT |
| 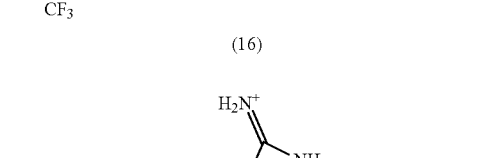 (18) | NT | NT | NT | +++ | ND | + or greater |

TABLE 1-continued

Na_v Isoform Potency and Selectivity

All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system. Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 μM < +++ ≤ 100 μM < ++ ≤ 250 μM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| (19) | NT | NT | NT | +++ | ND | + or greater |
| (20) | ++++ | ++ | +++ | NT | NT | NT |
| (21) | +++ | +++ | + | NT | NT | NT |
| (22) | ++++ | +++ | ++ | NT | NT | NT |

TABLE 1-continued

Na_v Isoform Potency and Selectivity

All data was measured in HEK cells. Column 1 provides $IC_{50}$ data for $Na_v$ 1.7 as measured using an IonFlux 16 automated patch clamp system. Column 2 provides $IC_{50}$ data for $Na_v$ 1.4 as measured using an IonFlux 16 automated patch clamp system Column 3 provides selectivity data for column 1 over column 2. Column 4 provides $IC_{50}$ data for $Na_v$ 1.7 as measured using using the patch-clamp technique in the whole-cell configuration with a HEKA EPC 9 amplifier. Column 5 provides $IC_{50}$ data for $Na_v$ 1.4 as measured using the patch-clamp technique in the whole-cell configuration with a HEKA EPC 9 amplifier. Column 6 provides selectivity data for column 4 over column 5. $IC_{50}$ results are provided in Table 1. ND means not detectable. NT means not tested. Potency is provided as follows: ++++ ≤ 10 μM < +++ ≤ 100 μM < ++ ≤ 250 μM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| (23) | ++++ | ++++ | ++ | NT | NT | NT |
| (24) | NT | NT | NT | ++++ | +++ | +++ |
| (25) | NT | NT | NT | ++++ | +++ | ++++ |
| (26) | NT | NT | NT | ++++ | +++ | +++ |

TABLE 1-continued

Na$_v$ Isoform Potency and Selectivity

All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 μM < +++ ≤ 100 μM < ++ ≤ 250 μM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| 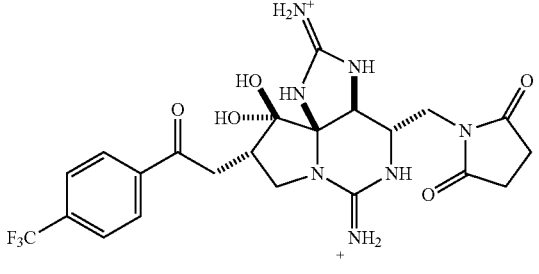 (27) | NT | NT | NT | ++++ | +++ | +++ |
| 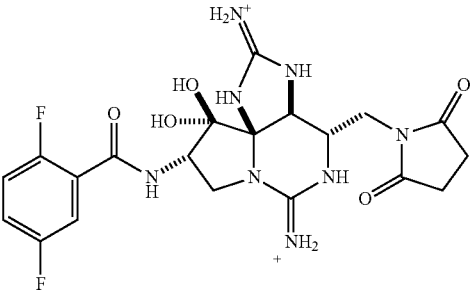 (28) | NT | NT | NT | ++++ | ++ | +++ |
| 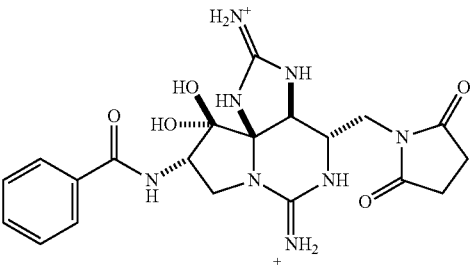 (29) | NT | NT | NT | ++++ | +++ | ++ |
| 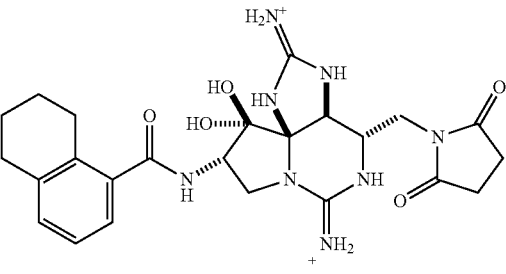 (30) | NT | NT | NT | ++++ | +++ | ++++ |

TABLE 1-continued

Na$_v$ Isoform Potency and Selectivity

All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 μM < +++ ≤ 100 μM < ++ ≤ 250 μM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| 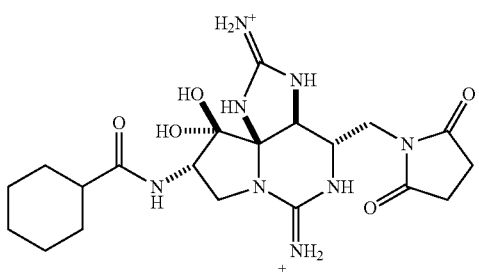 (31) | +++ | +++ | + | NT | NT | NT |
| 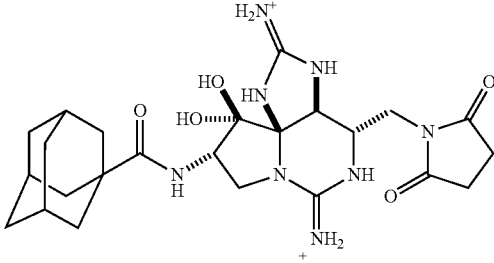 (32) | NT | NT | NT | +++ | +++ | + |
| 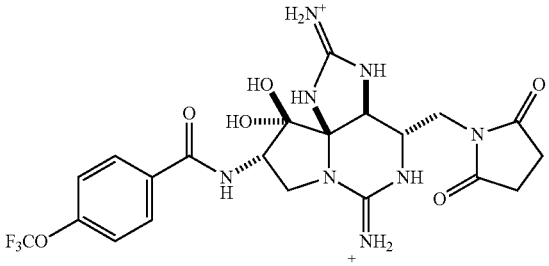 (33) | NT | NT | NT | +++ | +++ | ++ |
| 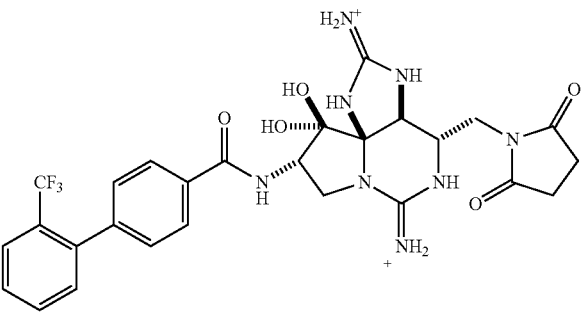 (35) | NT | NT | NT | +++ | +++ | ++ |

TABLE 1-continued

Na$_v$ Isoform Potency and Selectivity
All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 μM < +++ ≤ 100 μM < ++ ≤ 250 μM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| 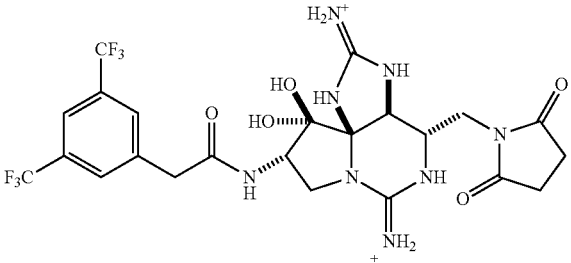 (36) | NT | NT | NT | +++ | +++ | + |
| 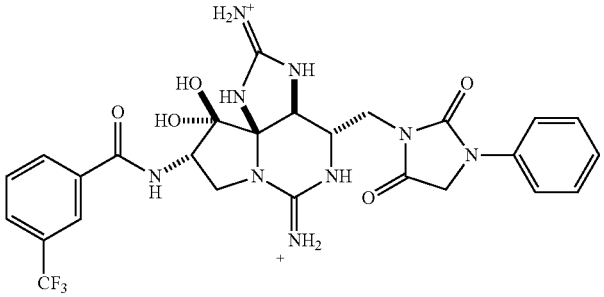 (37) | NT | NT | NT | ++++ | +++ | ++++ |
| 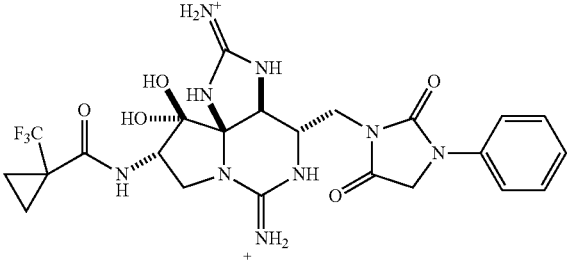 (38) | NT | NT | NT | +++ | +++ | ++ |
| 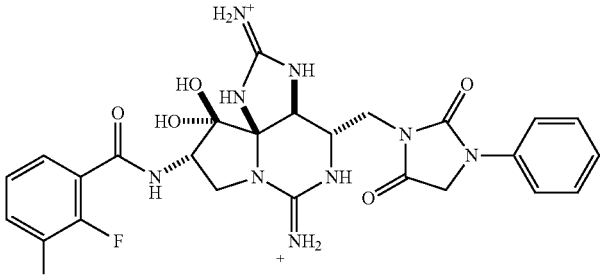 (39) | NT | NT | NT | ++++ | +++ | +++ |

TABLE 1-continued

Na$_v$ Isoform Potency and Selectivity

All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 µM < +++ ≤ 100 µM < ++ ≤ 250 µM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| 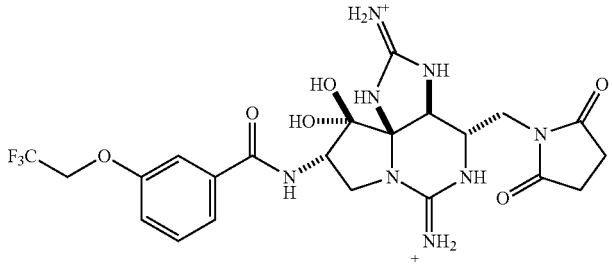 (40) | NT | NT | NT | ++++ | +++ | +++ |
| 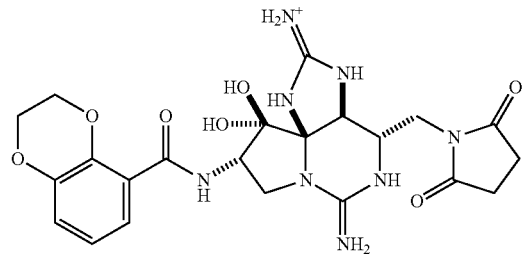 (50) | NT | NT | NT | ++++ | ++++ | ++++ |
| 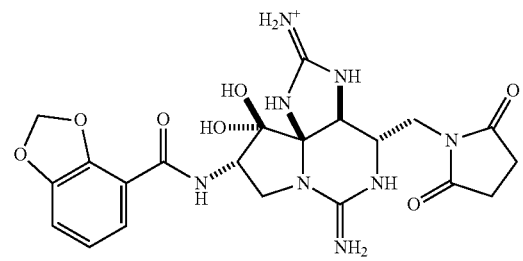 (52) | NT | NT | NT | ++++ | ++ | ++++ |
| 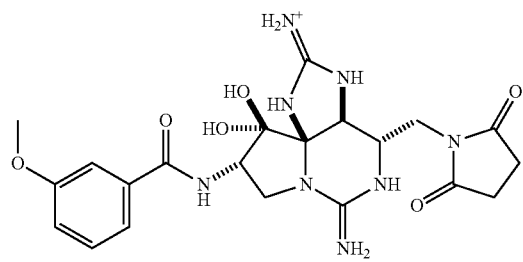 (53) | NT | NT | NT | ++++ | +++ | ++++ |

TABLE 1-continued

Na$_v$ Isoform Potency and Selectivity
All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 μM < +++ ≤ 100 μM < ++ ≤ 250 μM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| 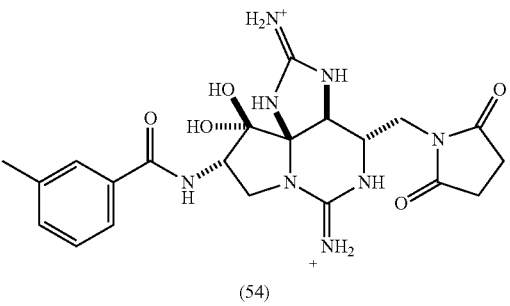 (54) | NT | NT | NT | ++++ | +++ | ++++ |
| 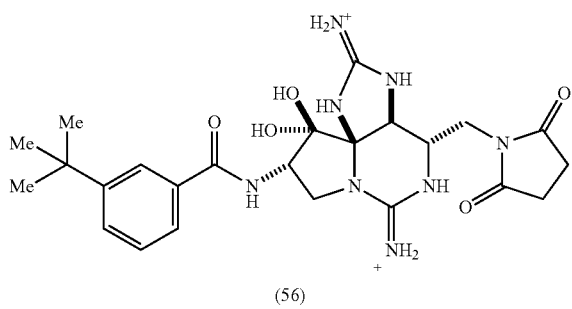 (56) | NT | NT | NT | ++++ | +++ | ++++ |
| 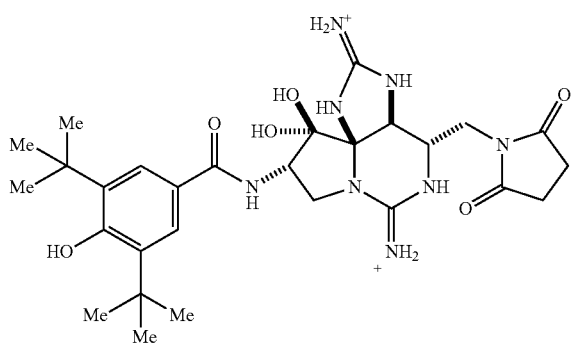 (58) | NT | NT | NT | ND | +++ | + |
| 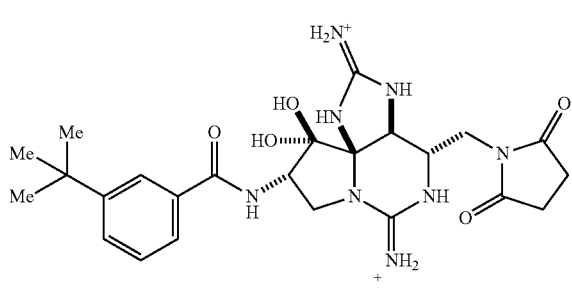 (60) | NT | NT | NT | ++++ | +++ | +++ |

TABLE 1-continued

Na$_v$ Isoform Potency and Selectivity

All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 μM < +++ ≤ 100 μM < ++ ≤ 250 μM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| 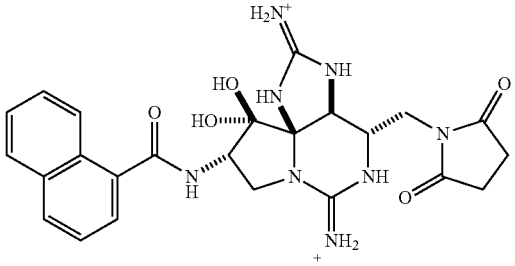 (62) | NT | NT | NT | ++++ | +++ | +++ |
| 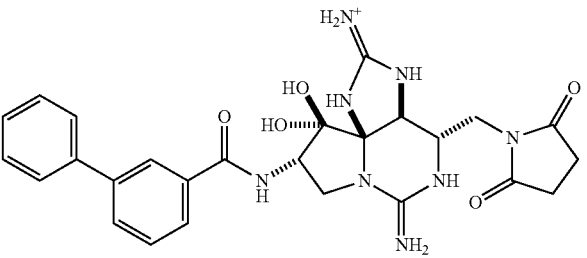 (64) | NT | NT | NT | ++++ | +++ | ++++ |
| 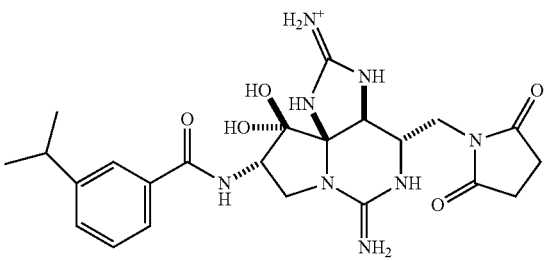 (65) | NT | NT | NT | ++++ | ++++ | ++ |
| 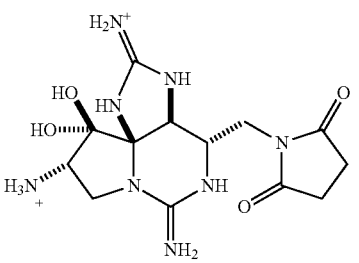 (66) | NT | NT | NT | ++++ | ++++ | + |

TABLE 1-continued

Na$_v$ Isoform Potency and Selectivity

All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 μM < +++ ≤ 100 μM < ++ ≤ 250 μM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| 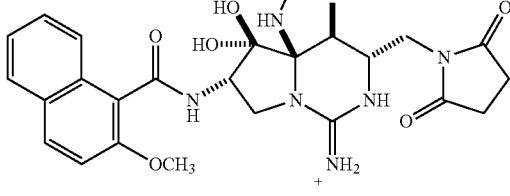 (67) | NT | NT | NT | ++++ | +++ | ++ |
| 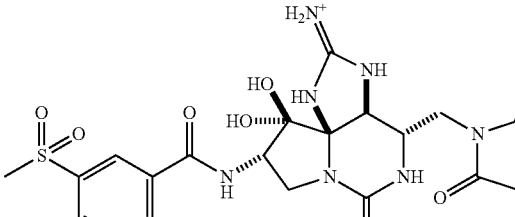 (68) | NT | NT | NT | ++++ | +++ | +++ |
| 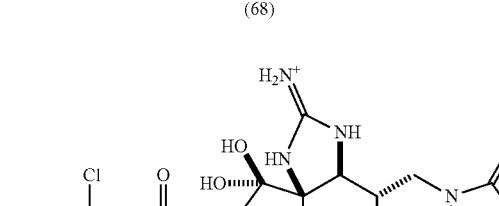 (69) | NT | NT | NT | ++++ | +++ | ++++ |
| 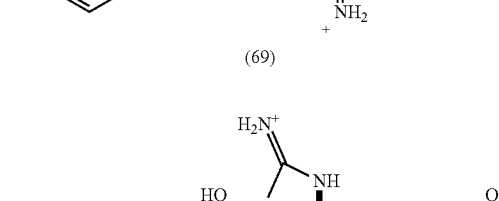 (70) | NT | NT | NT | +++ | + | +++ |

TABLE 1-continued

Na$_v$ Isoform Potency and Selectivity

All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 µM < +++ ≤ 100 µM < ++ ≤ 250 µM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| 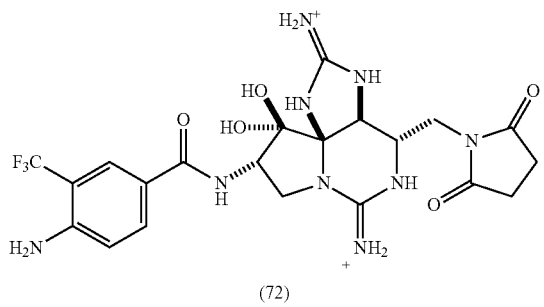 (72) | NT | NT | NT | ++++ | +++ | ++ |
| 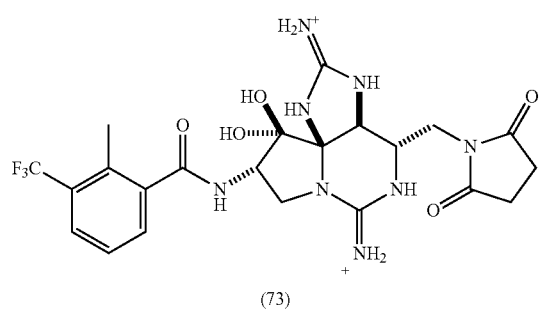 (73) | NT | NT | NT | ++++ | +++ | +++ |
| 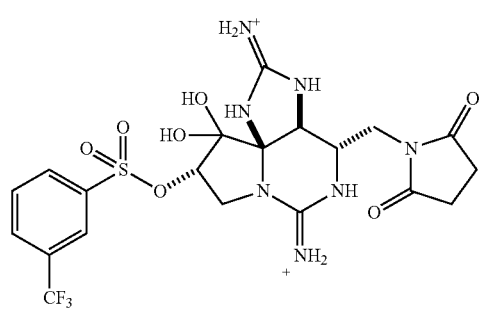 (74) | NT | NT | NT | ND | ND | ND |
| 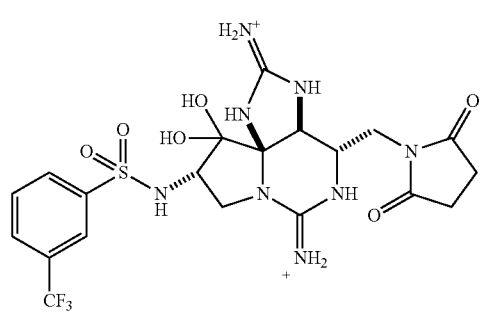 (75) | NT | NT | NT | ND | ND | ND |

TABLE 1-continued

Na$_v$ Isoform Potency and Selectivity

All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 µM < +++ ≤ 100 µM < ++ ≤ 250 µM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| 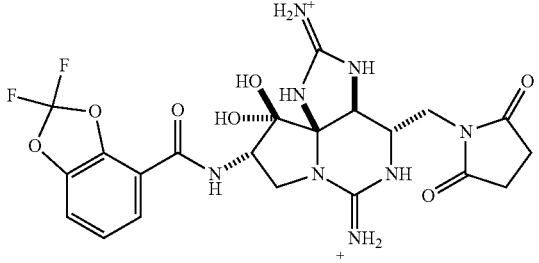 (77) | NT | NT | NT | ++++ | ND | ++++ |
| 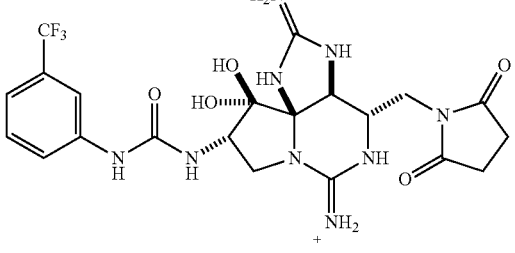 (78) | NT | NT | NT | ND | ND | ND |
| 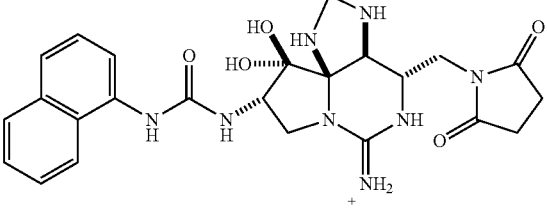 (79) | NT | NT | NT | +++ | ND | + or greater |
| 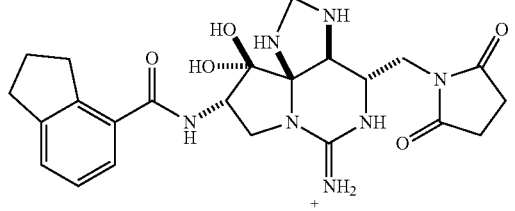 (80) | NT | NT | NT | ++++ | ND | ++++ |

TABLE 1-continued

Na$_v$ Isoform Potency and Selectivity

All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 µM < +++ ≤ 100 µM < ++ ≤ 250 µM < +. Selectivity is provided as follows: + ≤ 1 fold < ++ ≤ 10 fold < +++ ≤ 50 fold < ++++.

| Compound | 1 | 2 | 3 | 4 | 5 | 6 |
| --- | --- | --- | --- | --- | --- | --- |
| (81) | NT | NT | NT | ++++ | ND | + or greater |
| (83) | NT | NT | NT | ++++ | ++++ | ++++ |
| (84) | NT | NT | NT | ++++ | ND | ++ or greater |
| (85) | NT | NT | NT | ++++ | +++ | ++++ |

TABLE 1-continued

Na$_v$ Isoform Potency and Selectivity

All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 μM < +++ ≤ 100 μM < ++ ≤ 250 μM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| (86) | NT | NT | NT | +++ | +++ | ++ |
| (88) | NT | NT | NT | +++ | ND | ++ or greater |
| (90) | NT | NT | NT | +++ | +++ | ++ |
| (91) | NT | NT | NT | +++ | +++ | +++ |

TABLE 1-continued

Na$_v$ Isoform Potency and Selectivity

All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 μM < +++ ≤ 100 μM < ++ ≤ 250 μM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| 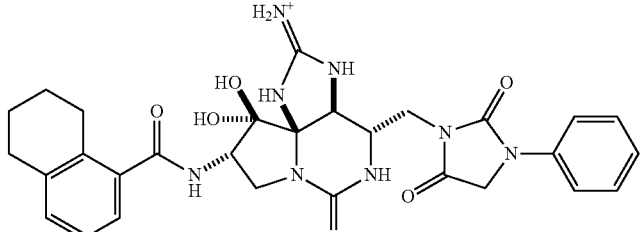 (92) | NT | NT | NT | ++++ | +++ | ++++ |
| 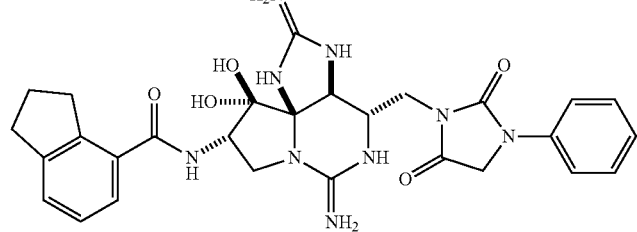 (93) | NT | NT | NT | ++++ | ND | ++++ |
| 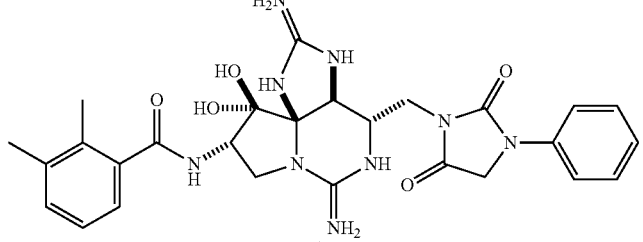 (94) | NT | NT | NT | ++++ | +++ | ++++ |
| 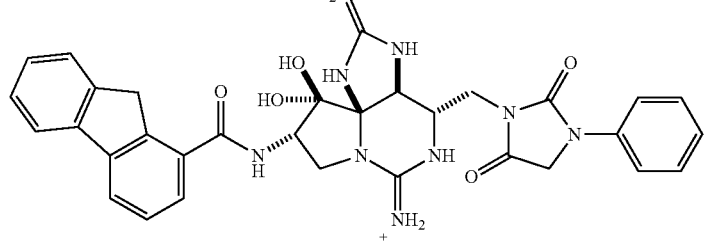 (95) | NT | NT | NT | ++++ | ++++ | +++ |

TABLE 1-continued

Na$_v$ Isoform Potency and Selectivity

All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 μM < +++ ≤ 100 μM < ++ ≤ 250 μM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| 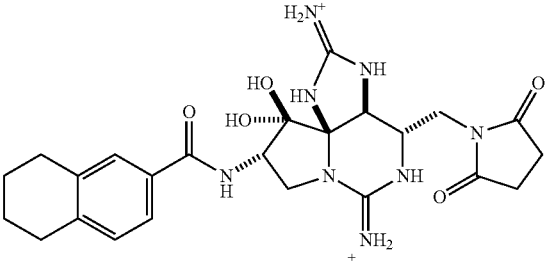 (96) | NT | NT | NT | ++++ | +++ | ++++ |
| 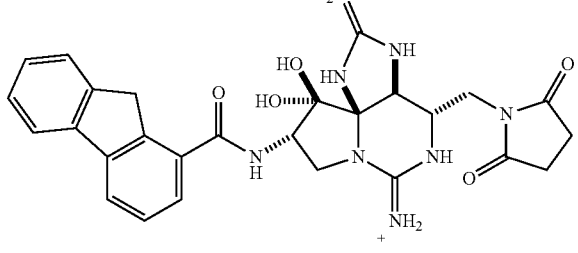 (97) | NT | NT | NT | ++++ | +++ | ++++ |
| 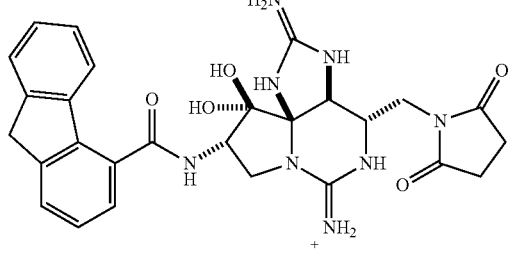 (98) | NT | NT | NT | ++++ | +++ | ++++ |
| 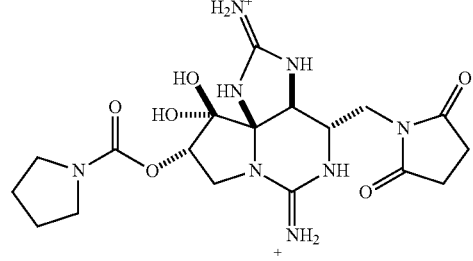 (99) | NT | NT | NT | ++++ | ND | +++ or greater |

TABLE 1-continued

Na$_v$ Isoform Potency and Selectivity

All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 μM < +++ ≤ 100 μM < ++ ≤ 250 μM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| (101) | NT | NT | NT | ++++ | +++ | ++ |
| (102) | NT | NT | NT | ++++ | ND | +++ or greater |
| (103) | NT | NT | NT | ++++ | +++ | +++ |
| (104) | NT | NT | NT | ++++ | +++ | +++ |

TABLE 1-continued

Na$_v$ Isoform Potency and Selectivity

All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 μM < +++ ≤ 100 μM < ++ ≤ 250 μM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| (105) | NT | NT | NT | +++ | ND | ++ or greater |
| (106) | NT | NT | NT | ++++ | +++ | +++ |
| (107) | NT | NT | NT | +++ | ++ | ++ |
| (108) | NT | NT | NT | ++++ | ND | +++ or greater |

TABLE 1-continued

Na$_v$ Isoform Potency and Selectivity
All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system Column 3 provides selectivity data for column 1 over column 2. Column 4 provides IC$_{50}$ data for Na$_v$ 1.7 as measured using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 μM < +++ ≤ 100 μM < ++ ≤ 250 μM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| 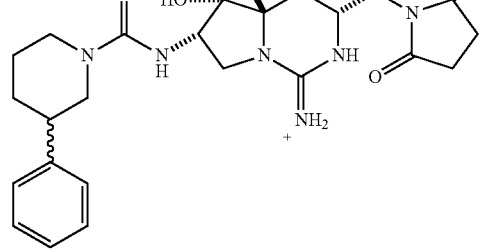 (110) | NT | NT | NT | +++ | +++ | ++ |
| 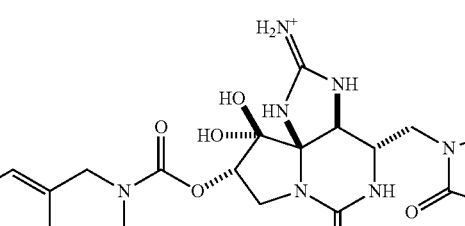 (111) | NT | NT | NT | ++++ | +++ | ++ |
| 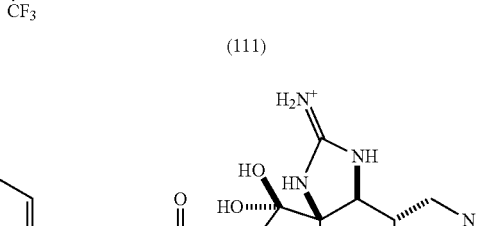 (115) | NT | NT | NT | ++++ | +++ | ++ |
| 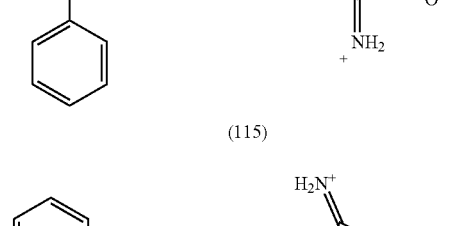 (116) | NT | NT | NT | ++++ | +++ | ++ |

TABLE 1-continued

Na$_v$ Isoform Potency and Selectivity

All data was measured in HEK cells. Column 1 provides IC$_{50}$ data for Na$_v$ 1.7 as measured using an IonFlux 16 automated patch clamp system. Column 2 provides IC$_{50}$ data for Na$_v$ 1.4 as measured using an IonFlux 16 automated patch clamp system. Column 3 provides selectivity data for column 1 over column 2. Column 4 provides IC$_{50}$ data for Na$_v$ 1.7 as measured using the patch-clamp technique in the whole-cell configuration with a HEKA EPC 9 amplifier. Column 5 provides IC$_{50}$ data for Na$_v$ 1.4 as measured using the patch-clamp technique in the whole-cell configuration with a HEKA EPC 9 amplifier. Column 6 provides selectivity data for column 4 over column 5. IC$_{50}$ results are provided in Table 1. ND means not detectable. NT means not tested. Potency is provided as follows: ++++ ≤ 10 µM < +++ ≤ 100 µM < ++ ≤ 250 µM < +. Selectivity is provided as follows: + ≤ 1 fold < ++ ≤ 10 fold < +++ ≤ 50 fold < ++++.

| Compound | 1 | 2 | 3 | 4 | 5 | 6 |
|---|---|---|---|---|---|---|
| 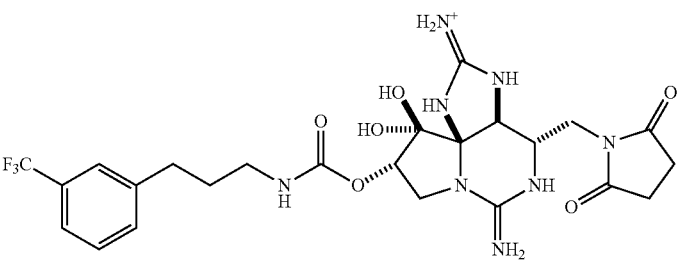 (117) | NT | NT | NT | ++++ | +++ | +++ |
| 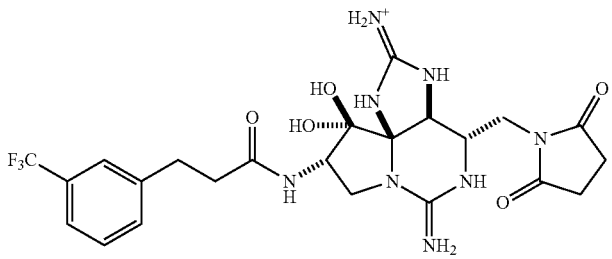 (118) | NT | NT | NT | +++ | ++ | ++ |
| 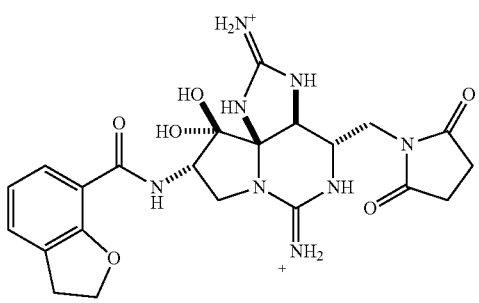 (120) | NT | NT | NT | ++++ | + | ++++ |

All publications, patents, and patent applications cited in this specification are herein incorporated by reference as if each individual publication, patent, or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the claimed subject matter is limited solely by the scope of the following claims, including equivalents thereof.

What is claimed is:

1. A Compound of Formula (I):

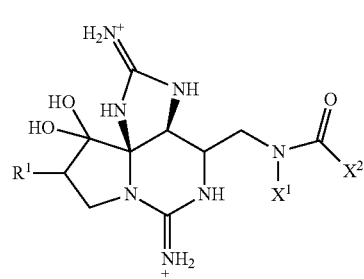

(I)

where $R^1$ is H, OH, —OS(O)$_3^-$, —OS(O)$_2R^5$, —OC(O)R$^6$, —NR$^7$C(O)R$^{7a}$, —OC(O)NR$^{10}$R$^{10a}$, —NR$^{11}$R$^{11a}$, —NH$_3^+$, —NR$^{13}$S(O)$_2$R$^{13a}$, or —NR$^{14}$C(O)NR$^{14a}$R$^{14b}$;

$X^1$ is $R^3$ and $X^2$ is $R^9$; or $X^1$ and $X^2$ together with the —NC(O)— to which they are attached form a 5 or 6-membered ring where $X^1$, $X^2$, and the one or two additional ring atoms are independently selected from —C(O)—, —O—, —S—, —NR$^8$—, and —C(R$^4$)(R$^{4a}$)— provided that only one is selected from —O—, —S—, and —NR$^8$—; and where the 5 or 6-membered ring is optionally fused at two adjacent carbon atoms, or is optionally fused at one carbon atom and one nitrogen atom which are adjacent to each other, to a form a saturated or unsaturated 6-12 membered bicyclic ring; where the 1, 2, 3, 4, 5, or 6 additional bicyclic ring atoms are independently —CR$^{12}$= or —C(R$^{12}$)$_2$—; or $X^1$ and $X^2$ together with the —NC(O)— to which they are attached form 1,3-dioxo-hexahydro-1H-4,7-methanoisoindolyl;

each $R^4$ and $R^{4a}$ is independently H; C$_{1-6}$alkyl; or when the 6-12 membered ring is fused at a —C(R$^4$)(R$^{4a}$—, one or both of the $R^4$ and $R^{4a}$ on the —C(R$^4$)(R$^{4a}$)— form a single or double bond with an adjacent ring atom;

$R^8$ is hydrogen; C$_{1-6}$alkyl; phenyl optionally substituted with 1, 2, or 3 groups independently selected from halo, C$_{1-6}$alkyl, halo-C$_{1-6}$alkyl, hydroxy, C$_{1-6}$alkoxy, halo-C$_{1-6}$alkoxy, nitro, and cyano; or when the 6-12 membered ring is fused at an —NR$^8$—, the $R^8$ forms a single bond with an adjacent ring atom;

each $R^{12}$ is independently hydrogen, halo, C$_{1-6}$alkyl, halo-C$_{1-6}$alkyl, or aryl;

$R^3$ is —C(O)C$_{1-6}$alkyl, —C(O)OC$_{1-6}$alkyl, or —C(O)phenyl where the phenyl is optionally substituted with one or two groups independently selected from halo, C$_{1-6}$alkyl, halo-C$_{1-6}$alkyl, C$_{1-6}$alkoxy, and aryl;

$R^5$ is H, C$_{1-6}$alkyl, or aryl optionally substituted with 1, 2, 3, or 4 R$^{5a}$;

each $R^{5a}$, when present, is independently halo, C$_{1-6}$alkyl, halo-C$_{1-6}$alkyl, hydroxy, C$_{1-6}$alkoxy, halo-C$_{1-6}$alkoxy, C$_{1-6}$alkylthio, halo-C$_{1-6}$alkylthio, C$_{1-6}$alkylsulfinyl, halo-C$_{1-6}$alkylsulfinyl, C$_{1-6}$alkylsulfonyl, halo-C$_{1-6}$alkylsulfonyl, nitro, amino, C$_{1-6}$alkylamino, di-C$_{1-6}$alkylamino, phenyl, or cyano;

$R^9$ is C$_{1-6}$alkyl, C$_{1-6}$alkoxy, or phenyl where the phenyl is optionally substituted with one or two groups independently selected from halo, C$_{1-6}$alkyl, halo-C$_{1-6}$alkyl, C$_{1-6}$alkoxy, and aryl;

$R^6$ is C$_{1-6}$alkyl; aryl optionally substituted with 1, 2, 3, or 4 R$^{6a}$; aralkyl where the aryl is optionally substituted with 1, 2, 3, or 4 R$^{6a}$; heteroaryl optionally substituted with 1, 2, 3, or 4 R$^{6a}$; heterocyclic optionally substituted with 1, 2, 3, or 4 R$^{6a}$; biphenyl optionally substituted on either ring with 1, 2, or 3 R$^{6a}$; or cycloalkyl optionally substituted with 1, 2, 3, or 4 groups independently selected from C$_{1-6}$alkyl and halo-C$_{1-6}$alkyl;

each $R^{6a}$, when present, is independently halo, C$_{1-6}$alkyl, halo-C$_{1-6}$alkyl, hydroxy, C$_{1-6}$alkoxy, halo-C$_{1-6}$alkoxy, nitro, C$_{1-6}$alkylthio, halo-C$_{1-6}$alkylthio, C$_{1-6}$alkylsulfinyl, halo-C$_{1-6}$alkylsulfinyl, C$_{1-6}$alkylsulfonyl, halo-C$_{1-6}$alkylsulfonyl, amino, C$_{1-6}$alkylamino, di-C$_{1-6}$alkylamino, phenyl, or cyano;

$R^7$ is hydrogen or C$_{1-6}$alkyl;

$R^7$a is C$_{1-6}$alkyl; aryl optionally substituted with 1, 2, 3, or 4 R$^{7b}$; aralkyl where the aryl is optionally substituted with 1, 2, 3, or 4 R$^{7b}$; heteroaryl optionally substituted with 1, 2, 3, or 4 R$^{7b}$; heterocyclic optionally substituted with 1, 2, 3, or 4 R$^{7b}$; biphenyl optionally substituted on either ring with 1, 2, or 3 R$^{7b}$; or cycloalkyl optionally substituted with 1, 2, 3, or 4 groups independently selected from C$_{1-6}$alkyl and halo-C$_{1-6}$alkyl;

each $R^{7b}$, when present, is independently halo, C$_{1-6}$alkyl, halo-C$_{1-6}$alkyl, hydroxy, C$_{1-6}$alkoxy, halo-C$_{1-6}$alkoxy, nitro, C$_{1-6}$alkylthio, halo-C$_{1-6}$alkylthio, C$_{1-6}$alkylsulfinyl, halo-C$_{1-6}$alkylsulfinyl, C$_{1-6}$alkylsulfonyl, halo-C$_{1-6}$alkylsulfonyl, amino, C$_{1-6}$alkylamino, di-C$_{1-6}$alkylamino, phenyl, or cyano;

$R^{10}$ is hydrogen or C$_{1-6}$alkyl;

$R^{10a}$ is C$_{1-6}$alkyl; aryl optionally substituted with 1, 2, 3, or 4 R$^{10b}$; aralkyl where the aryl is optionally substituted with 1, 2, 3, or 4 R$^{10b}$; phenylcarbonyl where the phenyl is optionally substituted with 1, 2, or 3 R$^{10b}$; heteroaryl optionally substituted with 1, 2, 3, or 4 R$^{10b}$; heterocyclic optionally substituted with 1, 2, 3, or 4 R$^{10b}$; biphenyl optionally substituted on either ring with 1, 2, 3, or 4 R$^{10b}$, or cycloalkyl optionally substituted with 1, 2, 3, or 4 groups independently selected from C$_{1-6}$alkyl and halo-C$_{1-6}$alkyl;

each $R^{10b}$, when present, is independently halo, C$_{1-6}$alkyl, halo-C$_{1-6}$alkyl, hydroxy, C$_{1-6}$alkoxy, halo-C$_{1-6}$alkoxy, nitro, C$_{1-6}$alkylthio, halo-C$_{1-6}$alkylthio, C$_{1-6}$alkylsulfinyl, halo-C$_{1-6}$alkylsulfinyl, C$_{1-6}$alkylsulfonyl, halo-C$_{1-6}$alkylsulfonyl, amino, C$_{1-6}$alkylamino, di-C$_{1-6}$alkylamino, phenyl, or cyano;

$R^{11}$ is hydrogen or C$_{1-6}$alkyl;

$R^{11a}$ is C$_{1-6}$alkyl; aryl optionally substituted with 1, 2, 3, or 4 R$^{11b}$; aralkyl where the aryl is optionally substituted with 1, 2, 3, or 4 R$^{11b}$; heteroaryl optionally substituted with 1, 2, 3, or 4 R$^{11b}$; heterocyclic optionally substituted with 1, 2, 3, or 4 R$^{11b}$; biphenyl optionally substituted on either ring with 1, 2, 3, or 4 R$^{11b}$; or cycloalkyl optionally substituted with 1, 2, or 3 groups independently selected from C$_{1-6}$alkyl and halo-C$_{1-6}$alkyl; and each $R^{11b}$, when present, is independently halo, C$_{1-6}$alkyl, halo-C$_{1-6}$alkyl, hydroxy, C$_{1-6}$alkoxy, halo-C$_{1-6}$alkoxy, nitro, C$_{1-6}$alkylthio, halo-C$_{1-6}$alkylthio, C$_{1-6}$alkylsulfinyl, halo-C$_{1-6}$alkylsulfinyl, C$_{1-6}$alkylsulfonyl, halo-C$_{1-6}$alkylsulfonyl, amino, C$_{1-6}$alkylamino, di-C$_{1-6}$alkylamino, phenyl, or cyano;

$R^{13}$ is hydrogen or C$_{1-6}$alkyl;

$R^{13a}$ is C$_{1-6}$alkyl; aryl optionally substituted with 1, 2, 3, or 4 R$^{13b}$; aralkyl where the aryl is optionally substituted with 1, 2, 3, or 4 R$^{13b}$; heteroaryl optionally substituted with 1, 2, 3, or 4 R$^{13b}$; heterocyclic optionally substituted with 1, 2, 3, or 4 R$^{13b}$; biphenyl optionally substituted on either ring with 1, 2, 3, or 4 R$^{13b}$; or cycloalkyl optionally substituted with 1, 2, 3, or 4 groups independently selected from C$_{1-6}$alkyl and halo-C$_{1-6}$alkyl;

each $R^{13b}$, when present, is independently halo, C$_{1-6}$alkyl, halo-C$_{1-6}$alkyl, hydroxy, C$_{1-6}$alkoxy, halo-C$_{1-6}$alkoxy, C$_{1-6}$alkylthio, halo-C$_{1-6}$alkylthio, C$_{1-6}$alkylsulfinyl, halo-C$_{1-6}$alkylsulfinyl, C$_{1-6}$alkylsulfonyl, halo-C$_{1-6}$alkylsulfonyl, nitro, amino, C$_{1-6}$alkylamino, di-C$_{1-6}$alkylamino, phenyl, or cyano;

$R^{14}$ is hydrogen or C$_{1-6}$alkyl;

$R^{14a}$ is hydrogen or C$_{1-6}$alkyl;

$R^{14b}$) is $C_{1-6}$alkyl; aryl optionally substituted with 1, 2, 3, or 4 $R^{14c}$; aralkyl where the aryl is optionally substituted with 1, 2, 3, or 4 $R^{14c}$; heteroaryl optionally substituted with 1, 2, 3, or 4 $R^{14c}$; heterocyclic optionally substituted with 1, 2, 3, or 4 $R^{14c}$; biphenyl optionally substituted on either ring with 1, 2, 3, or 4 $R^{14c}$; or cycloalkyl optionally substituted with 1, 2, 3, or 4 groups independently selected from $C_{1-6}$alkyl and halo-$C_{1-6}$alkyl; and each $R^{14c}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano; or a pharmaceutically acceptable salt, stereoisomer, tautomer, or mixture thereof.

2. The Compound of claim 1 where the compound is according to Formula (Ia):

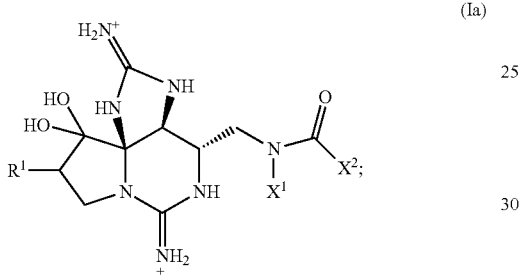

(Ia)

or a pharmaceutically acceptable salt, stereoisomer, tautomer, or mixture thereof.

3. The Compound of claim 1 where the compound is according to Formula (Ib):

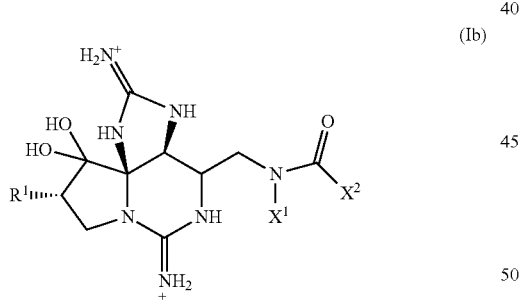

(Ib)

or a pharmaceutically acceptable salt, stereoisomer, tautomer, or mixture thereof.

4. The Compound of claim 1 where
$X^1$ is $R^3$ and $X^2$ is $R^9$; or
$X^1$ and $X^2$ together with the —NC(O)— to which they are attached form

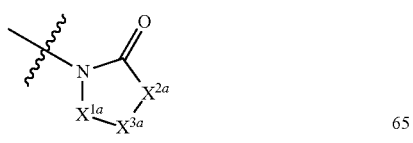

where $X^{1a}$ is —O—, —CH$_2$—, or —C(O)—; $X^{2a}$ is —S—, —NR$^8$— or —C(R$^4$)(R$^{4a}$)—, and $X^{3a}$ is one or two groups independently selected from —O—, —S—, —NR$^8$—, and —C(R$^4$)(R$^{4a}$)— provided that only one atom of $X^{1a}$, $X^{2a}$, and $X^{3a}$ is selected from —O—, —S—, and —NR$^8$—; and where the

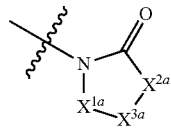

ring is optionally fused at $X^{2a}$ and at the adjacent atom in $X^{3a}$ to form a saturated or unsaturated, 6-12 membered bicyclic ring when 1) $X^{2a}$ is —NR$^8$— and $X^{3a}$ is —C(R$^4$)(R$^{4a}$)— or —C(R$^4$)(R$^{4a}$)—C(R$^4$)(R$^{4a}$)— or 2) $X^{2a}$ is —C(R$^4$)(R$^{4a}$)— and $X^{3a}$ is —C(R$^4$)(R$^{4a}$)—, —NR$^8$—, —C(R$^4$)(R$^{4a}$)—C(R$^4$)(R$^{4a}$)—, —C(R$^4$)(R$^{4a}$)—NR$^8$—, or —NR$^8$—C(R$^4$)(R$^{4a}$)—; and where the 1, 2, 3, 4, 5, or 6 additional ring atoms are independently —CR$^{12}$= or —C(R$^{12}$)$_2$—; or a pharmaceutically acceptable salt, stereoisomer, tautomer, or mixture thereof.

5. The Compound of claim 1 where $X^1$ is $R^3$ and $X^2$ is $R^9$.

6. The Compound of claim 1 where $X^1$ and $X^2$ together with the —NC(O)— to which they are attached form

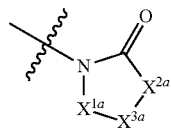

where $X^{1a}$ is —O—, —CH$_2$—, or —C(O)—; $X^{2a}$ is —S—, —NR$^8$—, or —C(R$^4$)(R$^{4a}$)—; and $X^{3a}$ is one or two groups independently selected from —O—, —S—, —NR$^8$—, and —C(R$^4$)(R$^{4a}$)— provided that only one atom of $X^{1a}$, $X^{2a}$, and $X^{3a}$ is selected from —O—, —S—, and —NR$^8$—; and where the

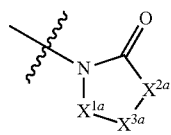

ring is optionally fused at $X^{2a}$ and at the adjacent atom in $X^{3a}$ to form a saturated or unsaturated, 6-12 membered bicyclic ring when 1) $X^{2a}$ is —NR$^8$— and $X^{3a}$ is —C(R$^4$)(R$^{4a}$)— or —C(R$^4$)(R$^{4a}$)—C(R$^4$)(R$^{4a}$)13 or 2) $X^{2a}$ is —C(R$^4$)(R$^{4a}$)— and $X^{3a}$ is —C(R$^4$)(R$^{4a}$)—, —NR$^8$—, —C(R$^4$)(R$^{4a}$)—C(R$^4$)(R$^{4a}$), —C(R$^4$)(R$^{4a}$)—NR$^8$—, or —NR$^8$—C(R$^4$)(R$^{4a}$)—; and where the three or four additional ring atoms are independently —CR$^{12}$= or —C(R$^{12}$)$_2$—;

each $R^4$ and $R^{4a}$ is independently H; $C_{1-6}$alkyl; or when the 6-12 membered ring is fused at a —C(R$^4$)(R$^{4a}$)—, one or both of the R$^4$ and R$^{4a}$ on the —C(R$^4$)(R$^{4a}$)— form a single or double bond with an adjacent ring atom;

$R^8$ is hydrogen; $C_{1-6}$alkyl; phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano; or when the 6-12 membered ring is fused at an —$NR^8$—, the $R^8$ forms a single bond with an adjacent ring atom; and each $R^{12}$ is independently hydrogen, halo, $C_{1-6}$alkyl, halo-$C_{1-6}$alkyl, or aryl; or a pharmaceutically acceptable salt, stereoisomer, tautomer, or mixture thereof.

7. The Compound of claim 1 where $X^1$ and $X^2$ together with the —NC(O)— to which they are attached form a 5-membered ring where the 5-membered ring is optionally fused at two adjacent carbon atoms and is

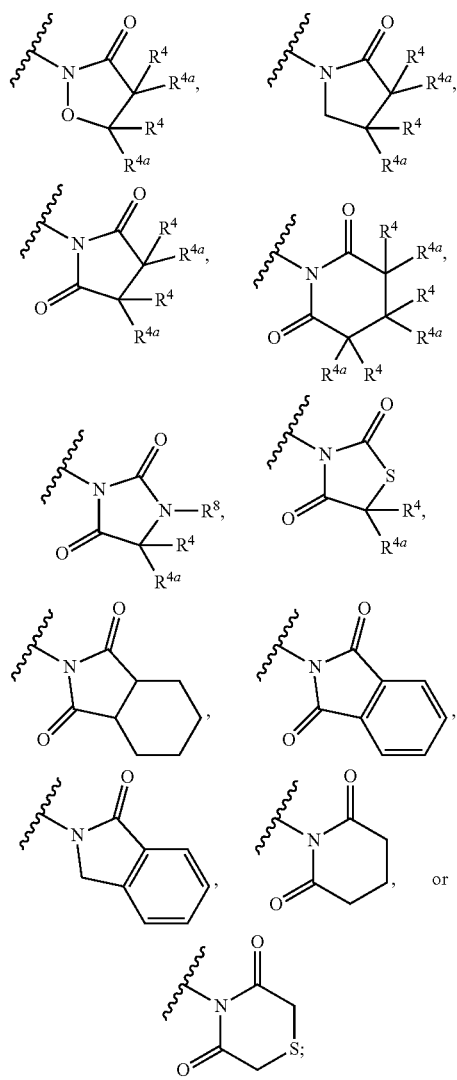

or a pharmaceutically acceptable salt, stereoisomer, tautomer, or mixture thereof.

8. The Compound of claim 1 where $X^1$ and $X^2$ together with the —NC(O)— to which they are attached form a 5-membered ring where the 5-membered ring is optionally fused at two adjacent carbon atoms and is

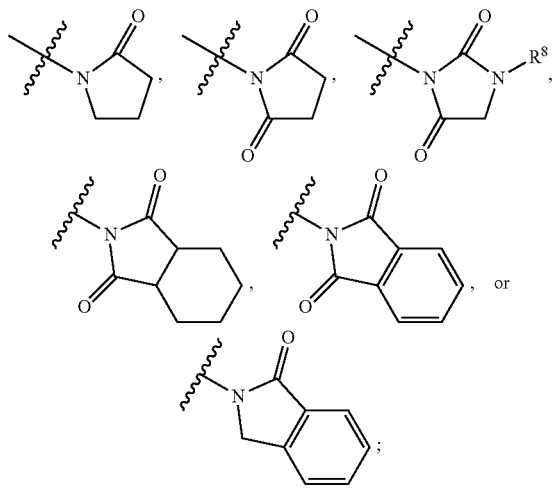

or a pharmaceutically acceptable salt, stereoisomer, tautomer, or mixture thereof.

9. The Compound of claim 1 where $X^1$ and $X^2$ together with the —NC(O)— to which they are attached form a 5-membered ring which is or a pharmaceutically acceptable salt, stereoisomer, tautomer, or mixture thereof.

10. The Compound of claim 7 where $R^5$ is $C_{1-6}$alkyl or aryl optionally substituted with 1, 2, 3, or 4 $R^5$;

$R^6$ is aryl optionally substituted with 1, 2, 3, or 4 $R^{6a}$; or heterocyclic optionally substituted with 1, 2, 3, or 4 $R^{6a}$;

$R^7a$ is aryl optionally substituted with 1, 2, 3, or 4 $R^{7b}$; or heterocyclic optionally substituted with 1, 2, 3, or 4 $R^{7b}$;

$R^{10a}$ is aryl optionally substituted with 1, 2, 3, or 4 $R^{10b}$; or heterocyclic optionally substituted with 1, 2, 3, or 4 $R^{10b}$;

$R^{11a}$ is aryl optionally substituted with 1, 2, 3, or 4 $R^{11b}$; or heterocyclic optionally substituted with 1, 2, 3, or 4 $R^{11b}$;

$R^{13a}$ is aryl optionally substituted with 1, 2, 3, or 4 $R^{13b}$; or heterocyclic optionally substituted with 1, 2, 3, or 4 $R^{13b}$; and $R^{14b}$ is aryl optionally substituted with 1, 2, 3, or 4 $R^{14c}$; or heterocyclic optionally substituted with 1, 2, 3, or 4 $R^{14c}$.

11. The Compound of claim 1 where $R^1$ is —$OS(O)_2R^5$, —$OC(O)^6$, —$NR^7C(O)NR^{7a}$, —$OC(O)NR^{10}R^{10a}$, —$NR^{11}R^{11a}$, —$NR^{13}S(O)_2R^{13a}$, or —$NR^{14}C(O)NR^{14a}R^{14b}$.

12. The Compound of claim 1 where $R^1$ is —$OC(O)R^6$ or —$NR^7C(O)R^{7a}$.

13. The Compound of claim 1 where $R^7$, $R^{10}$, $R^{11}$, $R^{13}$, $R^{14}$, and $R^{14a}$ are hydrogen.

14. The Compound of claim 1 where the aryl in $R^1$ is phenyl, naphthyl, tetrahydronaphthyl, fluorenyl, or indanyl; each of which is optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, $C_{1-6}$alkylthio, $C_{1-6}$alkylsulfonyl, and amino.

15. The Compound of claim 1 where the heterocyclic in $R^1$ is benzo-1,4-dioxanyl, benzodioxolyl, indolinyl, 2-oxo-indolinyl, pyrrolidinyl, piperidinyl, 2,3-dihydrobenzofuranyl, or decahydroquinolinyl; each of which is optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, and phenyl.

16. The compound of claim 1 where the Compound is selected from the compounds of Formula 1-122:

(1)

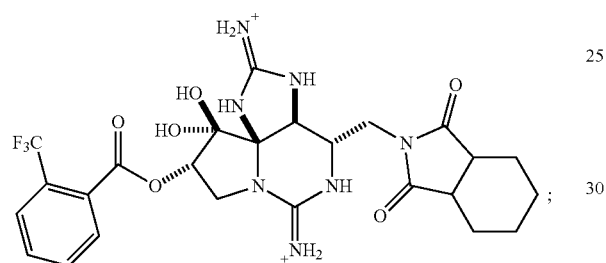

(2)

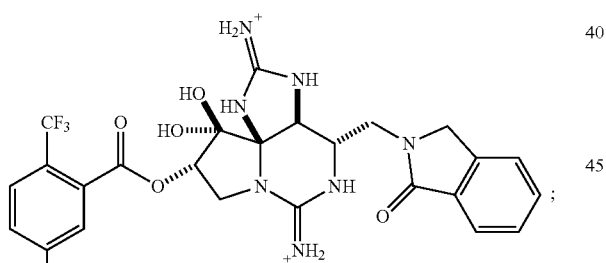

(3)

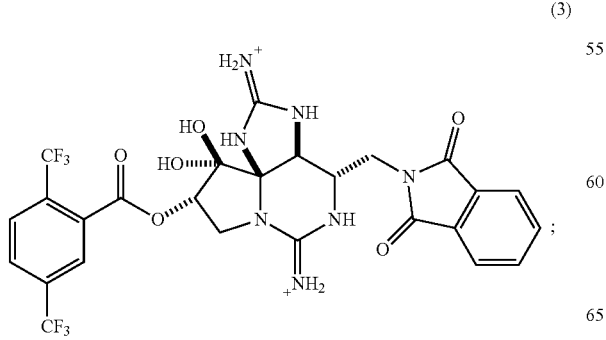

-continued (4)

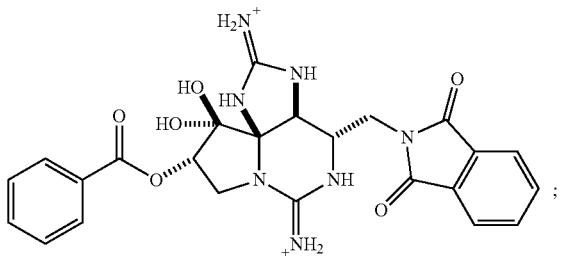

(5)

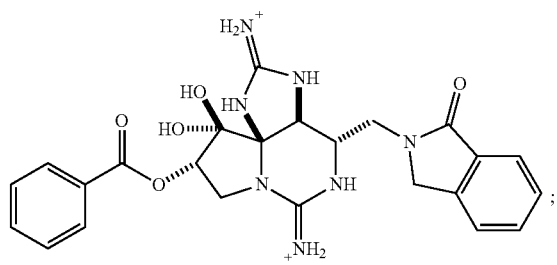

(6)

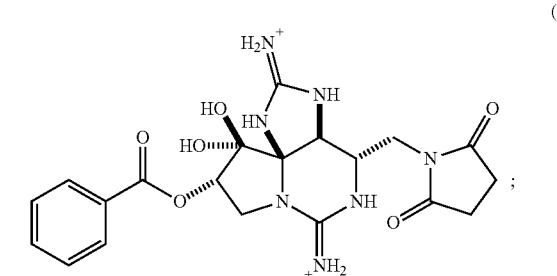

(7)

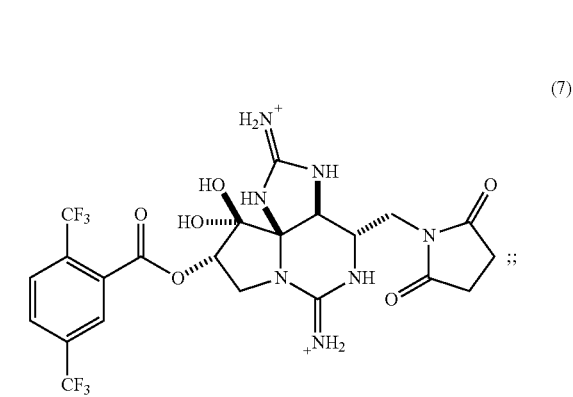

(8)

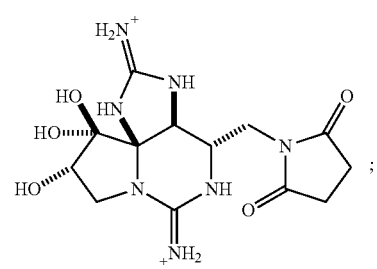

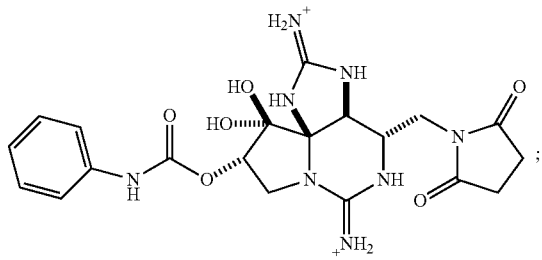 (9)
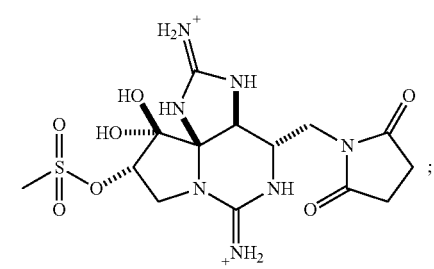 (10)
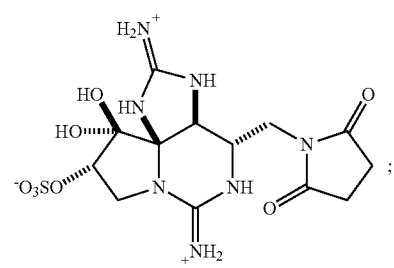 (11)
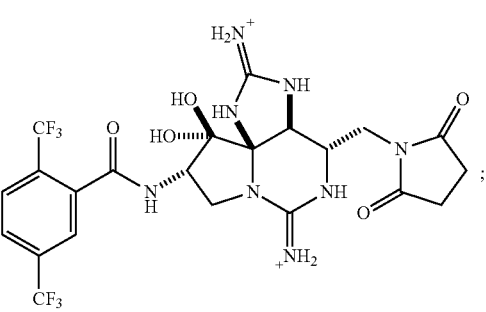 (12)
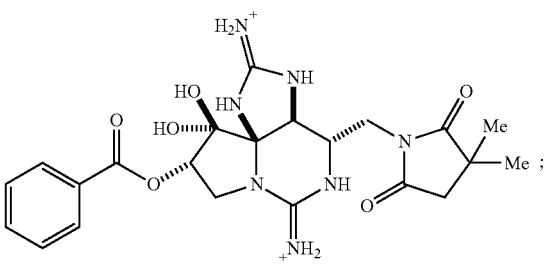 (13)
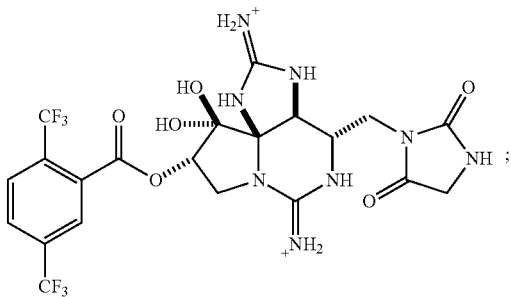 (14)
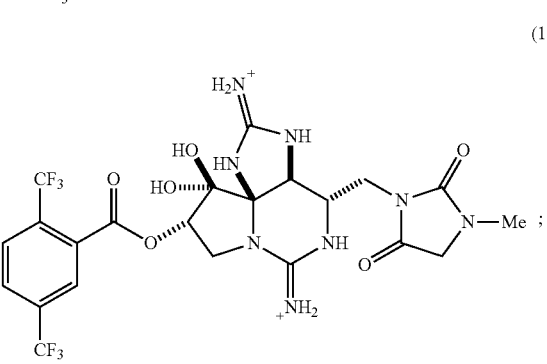 (15)
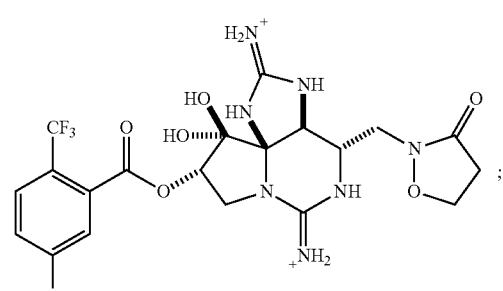 (16)
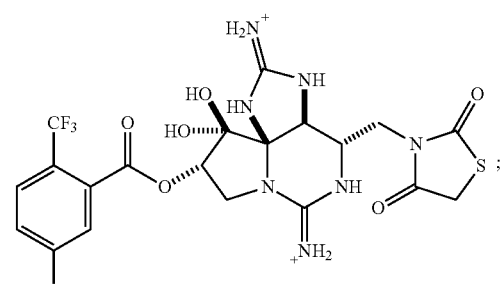 (17)
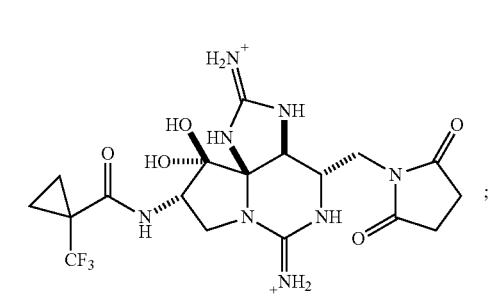 (18)

(19) 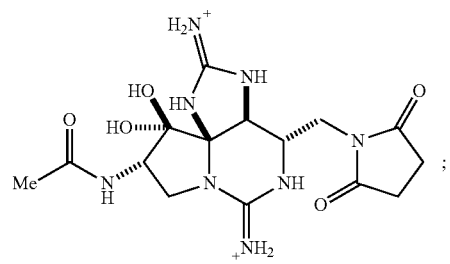
(20) 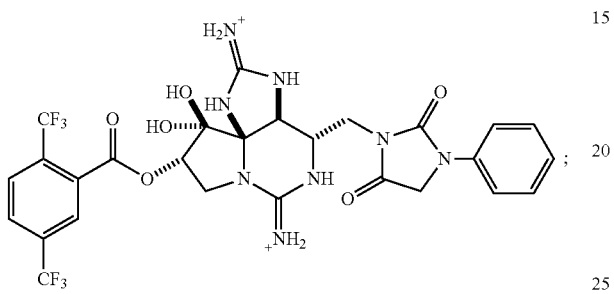
(21) 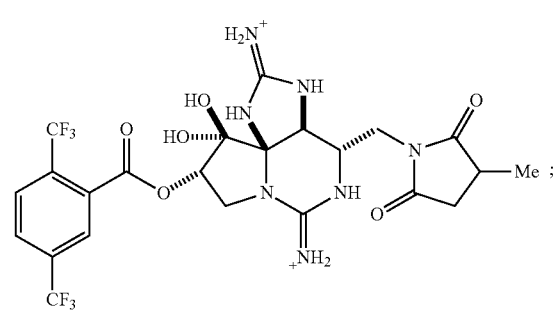
(22) 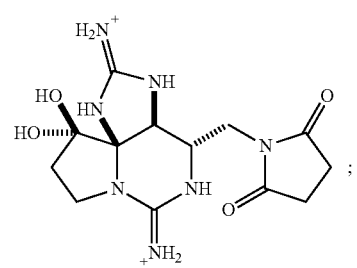
(23) 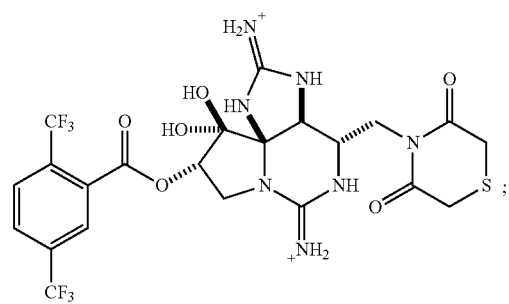
(24) 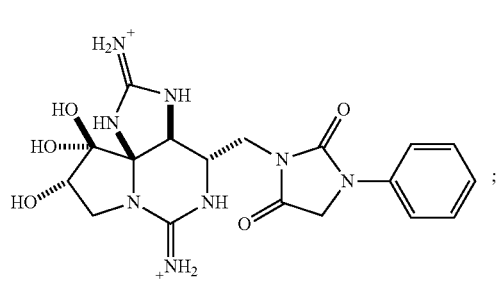
(25) 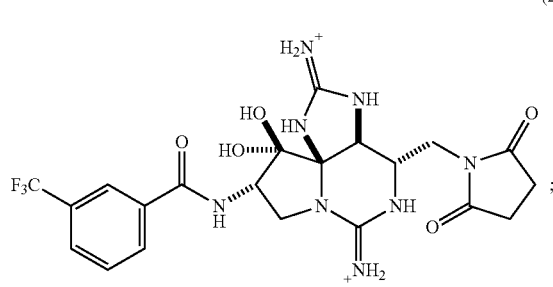
(26) 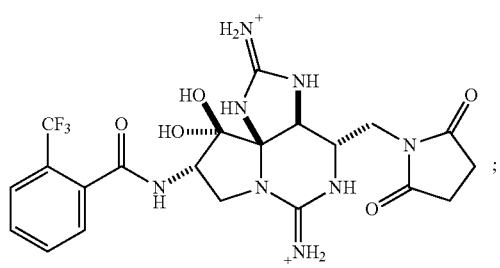
(27) 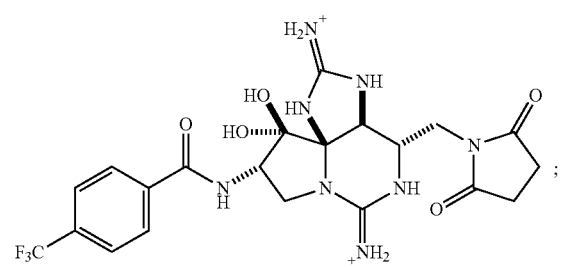
(28) 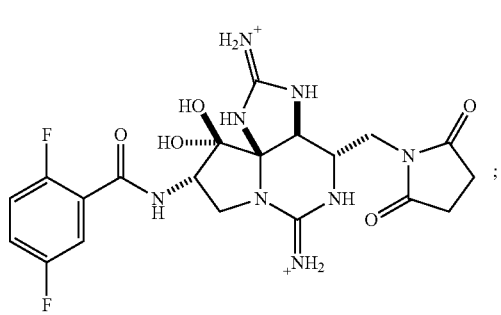

(29)
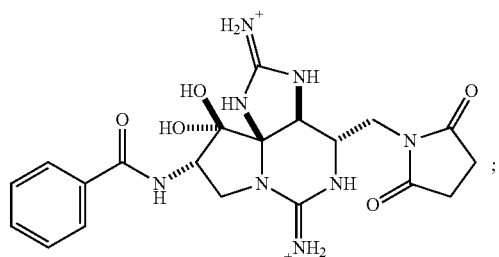
(30)
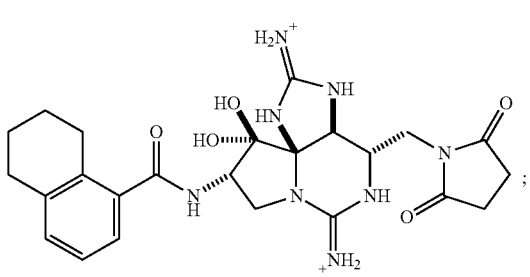
(31)
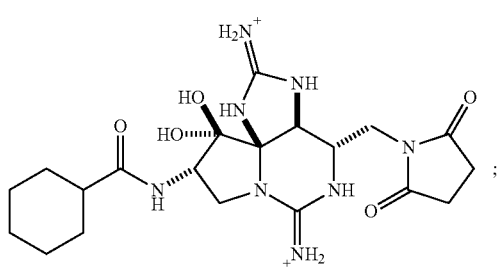
(32)
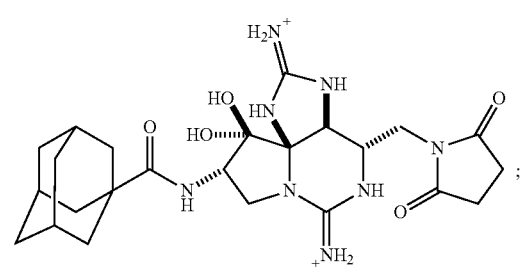
(33)
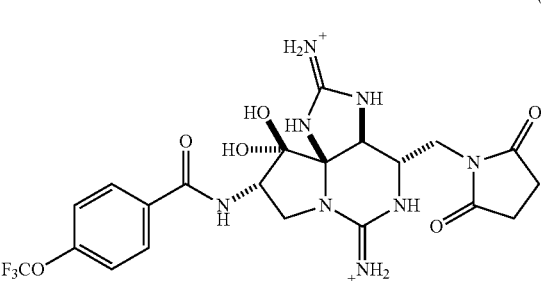
(34)
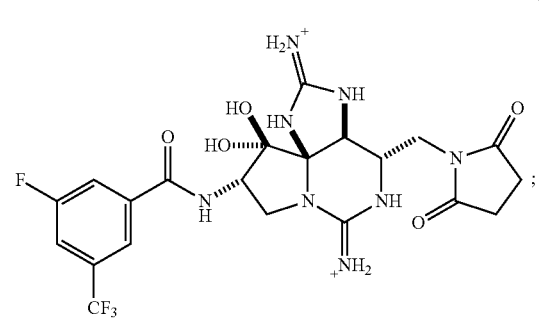
(35)
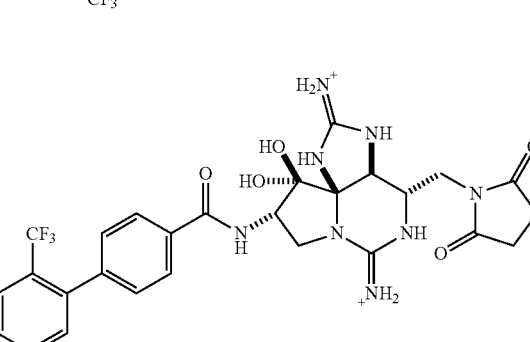
(36)
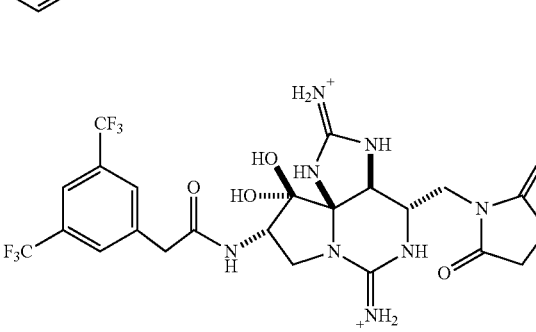
(37)
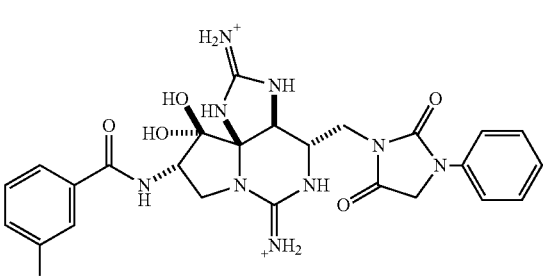
(38)
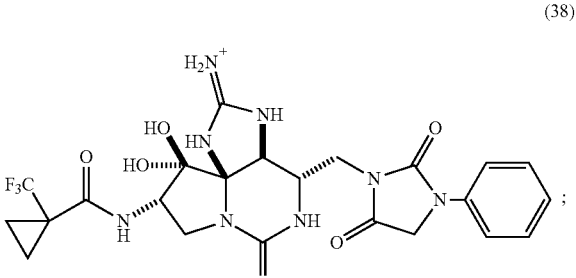

-continued
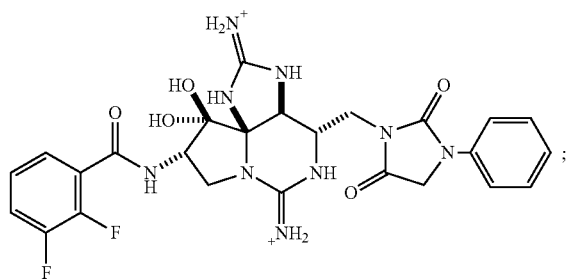
(39)
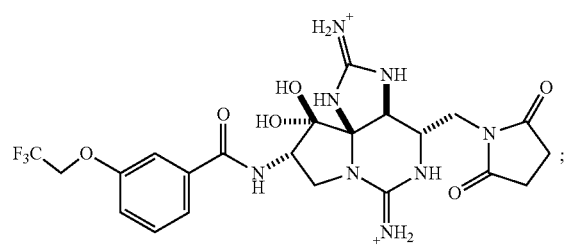
(40)
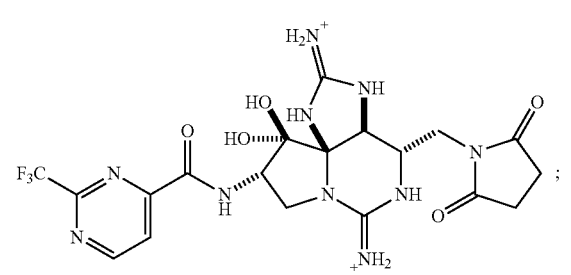
(41)
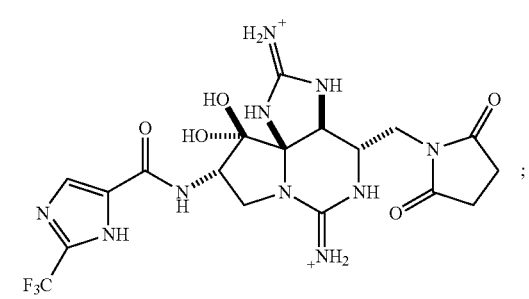
(42)
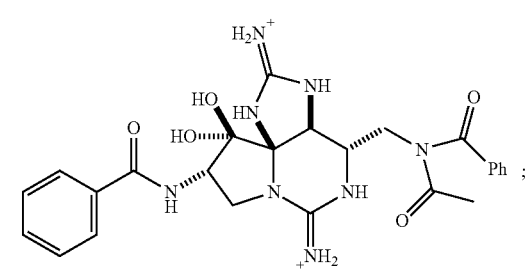
(43)
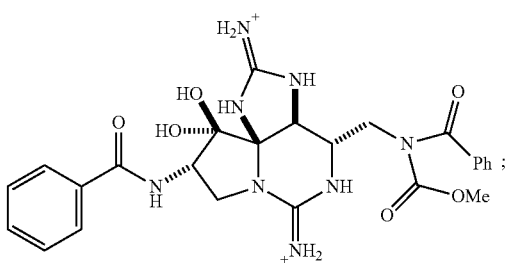
(44)
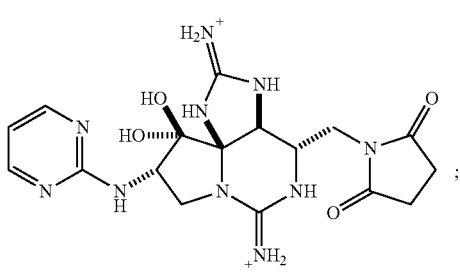
(45)
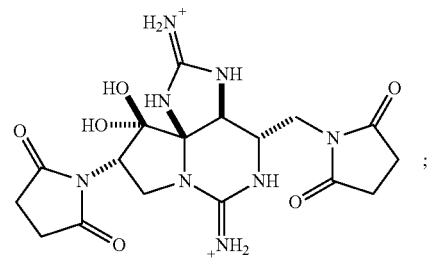
(46)
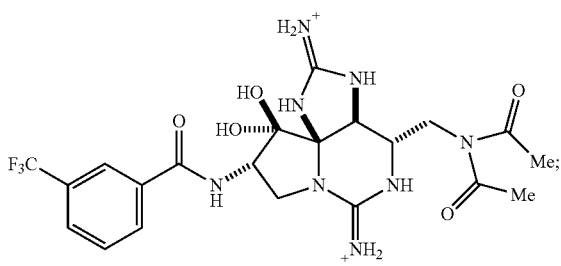
(47)
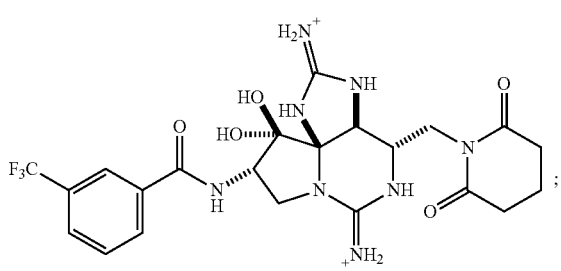
(48)

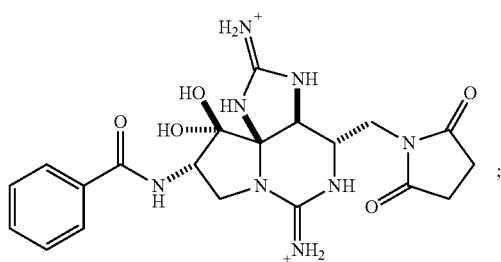
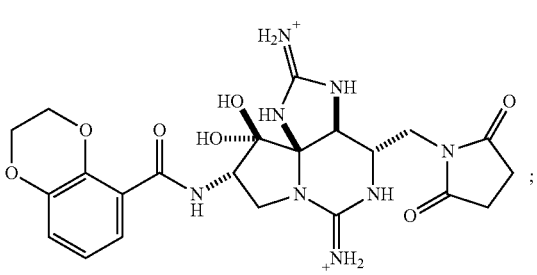
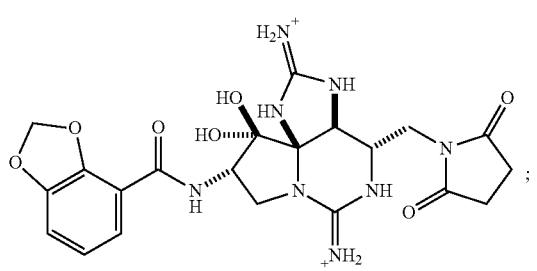
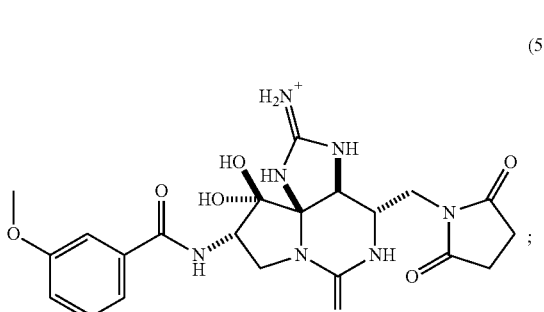
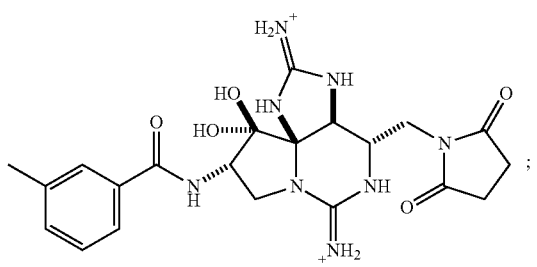
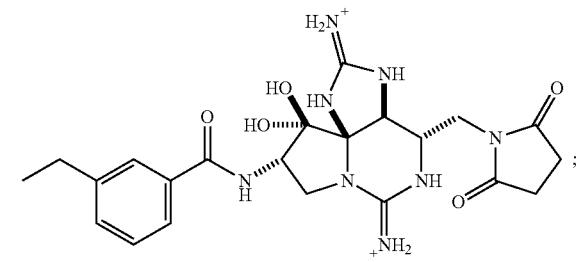
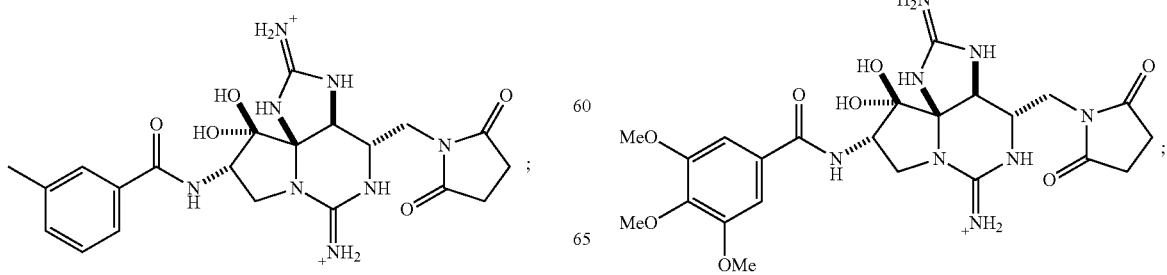

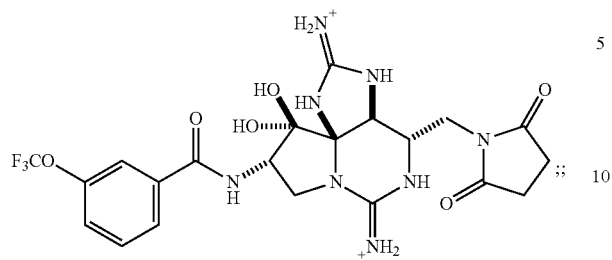
(60)
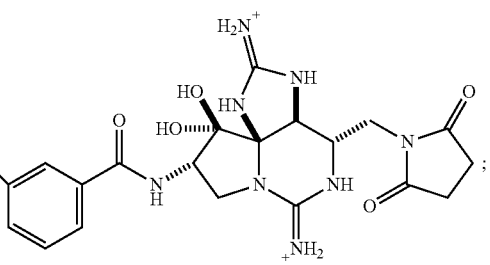
(65)
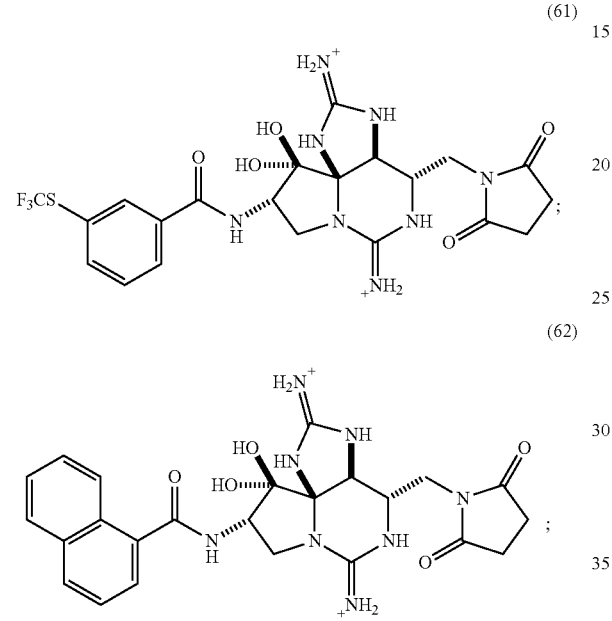
(61)
(62)
(63)
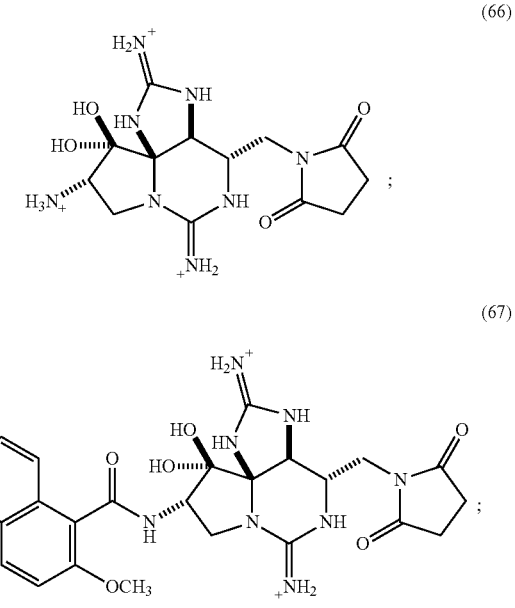
(66)
(67)
(68)
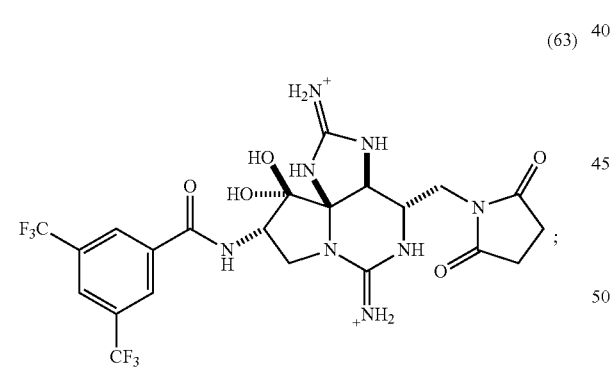
(64)
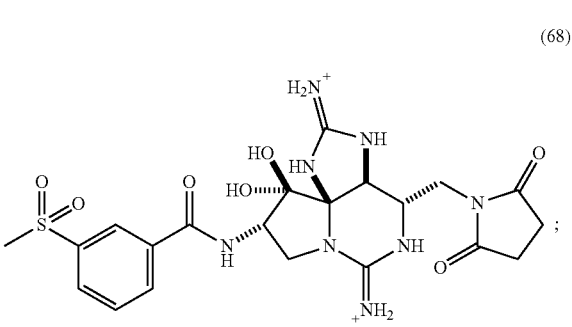
(69)

-continued
(70)
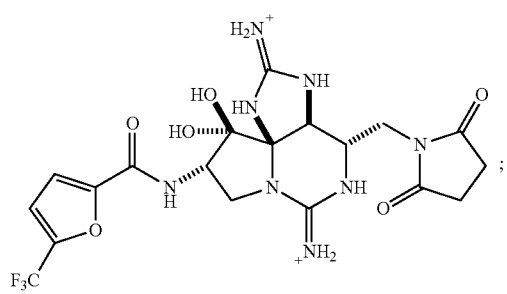
(71)
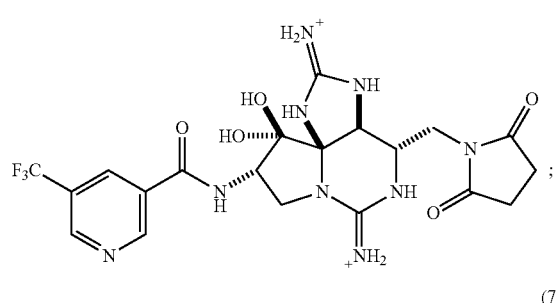
(72)
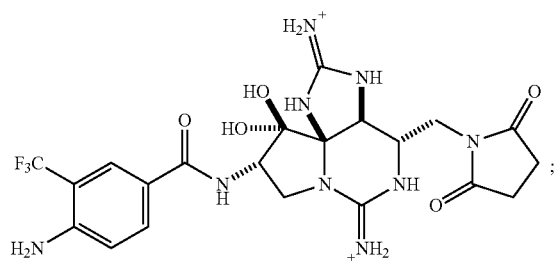
(73)
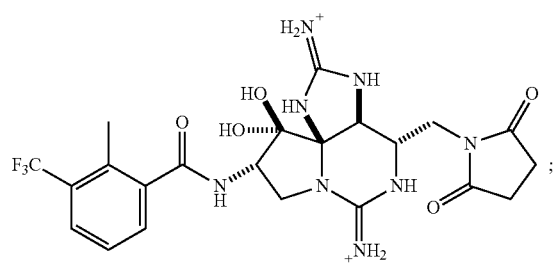
(74)
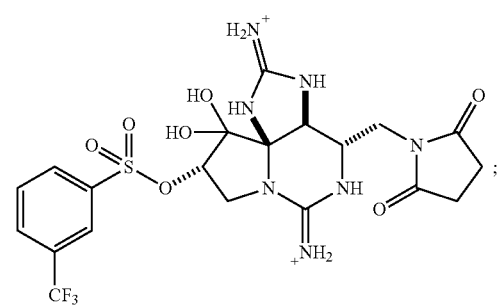
-continued
(75)
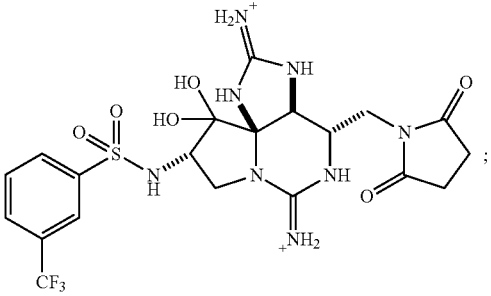
(76)
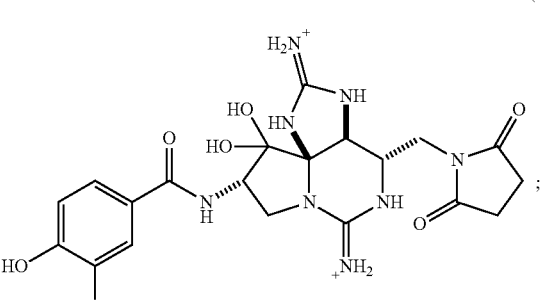
(77)
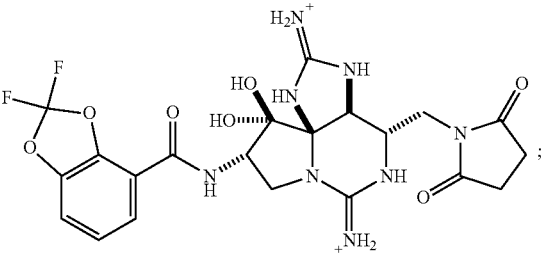
(78)
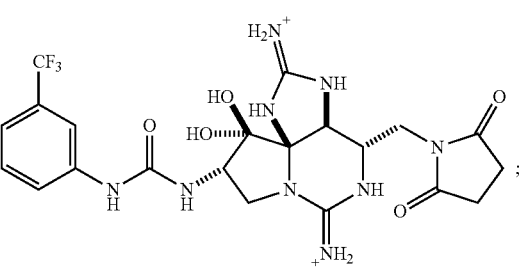
(79)
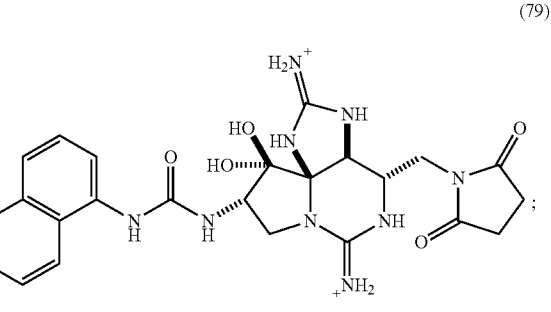

-continued
(80)
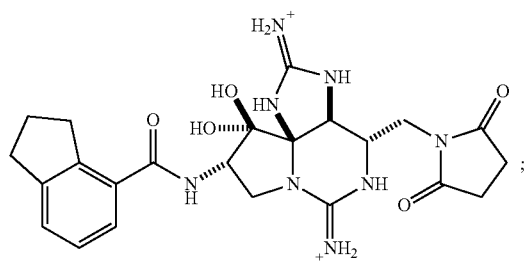
(81)
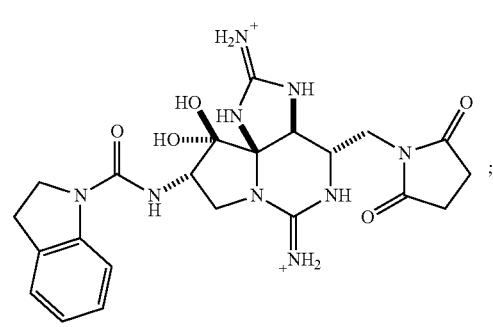
(82)
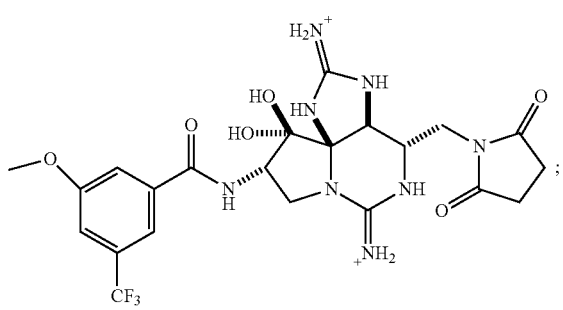
(83)
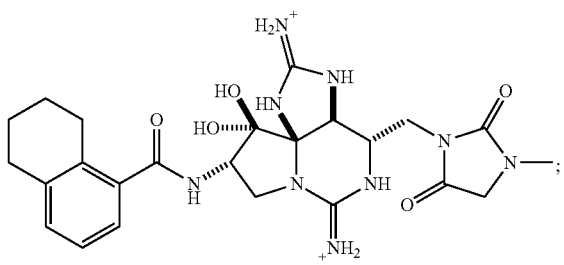
(84)
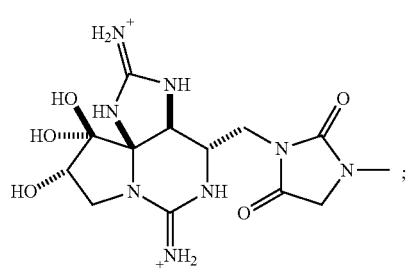
-continued
(85)
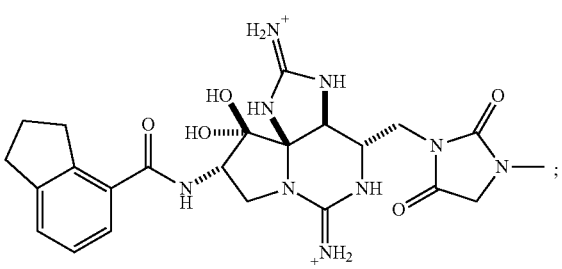
(86)
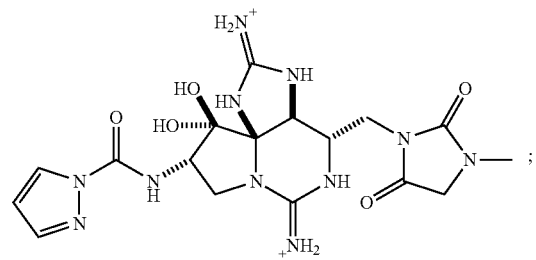
(87)
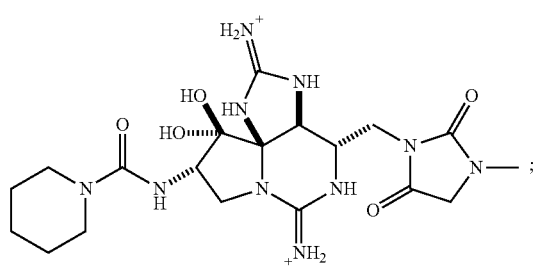
(88)
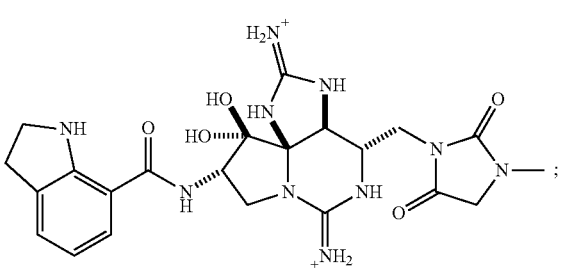
(89)
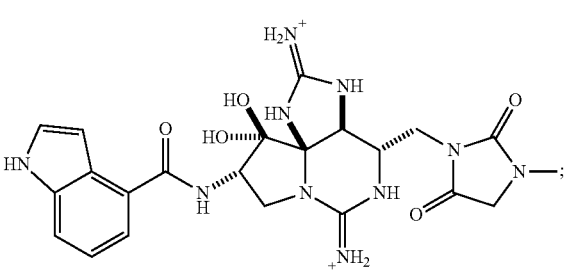

-continued
(90)
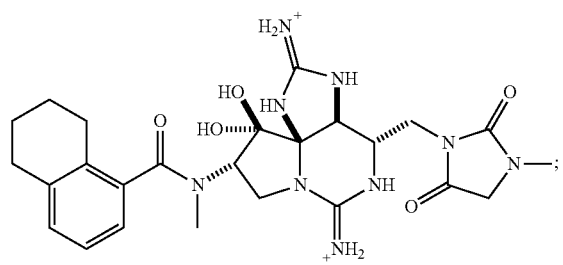
(91)
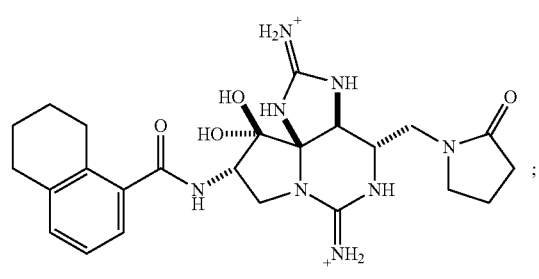
(92)
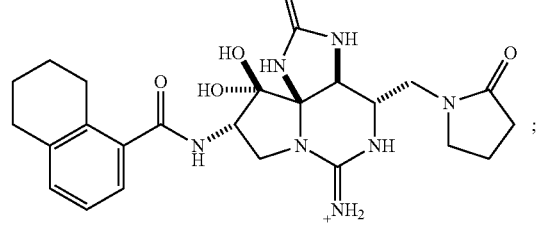
(93)
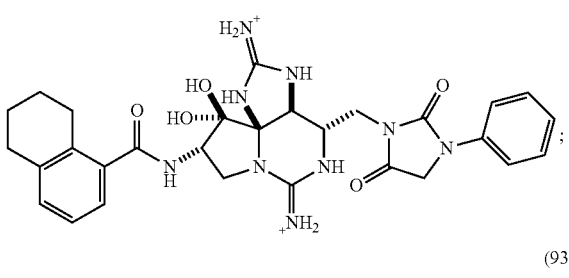
(94)
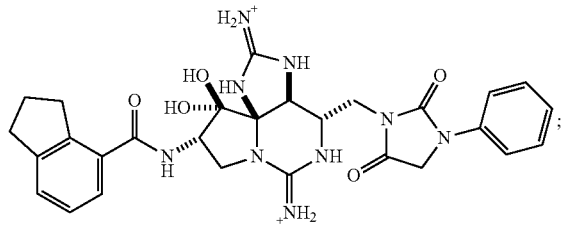
(95)
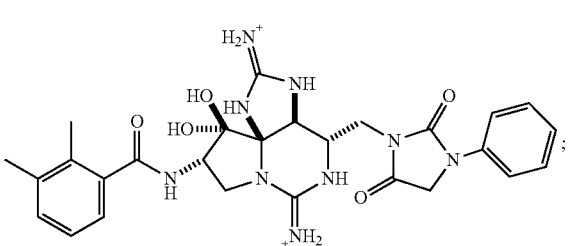
-continued
(96)
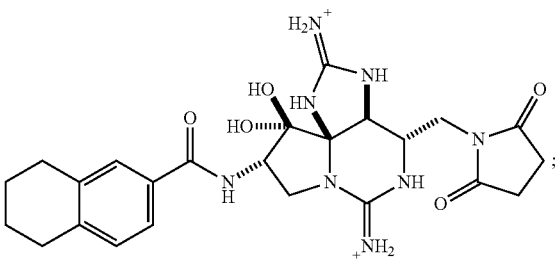
(97)
(98)
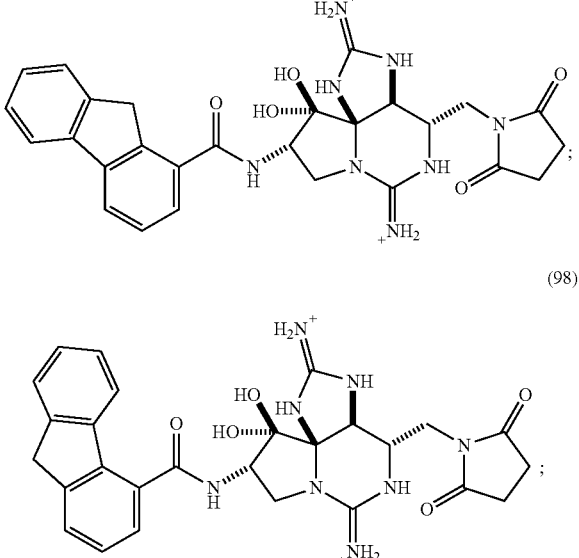
(99)
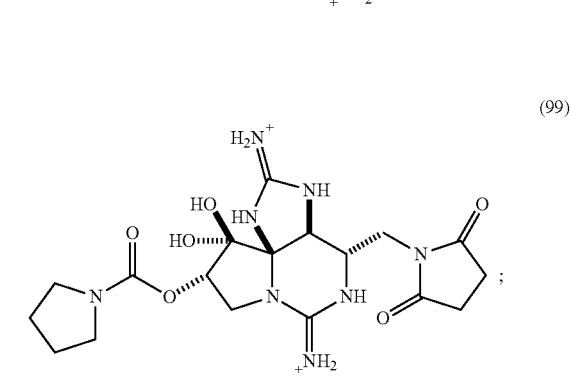
(100)
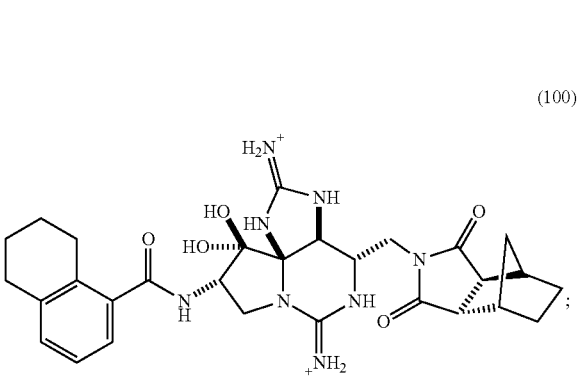

(101)
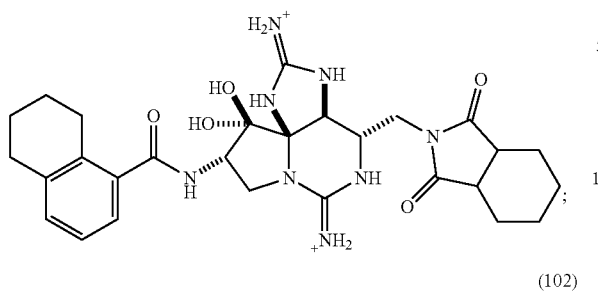
(102)
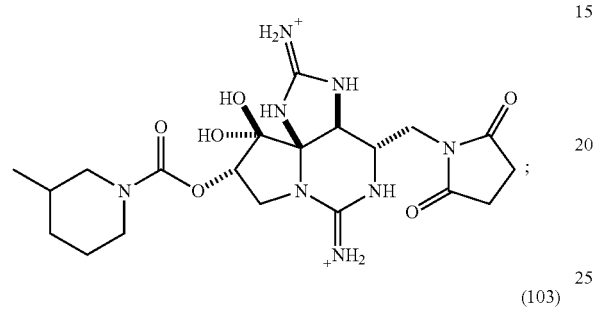
(103)
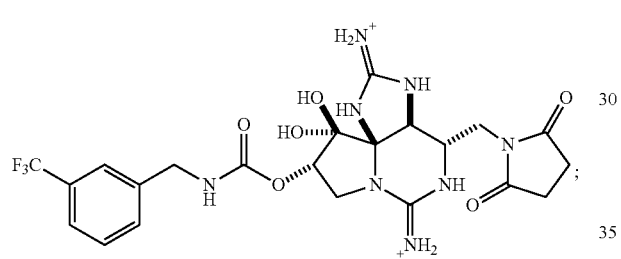
(104)
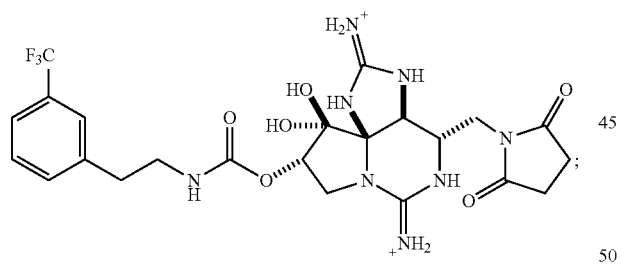
(105)
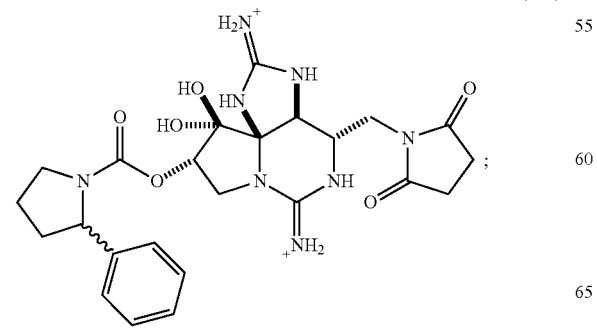
(106)
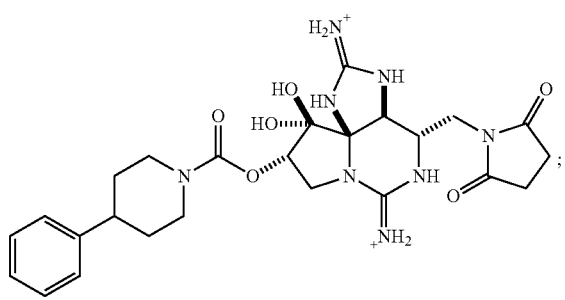
(107)
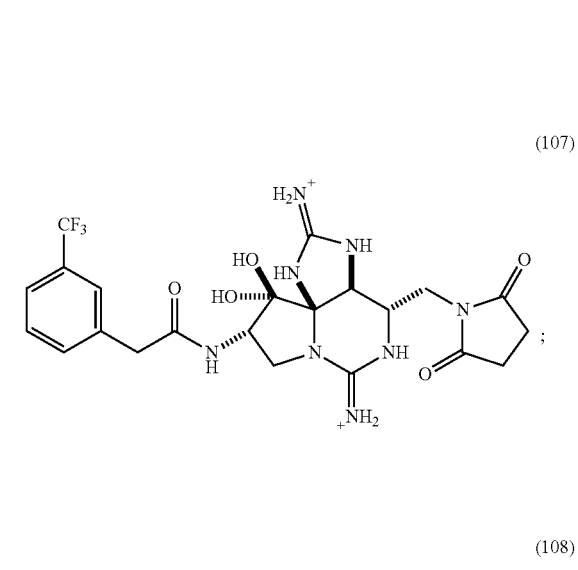
(108)
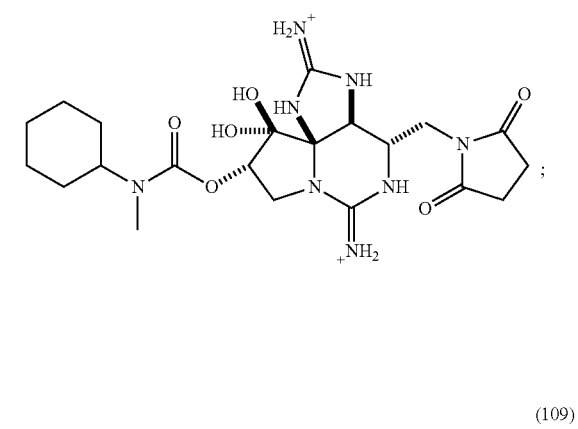
(109)
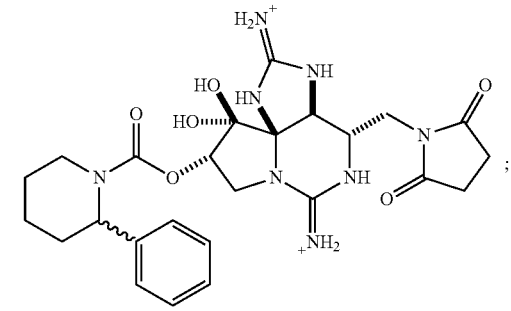

(110) 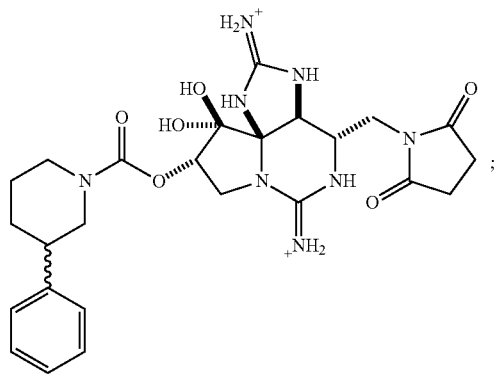
(114) 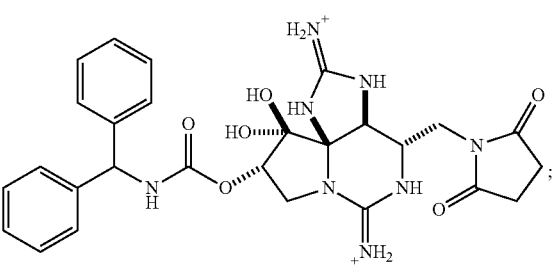
(111) 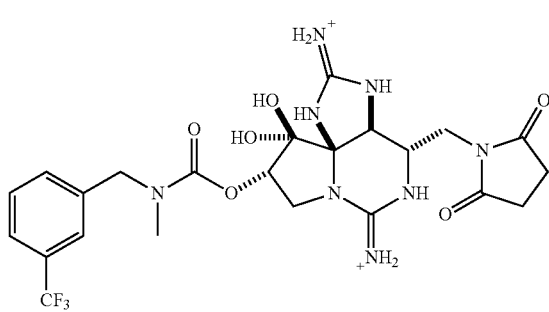
(115) 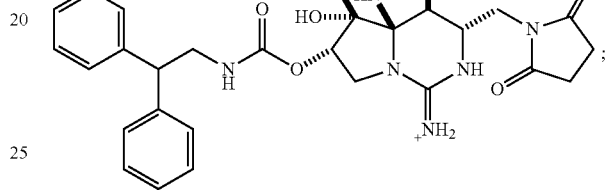
(112) 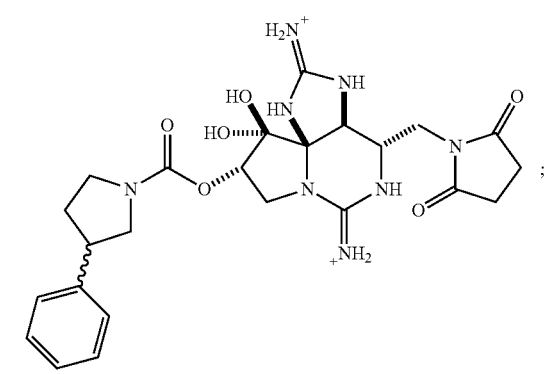
(116) 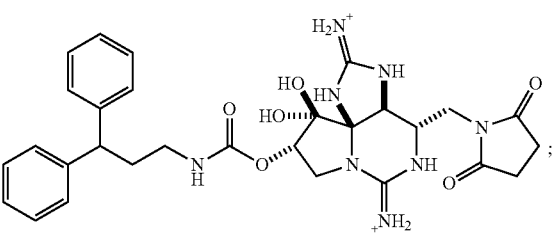
(117) 
(113) 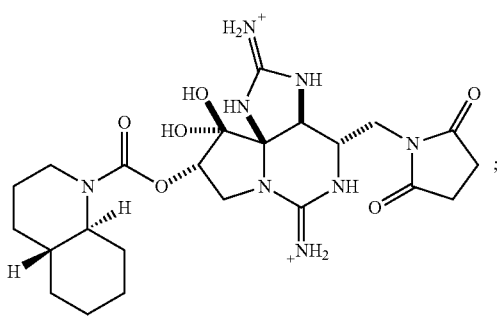
(118) 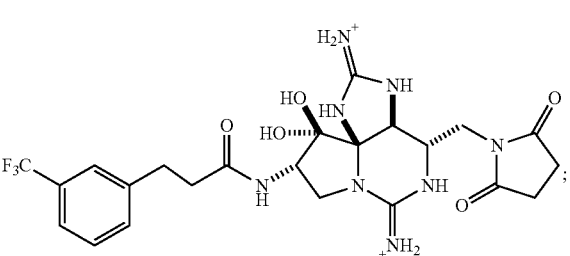

-continued (119)
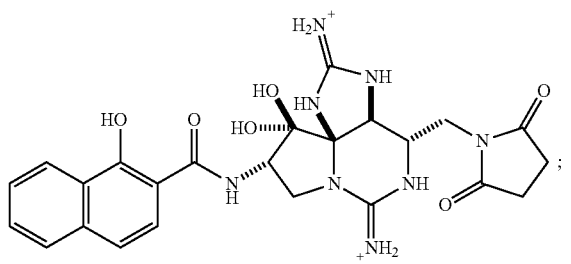

(120)
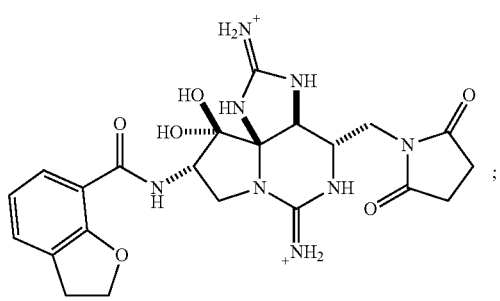

(121)
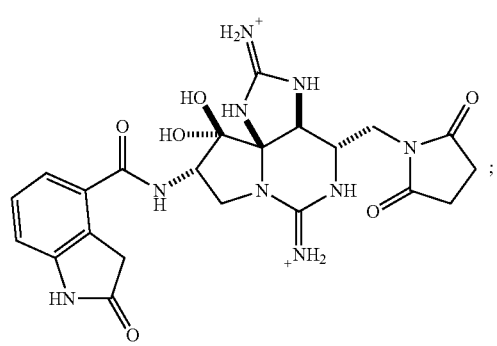

(122)
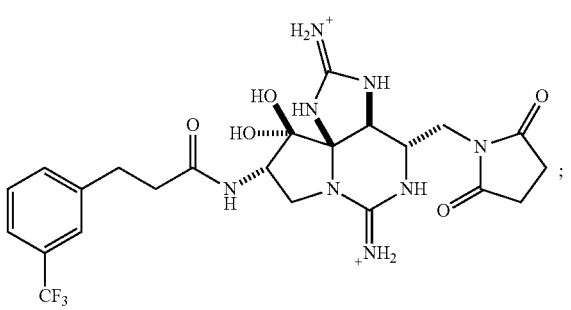

or a pharmaceutically acceptable salt, stereoisomer, tautomer, or mixture thereof.

17. A pharmaceutical composition comprising the compound of claim 1 and a pharmaceutically acceptable excipient, carrier or diluent.

18. The pharmaceutical composition of claim 17, wherein the composition is an oral or injectable formulation.

19. A method for the treatment of a condition associated with voltage-gated sodium channel function in a mammal, comprising the administration of a therapeutically effective amount of a compound of claim 1.

20. The method of claim 19, wherein the mammal is a human.

21. The method of claim 19 where the condition is pain.

22. The method of claim 19 where the condition is associated with pain.

23. The method of claim 22 where the condition is selected from erythromelalgia, diabetic peripheral neuropathy, paroxysmal extreme pain disorder, complex regional pain syndrome, trigeminal neuralgia, multiple sclerosis, osteoarthritis, postherpetic neuralgia, cancer pain, cluster headache, migraine, sciatica, endometriosis, fibromyalgia, and postsurgical pain.

24. The method of claim 19 where the condition is selected from epilepsy, Parkinson's disease, a mood disorder, psychosis, amyotropic lateral sclerosis, glaucoma, ischemia, a spasticity disorder, and obsessive compulsive disorder.

25. A compound of Formula Xe

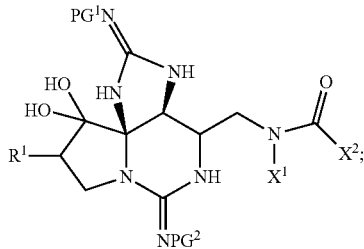

Xe or a salt thereof, where
PG$^1$ is a nitrogen-protecting group and is 9-fluorenylmethyloxycarbonyl (Fmoc), tert-butoxycarbonyl (Boc), benzyloxycarbonyl (CBz), acetyl, trichloroacetyl, trifluoroacetyl, —C(O)OCH$_2$CCl$_3$ (Troc), p-methoxyphenyl, benzyl, p-methoxybenzyl, p-methoxybenzylcarbonyl, triphenylmethyl, benzylidenyl, 2,2,2-trichloroethoxysulfonyl (Tces), p-methoxybenzenesulfonyl (Mbs) or p-toluenesulfonyl (tosyl);
PG$^2$ is a nitrogen-protecting group and is 9-fluorenylmethyloxycarbonyl (Fmoc), tert-butoxycarbonyl (Boc), benzyloxycarbonyl (CBz), acetyl, trichloroacetyl, trifluoroacetyl, —C(O)OCH$_2$CCl$_3$ (Troc), p-methoxyphenyl, benzyl, p-methoxybenzyl, p-methoxybenzylcarbonyl, triphenylmethyl, benzylidenyl, 2,2,2-trichloroethoxysulfonyl (Tces), p-methoxybenzenesulfonyl (Mbs) or p-toluenesulfonyl (tosyl);
R$^1$ is —OS(O)$_2$R$^5$, —OC(O)R$^6$, —NR$^7$C(O)R$^{7a}$, —OC(O)NR$^{10}$R$^{10a}$, —NR$^{11}$R$^{11a}$, —NR$^{13}$S(O)$_2$R$^{13a}$, or —NR$^{14}$C(O)NR$^{14a}$R$^{14b}$;
X$^1$ is R$^3$ and X$^2$ is R$^9$; or
X$^1$ and X$^2$ together with the —NC(O)— to which they are attached form

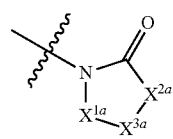

where X$^{1a}$ is —O—, —CH$_2$—, or —C(O)—; X$^{2a}$ is —S—, —NR$^8$—, or —C(R$^4$)(R$^{4a}$)—; and X$^{3a}$ is one or two groups independently selected from —O—, —S—, —NR$^8$—, and —C(R$^4$)(R$^{4a}$)— provided that only one atom of $X^{1a}$, $X^{2a}$, and $X^{3a}$ is selected from —O—, —S—, and —$NR^8$—; and where the

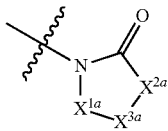

ring is optionally fused at $X^{2a}$ and at the adjacent atom in $X^{3a}$ to form a saturated or unsaturated, 6-12 membered bicyclic ring when 1) $X^{2a}$ is —$NR^8$— and $X^{3a}$ is —$C(R^4)(R^{4a})$— or —$C(R^4)(R^{4a})$—$C(R^4)(R^{4a})$— or 2) $X^{2a}$ is —$C(R^4)(R^{4a})$— and $X^{3a}$ is —$C(R^4)(R^{4a})$—, —$NR^8$—, —$C(R^4)(R^{4a})$—$C(R^4)(R^{4a})$—, —$C(R^4)(R^{4a})$—$NR^8$—, or —$NR^8$—$C(R^4)(R^{4a})$—; and where the three or four additional bicyclic ring atoms are independently —$CR^{12}$= or —$C(R^{12})_2$—;

each $R^4$ and $R^{4a}$ is independently H; $C_{1-6}$alkyl; or when the 6-12 membered ring is fused at a —$C(R^4)(R^{4a})$—, one or both of the $R^4$ and $R^{4a}$ on the —$C(R^4)(R^{4a})$— form a single or double) bond with an adjacent ring atom;

$R^8$ is hydrogen; $C_{1-6}$alkyl; phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano; or when the 6-12 membered ring is fused at an —$NR^8$—, the $R^8$ forms a single bond with an adjacent ring atom;

each $R^{12}$ is independently hydrogen, halo, $C_{1-6}$alkyl, halo-$C_{1-6}$alkyl, or aryl;

$R^3$ is —$C(O)C_{1-6}$alkyl, —$C(O)OC_{1-6}$alkyl, or —$C(O)$phenyl where the phenyl is optionally substituted with one or two groups independently selected from halo, $C_{1-6}$alkyl, halo-$C_{1-6}$alkyl, $C_{1-6}$alkoxy, and aryl;

$R^9$ is $C_{1-6}$alkyl, $C_{1-6}$alkoxy, or phenyl where the phenyl is optionally substituted with one or two groups independently selected from halo, $C_{1-6}$alkyl, halo-$C_{1-6}$alkyl, $C_{1-6}$alkoxy, and aryl;

$R^5$ is H, $C_{1-6}$alkyl, or aryl optionally substituted with 1, 2, 3, or 4 $R^{5a}$;

each $R^{5a}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;

$R^6$ is $C_{1-6}$alkyl; aryl optionally substituted with 1, 2, 3, or 4 $R^{6a}$; aralkyl where the aryl is optionally substituted with 1, 2, 3, or 4 $R^{6a}$; heteroaryl optionally substituted with 1, 2, 3, or 4 $R^{6a}$; heterocyclic optionally substituted with 1, 2, 3, or 4 $R^{6a}$; biphenyl optionally substituted on either ring with 1, 2, 3, or 4 $R^{6a}$; or cycloalkyl optionally substituted with 1, 2, or 3 groups independently selected from $C_{1-6}$alkyl and halo-$C_{1-6}$alkyl;

each $R^{6a}$, when present, is independently halo, $C_{1-6}$alkyl, halo-$C_{1-6}$alkyl, hydroxy, $C_{1-6}$alkoxy, halo-$C_{1-6}$alkoxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, phenyl, or cyano;

$R^7$ is hydrogen or $C_{1-6}$alkyl;

$R^{7a}$ is $C_{1-6}$alkyl; aryl optionally substituted with 1, 2, 3, or 4 $R^{7b}$; aralkyl where the aryl is optionally substituted with 1, 2, 3, or 4 $R^{7b}$; heteroaryl optionally substituted with 1, 2, 3, or 4 $R^{7b}$; heterocyclic optionally substituted with 1, 2, 3, or 4 $R^{7b}$; biphenyl optionally substituted on either ring with 1, 2, 3, or 4 $R^{7b}$; or cycloalkyl optionally substituted with 1, 2, 3, or 4 groups independently selected from $C_{1-6}$alkyl and halo-$C_{1-6}$alkyl;

each $R^{7b}$, when present, is independently halo, $C_{1-6}$alkyl, halo-$C_{1-6}$alkyl, hydroxy, $C_{1-6}$alkoxy, halo-$C_{1-6}$alkoxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, phenyl, or cyano; and $R^{10}$ is hydrogen or $C_{1-6}$alkyl;

$R^{10a}$ is $C_{1-6}$alkyl; aryl optionally substituted with 1, 2, 3, or 4 $R^{10b}$; aralkyl where the aryl is optionally substituted with 1, 2, 3, or 4 $R^{10b}$; phenylcarbonyl where the phenyl is optionally substituted with 1, 2, 3, or 4 $R^{10b}$; heteroaryl optionally substituted with 1, 2, 3, or 4 $R^{10b}$; heterocyclic optionally substituted with 1, 2, 3, or 4 $R^{10b}$; biphenyl optionally substituted on either ring with 1, 2, 3, or 4 $R^{10b}$; or cycloalkyl optionally substituted with 1, 2, 3, or 4 groups independently selected from $C_{1-6}$alkyl and halo-$C_{1-6}$alkyl;

each $R^{10b}$, when present, is independently halo, $C_{1-6}$alkyl, halo-$C_{1-6}$alkyl, hydroxy, $C_{1-6}$alkoxy, halo-$C_{1-6}$alkoxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, phenyl, or cyano;

$R^{11}$ is hydrogen or $C_{1-6}$alkyl;

$R^{11a}$ is $C_{1-6}$alkyl; aryl optionally substituted with 1, 2, 3, or 4 $R^{11b}$; aralkyl where the aryl is optionally substituted with 1, 2, 3, or 4 $R^{11b}$; heteroaryl optionally substituted with 1, 2, 3, or 4 $R^{11b}$; heterocyclic optionally substituted with 1, 2, 3, or 4 $R^{11a}$; biphenyl optionally substituted on either ring with 1, 2, 3, or 4 $R^{11b}$; or cycloalkyl optionally substituted with 1, 2, 3, or 4 groups independently selected from $C_{1-6}$alkyl and halo-$C_{1-6}$alkyl;

each $R^{11b}$, when present, is independently halo, $C_{1-6}$alkyl, halo-$C_{1-6}$alkyl, hydroxy, $C_{1-6}$alkoxy, halo-$C_{1-6}$alkoxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, phenyl, or cyano;

$R^{13}$ is hydrogen or $C_{1-6}$alkyl;

$R^{13a}$ is $C_{1-6}$alkyl; aryl optionally substituted with 1, 2, 3, or 4 $R^{13b}$; aralkyl where the aryl is optionally substituted with 1, 2, 3, or 4 $R^{13b}$; heteroaryl optionally substituted with 1, 2, 3, or 4 $R^{13b}$; heterocyclic optionally substituted with 1, 2, 3, or 4 $R^{13b}$; biphenyl optionally substituted on either ring with 1, 2, 3, or 4 $R^{13b}$; or cycloalkyl optionally substituted with 1, 2, 3, or 4 groups independently selected from $C_{1-6}$alkyl and halo-$C_{1-6}$alkyl;

each $R^{13b}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;

$R^{14}$ is hydrogen or $C_{1-6}$alkyl;

$R^{14a}$ is hydrogen or $C_{1-6}$alkyl;

$R^{14b}$ is $C_{1-6}$alkyl; aryl optionally substituted with 1, 2, 3, or 4 $R^{14c}$; aralkyl where the aryl is optionally substituted with 1, 2, 3, or 4 $R^{14c}$; heteroaryl optionally substituted with 1, 2, 3, or 4 $R^{14c}$; heterocyclic optionally substituted with 1, 2, 3, or 4 $R^{14c}$; biphenyl optionally substituted on either ring with 1, 2, 3, or 4 $R^{14c}$; or cycloalkyl optionally substituted with 1, 2, 3, or 4 groups independently selected from $C_{1-6}$alkyl and halo-$C_{1-6}$alkyl; and each $R^{14c}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano.

26. A method of preparing a compound of Formula (I) comprising
a) deprotecting a compound of Formula Xe

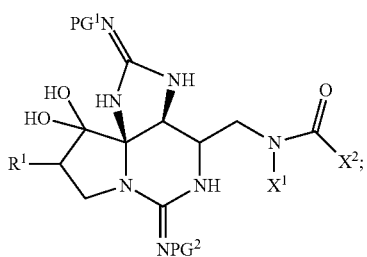

where
PG$^1$ is a nitrogen-protecting group and is 9-fluorenylmethyloxycarbonyl (Fmoc), tert-butoxycarbonyl (Boc), benzyloxycarbonyl (CBz), acetyl, trichloroacetyl, trifluoroacetyl, —C(O)OCH$_2$CCl$_3$ (Troc), p-methoxyphenyl, benzyl, p-methoxybenzyl, p-methoxybenzylcarbonyl, triphenylmethyl, benzylidenyl, 2,2,2-trichloroethoxysulfonyl (Tces), p-methoxybenzenesulfonyl (Mbs) or p-toluenesulfonyl (tosyl);

PG$^2$ is a nitrogen-protecting group and is 9-fluorenylmethyloxycarbonyl (Fmoc), tert-butoxycarbonyl (Boc), benzyloxycarbonyl (CBz), acetyl, trichloroacetyl, trifluoroacetyl, —C(O)OCH$_2$CCl$_1$ (Troc), p-methoxyphenyl, benzyl, p-methoxybenzyl, p-methoxybenzylcarbonyl, triphenylmethyl, benzylidenyl, 2,2,2-trichloroethoxysulfonyl (Tces), p-methoxybenzenesulfonyl (Mbs) or p-toluenesulfonyl (tosyl);

$R^1$ is —OS(O)$_2R^5$, —OC(O)R$^6$, —NR$^7$C(O)R$^{7a}$, —OC(O)NR$^{10}R^{10a}$, NR$^{11}R^{11a}$, —NR$^{13}$S(O)$_2R^{13a}$, or —NR$^{14}$C(O)NR$^{14a}R^{14b}$;

$X^1$ is $R^3$ and $X^2$ is $R^9$; or
$X^1$ and $X^2$ together with the —NC(O)— to which they are attached form

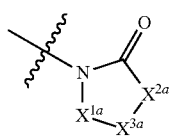

where $X^{1a}$ is —O—, —CH$_2$—, or —C(O)—; $X^{2a}$ is —S—, —NR$^8$—, or —C(R$^4$)(R$^{4a}$)—; and $X^{3a}$ is one or two groups independently selected from —O—, —S—, —NR$^8$—, and —C(R$^4$)(R$^{4a}$)— provided that only one atom of $X^{1a}$, $X^{2a}$, and $X^{3a}$ is selected from —O—, —S—, and —NR$^8$—; and where the

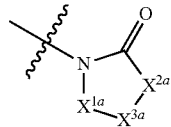

ring is optionally fused at $X^{2a}$ and at the adjacent atom in $X^{3a}$ to form a saturated or unsaturated, 6-12 membered bicyclic ring when 1) $X^{2a}$ is —NR$^8$— and $X^{3a}$ is —C(R$^4$)(R$^{4a}$)— or —C(R$^4$)(R$^{4a}$)—C(R$^4$)(R$^{4a}$)— or 2) $X^{2a}$ is —C(R$^4$)(R$^{4a}$)— and $X^{3a}$ is —C(R$^4$)(R$^{4a}$)—, —NR$^8$—, —C(R$^4$)(R$^{4a}$)—C(R$^4$)(R$^{4a}$)—, —C(R$^4$)(R$^{4a}$)—NR$^8$—, or —NR$^8$—C(R$^4$)(R$^{4a}$)—; and where the three or four additional ring atoms are independently —CR$^{12}$= or —C(R$^{12}$)$_2$—;

each $R^4$ and $R^{4a}$ is independently H; $C_{1-6}$alkyl; or when the 6-12 membered ring is fused at a —C(R$^4$)(R$^{4a}$)—, one or both of the $R^4$ and $R^{4a}$ on the —C(R$^4$)(R$^{4a}$)— form a single or double bond with an adjacent ring atom;

$R^8$ is hydrogen; $C_{1-6}$alkyl; phenyl optionally substituted with 1, 2, or 3 groups independently selected from halo, $C_{1-6}$alkyl, halo-$C_{1-6}$alkyl, hydroxy, $C_{1-6}$alkoxy, halo-$C_{1-6}$alkoxy, nitro, and cyano; or when the 6-12 membered ring is fused at an —NR$^8$—, the $R^8$ forms a single bond with an adjacent ring atom;

each $R^{12}$ is independently hydrogen, halo, $C_{1-6}$alkyl, halo-$C_{1-6}$alkyl, or aryl;

$R^3$ is —C(O)C$_{1-6}$alkyl, —C(O)OC$_{1-6}$alkyl, or —C(O)phenyl where the phenyl is optionally substituted with one or two groups independently selected from halo, $C_{1-6}$alkyl, halo-$C_{1-6}$alkyl, $C_{1-6}$alkoxy, and aryl;

$R^9$ is $C_{1-6}$alkyl, $C_{1-6}$alkoxy, or phenyl where the phenyl is optionally substituted with one or two groups independently selected from halo, $C_{1-6}$alkyl, halo-$C_{1-6}$alkyl, $C_{1-6}$alkoxy, and aryl;

$R^5$ is H, $C_{1-6}$alkyl, or aryl optionally substituted with 1, 2, 3, or 4 $R^{5a}$;

each $R^{5a}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;

$R^6$ is $C_{1-6}$alkyl; aryl optionally substituted with 1, 2, 3, or 4 $R^{6a}$; aralkyl where the aryl is optionally substituted with 1, 2, 3, or 4 $R^{6a}$; heteroaryl optionally substituted with 1, 2, 3, or 4 $R^{6a}$; heterocyclic optionally substituted with 1, 2, 3, or 4 $R^{6a}$; biphenyl optionally substituted on either ring with 1, 2, 3, or 4 $R^{6a}$; or cycloalkyl optionally substituted with 1, 2, 3, or 4 groups independently selected from $C_{1-6}$alkyl and halo-$C_{1-6}$alkyl;

each $R^{6a}$, when present, is independently halo, $C_{1-6}$alkyl, halo-$C_{1-6}$alkyl, hydroxy, $C_{1-6}$alkoxy, halo-$C_{1-6}$alkoxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, phenyl, or cyano;

$R^7$ is hydrogen or $C_{1-6}$alkyl;

$R^{7a}$ is $C_{1-6}$alkyl; aryl optionally substituted with 1, 2, 3, or 4 $R^{7b}$; aralkyl where the aryl is optionally substituted with 1, 2, 3, or 4 $R^{7b}$; heteroaryl optionally substituted with 1, 2, 3, or 4 $R^{7b}$; heterocyclic optionally substituted with 1, 2, 3, or 4 $R^{7b}$; biphenyl optionally substituted on either ring with 1, 2, 3, or 4 $R^{7b}$; or cycloalkyl optionally substituted with 1, 2, 3, or 4 groups independently selected from $C_{1-6}$alkyl and halo-$C_{1-6}$alkyl;

each $R^7b$, when present, is independently halo, $C_{1-6}$alkyl, halo-$C_{1-6}$alkyl, hydroxy, $C_{1-6}$alkoxy, halo-$C_{1-6}$alkoxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, phenyl, or cyano; and $R^{10}$ is hydrogen or $C_{1-6}$alkyl;

$R^{10a}$ is $C_{1-6}$alkyl; aryl optionally substituted with 1, 2, 3, or 4 $R^{10b}$; aralkyl where the aryl is optionally substituted with 1, 2, 3, or 4 $R^{10b}$; phenylcarbonyl where the phenyl is optionally substituted with 1, 2, 3, or 4 $R^{10b}$; heteroaryl optionally substituted with 1, 2, 3, or 4 $R^{10b}$; heterocyclic optionally substituted with 1, 2, or 3 $R^{10b}$; biphenyl optionally substituted on either ring with 1, 2, 3, or 4 $R^{10b}$; or cycloalkyl optionally substituted with 1, 2, 3, or 4 groups independently selected from $C_{1-6}$alkyl and halo-$C_{1-6}$alkyl;

each $R^{10b}$, when present, is independently halo, $C_{1-6}$alkyl, halo-$C_{1-6}$alkyl, hydroxy, $C_{1-6}$alkoxy, halo-$C_{1-6}$alkoxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, phenyl, or cyano;

$R^{11}$ is hydrogen or $C_{1-6}$alkyl;

$R^{11a}$ is $C_{1-6}$alkyl; aryl optionally substituted with 1, 2, 3, or 4 $R^{11b}$; aralkyl where the aryl is optionally substituted with 1, 2, 3, or 4 $R^{11b}$; heteroaryl optionally substituted with 1, 2, 3, or 4 $R^{11b}$; heterocyclic optionally substituted with 1, 2, 3, or 4 $R^{11a}$; biphenyl optionally substituted on either ring with 1, 2, 3, or 4 $R^{11b}$; or cycloalkyl optionally substituted with 1, 2, 3, or 4 groups independently selected from $C_{1-6}$alkyl and halo-$C_{1-6}$alkyl;

each $R^{11b}$, when present, is independently halo, $C^{1-6}$alkyl, halo-$C_{1-6}$alkyl, hydroxy, $C_{1-6}$alkoxy, halo-$C_{1-6}$alkoxy, nitro, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, amino, $C_{1-6}$alkylamino, di-$C_{1-6}$alkylamino, phenyl, or cyano;

$R^{13}$ is hydrogen or $C_{1-6}$alkyl;

$R^{13a}$ is $C_{1-6}$alkyl; aryl optionally substituted with 1, 2, 3, or 4 $R^{13b}$; aralkyl where the aryl is optionally substituted with 1, 2, 3, or 4 $R^{13b}$; heteroaryl optionally substituted with 1, 2, 3, or 4 $R^{13b}$; heterocyclic optionally substituted with 1, 2, 3, or 4 $R^{13b}$; biphenyl optionally substituted on either ring with 1, 2, 3, or 4 $R^{13b}$; or cycloalkyl optionally substituted with 1, 2, 3, or 4 groups independently selected from $C_{1-6}$alkyl and halo-$C_{1-6}$alkyl;

each $R^{13b}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;

$R^{14}$ is hydrogen or $C_{1-6}$alkyl;

$R^{14a}$ is hydrogen or $C_{1-6}$alkyl;

$R^{14b}$ is $C_{1-6}$alkyl; aryl optionally substituted with 1, 2, 3, or 4 $R^{14c}$; aralkyl where the aryl is optionally substituted with 1, 2, 3, or 4 $R^{14c}$; heteroaryl optionally substituted with 1, 2, 3, or 4 $R^{14c}$; heterocyclic optionally substituted with 1, 2, 3, or 4 $R^{14c}$; biphenyl optionally substituted on either ring with 1, 2, 3, or 4 $R^{14c}$; or cycloalkyl optionally substituted with 1, 2, 3, or 4 groups independently selected from $C_{1-6}$alkyl and halo-$C_{1-6}$alkyl; and each $R^{14c}$, when present, is independently halo, $C_{1-6}$alkyl, halo-$C_{1-6}$alkyl, hydroxy, $C_{1-6}$alkoxy, halo-$C_{1-6}$alkoxy, $C_{1-6}$alkylthio, halo-$C_{1-6}$alkylthio, $C_{1-6}$alkylsulfinyl, halo-$C_{1-6}$alkylsulfinyl, $C_{1-6}$alkylsulfonyl, halo-$C_{1-6}$alkylsulfonyl, nitro, amino, $C_{1-6}$alkylamino, di-$C_{1-6}$alkylamino, phenyl, or cyano;

to yield a compound of Formula I; and b) optionally isolating the compound of Formula I.

27. The Compound of claim 25 where $PG^1$ is Tces, Mbs, or tosyl and $PG^2$ is trichloroacetyl or —C(O)OCH$_2$CCl$_3$.

28. The method of claim 26 where $PG^1$ is Tces, Mbs, or tosyl and $PG^2$ is trichloroacetyl or —C(O)OCH$_2$CCl$_3$.

29. The Compound of claim 1 where $X^1$ and $X^2$ together with the —NC(O)— to which they are attached form a 5-membered ring which is

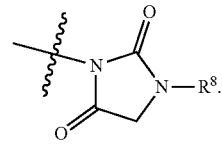

30. The Compound of claim 10 where $X^1$ and $X^2$ together with the —NC(O)— to which they are attached form a 5-membered ring which is

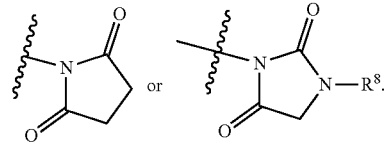

31. The Compound of claim 1 where $X^1$ and $X^2$ together with the —NC(O)— to which they are attached form a 5-membered ring which is

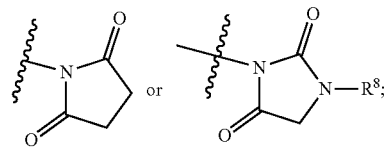

and $R^1$ is —OC(O)$R^6$ or —NR$^7$C(O)$R^{7a}$.

32. The Compound of claim 31 where $R^6$ is aryl optionally substituted with 1, 2, 3, or 4 $R^{6a}$; or heterocyclic optionally substituted with 1, 2, 3, or 4 $R^{6a}$; $R^7$ is hydrogen; and $R^{7a}$ is aryl optionally substituted with 1, 2, 3, or 4 $R^{7b}$; or heterocyclic optionally substituted with 1, 2, 3, or 4 $R^{7b}$.

* * * * *